(12) United States Patent
Sakaki et al.

(10) Patent No.: US 6,403,644 B1
(45) Date of Patent: *Jun. 11, 2002

(54) METHOD OF TREATING DISEASE WITH SULFONYLAMINO ACID DERIVATIVES

(75) Inventors: Katsuhito Sakaki; Hidekazu Kanazawa; Tsuneyuki Sugiura; Tohru Miyazaki; Hiroyukii Ohno, all of Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/709,439

(22) Filed: Nov. 13, 2000

Related U.S. Application Data

(62) Division of application No. 08/688,161, filed on Jul. 29, 1996, now Pat. No. 6,177,466.

(30) Foreign Application Priority Data

Jul. 28, 1995 (JP) .............................. 7-212556
Mar. 19, 1996 (JP) .............................. 8-090491

(51) Int. Cl.⁷ ..................... C07C 311/42; C07C 311/37; A61K 31/216
(52) U.S. Cl. ..................... 514/538; 514/542; 514/562; 560/12; 560/13; 562/430
(58) Field of Search ................. 514/538, 542, 514/562; 560/12, 13; 562/430

(56) References Cited

U.S. PATENT DOCUMENTS

| | | | |
|---|---|---|---|
| 5,017,610 A | 5/1991 | Imaki et al. | |
| 5,455,258 A | 10/1995 | Macpherson et al. | |
| 5,795,890 A | 8/1998 | Nakae et al. | |
| 6,177,466 B1 * | 1/2001 | Sakaki et al. | ............... 514/538 |

FOREIGN PATENT DOCUMENTS

| | | |
|---|---|---|
| WO | 9535275 | 12/1995 |
| WO | 9535276 | 12/1995 |
| WO | 9600214 | 1/1996 |

OTHER PUBLICATIONS

El–Sayed, J Serb Chem Soc 56 (6) 311–318; Date:1991.
Bilobrova Zh. Org. Khim. 7(10) 2168–71 Abstract; Date 1971.
Novel Inhibitors of Rat Lens Aldose Reductase: N–[[(Substituted amino)phenyl]sulfonyl]glycines, Charles A. Mayfield and Jack DeRuiter, Journal of Medicinal Chemistry, vol. 30, No. 9, pp. 1595–1598, 1987.
Inhibitors of matric metalloproteinases (MNP's), Beeley et al, Curr. Opin. Ther. Patents (1994) 4 (1):7–16, Current Drugs Ltd ISSN 0962–2594.
Inhibitory activity and mechanism of inhibition of the N–[[4–benzoylamino)phenyl]sulfonyl]amino acid aldose reductase inhibitors, DeRuiter et al, Biochemical Pharmacology, vol. 40, No. 10, pp. 2219–2226.

Some novel sulfanilyl amino acid derivatives, El–Sayed J. Serb. Chem. Soc. 56 (6) pp. 311–318 (1991).
Carboxylic acid analogues of suramin, potential filaricides, Nickel et al, Indian Journal of Chem., vol. 30B, Feb. 1991, pp. 182–187.
4–(4'–Substituted benzoyl) aminobenzenesulphonyl–L(+)–glutamic acids . . . , DeBnath et al, Indian Journal of chem., vol. 28B, Oct. 1989, pp. 843–847.

* cited by examiner

*Primary Examiner*—Floyd D. Higel
(74) *Attorney, Agent, or Firm*—Stevens, Davis, Miller & Mosher, LLP

(57) ABSTRACT

The present invention is related to:
(i) matrix metalloproteinase inhibitors containing sulfonylamino acid derivatives of the formula (Ia);

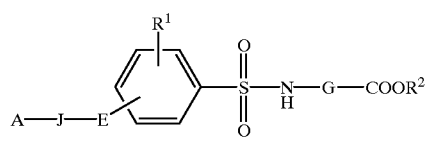

(Ia)

wherein $R^1$ is hydrogen, C1–4 alkyl; $R^2$ is hydrogen, C1–8 alkyl etc.; E is —$CONR^3$—, in which $R^3$ is hydrogen, C1–4 alkyl etc., —$NR^3CO$—, —CO—O—, —O—CO— etc.; A is hydrogen, C1–8 alkyl, C3–7 cycloalkyl, or Ar; J is bond, C2–4 alkylene etc.; G is —$(CH_2)_m$—, in which m is 2, 3 or 4, or

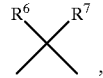

in which $R^6$ and $R^7$ is hydrogen, C1–8 alkyl etc.; and non-toxic salts thereof, (ii) sulfonylamino acid derivatives of the formula (Ib):

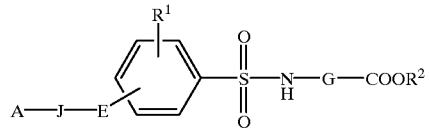

(Ib)

wherein all the symbols are the same meaning as (i); and non-toxic salts thereof, and (iii) process for the preparation of the compound of the formula (Ib).

The compounds of the formula (Ia) are useful for prevention and/or treatment of diseases induced by overexpression and excess activity of MMP. The diseases such as above, for example, are rheumatoid, arthrosteitis, unusual bone resorption, osteoporosis, periodontitis, interstitial nephritis, arteriosclerosis, pulmonary emphysema, cirrhosis, cornea injury, metastasis of, invasion of or growth of tumor cell, autoimmune disease (Crohn's disease, Sjogren's syndrome etc.), disease caused by vascular emigration or infiltration of leukocytes, arterialization.

8 Claims, No Drawings

METHOD OF TREATING DISEASE WITH SULFONYLAMINO ACID DERIVATIVES

This is a divisional of U.S. patent application Ser. No. 08/688,161 filed Jul. 29, 1996, now U.S. Pat. No. 6,177,466, issued Jan. 23, 2001, and incorporated herein by reference.

SUMMARY

This invention is related to sulfonylamino acid derivatives and matrix metalloproteinase inhibitors containing sulfonylamino acid derivatives as active ingredient. More particularly, this invention is related to:

(i) matrix metalloproteinase inhibitors containing sulfonylamino acid derivatives of the formula (Ia):

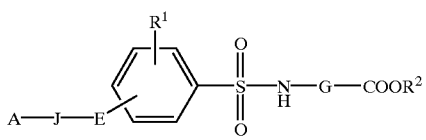

(Ia)

wherein all the symbols are the same meaning as hereinafter defined. and non-toxic salts thereof as active ingredient, (ii) novel sulfonylamino acid derivatives of the formula (Ib):

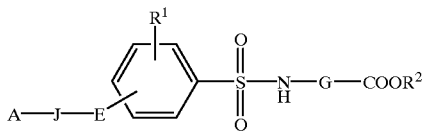

(Ib)

wherein all the symbols are the same meaning as hereinafter defined, and non-toxic salts thereof, and (iii) process for the preparation of the compounds of the formula (Ib).

BACKGROUND

The matrix metalloproteinases (MMPs) are neutral metalloproteinases and zinc ($Zn^{2+}$) is essential in the active site for their activation. They degrade collagen, laminin, proteoglycans, fibronectin, elastin, gelatin etc. under physiological conditions and therefore, are effective on growth and tissue remodeling of articulation tissue, bone tissue, connective tissue. At least 10 classes of MMPs which differ in primary structure are identified.

As common characters of each enzymes, MMPs
(1) have $Zn^{2+}$ in the active site and the activity depends on calcium ($Ca^{2+}$),
(2) are secreted as an inactive proenzyme and activated outside of cells,
(3) have high homology on amino acid sequence,
(4) have degradable ability on various extracellular matrix components in vivo,
(5) are regulated by tissue inhibitors of metalloproteinases (TIMP) which are specific to MMPs.

MMP inhibitors are useful for prevention and/or treatment of various diseases induced by overexpression and excess activation of MMP. Such diseases are, for example, rheumatoid, arthrosteitis, unusual bone resorption, osteoporosis, periodontitis, interstitial nephritis, arteriosclerosis, pulmonary emphysema, cirrhosis, cornea injury, metastasis of, invasion of or growth of tumor cells, autoimmune diseases (Crohn's disease, Sjogren's syndrome etc.), diseases caused by vascular emigration or infiltration of leukocytes, arterialization.

Related Arts

Some compounds possessing inhibitory activity against MMP are known. A sequence in the vicinity of cleavage site of collagen (Gly-Ile-Ala-Gly or Gly-Leu-Ala-Gly) has high affinity for collagenase.

A lot of research and development of substrate analogous MMP inhibitors, which are chemically modified so as to have zinc affinity groups on a cleaving site of substrate, are carried out energetically [Inhibitors of matrix metalloproteinases (MMP's), Nigel R A Beeley, Phillip R J Ansell, Andrew J P Docherty et. al., Curr. Opin. Ther. Patents., 4, 7–16 (1994), Current Drugs Ltd ISSN 0962-2594]. However, these substrate-analogues inhibitors might have various problems. Therefor, it is desired a non-peptide inhibitor and some compounds are reported.

For example, in the specification of EP 606046, arylsulfonamide derivatives of the formula (X):

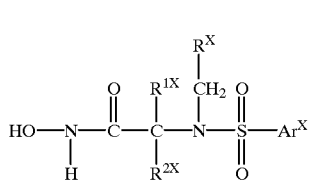

(X)

wherein (a) $Ar^X$ is carbocyclic or heterocyclic aryl; $R^X$ is hydrogen, lower alkyl, carbocyclic aryl-lower alkyl etc.; $R^{1X}$ is hydrogen, lower alkyl, carbocyclic aryl-lower alkyl etc.; $R^{2X}$ is hydrogen, lower alkyl; or (b) $R^X$ and $R^{1X}$ together with the chain to which they are attached form 1, 2, 3, 4-tetrahydro-isoquinoline, piperidine etc.; $Ar^X$ and $R^{2X}$ are the same meaning as (a); or (c) $R^{1X}$ and $R^{2X}$ together with the carbon to which they are attached form C3–7 cycloalkane, oxa-cyclohexane, thia-cyclohexane etc. which is unsubstituted or substituted by lower alkyl; and $Ar^X$ and $R^{2X}$ are the same meaning as (a); are disclosed to have inhibitory activity against matrix metalloproteinase.

Phenylsulfonylamino acid derivatives of the formula (Y):

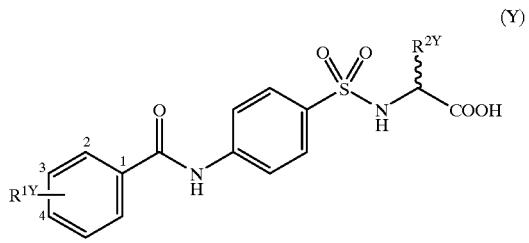

(Y)

wherein $R^{1Y}$ is hydrogen, $R^{2Y}$ is hydrogen;
$R^{1Y}$ is 4-methoxy, $R^{2Y}$ is hydrogen;
$R^{1Y}$ is 4-fluoro, $R^{2Y}$ is hydrogen;
$R^{1Y}$ is 4-nitro, $R^{2Y}$ is hydrogen;
$R^{1Y}$ is 3-nitro, $R^{2Y}$ is hydrogen;
$R^{1Y}$ is 2-nitro, $R^{2Y}$ is hydrogen;
$R^{1Y}$ is 4-formyl, $R^{2Y}$ is hydrogen;
$R^{1Y}$ is hydrogen, $R^{2Y}$ is (S)-phenyl;
$R^{1Y}$ is hydrogen, $R^{2Y}$ is (R)-phenyl;
$R^{1Y}$ is 4-methyl, $R^{2Y}$ is (S)-phenyl;
$R^{1Y}$ is 4-methyl, $R^{2Y}$ is (R)-phenyl;
$R^{1Y}$ is 4-methoxy, $R^{2Y}$ is (S)-phenyl;

$R^{1Y}$ is 4-methoxy, $R^{2Y}$ is (R)-phenyl;
$R^{1Y}$ is 4-fluoro, $R^{2Y}$ is (S)-phenyl;
$R^{1Y}$ is 4-fluoro, $R^{2Y}$ is (R)-phenyl;
$R^{1Y}$ is 4-nitro, $R^{2Y}$ is (S)-phenyl; or
$R^{1Y}$ is 4-nitro, $R^{2Y}$ is (R)-phenyl;
are disclosed to have inhibitory activity against aldose reductase [Biochemical Pharmacology, 40, 2219–2226 (1990)].

In the specification of EP3471 68, p-substituted phenyl ester of pivalic acid derivatives of the formula (Z):

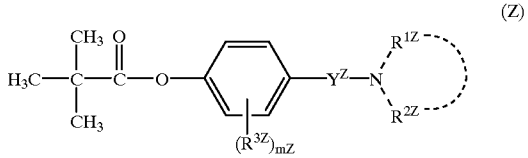

wherein $Y^Z$ is sulfonyl (—SO$_2$—) or carbonyl (—CO—); $R^{1Z}$ and $R^{2Z}$, same or different, is hydrogen, C1–16 alkyl which may be substituted by carboxy (—COOH); $R^{3Z}$ is hydrogen, hydroxy, C1–6 alkyl, halogen, C1–4 alkoxy or C2–5 acyloxy; $m^Z$ is 1–4; are disclosed to have inhibitory activity against elastase.

The following compounds are disclosed to possess antimicrobial activity [J. Serb. Chem. Soc. 56(6), 311–318 (1991)].
N-[[4-(2, 4-Dichlorobenzoylamino)phenyl]sulfonyl] glycine,
N-[[4-(2, 4-Dichlorobenzoylamino)phenyl]sulfonyl]-D, L-alanine,
N-[[4-(2, 4-Dichlorobenzoylamino)phenyl]sulfonyl]-β-alanine,
N-[[4-(2, 4-Dichlorobenzoylamino)phenyl]sulfonyl]-L-valine,
N-[[4-(2, 4-Dichlorobenzoylamino)phenyl]sulfonyl]-D, L-valine,
N-[[4-(2, 4-Dichlorobenzoylamino)phenyl]sulfonyl]-L-leucine,
N-[[4-(2, 4-Dichlorobenzoylamino)phenyl]sulfonyl]-D, L-leucine,
N-[[4-(2, 4-Dichlorobenzoylamino)phenyl]sulfonyl]-D, L-serine,
N-[[4-(2, 4-Dichlorobenzoylamino)phenyl]sulfonyl]-L-phenylalanine,
N-[[4-(2, 4-Dichlorobenzoylamino)phenyl]sulfonyl]-L-tyrosine,
N-[[4-(2, 4-Dichlorobenzoylamino)phenyl]sulfonyl]-D, L-alanine methyl ester,
N-[[4-(2,4-Dichlorobenzoylamino)phenyl]sulfonyl]-L-valine methyl ester,
N-[[4-(2, 4-Dichlorobenzoylamino)phenyl]sulfonyl]-D, L-valine methyl ester,
N-[[4-(2, 4-Dichlorobenzoylamino)phenyl]sulfonyl]-L-leucine methyl ester,
N-[[4-(2, 4-Dichlorobenzoylamino)phenyl]sulfonyl]-D, L-serine methyl ester, and
N-[[4-(2, 4-Dichlorobenzoylamino)phenyl]sulfonyl]-L-tyrosine methyl ester.

The following compounds are disclosed to possess antifilarial activity [Indian J. Chem. 30B, 182–187 (1991)].
N-[[4-(3-Nitrobenzoylamino)phenyl]sulfonyl]-L-aspartic acid,
N-[[3-(3-Nitrobenzoylamino)phenyl]sulfonyl]-L-aspartic acid,
N-[[4-(3-Aminobenzoylamino)phenyl]sulfonyl]-L-aspartic acid and
N-[[3-(3-Aminobenzoylamino)phenyl]sulfonyl]-L-aspartic acid.

The following compounds are disclosed to possess antineoplastic activity [Indian J. Chem. 28B. 843–847 (1989)].
N-[[4-(Benzoylamino)phenyl]sulfonyl]-L-glutamic acid,
N-[[4-(4-Chlorobenzoylamino)phenyl]sulfonyl]-L-glutamic acid and
N-[[4-(4-Nitrobenzoylamino)phenyl]sulfonyl]-L-glutamic acid.

Purpose of invention

Energetic investigations have been carried out in order to make a matrix metalloproteinase inhibitor, the present inventors have found that a series of sulfonylamino acid derivatives of the formula (Ia) have inhibitory activity against matrix metalloproteinase and have accomplished the present invention.

Sulfonylamino acid derivatives of the formula (Ia) of the present invention are not known as matrix metalloproteinase inhibitors at all. And sulfonylamino acid derivatives of the formula (Ib) of the present invention are novel compounds that are not known at all.

Moreover, the compounds of the present invention possess, especially, a selective inhibitory activity against gelatinases classified in matrix metalloproteinases.

Disclosure of the Invention

The present invention is related to:
(i) matrix metalloproteinase inhibitors containing sulfonylamino acid derivatives of the formula (Ia):

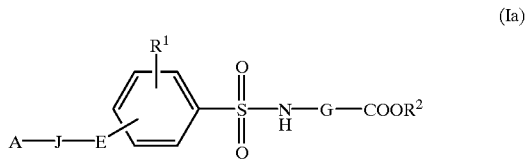

wherein
$R^1$ is hydrogen, or C1–4 alkyl;
$R^2$ is (1) hydrogen, (2) C1–8 alkyl, (3) phenyl, or (4) C1–4 alkyl substituted by phenyl, —OCOR$^{16}$, in which R$^{16}$ is C1–4 alkyl; or —CONR$^{17}$R$^{18}$, in which R$^{17}$ and R$^{18}$ each, independently, is hydrogen or C1–4 alkyl;
E is (1) —CONR$^3$—, in which R$^3$ is hydrogen, C1–4 alkyl, phenyl, C1–4 alkyl substituted by phenyl;
(2) —NR$^3$CO—, in which R$^3$ is the same meaning as hereinbefore defined;
(3) —CO—O—,
(4) —O—CO—,
(5) —NR$^3$—CO—NR$^3$—, in which R$^3$ is the same meaning as hereinbefore defined;
(6) —CO—CH$_2$—,
(7) —CO—,
(8) —O—CO—NR$^3$—, in which R$^3$ is the same meaning as hereinbefore defined;
(9) —NR$^3$—CO—O—, in which R$^3$ is the same meaning as hereinbefore defined;
(10) —O—CO—O—,
(11) —CS—NR$^3$—, in which R$^3$ is the same meaning as hereinbefore defined;
(12) —NR$^3$—CS—, in which R$^3$ is the same meaning as hereinbefore defined;
(13) —NR$^3$—CS—NR$^3$—, in which R$^3$ is the same meaning as hereinbefore defined;
(14) —O—CS—NR$^3$—, in which R$^3$ is the same meaning as hereinbefore defined;
(15) —NR$^3$—CS—O—, in which R$^3$ is the same meaning as hereinbefore defined;

(16) —CS—O—,
(17) —O—CS—,
(18) —O—CS—O—,

A is (1) hydrogen, (2) C1–8 alkyl, (3) C3–7 cycloalkyl, or (4) Ar, in which Ar is carbocyclic aryl or heterocyclic aryl, and these ring may be substituted by 1–3 of C1–15 alkyl, C1–15 alkoxy, halogen, nitro, cyano, guanidino, amidino, hydroxy, benzyloxy, —NR$^9$R$^{10}$, in which R$^9$ and R$^{10}$ each, independently, is hydrogen or C1–4 alkyl; —COOR$^{11}$, in which R$^{11}$ is hydrogen or C1–4 alkyl; trifluoromethyl, phenyl or heterocyclic ring;

J is (1) bond, (2) C2–4 alkylene, (3) C2–4 alkenylene, or (4)

in which
R$^4$ and R$^5$ each, independently, is (i) hydrogen, (ii) C1–4 alkyl, (iii) C1–4 alkoxy, or
R$^4$ and R$^5$, taken together with the carbon to which they are attached, is C3–7 cycloalkyl,
G is (1)—(CH$_2$)$_m$—, in which m is 2, 3 or 4, or (2)

in which R$^6$ and R$^7$ each, independently, is (i) hydrogen, (ii) C1–8 alkyl, (iii) —COOR$^8$, in which R$^8$ is hydrogen, C1–8 alkyl, phenyl, C1–4 alkyl substituted by phenyl; (iv) Ar, in which Ar is the same meaning as hereinbefore defined; (v) heterocyclic ring, (vi) C1–8 alkyl substituted by —COOR$^8$, in which R$^8$ is the same meaning as hereinbefore defined; C1–4 alkoxy, hydroxy, benzyloxy, —NR$^{12}$R$^{13}$, in which R$^{12}$ and R$^{13}$ each, independently, is hydrogen or C1–4 alkyl; —NR$^{14}$COOR$^{15}$, in which R$^{14}$ is hydrogen or C1–4 alkyl, R$^{15}$ is hydrogen, C1–8 alkyl, phenyl, C1–4 alkyl substituted by phenyl; Ar or heterocyclic ring; with the proviso that one of carbon in C1–8 alkyl may be replaced by one of sulfur, or R$^8$ and R$^7$, taken together with the carbon to which they are attached, is C3–7 cycloalkyl; a compound in which E is —O—CO—NR$^3$—, —O—CO—O—, —O—CS—NR$^3$—, or —O—CS—O—, J is a bond and A is hydrogen, is excluded; and non-toxic salts thereof, (ii) novel sulfonylamino acid derivatives of the formula (Ib):

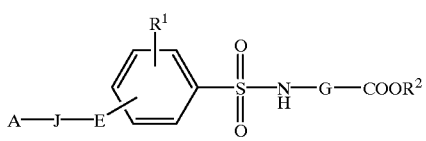

(Ib)

wherein
R$^1$ is hydrogen, or C1–4 alkyl;
R$^2$ is (1) hydrogen, (2) C1–8 alkyl, (3) phenyl, or (4) C1–4 alkyl substituted by phenyl, —OCOR$^{16}$, in which R$^{16}$ is C1–4 alkyl; or —CONR$^{17}$R$^{18}$, in which R$^{17}$ and R$^{18}$ each independently, is hydrogen or C1–4 alkyl;
E is (1) —CONR$^3$—, in which R$^3$ is hydrogen, C1–4 alkyl, phenyl, C1–4 alkyl substituted by phenyl;

(2) —NR$^3$CO—, in which R$^3$ is the same meaning as hereinbefore defined;
(3) —CO—O—,
(4) —O—CO—,
(5) —NR$^3$CO—NR$^3$—, in which R$^3$ is the same meaning as hereinbefore defined;
(6) —CO—CH$_2$—,
(7) —CO—,
(8) —O—CO—NR$^3$—, in which R$^3$ is the same meaning as hereinbefore defined;
(9) —NR$^3$—CO—O—, in which R$^3$ is the same meaning as hereinbefore defined;
(10) —O—CO—O—,
(12) —CS—NR$^3$—, in which R$^3$ is the same meaning as hereinbefore defined;
(12) —NR$^3$—CS—, in which R$^3$ is the same meaning as hereinbefore defined;
(13) —NR$^3$—CS—NR$^3$—, in which R$^3$ is the same meaning as hereinbefore defined;
(14) —O—CS—NR$^3$—, in which R$^3$ is the same meaning as hereinbefore defined;
(15) —NR$^3$—CS—O, in which R$^3$ is the same meaning as hereinbefore defined;
(16) —CS—O—,
(17) —O—CS—,
(18) —O—CS—O—, A is (1) hydrogen, (2) C1–8 alkyl, (3) C3–7 cycloalkyl, or (4) Ar, in which Ar is carbocyclic aryl or heterocyclic aryl, and these ring may be substituted by 1–3 of C1–15 alkyl, C1–15 alkoxy, halogen, nitro, cyano, guanidino, amidino, hydroxy, benzyloxy, —NR$^9$R$^{10}$, in which R$^9$ and R$^{10}$ each, independently, is hydrogen or C1–4 alkyl; —COOR$^{11}$, in which R$^{11}$ is hydrogen or C1–4 alkyl; trifluoromethyl, phenyl or heterocyclic ring;

J is (1) bond, (2) C2–4 alkylene, (3) C2–4 alkenylene, or (4)

in which
R$^4$ and R$^5$ each, independently, is (i) hydrogen, (ii) C1–4 alkyl, (iii) C1–4 alkoxy, or
R$^4$ and R$^5$, taken together with the carbon to which they are attached, is C3–7 cycloalkyl,
G is (1) —(CH$_2$)$_m$—, in which m is 2, 3 or 4, or (2)

in which R$^6$ and R$^7$ each, independently, is (i) hydrogen, (ii) C1–8 alkyl, (iii) —COOR$^8$, in which R$^8$ is hydrogen, C1–8 alkyl, phenyl, C1–4 alkyl substituted by phenyl; (iv) Ar, in which Ar is the same meaning as hereinbefore defined; (v) heterocyclic ring, (vi) C1–8 alkyl substituted by —COOR$^8$, in which R$^8$ is the same meaning as hereinbefore defined; C1–4 alkoxy, hydroxy, benzyloxy, —NR$^{12}$R$^{13}$, in which R$^{12}$ and R$^{13}$ each, independently, is hydrogen or C1–4 alkyl; —NR$^{14}$COOR$^{15}$, in which R$^{14}$ is hydrogen or C1–4 alkyl, R$^{15}$ is hydrogen, C1–8 alkyl, phenyl, C1–4 alkyl substituted by phenyl; Ar or heterocyclic ring; with the proviso that one of carbon in C1–8 alkyl may be replaced by one of sulfur; or R$^6$ and R$^7$, taken together with the carbon to which they are attached, is C3–7 cycloalkyl; and non-toxic salts thereof;

with the proviso that a compound in which E is —O—CO—NR³—, —O—CO—O—, —O—CS—NR³— or —O—CS—O—, J is a bond and A is hydrogen, is excluded and the following compounds are excluded:

(1) N-[[4-(Benzoylamino)phenyl]sulfonyl]glycine,
(2) N-[[3-(Benzoylamino)phenyl]sulfonyl]glycine,
(3) N-[[2-(Benzoylamino)phenyl]sulfonyl]glycine,
(4) N-[[4-(Acetylamino)phenyl]sulfonyl]glycine,
(5) N-[[4-(Phenylacetylamino)phenyl]sulfonyl] glycine,
(6) N-[[4-[(Phenylethylcarbonyl)amino]phenyl] sulfonyl]glycine,
(7) N-[[4-(Cinnamoylamino)phenyl]sulfonyl]glycine,
(8) N-[[4-(N-Phenylureido)phenyl]sulfonyl]glycine,
(9) N-[[4-(N-Phenylthioureido)amino]phenyl] sulfonyl]glycine,
(10) N-[[4-[(Benzyloxycarbonyl)amino]phenyl] sulfonyl]glycine,
(11) N-[[4-[(Phenyloxymethylcarbonyl)amino]phenyl] sulfonyl]glycine,
(12) N-[[4-[(Benzyloxymethylcarbonyl)amino]phenyl] sulfonyl]glycine,
(13) N-[[4-(4-Methoxybenzoylamino)phenyl]sulfonyl] glycine,
(14) N-[[4-(4-Fluorobenzoylamino)phenyl]sulfonyl] glycine,
(15) N-[[4-(4-Nitrobenzoylamino)phenyl]sulfonyl] glycine,
(16) N-[[4-(3-Nitrobenzoylamino)phenyl]sulfonyl] glycine,
(17) N-[[4-(2-Nitrobenzoylamino)phenyl]sulfonyl] glycine,
(18) N-[[4-(4-Formylbenzoylamino)phenyl]sulfonyl] glycine,
(19) N-[[4-(Benzoylamino)phenyl]sulfonyl]-D-α-phenylglycine,
(20) N-[[4-(Benzoylamino)phenyl]sulfonyl]-L-α-phenylglycine,
(21) N-[[4-(4-Methylbenzoylamino)phenyl]sulfonyl]-D-α-phenylglycine,
(22) N-[[4-(4-Methylbenzoylamino)phenyl]sulfonyl]-L-α-phenylglycine,
(23) N-[[4-(4-Methoxybenzoylamino)phenyl] sulfonyl]-D-α-phenylglycine,
(24) N-[[4-(4-Methoxybenzoylamino)phenyl] sulfonyl]-L-α-phenylglycine,
(25) N-[[4-(4-Fluorobenzoylamino)phenyl]sulfonyl]-D-α-phenylglycine,
(26) N-[[4-(4-Fluorobenzoylamino)phenyl]sulfonyl]-L-α-phenylglycine,
(27) N-[[4-(4-Nitrobenzoylamino)phenyl]sulfonyl]-D-α-phenylglycine,
(28) N-[[4-(4-Nitrobenzoylamino)phenyl]sulfonyl]-L-α-phenylglycine,
(29) N-[(4-Pivaloyloxyphenyl)sulfonyl]-D, L-α-phenylglycine,
(30) N-[(4-Pivaloyloxyphenyl)sulfonyl]-D, L-phenylalanine,
(31) N-[[4-(2, 4-Dichlorobenzoylamino)phenyl] sulfonyl]glycine,
(32) N-[[4-(2, 4-Dichlorobenzoylamino)phenyl] sulfonyl]-D, L-alanine,
(33) N-[[4-(2, 4-Dichlorobenzoylamino)phenyl] sulfonyl]-β-alanine,
(34) N-[[4-(2, 4-Dichlorobenzoylamino)phenyl] sulfonyl]-L-valine,
(35) N-[[4-(2, 4-Dichlorobenzoylamino)phenyl] sulfonyl]-D, L-valine,
(36) N-[[4-(2, 4-Dichlorobenzoylamino)phenyl] sulfonyl]-L-leucine,
(37) N-[[4-(2, 4-Dichlorobenzoylamino)phenyl] sulfonyl]-D, L-leucine,
(38) N-[[4-(2, 4-Dichlorobenzoylamino)phenyl] sulfonyl]-D, L-serine,
(39) N-[[4-(2, 4-Dichlorobenzoylamino)phenyl] sulfonyl]-L-phenylalanine,
(40) N-[[4-(2, 4-Dichlorobenzoylamino)phenyl] sulfonyl]-L-tyrosine,
(41) N-[[4-(2, 4-Dichlorobenzoylamino)phenyl] sulfonyl]-D, L-alanine methyl ester,
(42) N-[[4-(2,4-Dichlorobenzoylamino)phenyl] sulfonyl]-L-valine methyl ester,
(43) N-[[4-(2, 4-Dichlorobenzoylamino)phenyl] sulfonyl]-D, L-valine methyl ester,
(44) N-[[4-[[(2, 4-Dichlorobenzoylamino)phenyl] sulfonyl]-L-leucine methyl ester,
(45) N-[[4-(2, 4-Dichlorobenzoylamino)phenyl] sulfonyl]-D, L-serine methyl ester,
(46) N-[[4-(2, 4-Dichlorobenzoylamino)phenyl] sulfonyl]-L-tyrosine methyl ester,
(47) N-[[4-(3-Nitrobenzoylamino)phenyl]sulfonyl]-L-aspartic acid,
(48) N-[[3-(3-Nitrobenzoylamino)phenyl]sulfonyl]-L-aspartic acid,
(49) N-[[4-(3-Aminobenzoylamino)phenyl]sulfonyl]-L-aspartic acid,
(50) N-[[3-(3-Aminobenzoylamino)phenyl]sulfonyl]-L-aspartic acid,
(51) N-[[4-(Benzoylamino)phenyl]sulfonyl]-L-glutamic acid,
(52) N-[[4-(4-Chlorobenzoylamino)phenyl]sulfonyl]-L-glutamic acid,
(53) N-[[4-(4-Nitrobenzoylamino)phenyl]sulfonyl]-L-glutamic acid,
(54) N-[[4-[2-(4-(1-Pyrrolidinyl)phenyl]butyryloxy] phenyl]sulfonyl]-D,L-3-morpholinoalanine ethyl ester,
(55) N-[[4-[2-(4-(1-Nitrophenyl)butyryloxy]phenyl] sulfonyl]-D,L-3-morpholino alanine ethyl ester,
(56) N-[[4-(2-Methoxy-2-phenylacetyloxy)phenyl] sulfonyl]-D,L-3-morpholino alanine ethyl ester,
(57) N-[[4-[[[1-(4-Nitrophenyl)cyclobutyl]carbonyl] oxy]phenyl]sulfonyl]-D,L-3-morpholinoalanine ethyl ester,
(58) N-[[3-Methyl-4-[2-[4-(1-Pyrrolidinyl)phenyl] butyryloxy]phenyl]sulfonyl]-t-butoxycarbonyl-L-lysine,
(59) N-[[4-(2-Phenylbutyryloxy)phenyl]sulfonyl] glycine,
(60) N-[[4-[2-[4-(1-Pyrrolidinyl)phenyl]butyryloxy] phenyl]sulfonyl]-D,L-phenyl alanine,
(61) N-[[4-[2-[4-(1-Pyrrolidinyl)phenyl]butyryloxy] phenyl]sulfonyl]-D,L-aspartic acid,
(62) N-[[4-[[[1-(4-Nitrophenyl)cyclobutyl]carbonyl] oxy]phenyl]sulfonyl]-D, L-aspartic acid,
(63) 1-[[4-[2-[4-(1-Pyrrolidinyl)phenyl]butyryloxy] phenyl]sulfonylamide]-1-cyclopropanecarboxylic acid,
(64) N-[[4-[2-[4-(1-Pyrrolidinyl)phenyl]butyryloxy] phenyl]sulfonyl]-D,L-2-(2-furanyl)glycine,
(65) N-[[4-[2-[4-(1-Pyrrolidinyl)phenyl]butyryloxy] phenyl]sulfonyl]-D,L-2-(2-thienyl)glycine,
(66) N-[[4-[2-[4-(1-Pyrrolidinyl)phenyl]butyryloxy] phenyl]sulfonyl]-L-valine,

(67) N-[[4-[2-[4-(1-Pyrrolidinyl)phenyl]butyryloxy]phenyl]sulfonyl]-S-carboxymethyl-L-cysteine,

(68) N-[[4-[2-Ethyl-2-(4-methoxyphenyl)butyryloxy]phenyl]sulfonyl]-glycine,

(69) N-[[3-Methyl-4-[2-[4-(1-Pyrrolidinyl)phenyl]butyryloxy]phenyl]sulfonyl]-L-lysine,

(70) 5-[N-[[3-Methyl-4-[2-[4-(1-pyrrolidinyl)phenyl]butylyloxy]phenyl]sulfonyl]amino]pentanoic acid, and

(71) N-[[(3-Methyl-4-pivaloyloxy)phenyl]sulfonyl]-β-alanine, or (iii) a process for the preparation of sulfonylamino acid derivatives of the formula (Ib) and non-toxic salts thereof.

Unless otherwise specified, all isomers are included in the present invention. For example, alkyl, alkoxy and alkylene includes straight and branched ones. Isomers occurred by the existence of asymmetric carbon(s) e.g. branched alkyl are also included within the present invention.

In the formula (Ia) and (Ib), C1–4 alkyl represented by $R^1$, $R^3$, $R^4$, $R^5$, $R^9$, $R^{10}$, $R^{11}$, $R^{12}$, $R^{13}$, $R^{14}$, $R^{16}$, $R^{17}$, or $R^{18}$ mean methyl, ethyl, propyl, butyl and isomeric groups thereof.

In the formula (Ia) and (Ib), C1–8 alkyl represented by $R^2$, $R^6$, $R^7$, $R^8$, $R^{15}$, A mean methyl, ethyl, propyl, butyl, pentyl, hexyl, heptyl, octyl and isomeric groups thereof.

In the formula (Ia) and (Ib), C1–4 alkyl substituted by phenyl represented by $R^2$, $R^3$, $R^8$, $R^{15}$ mean methyl, ethyl, propyl, butyl and isomeric groups thereof substituted by 1 of phenyl.

In the formula (Ia) and (Ib), C1–4 alkoxy represented by $R^4$, $R^5$, $R^6$, $R^7$ mean methoxy, ethoxy, propoxy, butoxy and isomeric groups thereof.

In the formula (Ia) and (Ib), C1–15 alkyl as substituents of Ar mean methyl, ethyl, propyl, butyl, pentyl, hexyl, heptyl, octyl, nonyl, decyl, undecyl, dodecyl, tridecyl, tetradecyl, pentadecyl and isomeric groups thereof.

In the formula (Ia) and (Ib), C1–15 alkoxy as substituents of Ar mean methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy and isomeric groups thereof.

In the formula (Ia) and (Ib), halogen as substituents of Ar is fluorine, chlorine, bromine and iodine.

In the formula (Ia) and (Ib), C2–4 alkylene represented by J means ethylene, trimethylene, tetramethylene and isomeric groups thereof.

In the formula (Ia) and (Ib), C2–4 alkenylene represented by J means vinylene, propenylene, butenylene, butadinylene and isomeric groups thereof.

In the formula (Ia) and (Ib), C3–7 cycloalkyl represented by $R^4$ and $R^5$, taken together with carbon to which they are attached, $R^6$ and $R^7$, taken together with carbon to which they are attached or A mean cyclopropyl, cyclobutyl, cyclopentyl, cyclohexyl and cycloheptyl.

In the formula (Ia) and (Ib), carbocyclic aryl represented by A, Ar in $R^6$ and $R^7$ mean C5–10 carbocyclic aryl, for example, benzene, pentalene, indene, naphthalene, azulene.

In the formula (Ia) and (Ib), heterocyclic aryl represented by A, e in $R^6$ and $R^7$ mean C5–15 membered mono- or bi-heterocyclic aryl containing 1–2 of nitrogen, 1 of oxygen and/or 1 of sulfur, for example, pyrrole, imidazole, pyrazole, pyridine, pyrazine, pyrimidine, pyridazine, azepine, diazepine, furan, pyran, oxepin, oxazepine, thioptiene, thiain (thiopyran), thiepin, oxazole, isoxazole, thiazole, isothiazole, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzoimidazole.

In the formula (Ia) and (Ib), heterocyclic ring represented by $R^6$ and $R^7$ and as substituents of Ar mean C5–15 membered mono- or bi-heterocyclic ring containing 1–2 of nitrogen, 1 of oxygen and/or 1 of sulfur. The heterocyclic ring are contained partially or fully saturated ring which is above C5–15 membered mono- or bi-heterocyclic aryl containing 1–2 of nitrogen, 1 of oxygen and/or 1 of sulfur, for example, pyrroline, pyrrolidine, imidazoline, imidazolidine, pyrazoline, pyrazolidine, piperidine, piperazine, tetrahydropyrimidine, tetrahydropyridazine, dihydrofuran, tetrahydrofuran, dihydropyran, tetrahydropyran, dihydrothiophene, tetrahydrothiophene, dihydrothiain (dihydrothiopyran), tetrahydrothiain (tetrahydrothiopyran), dihydrooxazole, tetrahydrooxazole, dihydroisoxazole, tetrahydroisoxazole, dihydrothiazole, tetrahydrothiazole, dihydroisothiazole, tetrahydroisothiazole, morpholine, thiomorpholine, indoline, isoindoline, dihydrobenzofuran, perhydrobenzofuran, dihydroisobenzofuran, perhydrobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzimidazole, perhydrobenzimidazole.

In the present invention, it means that E bonds to benzene ring at the right side and to J at the left side. For example, when E is —CO—$NR^3$—, it means J—CO—$NR^3$—benzene ring.

Salts

Non-toxic salts of the present invention are contained all pharmaceutically acceptable salts, for example, general salts, acid addition salts, hydrate salts.

The compounds of the formula (Ia) and (Ib) of the present invention may be converted into the corresponding salts. Non-toxic and water-soluble salts are preferable. Suitable salts, for example, are as follows: salts of alkaline metals (sodium, potassium etc.), salts of alkaline earth metals (calcium, magnesium etc.), ammonium salts, salts of pharmaceutically acceptable organic amines (tetramethylammonium, triethylamine, methylamine, dimethylamine, cyclopentylamine, benzylamine, phenethylamine, piperidine, monoethanolamine, diethanolamine, tris(hydroxymethyl)amine, lysine, arginine, N-methyl-D-glucamine etc.).

The compounds of the formula (Ia) and (Ib) may be converted into the corresponding acid addition salts. Non-toxic and water-soluble salts are preferable. Suitable salts, for example, are as follows: salts of inorganic acids e.g. hydrochloride, hydrobromide, hydroiodide, sulfate, phosphate, nitrate; salts of organic acids e.g. acetate, trifluoroacetate, lactate, tartarate, oxalate, fumarate, maleate, citrate, benzoate, methanesulphonate, ethanesulphonate, benzenesulphonate, toluenesulphonate, isethionate, glucuronate, gluconate.

The compounds of the formula (Ia) and (Ib) and salts thereof may be converted into the corresponding hydrate by conventional manner.

In the compound of the present invention of the formula (Ia) and (Ib), sulfonylamino acid derivatives of the following formula, ester derivatives thereof and non-toxic salts thereof are preferable:

the formula I(1):

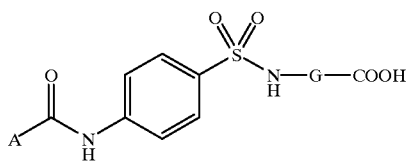

I(1)

wherein A and G are the same meaning as hereinbefore defined, the formula I(2):

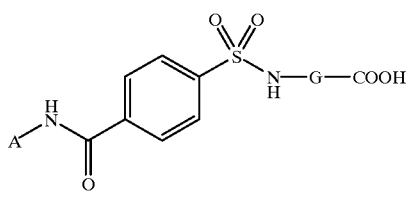

I(2)

wherein A and G are the same meaning as hereinbefore defined, the formula I(3):

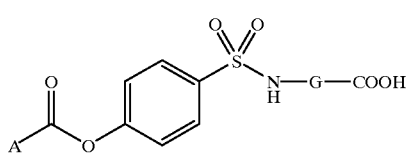

I(3)

wherein A and G are the same meaning as hereinbefore defined, the formula I(4):

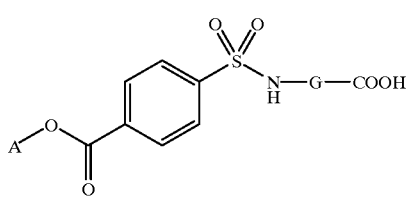

I(4)

wherein A and G are the same meaning as hereinbefore defined, the formula I(5):

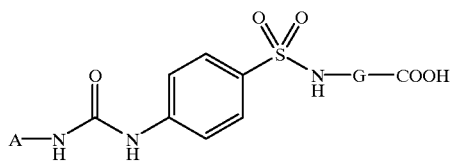

I(5)

wherein A and G are the same meaning as hereinbefore defined, the formula I(6):

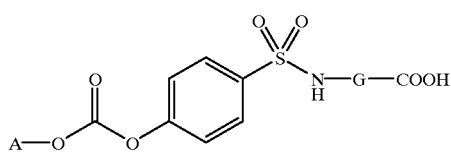

I(6)

wherein A and G are the same meaning as hereinbefore defined, the formula I(7):

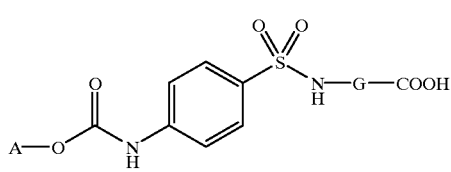

I(7)

wherein A and G are the same meaning as hereinbefore defined, the formula I(8):

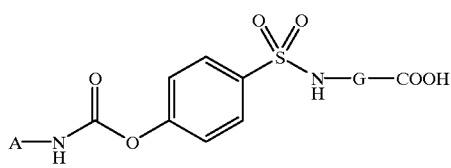

I(8)

wherein A and G are the same meaning as hereinbefore defined, the formula I(9):

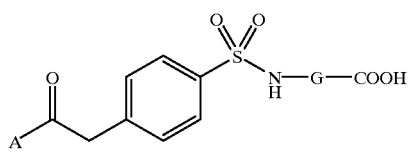

I(9)

wherein A and G are the same meaning as hereinbefore defined, the formula I(10):

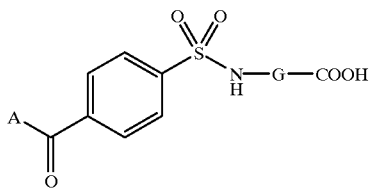

wherein A and G are the same meaning as hereinbefore defined, the formula I(11):

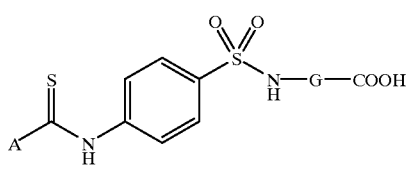

wherein A and G are the same meaning as hereinbefore defined, the formula I(12):

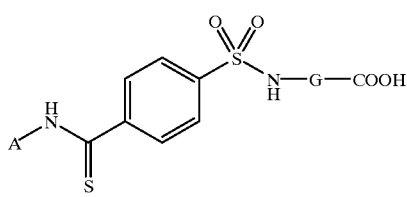

wherein A and G are the same meaning as hereinbefore defined, the formula I(13):

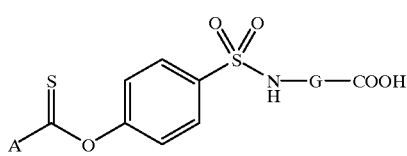

wherein A and G are the same meaning as hereinbefore defined, the formula I(14):

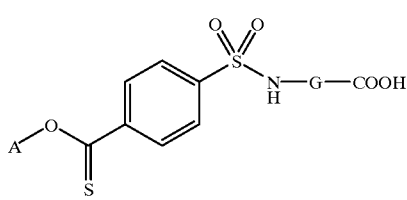

wherein A and G are the same meaning as hereinbefore defined, the formula I(15):

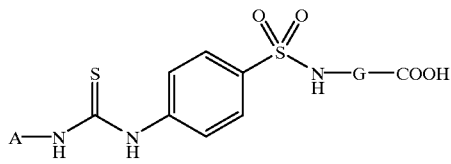

wherein A and G are the same meaning as hereinbefore defined, the formula I(16):

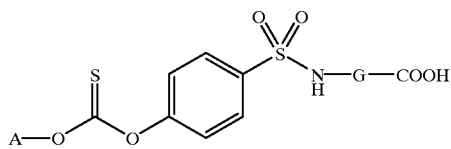

wherein A and G are the same meaning as hereinbefore defined, the formula I(17):

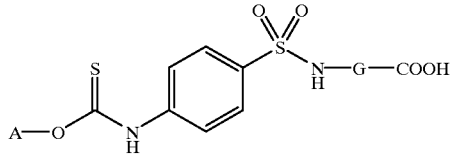

wherein A and G are the same meaning as hereinbefore defined, the formula I(18):

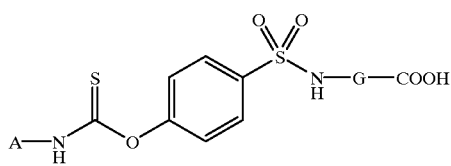

wherein A and G are the same meaning as hereinbefore defined, the formula I(19):

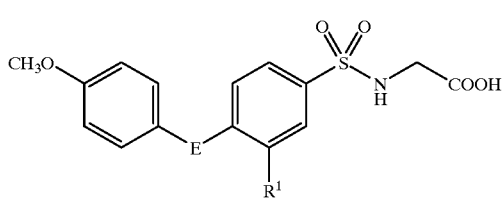

wherein $R^1$ and E are the same meaning as hereinbefore defined, the formula I(20):

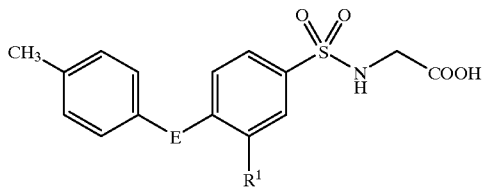

wherein $R^1$ and E are the same meaning as hereinbefore defined, the formula I(21):

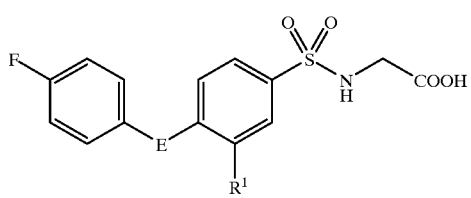

wherein $R^1$ and E are the same meaning as hereinbefore defined, the formula I(22):

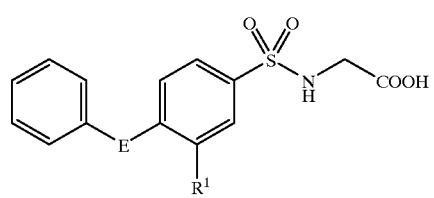

wherein $R^1$ and E are the same meaning as hereinbefore defined, and the formula I(23):

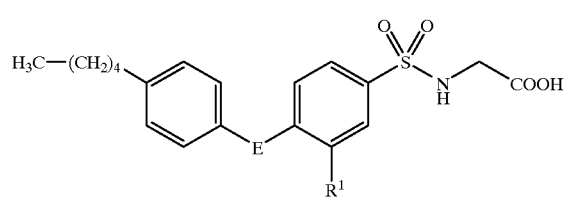

wherein $R^1$ and E are the same meaning as hereinbefore defined, and the formula I(24):

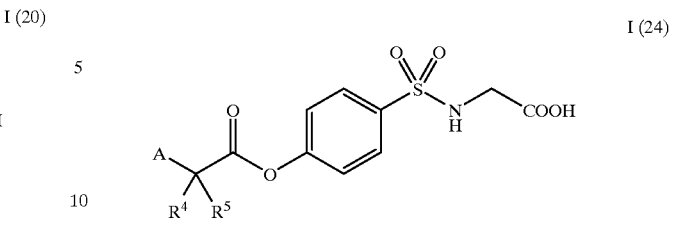

wherein A, $R^4$ and $R^5$ are the same meaning as hereinbefore defined.

The preferable specific compounds of the formula (Ia) and (Ib) are the compounds in table 1–23 and the compounds which are described chemical name thereof, ester derivatives thereof and non-toxic salts thereof and example compounds.

TABLE 1

(1A)

| No. | A | G |
|---|---|---|
| 1 | phenyl | $H_3C$-CH($CH_3$)-CH-$CH_3$ (isobutyl-like) |
| 2 | phenyl | -CH($CH_3$)-CH$_2$-CH($CH_3$)$_2$ |
| 3 | phenyl | -CH$_2$-CH$_2$-phenyl |
| 4 | 4-methylphenyl | $H_3C$-CH($CH_3$)-CH-$CH_3$ |
| 5 | 4-methylphenyl | -CH($CH_3$)-CH$_2$-CH($CH_3$)$_2$ |

TABLE 1-continued
(1A)
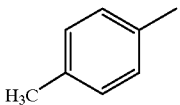
| No. | A | G |
|---|---|---|
| 6 | 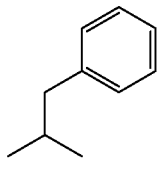 | 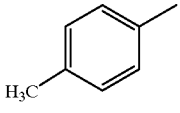 |
| 7 | 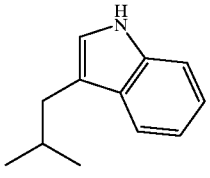 | 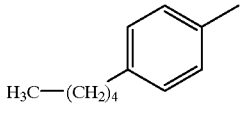 |
| 8 | 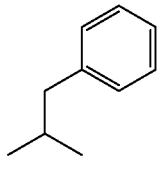 | 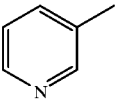 |
| 9 | 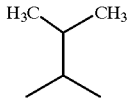 | 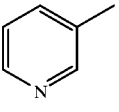 |
| 10 | 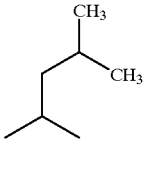 | 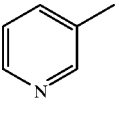 |
| 11 | 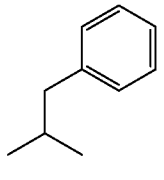 | 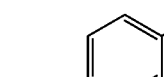 |
TABLE 2
(1B)
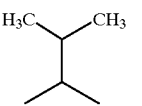
| No. | A | G |
|---|---|---|
| 1 | 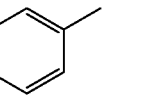 | 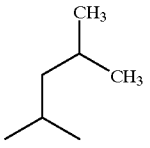 |
| 2 | 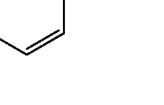 | 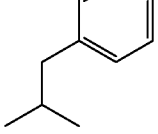 |
| 3 | 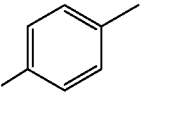 | 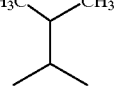 |
| 4 | 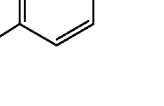 | 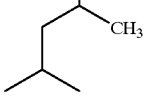 |
| 5 | 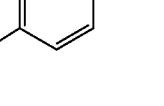 | 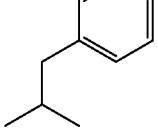 |
| 6 | 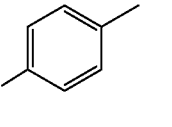 | 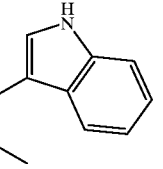 |
| 7 | 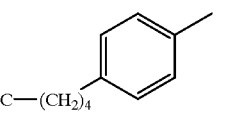 | 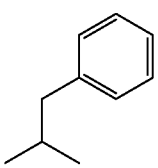 |
| 8 | | |

TABLE 2-continued (1B)

[Structure: A-NH-C(=O)-C6H4-S(=O)2-NH-G-COOH]

| No. | A | G |
|---|---|---|
| 9 | 3-pyridyl | isopropyl-CH(CH3)- (H3C,CH3 branched) |
| 10 | 3-pyridyl | CH3-CH(CH3)-CH2-CH(CH3)- |
| 11 | 3-pyridyl | -CH2-CH(CH3)-phenyl (isobutylphenyl) |

TABLE 3

(1C)

[Structure: A-C(=O)-O-C6H4-S(=O)2-NH-G-COOH]

| No. | A | G |
|---|---|---|
| 1 | phenyl | H3C-CH(CH3)-CH(CH3)- |
| 2 | phenyl | CH3-CH(CH3)-CH2-CH(CH3)- |
| 3 | phenyl | -CH2-CH(CH3)-phenyl |
| 4 | 4-methylphenyl (p-tolyl) | H3C-CH(CH3)-CH(CH3)- |

TABLE 3-continued (1C)

[Structure: A-C(=O)-O-C6H4-S(=O)2-NH-G-COOH]

| No. | A | G |
|---|---|---|
| 5 | 4-methylphenyl | CH3-CH(CH3)-CH2-CH(CH3)- |
| 6 | 4-methylphenyl | -CH2-CH(CH3)-phenyl |
| 7 | 4-methylphenyl | indol-3-yl-CH2-CH(CH3)- |
| 8 | 4-pentylphenyl (H3C-(CH2)4-) | -CH2-CH(CH3)-phenyl |
| 9 | 3-pyridyl | H3C-CH(CH3)-CH(CH3)- |
| 10 | 3-pyridyl | CH3-CH(CH3)-CH2-CH(CH3)- |
| 11 | 3-pyridyl | -CH2-CH(CH3)-phenyl |

TABLE 4

(1D)

A structure showing: A—O—C(=O)—[phenyl]—S(=O)₂—N(H)—G—COOH

| No. | A | G |
|-----|---|---|
| 1 | phenyl | —CH(CH₃)—CH(CH₃)₂ (H₃C, CH₃ branched) |
| 2 | phenyl | —CH₂—CH(CH₃)—CH(CH₃)₂ |
| 3 | phenyl | —CH(CH₂Ph)—CH(CH₃)₂ (benzyl isobutyl) |
| 4 | 4-methylphenyl | —CH(CH₃)—CH(CH₃)₂ |
| 5 | 4-methylphenyl | —CH₂—CH(CH₃)—CH(CH₃)₂ |
| 6 | 4-methylphenyl | benzyl isobutyl |
| 7 | 4-methylphenyl | 3-(1H-indolyl)methyl isobutyl |
| 8 | 4-(H₃C—(CH₂)₄)phenyl | benzyl isobutyl |

TABLE 4-continued (1D)

| No. | A | G |
|-----|---|---|
| 9 | 3-pyridyl | —CH(CH₃)—CH(CH₃)₂ |
| 10 | 3-pyridyl | —CH₂—CH(CH₃)—CH(CH₃)₂ |
| 11 | 3-pyridyl | benzyl isobutyl |

TABLE 5

(1E)

A structure showing: A—NH—C(=O)—NH—[phenyl]—S(=O)₂—N(H)—G—COOH

| No. | A | G |
|-----|---|---|
| 1 | phenyl | —CH(CH₃)—CH(CH₃)₂ |
| 2 | phenyl | —CH₂—CH(CH₃)—CH(CH₃)₂ |
| 3 | phenyl | benzyl isobutyl |
| 4 | 4-methylphenyl | —CH(CH₃)—CH(CH₃)₂ |

TABLE 5-continued
(1E)
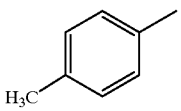
| No. | A | G |
|---|---|---|
| 5 | 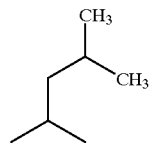 | 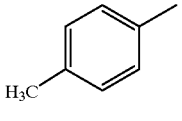 |
| 6 | 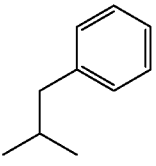 | 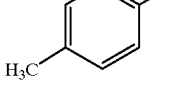 |
| 7 | 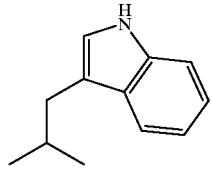 | 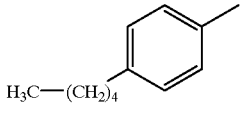 |
| 8 | 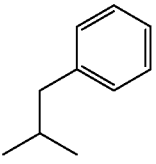 | 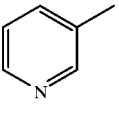 |
| 9 | 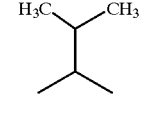 | 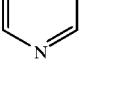 |
| 10 | 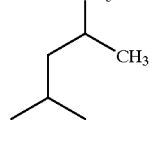 | 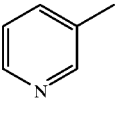 |
| 11 | 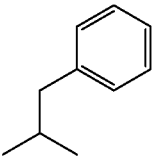 | 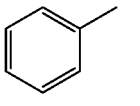 |
TABLE 6
(1F)
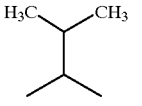
| No. | A | G |
|---|---|---|
| 1 | 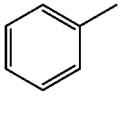 | 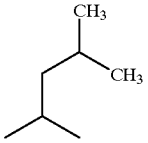 |
| 2 | 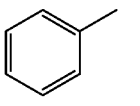 | 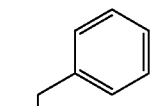 |
| 3 | 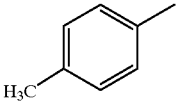 | 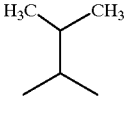 |
| 4 | 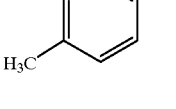 | 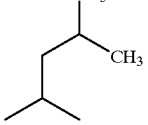 |
| 5 | 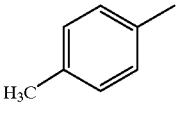 | 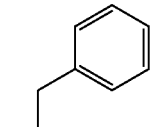 |
| 6 | 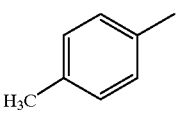 | 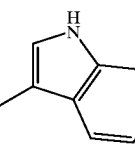 |
| 7 | 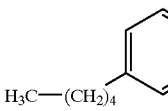 | 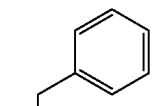 |
| 8 | H₃C—(CH₂)₄— | |

TABLE 6-continued (1F)

Structure: A-O-C(=O)-O-[C6H4]-S(=O)2-NH-G-COOH

| No. | A | G |
|---|---|---|
| 9 | 3-pyridyl | -CH(CH3)2 (isopropyl-like, H3C-CH-CH3) |
| 10 | 3-pyridyl | -CH2-CH(CH3)-CH2-CH(CH3)2 type |
| 11 | 3-pyridyl | -CH2-CH(CH3)-CH2-C6H5 |

TABLE 7

(1G)

Structure: A-O-C(=O)-NH-[C6H4]-S(=O)2-NH-G-COOH

| No. | A | G |
|---|---|---|
| 1 | phenyl | H3C-CH-CH3 isopropyl branched |
| 2 | phenyl | -CH2-CH(CH3)-CH2-CH(CH3)2 |
| 3 | phenyl | -CH2-CH(CH3)-CH2-C6H5 |
| 4 | 4-methylphenyl (p-tolyl) | H3C-CH-CH3 isopropyl branched |

TABLE 7-continued (1G)

| No. | A | G |
|---|---|---|
| 5 | 4-methylphenyl | isobutyl-like branched |
| 6 | 4-methylphenyl | -CH2-CH(CH3)-CH2-C6H5 |
| 7 | 4-methylphenyl | 3-(1H-indolyl)methyl-isobutyl |
| 8 | 4-pentylphenyl (H3C-(CH2)4-C6H4-) | -CH2-CH(CH3)-CH2-C6H5 |
| 9 | 3-pyridyl | H3C-CH-CH3 isopropyl branched |
| 10 | 3-pyridyl | -CH2-CH(CH3)-CH2-CH(CH3)2 |
| 11 | 3-pyridyl | -CH2-CH(CH3)-CH2-C6H5 |

TABLE 8

(1H)

[Structure: A-NH-C(=O)-O-C6H4-S(=O)2-NH-G-COOH]

| No. | A | G |
|-----|---|---|
| 1 | phenyl | (H3C)(CH3)CH-CH(CH3)- (3-methylbutan-2-yl) |
| 2 | phenyl | isohexyl (CH3)2CH-CH2-CH(CH3)- |
| 3 | phenyl | 2-methyl-1-phenylpropyl (PhCH2CH(iPr)-) |
| 4 | 4-methylphenyl | (H3C)(CH3)CH-CH(CH3)- |
| 5 | 4-methylphenyl | isohexyl |
| 6 | 4-methylphenyl | 2-methyl-1-phenylpropyl |
| 7 | 4-methylphenyl | 3-(1H-indol-3-yl)-2-methylpropyl |
| 8 | 4-pentylphenyl (H3C-(CH2)4-C6H4-) | 2-methyl-1-phenylpropyl |

TABLE 8-continued (1H)

[Structure: A-NH-C(=O)-O-C6H4-S(=O)2-NH-G-COOH]

| No. | A | G |
|-----|---|---|
| 9 | pyridin-3-yl | (H3C)(CH3)CH-CH(CH3)- |
| 10 | pyridin-3-yl | isohexyl |
| 11 | pyridin-3-yl | 2-methyl-1-phenylpropyl |

TABLE 9

(1J)

[Structure: A-C(=O)-CH2-C6H4-S(=O)2-NH-G-COOH]

| No. | A | G |
|-----|---|---|
| 1 | phenyl | (H3C)(CH3)CH-CH(CH3)- |
| 2 | phenyl | isohexyl |
| 3 | phenyl | 2-methyl-1-phenylpropyl |
| 4 | 4-methylphenyl | (H3C)(CH3)CH-CH(CH3)- |

TABLE 9-continued
(1J)
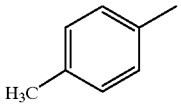
| No. | A | G |
|---|---|---|
| 5 | 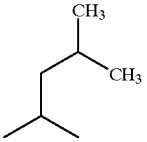 | 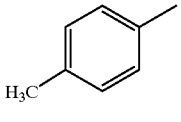 |
| 6 | 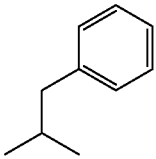 | 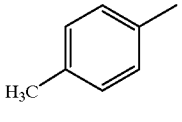 |
| 7 | 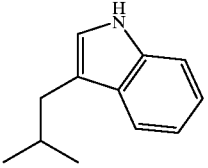 | 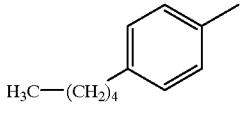 |
| 8 | 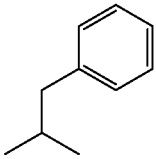 | 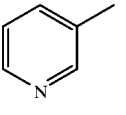 |
| 9 | 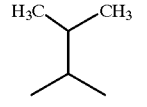 | 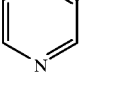 |
| 10 | 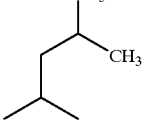 | 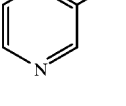 |
| 11 | 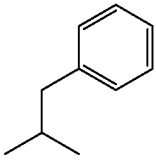 | 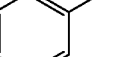 |
TABLE 10
(1K)
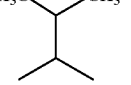
| No. | A | G |
|---|---|---|
| 1 | 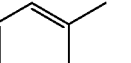 | 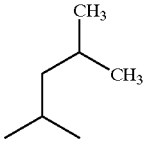 |
| 2 | 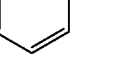 | 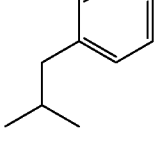 |
| 3 | 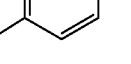 | 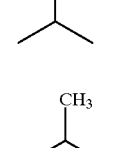 |
| 4 |  | 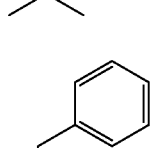 |
| 5 | 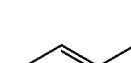 | 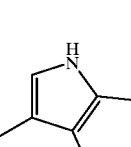 |
| 6 | 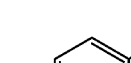 | 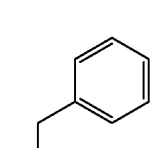 |
| 7 |  |  |
| 8 | | |

TABLE 10-continued
(1K)
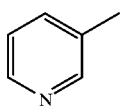
| No. | A | G |
|-----|---|---|
| 9 | 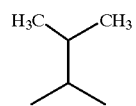 | 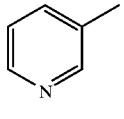 |
| 10 | 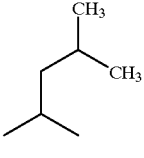 | 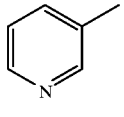 |
| 11 | 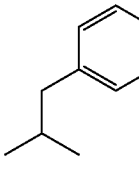 | 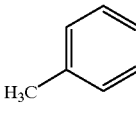 |
TABLE 11
(1L)
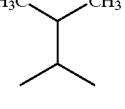
| No. | A | G |
|-----|---|---|
| 1 | 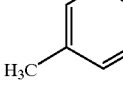 | 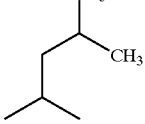 |
| 2 | 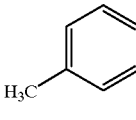 | 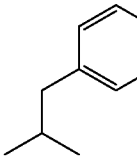 |
| 3 | 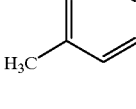 | 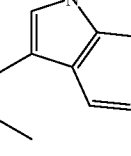 |
| 4 | 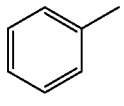 | 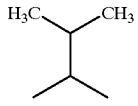 |
| 5 | 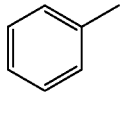 | 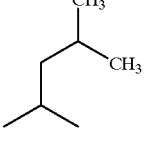 |
| 6 | 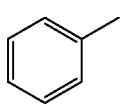 | 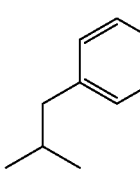 |
| 7 | 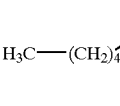 | 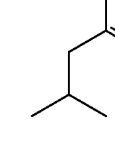 |
| 8 | 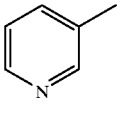 | 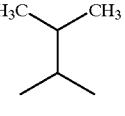 |
| 9 | 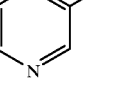 | 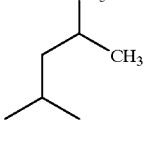 |
| 10 | 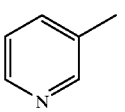 | 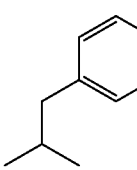 |

TABLE 12
(1M)
| No. | A | G |
|---|---|---|
| 1 | 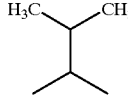 | 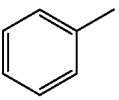 |
| 2 | 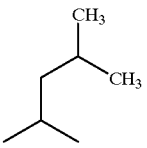 | 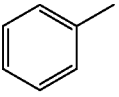 |
| 3 | 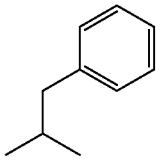 | 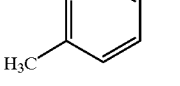 |
| 4 |  | 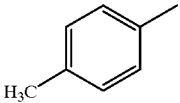 |
| 5 | 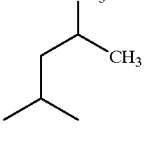 | 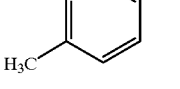 |
| 6 | 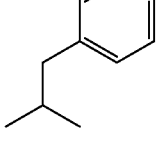 | 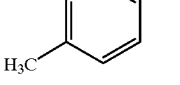 |
| 7 | 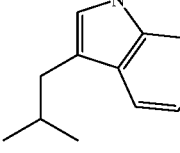 | 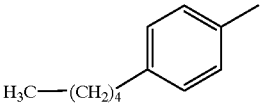 |
| 8 | 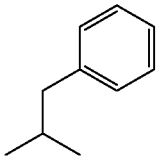 | 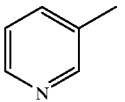 |
TABLE 12-continued
(1M)
| No. | A | G |
|---|---|---|
| 9 | 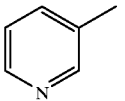 | 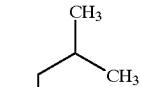 |
| 10 | 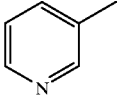 | 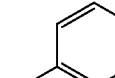 |
| 11 | 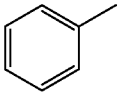 |  |
TABLE 13
(1N)
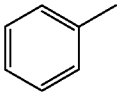
| No. | A | G |
|---|---|---|
| 1 | 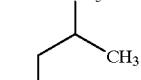 | H₃C  CH₃ |
| 2 | 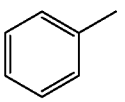 | 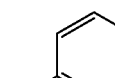 |
| 3 | (pyridyl) | (phenyl-isobutyl) |

TABLE 13-continued
(1N)
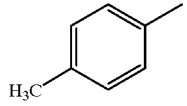
| No. | A | G |
|---|---|---|
| 4 | 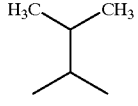 | 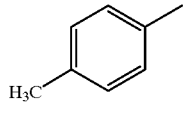 |
| 5 | 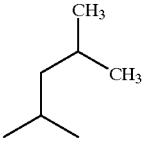 | 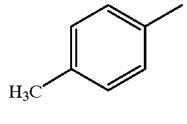 |
| 6 | 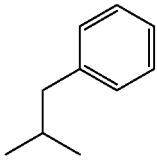 | 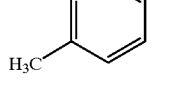 |
| 7 | 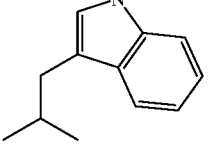 | 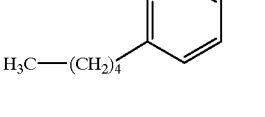 |
| 8 | 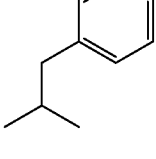 | 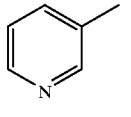 |
| 9 | 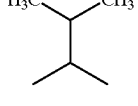 | 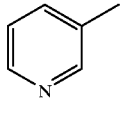 |
| 10 | 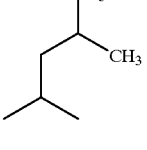 | 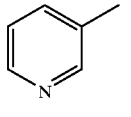 |
| 11 | 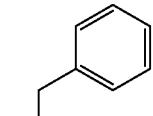 | 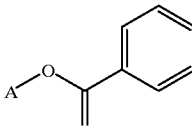 |
TABLE 14
(1P)
| No. | A | G |
|---|---|---|
| 1 | 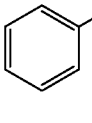 | 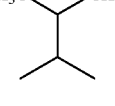 |
| 2 | 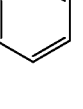 | 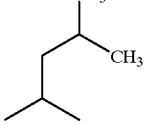 |
| 3 | 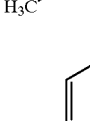 | 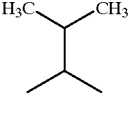 |
| 4 | 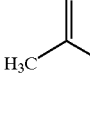 | 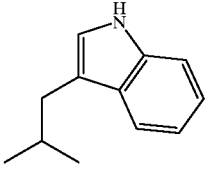 |
| 5 | 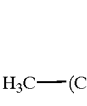 | 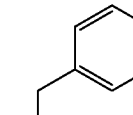 |
| 6 | | |
| 7 | | |
| 8 | | |

TABLE 14-continued (1P)

| No. | A | G |
|---|---|---|
| 9 | 3-pyridyl | isopropyl-CH(CH3)- (H3C, CH3) |
| 10 | 3-pyridyl | 2,4-dimethylpentyl (CH3, CH3 branched) |
| 11 | 3-pyridyl | isobutylbenzyl (phenyl-CH2-CH(CH3)2... benzyl with isobutyl) |

TABLE 15

(1Q)

| No. | A | G |
|---|---|---|
| 1 | phenyl | H3C-CH(CH3)- CH(CH3)-... (isopropyl-CH(CH3)) |
| 2 | phenyl | CH3, CH3 branched chain |
| 3 | phenyl | phenyl-CH2-CH(CH3)-CH2- |

TABLE 15-continued (1Q)

| No. | A | G |
|---|---|---|
| 4 | 4-methylphenyl | H3C, CH3 (isopropyl-CH(CH3)) |
| 5 | 4-methylphenyl | CH3, CH3 branched |
| 6 | 4-methylphenyl | phenyl-CH2-CH(CH3)-CH2- |
| 7 | 4-methylphenyl | 1H-indol-3-yl-CH2-CH(CH3)- |
| 8 | 4-pentylphenyl (H3C-(CH2)4-) | phenyl-CH2-CH(CH3)-CH2- |
| 9 | 3-pyridyl | H3C, CH3 (isopropyl-CH(CH3)) |
| 10 | 3-pyridyl | CH3, CH3 branched |
| 11 | 3-pyridyl | phenyl-CH2-CH(CH3)-CH2- |

TABLE 16

(1R)

| No. | A | G |
|-----|---|---|
| 1 | phenyl | isopropyl-CH(CH₃)- (3-methylbut-2-yl) |
| 2 | phenyl | 4-methylpentan-2-yl |
| 3 | phenyl | 2-methyl-1-phenylpropyl (isobutyl-benzyl) |
| 4 | 4-methylphenyl | 3-methylbut-2-yl |
| 5 | 4-methylphenyl | 4-methylpentan-2-yl |
| 6 | 4-methylphenyl | 2-methyl-1-phenylpropyl |
| 7 | 4-methylphenyl | (1H-indol-3-yl)-isobutyl-methyl |
| 8 | 4-pentylphenyl | 2-methyl-1-phenylpropyl |

TABLE 16-continued (1R)

| No. | A | G |
|-----|---|---|
| 9 | pyridin-3-yl | 3-methylbut-2-yl |
| 10 | pyridin-3-yl | 4-methylpentan-2-yl |
| 11 | pyridin-3-yl | 2-methyl-1-phenylpropyl |

TABLE 17

(1S)

| No. | A | G |
|-----|---|---|
| 1 | phenyl | 3-methylbut-2-yl |
| 2 | phenyl | 4-methylpentan-2-yl |
| 3 | phenyl | 2-methyl-1-phenylpropyl |

TABLE 17-continued (1S)

| No. | A | G |
|-----|---|---|
| 4 | 4-methylphenyl | isopropyl-CH(CH3)- (H3C,CH3 branch) |
| 5 | 4-methylphenyl | isobutyl-CH2- |
| 6 | 4-methylphenyl | benzyl (CH2-Ph) |
| 7 | 4-methylphenyl | (1H-indol-3-yl)methyl |
| 8 | 4-pentylphenyl | benzyl |
| 9 | pyridin-3-yl | H3C,CH3 branch |
| 10 | pyridin-3-yl | isobutyl type |
| 11 | pyridin-3-yl | isobutyl |

TABLE 18

(1T)

| No. | A | G |
|-----|---|---|
| 1 | phenyl | H3C,CH3 branch |
| 2 | phenyl | isobutyl type |
| 3 | phenyl | benzyl |
| 4 | 4-methylphenyl | H3C,CH3 branch |
| 5 | 4-methylphenyl | isobutyl type |
| 6 | 4-methylphenyl | benzyl |
| 7 | 4-methylphenyl | (1H-indol-3-yl)methyl |
| 8 | 4-pentylphenyl | benzyl |

TABLE 18-continued (1T)

| No. | A | G |
|-----|---|---|
| 9 | 3-pyridyl (methyl) | H₃C-CH(CH₃)-CH(CH₃)- |
| 10 | 3-pyridyl (methyl) | -CH₂-CH(CH₃)-CH₂-CH(CH₃)₂ |
| 11 | 3-pyridyl (methyl) | -CH₂-CH(CH₃)-CH₂-C₆H₅ |

TABLE 19

(1U)

| NO. | E | R¹ |
|-----|---|-----|
| 1 | —CO—NH— | CH₃ |
| 2 | —CO—NH— | CH(CH₃)₂ |
| 3 | —NH—CO— | CH₃ |
| 4 | —NH—CO— | CH(CH₃)₂ |
| 5 | —CO—O— | CH₃ |
| 6 | —CO—O— | CH(CH₃)₂ |
| 7 | —O—CO— | CH₃ |
| 8 | —O—CO— | CH(CH₃)₂ |
| 9 | —NH—CO—NH— | CH₃ |
| 10 | —NH—CO—NH— | CH(CH₃)₂ |
| 11 | —O—CO—O— | CH₃ |
| 12 | —O—CO—O— | CH(CH₃)₂ |
| 13 | —O—CO—NH— | CH₃ |
| 14 | —O—CO—NH— | CH(CH₃)₂ |
| 15 | —NH—CO—O— | CH₃ |
| 16 | —NH—CO—O— | CH(CH₃)₂ |
| 17 | —CO—CH₂— | CH₃ |
| 18 | —CO—CH₂— | CH(CH₃)₂ |
| 19 | —CO— | CH₃ |
| 20 | —CO— | CH(CH₃)₂ |
| 21 | —CS—NH— | CH₃ |
| 22 | —CS—NH— | CH(CH₃)₂ |
| 23 | —NH—CS— | CH₃ |
| 24 | —NH—CS— | CH(CH₃)₂ |
| 25 | —CS—O— | CH₃ |
| 26 | —CS—O— | CH(CH₃)₂ |

TABLE 19-continued (1U)

| NO. | E | R¹ |
|-----|---|-----|
| 27 | —O—CS— | CH₃ |
| 28 | —O—CS— | CH(CH₃)₂ |
| 29 | —NH—CS—NH— | CH₃ |
| 30 | —NH—CS—NH— | CH(CH₃)₂ |
| 31 | —O—CS—O— | CH₃ |
| 32 | —O—CS—O— | CH(CH₃)₂ |
| 33 | —O—CS—NH— | CH₃ |
| 34 | —O—CS—NH— | CH(CH₃)₂ |
| 35 | —NH—CS—O— | CH₃ |
| 36 | —NH—CS—O— | CH(CH₃)₂ |

TABLE 20

(1W)

| NO. | E | R¹ |
|-----|---|-----|
| 1 | —CO—NH— | CH₃ |
| 2 | —CO—NH— | CH(CH₃)₂ |
| 3 | —NH—CO— | CH₃ |
| 4 | —NH—CO— | CH(CH₃)₂ |
| 5 | —CO—O— | CH₃ |
| 6 | —CO—O— | CH(CH₃)₂ |
| 7 | —O—CO— | CH₃ |
| 8 | —O—CO— | CH(CH₃)₂ |
| 9 | —NH—CO—NH— | CH₃ |
| 10 | —NH—CO—NH— | CH(CH₃)₂ |
| 11 | —O—CO—O— | CH₃ |
| 12 | —O—CO—O— | CH(CH₃)₂ |
| 13 | —O—CO—NH— | CH₃ |
| 14 | —O—CO—NH— | CH(CH₃)₂ |
| 15 | —NH—CO—O— | CH₃ |
| 16 | —NH—CO—O— | CH(CH₃)₂ |
| 17 | —CO—CH₂— | CH₃ |
| 18 | —CO—CH₂— | CH(CH₃)₂ |
| 19 | —CO— | CH₃ |
| 20 | —CO— | CH(CH₃)₂ |
| 21 | —CS—NH— | CH₃ |
| 22 | —CS—NH— | CH(CH₃)₂ |
| 23 | —NH—CS— | CH₃ |
| 24 | —NH—CS— | CH(CH₃)₂ |
| 25 | —CS—O— | CH₃ |
| 26 | —CS—O— | CH(CH₃)₂ |
| 27 | —O—CS— | CH₃ |
| 28 | —O—CS— | CH(CH₃)₂ |
| 29 | —NH—CS—NH— | CH₃ |
| 30 | —NH—CS—NH— | CH(CH₃)₂ |
| 31 | —O—CS—O— | CH₃ |
| 32 | —O—CS—O— | CH(CH₃)₂ |
| 33 | —O—CS—NH— | CH₃ |
| 34 | —O—CS—NH— | CH(CH₃)₂ |
| 35 | —NH—CS—O— | CH₃ |
| 36 | —NH—CS—O— | CH(CH₃)₂ |

TABLE 21

(IY)

[Structure: 4-methoxyphenyl-E-phenyl-SO2-NH-CH2-COOH]

| NO. | E | R¹ |
|---|---|---|
| 1 | —CO—NH— | CH₃ |
| 2 | —CO—NH— | CH(CH₃)₂ |
| 3 | —NH—CO— | CH₃ |
| 4 | —NH—CO— | CH(CH₃)₂ |
| 5 | —CO—O— | CH₃ |
| 6 | —CO—O— | CH(CH₃)₂ |
| 7 | —O—CO— | CH₃ |
| 8 | —O—CO— | CH(CH₃)₂ |
| 9 | —NH—CO—NH— | CH₃ |
| 10 | —NH—CO—NH— | CH(CH₃)₂ |
| 11 | —O—CO—O— | CH₃ |
| 12 | —O—CO—O— | CH(CH₃)₂ |
| 13 | —O—CO—NH— | CH₃ |
| 14 | —O—CO—NH— | CH(CH₃)₂ |
| 15 | —NH—CO—O— | CH₃ |
| 16 | —NH—CO—O— | CH(CH₃)₂ |
| 17 | —CO—CH₂— | CH₃ |
| 18 | —CO—CH₂— | CH(CH₃)₂ |
| 19 | —CO— | CH₃ |
| 20 | —CO— | CH(CH₃)₂ |
| 21 | —CS—NH— | CH₃ |
| 22 | —CS—NH— | CH(CH₃)₂ |
| 23 | —NH—CS— | CH₃ |
| 24 | —NH—CS— | CH(CH₃)₂ |
| 25 | —CS—O— | CH₃ |
| 26 | —CS—O— | CH(CH₃)₂ |
| 27 | —O—CS— | CH₃ |
| 28 | —O—CS— | CH(CH₃)₂ |
| 29 | —NH—CS—NH— | CH₃ |
| 30 | —NH—CS—NH— | CH(CH₃)₂ |
| 31 | —O—CS—O— | CH₃ |
| 32 | —O—CS—O— | CH(CH₃)₂ |
| 33 | —O—CS—NH— | CH₃ |
| 34 | —O—CS—NH— | CH(CH₃)₂ |
| 35 | —NH—CS—O— | CH₃ |
| 36 | —NH—CS—O— | CH(CH₃)₂ |

TABLE 22

(1Z)

[Structure: 4-methylphenyl-E-phenyl(R¹)-SO2-NH-CH2-COOH]

| NO. | E | R¹ |
|---|---|---|
| 1 | —CO—NH— | CH₃ |
| 2 | —CO—NH— | CH(CH₃)₂ |
| 3 | —NH—CO— | CH₃ |
| 4 | —NH—CO— | CH(CH₃)₂ |
| 5 | —CO—O— | CH₃ |
| 6 | —CO—O— | CH(CH₃)₂ |
| 7 | —O—CO— | CH₃ |
| 8 | —O—CO— | CH(CH₃)₂ |
| 9 | —NH—CO—NH— | CH₃ |
| 10 | —NH—CO—NH— | CH(CH₃)₂ |
| 11 | —O—CO—O— | CH₃ |
| 12 | —O—CO—O— | CH(CH₃)₂ |
| 13 | —O—CO—NH— | CH₃ |

TABLE 22-continued (1Z)

| NO. | E | R¹ |
|---|---|---|
| 14 | —O—CO—NH— | CH(CH₃)₂ |
| 15 | —NH—CO—O— | CH₃ |
| 16 | —NH—CO—O— | CH(CH₃)₂ |
| 17 | —CO—CH₂— | CH₃ |
| 18 | —CO—CH₂— | CH(CH₃)₂ |
| 19 | —CO— | CH₃ |
| 20 | —CO— | CH(CH₃)₂ |
| 21 | —CS—NH— | CH₃ |
| 22 | —CS—NH— | CH(CH₃)₂ |
| 23 | —NH—CS— | CH₃ |
| 24 | —NH—CS— | CH(CH₃)₂ |
| 25 | —CS—O— | CH₃ |
| 26 | —CS—O— | CH(CH₃)₂ |
| 27 | —O—CS— | CH₃ |
| 28 | —O—CS— | CH(CH₃)₂ |
| 29 | —NH—CS—NH— | CH₃ |
| 30 | —NH—CS—NH— | CH(CH₃)₂ |
| 31 | —O—CS—O— | CH₃ |
| 32 | —O—CS—O— | CH(CH₃)₂ |
| 33 | —O—CS—NH— | CH₃ |
| 34 | —O—CS—NH— | CH(CH₃)₂ |
| 35 | —NH—CS—O— | CH₃ |
| 36 | —NH—CS—O— | CH(CH₃)₂ |

TABLE 23

(1AA)

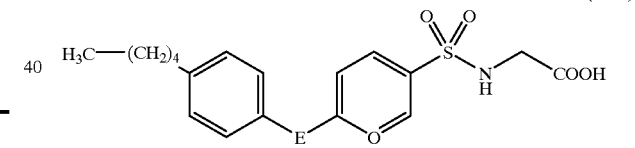

| NO. | E | R¹ |
|---|---|---|
| 1 | —CO—NH— | CH₃ |
| 2 | —CO—NH— | CH(CH₃)₂ |
| 3 | —NH—CO— | CH₃ |
| 4 | —NH—CO— | CH(CH₃)₂ |
| 5 | —CO—O— | CH₃ |
| 6 | —CO—O— | CH(CH₃)₂ |
| 7 | —O—CO— | CH₃ |
| 8 | —O—CO— | CH(CH₃)₂ |
| 9 | —NH—CO—NH— | CH₃ |
| 10 | —NH—CO—NH— | CH(CH₃)₂ |
| 11 | —O—CO—O— | CH₃ |
| 12 | —O—CO—O— | CH(CH₃)₂ |
| 13 | —O—CO—NH— | CH₃ |
| 14 | —O—CO—NH— | CH(CH₃)₂ |
| 15 | —NH—CO—O— | CH₃ |
| 16 | —NH—CO—O— | CH(CH₃)₂ |
| 17 | —CO—CH₂— | CH₃ |
| 18 | —CO—CH₂— | CH(CH₃)₂ |
| 19 | —CO— | CH₃ |
| 20 | —CO— | CH(CH₃)₂ |
| 21 | —CS—NH— | CH₃ |
| 22 | —CS—NH— | CH(CH₃)₂ |
| 23 | —NH—CS— | CH₃ |
| 24 | —NH—CS— | CH(CH₃)₂ |
| 25 | —CS—O— | CH₃ |
| 26 | —CS—O— | CH(CH₃)₂ |

TABLE 23-continued (1AA)

H₃C—(CH₂)₄—[phenyl]—E—[pyranyl]—SO₂—NH—CH₂—COOH

| NO. | E | R¹ |
|---|---|---|
| 27 | —O—CS— | CH₃ |
| 28 | —O—CS— | CH(CH₃)₂ |
| 29 | —NH—CS—NH— | CH₃ |
| 30 | —NH—CS—NH— | CH(CH₃)₂ |
| 31 | —O—CS—O— | CH₃ |
| 32 | —O—CS—O— | CH(CH₃)₂ |
| 33 | —O—CS—NH— | CH₃ |
| 34 | —O—CS—NH— | CH(CH₃)₂ |
| 35 | —NH—CS—O— | CH₃ |
| 36 | —NH—CS—O— | CH(CH₃)₂ |

(1) N-[[4-(Benzoylamino)phenyl]sulfonyl]glycine,
(2) N-[[3-(Benzoylamino)phenyl]sulfonyl]glycine,
(3) N-[[2-(Benzoylamino)phenyl]sulfonyl]glycine,
(4) N-[[4-(Acetylamino)phenyl]sulfonyl]glycine,
(5) N-[[4-(Phenylacetylamino)phenyl]sulfonyl]glycine,
(6) N-[[4-[(Phenylethylcarbonyl)amino]phenyl]sulfonyl]glycine,
(7) N-[[4-(Cinnamoylamino)phenyl]sulfonyl]glycine,
(8) N-[[4-(N-Phenylureido)phenyl]sulfonyl]glycine,
(9) N-[[4-(N-Phenylthioureido)amino]phenyl]sulfonyl]glycine,
(10) N-[[4-[(Benzyloxycarbonyl)amino]phenyl]sulfonyl]glycine,
(11) N-[[4-[(Phenyloxymethylcarbonyl)amino]phenyl]sulfonyl]glycine,
(12) N-[[4-[(Benzyloxymethylcarbonyl)amino]phenyl]sulfonyl]glycine,
(13) N-[[4-(4-Methoxybenzoylamino)phenyl]sulfonyl]glycine,
(14) N-[[4-(4-Fluorobenzoylamino)phenyl]sulfonyl]glycine,
(15) N-[[4-(4-Nitrobenzoylamino)phenyl]sulfonyl]glycine,
(16) N-[[4-(3-Nitrobenzoylamino)phenyl]sulfonyl]glycine,
(17) N-[[4-(2-Nitrobenzoylamino)phenyl]sulfonyl]glycine,
(18) N-[[4-(4-Formylbenzoylamino)phenyl]sulfonyl]glycine,
(19) N-[[4-(Benzoylamino)phenyl]sulfonyl]-D-α-phenylglycine,
(20) N-[[4-(Benzoylamino)phenyl]sulfonyl]-L-α-phenylglycine,
(21) N-[[4-(4-Methylbenzoylamino)phenyl]sulfonyl]-D-α-phenylglycine,
(22) N-[[4-(4-Methylbenzoylamino)phenyl]sulfonyl]-L-α-phenylglycine,
(23) N-[[4-(4-Methoxybenzoylamino)phenyl]sulfonyl]-D-α-phenylglycine,
(24) N-[[4-(4-Methoxybenzoylamino)phenyl]sulfonyl]-L-α-phenylglycine,
(25) N-[[4-(4-Fluorobenzoylamino)phenyl]sulfonyl]-D-α-phenylglycine,
(26) N-[[4-(4-Fluorobenzoylamino)phenyl]sulfonyl]-L-α-phenylglycine,
(27) N-[[4-(4-Nitrobenzoylamino)phenyl]sulfonyl]-D-α-phenylglycine,
(28) N-[[4-(4-Nitrobenzoylamino)phenyl]sulfonyl]-L-α-phenylglycine,
(29) N-[(4-Pivatoyloxyphenyl)sulfonyl]-D, L-α-phenylglycine,
(30) N-[(4-Pivaloyloxyphenyl)sulfonyl]-D, L-phenylalanine,
(31) N-[[4-(2, 4-Dichlorobenzoylamino)phenyl]sulfonyl]glycine,
(32) N-[[4-(2, 4-Dichlorobenzoylamino)phenyl]sulfonyl]-D, L-alanine,
(33) N-[[4-(2, 4-Dichlorobenzoylamino)phenyl]sulfonyl]-β-alanine,
(34) N-[[4-(2, 4-Dichlorobenzoylamino)phenyl]sulfonyl]-L-valine,
(35) N-[[4-(2, 4-Dichlorobenzoylamino)phenyl]sulfonyl]-D, L-valine,
(36) N-[[4-(2, 4-Dichlorobenzoylamino)phenyl]sulfonyl]-L-leucine,
(37) N-[[4-(2, 4-Dichlorobenzoylamino)phenyl]sulfonyl]-D, L-leucine,
(38) N-[[4-(2, 4-Dichlorobenzoylamino)phenyl]sulfonyl]-D, L-serine,
(39) N-[[4-(2, 4-Dichlorobenzoylamino)phenyl]sulfonyl]-L-phenylalanine,
(40) N-[[4-(2, 4-Dichlorobenzoylamino)phenyl]sulfonyl]-L-tyrosine,
(41) N-[[4-(2, 4-Dichlorobenzoylamino)phenyl]sulfonyl]-D, L-alanine methyl ester,
(42) N-[[4-(2,4-Dichlorobenzoylamino)phenyl]sulfonyl]-L-valine methyl ester,
(43) N-[[4-(2, 4-Dichlorobenzoylamino)phenyl]sulfonyl]-D, L-valine methyl ester,
(44) N-[[4-[[(2, 4-Dichlorobenzoylamino)phenyl]sulfonyl]-L-leucine methyl ester,
(45) N-[[4-(2, 4-Dichlorobenzoylamino)phenyl]sulfonyl]-D, L-serine methyl ester,
(46) N-[[4-(2, 4-Dichlorobenzoylamino)phenyl]sulfonyl]-L-tyrosine methyl ester,
(47) N-[[4-(3-Nitrobenzoylamino)phenyl]sulfonyl]-L-aspartic acid,
(48) N-[[3-(3-Nitrobenzoylamino)phenyl]sulfonyl]-L-aspartic acid,
(49) N-[[4-(3-Aminobenzoylamino)phenyl]sulfonyl]-L-aspartic acid,
(50) N-[[3-(3-Aminobenzoylamino)phenyl]sulfonyl]-L-aspartic acid,
(51) N-[[4-(Benzoylamino)phenyl]sulfonyl]-L-glutamic acid,
(52) N-[[4-(4-Chlorobenzoylamino)phenyl]sulfonyl]-L-glutamic acid,
(53) N-[[4-(4-Nitrobenzoylamino)phenyl]sulfonyl]-L-glutamic acid,
(54) N-[[4-[2-(4-(1-Pyrrolidinyl)phenyl]butyryloxy]phenyl]sulfonyl]-D,L-3-morpholinoalanine ethyl ester,
(55) N-[[4-[2-(4-(1-Nitrophenyl)butyryloxy]phenyl]sulfonyl]-D,L-3-morpholino alanine ethyl ester,
(56) N-[[4-(2-Methoxy-2-phenylacetyloxy)phenyl]sulfonyl]-D,L-3-morpholino alanine ethyl ester,
(57) N-[[4-[[[1-(4-Nitrophenyl)cyclobutyl]carbonyl]oxy]phenyl]sulfonyl]-D,L-3-morpholinoalanine ethyl ester,
(58) N-[[3-Methyl-4-[2-[4-(1-Pyrrolidinyl)phenyl]butyryloxy]phenyl]sulfonyl]-t-butoxycarbonyl-L-lysine,
(59) N-[[4-(2-Phenylbutyryloxy)phenyl]sulfonyl]glycine,
(60) N-[[4-[2-[4-(1-Pyrrolidinyl)phenyl]butyryloxy]phenyl]sulfonyl]-D,L-phenyl alanine,
(61) N-[[4-[2-[4-(1-Pyrrolidinyl)phenyl]butyryloxy]phenyl]sulfonyl]-D,L-aspartic acid,
(62) N-[[4-[[[1-(4-Nitrophenyl)cyclobutyl]carbonyl]oxy]phenyl]sulfonyl]-D, L-aspartic acid,

(63) 1-[[4-[2-[4-(1-Pyrrolidinyl)phenyl]butyryloxy]phenyl]sulfonylamide]-1-cyclopropanecarboxylic acid,
(64) N-[[4-[2-[4-(1-Pyrrolidinyl)phenyl]butyryloxy]phenyl]sulfonyl]-D,L-2-(2-furanyl)glycine,
(65) N-[[4-[2-[4-(1-Pyrrolidinyl)phenyl]butyryloxy]phenyl]sulfonyl]-D,L-2-(2-thienyl)glycine,
(66) N-[[4-[2-[4-(1-Pyrrolidinyl)phenyl]butyryloxy]phenyl]sulfonyl]-L-valine,
(67) N-[[4-[2-[4-(1-Pyrrolidinyl)phenyl]butyryloxy]phenyl]sulfonyl]-S-carboxymethyl-L-cysteine,
(68) N-[[4-[2-Ethyl-2-(4-methoxyphenyl)butyryloxy]phenyl]sulfonyl]-glycine,
(69) N-[[3-Methyl-4-[2-[4-(1-Pyrrolidinyl)phenyl]butyryloxy]phenyl]sulfonyl]-L-lysine,
(70) 5-[N-[[3-Methyl-4-[2-[4-(1-pyrrolidinyl)phenyl]butyryloxy]phenyl]sulfonyl]amino]pentanoic acid, and
(71) N-[[(3-Methyl-4-pivaloyloxy)phenyl]sulfonyl]-β-alanine.

Process for the preparation (1) In the compounds of the present invention of the formula (Ib), the compound in which A—J—E—, substituents of Ar in A, $R^6$ and $R^7$ in G, and —$COOR^2$ are not —COOH or group containing —COOH, and substituents of Ar in A, $R^6$ and $R^7$ in G are not amino, hydroxy or group containing them, that is the compound of the formula (Ib-1):

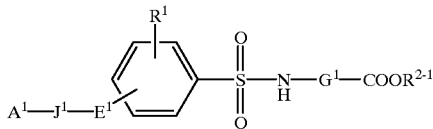

(Ib-1)

wherein $R^{2-1}$ is C1–8 alkyl, phenyl, or C1–4 alkyl substituent by phenyl or —$OCOR^{16}$, in which $R^{16}$ is the same meaning as hereinbefore defined; —$CONR^{17}R^{18}$ in which $R^{17}$ and $R^{18}$ are the same meaning as hereinbefore defined; $E^1$, $J^1$ and $A^1$ are the same meaning as E, J and A, with the proviso that when $E^1$ is —OCO—, or —OCS—, $J^1$ is not bond and $A^1$ is not hydrogen; $A^1$ and $G^1$ is the same meaning as A and G, with the proviso that substituents of Ar in $A^1$, $R^6$ and $R^7$ in $G^1$ are not —COOH, amino, hydroxy and groups containing them; and the other symbols are the same meaning as hereinbefore defined; may be prepared by following (a)–(k) methods.

(a) In the compounds of the formula (Ib-1), the compounds in which $E^1$ is —$CONR^3$—, that is the compounds of the formula (Ib-a):

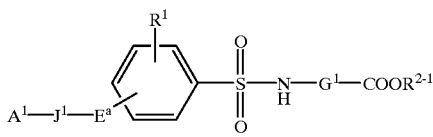

(Ib-a)

wherein $E^a$ is —CO—$NR^3$—, the other symbols are the same meaning as hereinbefore defined;

may be prepared by amidation of the compound of the formula (IIb-a):

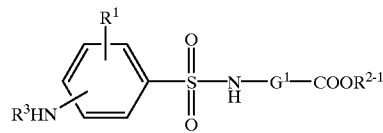

(IIb-a)

wherein all the symbols are the a same meaning as hereinbefore defined;
with the compound of the formula (IIIb-a):

$$A^1—J^1—COOH \qquad (III\ b\text{-}a)$$

wherein all the symbols are the same meaning as hereinbefore defined;
or, if necessary, followed by deprotection.

The method of amidation is known. It includes the method
(1) via acyl halide,
(2) via mixed acid anhydride,
(3) using condensing agent.

These methods are explained as follows.

(1) The method via acyl halide, for example, may be carried out in organic solvent (chloroform, methylene chloride, diethyl ether, tetrahydrofuran etc.) or without solvent, using an acid halide (oxalyl chloride, thionyl chloride etc.) at –20° C. to reflux temperature, and the obtained acyl halide derivative may be reacted with an amine in organic solvent (chloroform, methylene chloride, diethyl ether, tetrahydrofuran etc.) in the presence of a tertiary amine (pyridine, triethyl amine, dimethyl aniline, dimethylaminopyridine etc.) at 0–40° C.

(2) The method via mixed acid anhydride, for example, carboxylic acid may be reacted with an acid halide (pivaloyl chloride, tosyl chloride, mesyl chloride, ethyl chloroformate, isobutyl chloroformate etc.) in organic solvent (chloroform, methylene chloride, diethyl ether, tetrahydrofuran etc.) or without solvent, in the presence of a tertiary amine (pyridine, triethylamine, dimethylaniline, dimethylaminopyridine etc.) at –20° C.–40° C., and the obtained mixed acid anhydride derivative may be reacted with a corresponding amine in organic solvent (chloroform, methylene chloride, diethyl ether, tetrahydrofuran etc.) at 0–40° C.

(3) The method using condensing agent (1,3-dicyclohexylcarbodiimide (DCC), 1-ethyl-3-[3-(dimethylamino)propyl]carbodiimide (EDC), 2-chloro-1-methylpyridinium iodide etc.), for example, a carboxylic acid may be reacted with an amine in organic solvent (chloroform, methylene chloride, dimethylformamide, diethyl ether etc.) or without solvent, in the presence or absence of a tertiary amine (pyridine, triethylamine, dimethylaniline, dimethylaminopyridine etc.) using a condensing agent at 0–40° C.

The reaction described in (1), (2) and (3) must be carried out under an inert gas (argon, nitrogen etc.) to avoid water in order to obtain a preferable result.

The method of deprotection is known. It includes the method
(1) deprotection under alkaline condition,
(2) deprotection under acidic condition,
(3) hydrogenolysis,
and suitable condition is selected from (1), (2) or (3) depending on the character of protecting group.

These methods are explained as follows.

(1) Deprotection under alkaline condition, for example, may be carried out in organic solvent (methanol, tetrahydrofuran(THF), dioxane etc.), using an alkali metal hydroxide (potassium hydroxide, sodium hydroxide etc.), an alkali earth metal hydroxide (calcium hydroxide etc.) or a carbonate (sodium carbonate, potassium carbonate etc.), an aqueous solution thereof or mixture thereof at 0–40° C.

(2) Deprotection under acidic condition, for example, may be carried out in organic solvent (methylene chloride, chloroform, dioxane, ethyl acetate, acetic acid, water or two more mixture thereof etc.), using an organic acid (trifluoroacetic acid etc.), or an inorganic acid (hydrogen chloride, hydrogen bromide etc.) or mixture thereof at 0–120° C.

(3) Hydrogenolysis, for example, may be carried out in solvent [ether (tetrahydrofuran, dioxane, dimethoxyethane, diethyl ether etc.), alcohol (methanol, ethanol etc.), benzene (benzene, toluene etc.), amide (dimethylformamide etc.), water, ethyl acetate, acetic acid or two more mixture thereof etc.], in the presence of a catalyst (palladium on carbon, palladium black, palladium hydroxide, platinum dioxide, Raney-nickel etc.), in the presence or absence of an inorganic acid (hydrochloric acid, sulfuric acid, hypochlorous acid, boric acid, tetrafluoroboric acid etc.) or an organic acid (acetic acid, p-toluenesulfonic acid, oxalic acid, trifluoroacetic acid, formic acid etc.), at ordinary or elevated pressure of hydrogen gas or ammonium formate at 0–200° C.

(b) In the compounds of the formula (Ib-1), the compounds in which $E^1$ is —O—CO—NR$^3$—, that is the compounds of the formula (Ib-b):

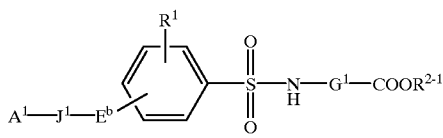

(Ib-b)

wherein $E^b$ is —O—CO—NR$^3$—, the other symbols are the same meaning as hereinbefore defined;

may be prepared by reacting the above compound of the formula (IIb-a) with the compound of the formula (IIIb-b):

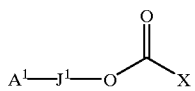

(IIIb-b)

wherein X is halogen, the other symbols are the same meaning as hereinbefore defined;

or, if necessary, followed by deprotection.

This type of reaction is known, for example, may be carried out in organic solvent (acetonitrile, tetrahydrofuran etc.) and in the presence or absence of water, using an organic base (4-dimethylaminopyridine etc.) or an inorganic base [alkali metal hydroxide (sodium hydroxide, potassium hydroxide etc.), alkali earth metal hydroxide (potassium hydroxide etc.), or carbonate (sodium carbonate, calcium carbonate etc.)] at 0–40° C.

The reaction of deprotection may be carried out by the same method as hereinbefore described.

(c) In the compounds of the formula (Ib-1), the compounds in which $E^1$ is —NR$^3$—CO—NR$^3$— or —NR$^3$—CS—NR$^3$—, that is the compounds of the formula (Ib-c):

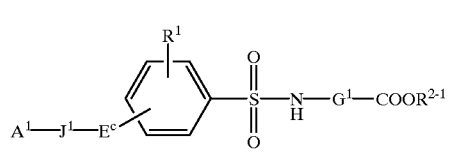

(Ib-c)

wherein $E^c$ is —NR$^3$—CO—NR$^3$— or —NR$^3$—CS—NR$^3$—, the other symbols are the same meaning as hereinbefore defined;

may be prepared by reacting the above compound of the formula (IIb-a) with the compound of the formula (IIIb-c):

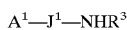

$A^1$—$J^1$—NHR$^3$ (III b-c)

wherein all the symbols are the same meaning as hereinbefore defined;

and with the compound of the formula (IVb-c):

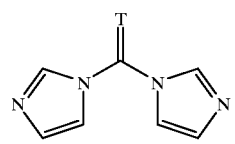

(IVb-c)

wherein T is oxygen or sulfur;

or, if necessary, followed by deprotection.

This type of reaction is known, for example, may be carried out in organic solvent (dimethylformamide, methylene chloride, tetrahydofuran etc.), in the presence or absence of an amine (triethylamine, pyridine, dimethylaminopyridine etc.) at 0–80° C.

The reaction of deprotection may be carried out by the same method as hereinbefore described.

Besides, it may be also prepared by reacting the above compound of the formula (IIb-a) with the compound of the formula (IIIb-c1):

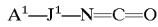

$A^1$—$J^1$—N=C=O (IIIb-c1)

wherein all the symbols are the same meaning as hereinbefore defined;

or with the compound of the formula (IIIb-c2):

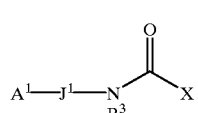

(IIIb-c2)

wherein all the symbols are the same meaning as hereinbefore defined;

or, if necessary, followed by deprotection.

This reaction is known, for example, may be carried out in organic solvent (acetone, chloroform, methyl chloride, benzene, tetrahydrofuran etc.), in the presence or absence of an amine (triethylamine, pyridine, dimethylaminopyridine etc.) at 0–80° C., or by the same method as (1) method acyl halide in amidation as hereinbefore defined.

The reaction of deprotection may be carried out by the same method as hereinbefore described.

(d) In the compounds of the formula (Ib-1), the compounds in which $E^1$ is —CO—O—, that is the compounds of the formula (Ib-d):

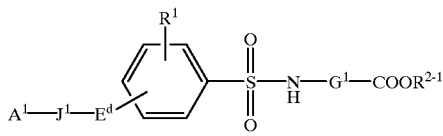

(Ib-d)

wherein $E^d$ is —CO—O—, the other symbols are the same meaning as hereinbefore defined;

may be prepared by esterification of the compound of the formula (IIb-d):

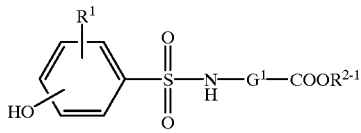

(IIb-d)

wherein all the symbols are the a same meaning as hereinbefore defined;

with the above compound of the formula (IIIb-a) or, if necessary, followed by deprotection.

The method of esterification is known. It includes the method
(1) via acyl halide,
(2) using mixed acid anhydride,
(3) using condensing agent.

These methods are explained as follows.

(1) Acyl haride may be prepared in organic solvent (chloroform, methylene chloride, diethyl ether, tetrahydrofuran etc.) or non-solvent, using an acid halide (oxalyl chloride, thionyl chloride etc.) at −20° C. to reflux temperature, and the obtained acyl halide derivative may be reacted with an alcohol derivative in organic solvent (chloroform, methylene chloride, diethyl ether, tetrahydrofuran etc.), in the presence of a tertiary amine (pyridine, triethylamine, dimethylaniline, dimethylaminopyridine etc.) at 0–40° C.

(2) Method using mixed acid anhydride, for example, carboxylic acid derivative may be reacted with acyl halide or acid derivative (ethyl chloroformate, isobutyl chloroformate etc.), in organic solvent (chloroform, methylene chloride, diethyl ether, tetrahydrofuran etc.) or without solvent, in the presence of a tertiary amine (pyridine, triethylamine, dimethylaniline, dimethylaminopyridine etc.), and the obtained mixed acid anhydride derivative may be reacted with alcohol derivative in organic solvent (chloroform, methylene chloride, diethyl ether, tetrahydrofuran etc.) at 0–40° C.

(3) Method using a condensing agent (DCC, EDC, 2-chloro-1-methylpyridinium iodide etc.), for example, carboxylic acid derivative may be reacted with alcohol derivative in organic solvent (chloroform, methylene chloride, dimethylformamide, diethyl ether etc.) or without solvent, in the presence or absence of a tertiary amine (pyridine, triethylamine, dimethylaniline, dimethylaminopyridine etc.), using a condensing agent at 0–40° C.

The reactions described in (1), (2) and (3) must be carried out under an inert gas (argon, nitrogen etc.) to avoid water in order to obtain a preferable result.

The reaction of deprotection may be carried out by the same method as hereinbefore described.

(e) In the compounds of the formula (Ib-1), the compounds in which $E^1$ is —O—CO—O—, that is the compounds of the formula (Ib-e):

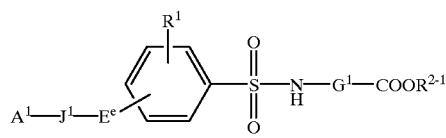

(Ib-e)

wherein $E^e$ is —O—CO—O—, the other symbols are the same meaning as hereinbefore defined;

may be prepared by reacting the above compound of the formula (IIb-d) with the above compound of the formula (IIIb-b) or, if necessary, followed by deprotection.

This reaction may be carried out by the same method as (b).

The reaction of deprotection may be carried out by the same method as hereinbefore described.

(f) In the compounds of the formula (Ib-1), the compounds in which $E^1$ is —$NR^3$—CO—, that is the compounds of the formula (Ib-f):

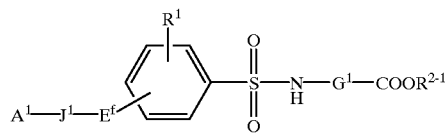

(Ib-f)

wherein $E^1$ is —$NR^3$—CO—, the other symbols are the same meaning as hereinbefore defined;

may be prepared by amidation of the compound of the formula (IIb-f):

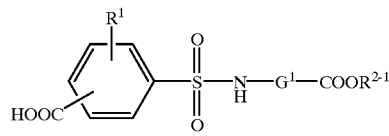

(IIb-f)

wherein all the symbols are the a same meaning as hereinbefore defined;

with the above compound of the formula (IIIb-c) or, if necessary, followed by deprotection.

This reaction of amidation may be carried out by the same method as (a).

The reaction of deprotection may be carried out by the same method as hereinbefore described.

(g) In the compounds of the formula (Ib-1), the compounds in which $E^1$ is —O—CO—, that is the compounds of the formula (Ib-g):

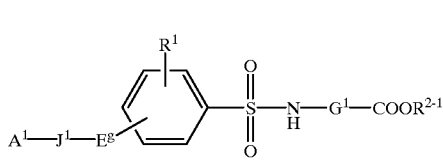 (Ib-g)

wherein $E^g$ is —O—CO—, the other symbols are the same meaning as hereinbefore defined;

may be prepared by esterification of the above compound of the formula (IIb-f) with the compound of the formula (IIIb-g):

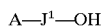 A—J¹—OH (III b-g)

wherein all the symbols are the same meaning as hereinbefore defined;

or, if necessary, followed by deprotection.

This reaction of esterification may be carried out by the same method as (d).

The reaction of deprotection may be carried out by the same method as hereinbefore described.

(h) In the compounds of the formula (Ib-1), the compounds in which $E^1$ is —NR³—CO—O—, that is the compounds of the formula (Ib-h):

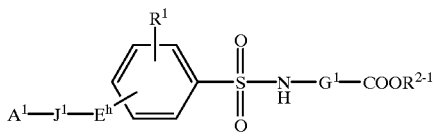 (Ib-h)

wherein $E^h$ is —NR³—CO—O—, the other symbols are the same meaning as hereinbefore defined;

may be prepared by reacting the compound of the formula (IIb-h):

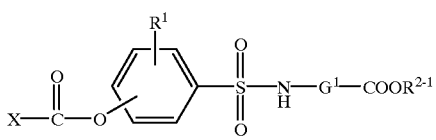 (IIb-h)

wherein all the symbols are the same meaning as hereinbefore defined;

with the above compound of the formula (IIIb-c) or, if necessary, followed by deprotection.

This reaction may be carried out by the same method as (b).

The reaction of deprotection may be carried out by the same method as hereinbefore described.

(j) In the compounds of the formula (Ib-1), the compounds in which $E^1$ is —CO— or —CO—CH₂— that is the compounds of the formula (Ib-j):

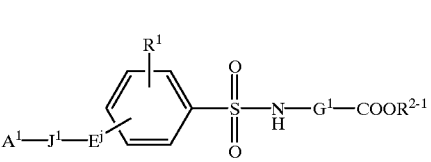 (Ib-j)

wherein $E^j$ is —CO— or —CO—CH₂—, the other symbols are the same meaning as hereinbefore defined;

may be prepared by reacting the compound of the formula (IIb-j-1):

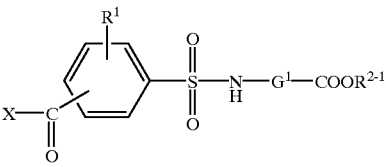 (IIb-j-1)

wherein all the symbols are the same meaning as hereinbefore defined;

or the compound of the formula (IIb-j-2):

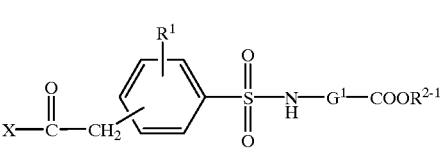 (IIb-j-2)

wherein all the symbols are the same meaning as hereinbefore defined;

with the compound of the formula (IIIb-j):

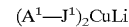 (A¹—J¹)₂CuLi (III b-j)

wherein all the symbols are the same meaning as hereinbefore defined;

or, if necessary, followed by deprotection.

This reaction using an organocopper agent is known, for example, an organocopper agent, which is prepared in organic solvent (tetrahydrofuran, ether etc.), using an organic lithium agent and an inorganic copper (copper iodide, copper cyanide etc.) at −78° C.–0° C., may be reacted with an acyl halide at −78° C.–0° C. The reactions must be carried out under an inert gas (argon, nitrogen etc.) to avoid water in order to obtain a preferable result.

The reaction of deprotection may be carried out by the same method as hereinbefore described.

(J-1) In the compounds of the formula (Ib-1), the compounds in which $E^1$ is —CO—NR$^3$—, —O—CO—NR$^3$—, —NR$^3$—CO—O—, —CO—O—, —CO—CH$_2$— or —O—CO—O—, that is the compounds of the formula (Ib-1-AA):

(Ib-1-AA)

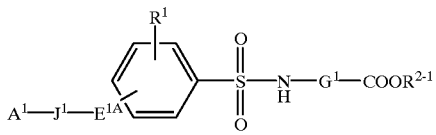

wherein $E^{1A}$ is —CO—NR$^3$—, —O—CO—NR$^3$—, —NR$^3$—CO—O—, —CO—O—, —CO—CH$_2$— or —O—CO—O— and the other symbols are the same meaning as hereinbefore defined;

may be prepared by amidation of the compound of the formula (XII):

(XII)

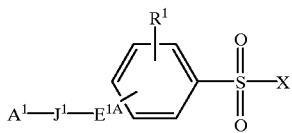

wherein all the symbols are the a same meaning as hereinbefore defined;

with the compound of the formula (XIII):

H$_2$N—G$^1$—COOR$^{2-1}$ (XIII)

wherein all the symbols are the same meaning as hereinbefore defined;

or, if necessary, followed by deprotection.

This amidation may be carried out by the same method via acyl halide as method (1) described in the part of amidation.

The reaction of deprotection may be carried out by the same method as hereinbefore described.

(J-2) In the compounds of the formula (Ib-1), the compounds in which $E^1$ is —CO—NR$^3$—, —NR$^3$—CO—, —NR$^3$—CO—NR$^3$—, —O—CO—NR$^3$— or —NR$^3$-CO—O—, that is the compounds of the formula (Ib-1-AB):

(Ib-1-AB)

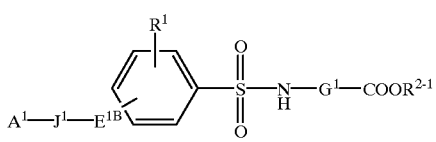

wherein $E^{1B}$ is —CO—NR$^3$—, —NR$^3$—CO—, —NR$^3$—CO—NR$^3$—, —O—CO—NR$^3$— or —NR$^3$—CO—O— and the other symbols are the same meaning as hereinbefore defined;

may be also prepared by conversion of —NH— into —N(R$^{3-1}$)—, wherein R$^{3-1}$ is C1–4 alkyl, phenyl or C1–4 alkyl substituted by phenyl; from the compound of the formula (Ib-1-AB1):

(Ib-1-AB1)

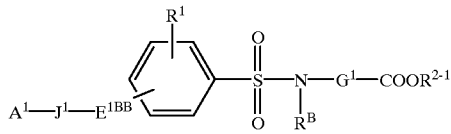

wherein $E^{1BB}$ is —CO—NH—, —NH—CO—, —NH—CO—NH—, —O—CO—NH— or —NH—CO—O—, $R^B$ is a protecting group of amino (e.g. t-butoxycarbonyl, benzyloxycarbonyl) and the other symbols are the same meaning as hereinbefore defined; and followed by deprotection of ($R^B$).

This reaction of conversion of —NH— to —N(R$^{3-1}$)— may be performed in an organic solvent (dimethylformamide etc.), in the presence of an base (sodium hydride etc.), using a corresponding R$^{3-1}$-halide at 0–40° C.

The reaction of deprotection may be carried out by the same method as hereinbefore described.

(k) In the compounds of the formula (Ib-1), the compounds in which $E^1$ is —CS—NR$^3$—, —NR$^3$—CS—, —NR$^3$—CS—NR$^3$—, —O—CS—NR$^3$—, —NR$^3$—CS—O—, —CS—O—, —O—CS— or —O—CS—O— that is the compounds of the formula (Ib-k):

(Ib-k)

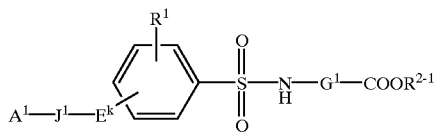

wherein $E^k$ is —CS—NR$^3$, —NR$^3$—CS—, —NR$^3$—CS—NR$^3$—, —O—CS—NR$^3$—, —NR$^3$—CS—O—, —CS—O—, —O—CS— or —O—CS—O— and the other symbols are the same meaning as hereinbefore defined;

may be prepared by reacting the compound which is prepared by the above method, of the formula (IIb-a), (Ib-b), (Ib-c), (Ib-d), (Ib-e), (Ib-f), (Ib-g) or (Ib-h), that is the compound of the formula (Ib-m):

(Ib-m)

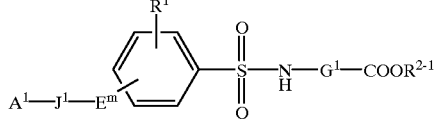

wherein $E^m$ is —CO—NR$^3$—, —NR$^3$—CO—, —NR$^3$—CO—NR$^3$—, —O—CO—NR$^3$—, —NR$^3$—CO—O—, —CO—O—, —O—CO— or —O—CO—O— and the other symbols are the same meaning as hereinbefore defined;

with Lawesson's reagent of the formula (IIIb-k):

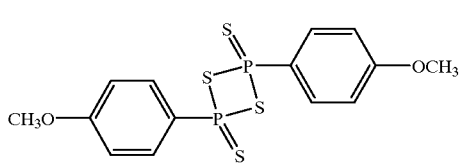
(IIIb-k)

or, if necessary, followed by deprotection.

This reaction using Lawesson's reagent is known, for example, may be carried out in organic solvent (dioxane, berizene, toluene, xylene etc.) at 20–150° C. The reactions must be carried out under an inert gas (argon, nitrogen etc.) to avoid water in order to obtain a preferable result.

The reaction of deprotection may be carried out by the same method as hereinbefore described.

(2) In the compounds of the present Invention of the formula (Ib), the compound in which at least one of A—J—E—, substituents of Ar in A, $R^6$ or $R^7$ in G, and —COOR$^2$ is —COOH or group containing —COOH, or at least one of substituents Ar in A, $R^6$ or $R^7$ in G is amino, hydroxy or group containing them, that is the compound of the formula (Ib-2):

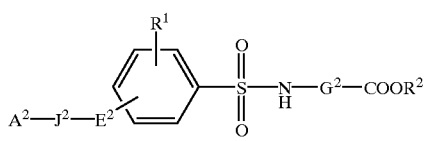
(Ib-2)

wherein $G^2$, $E^2$, $J^2$, and $A^2$ are the same meaning as G, E, J and A, with the proviso that at least one of $A^2$—$J^2$—$E^2$—, substituents of Ar in $A^2$, $R^6$ or $R^7$ in $G^2$, and —COOR$^2$ is —COOH or group containing —COOH, or at least one of substituents Ar in $A^2$, $R^6$ or $R^7$ in $G^2$ is amino, hydroxy or group containing them or $A^2$—J—$E^2$ is —CSOH, and the other symbols are the same meaning as hereinbefore defined; may be prepared by subjecting the compound of the formula (Ib-1) to deprotect. the reaction of deprotection may be carried out by the same method as hereinbefore described.

Besides, in the compounds of the present invention of the formula (Ib), the compound in which substituents of Ar in A is amino, that is the compounds of the formula (Ib-3):

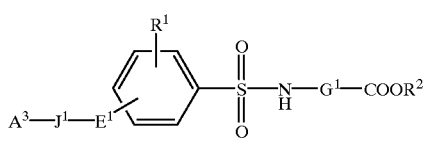
(Ib-3)

wherein $A^3$ is the same meaning as A, with the proviso that substituents of Ar in $A^3$ is amino and the other symbols are the same meaning as hereinbefore defined; may be prepared by subjecting the compound prepared by above methods of the formula (Ib-4):

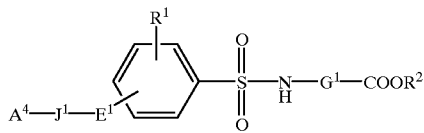
(Ib-4)

wherein $A^4$ is the same meaning as A, with the proviso that substituents of Ar in $A^4$ is nitro and the other symbols are the same meaning as hereinbefore defined; to hydrogenolysis.

Hydrogenolysis may be carried out by the same method as hereinbefore described.

The compound of the formula (IIb-a), (IIb-d), (IIb-f), (IIb-h), (IIb-j-1) or (IIb-j-2) may be prepared by known methods, methods of the following scheme 1–3 or methods in examples.

Scheme 1

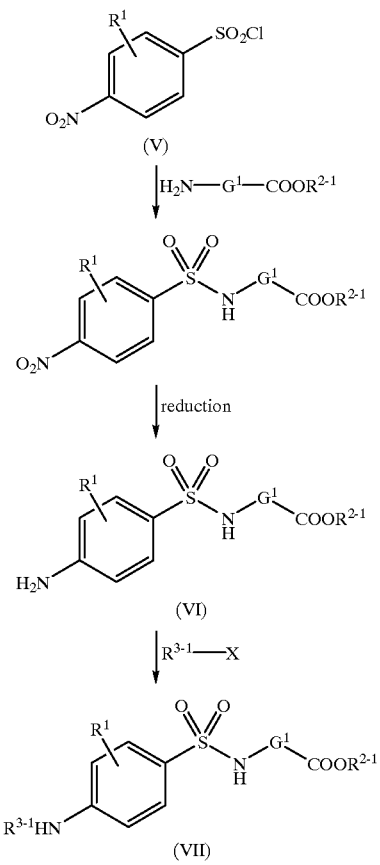

Scheme 2

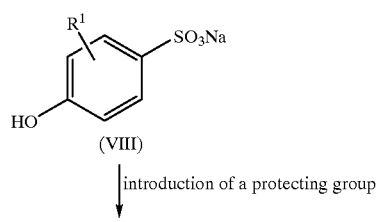

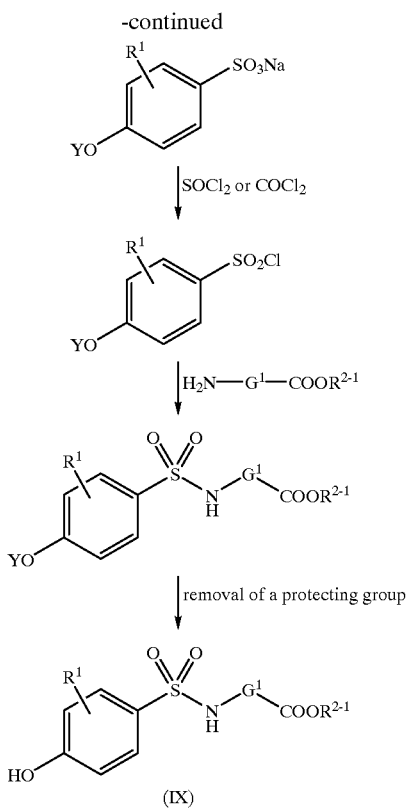

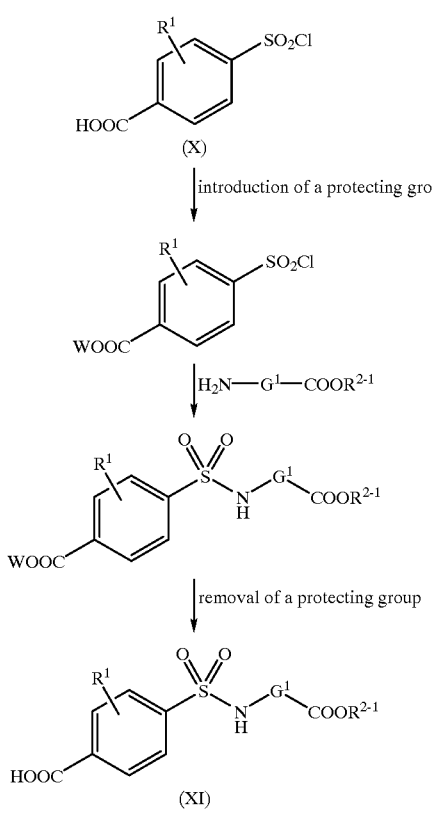

In the above scheme, Y is a protecting group of hydroxy (e.g. benzyl, benzyloxycarbonyl), W is a protecting group (e.g. benzyl, methyl) and the other symbols are the same meaning as hereinbefore defined.

In the above scheme, the compounds of the formula (VI) and (VII) are the partially compounds in the compounds of the formula (IIb-a). The compound of the formula (IX) is the partially compound in the compounds of the formula (IIb-d). The compound of the formula (XI) is the partially compound in the compounds of the formula (IIb-f).

Each reaction in the above scheme may be carried out by a known method. In the above scheme, the compound of the formula (V), (VIII) and (X) are known per se or may be prepared by known methods.

In each reaction in the present specification, products may be purified by conventional techniques. For example, purification may be carried out by distillation at atmospheric or reduced pressure, by high performance liquid chromatography, by thin layer chromatography or by column chromatography using silica gel or magnesium silicate, by washing or by recrystallization. Purification may be carried out after each reaction, or after a series of reactions.

The other starting materials and reagents in the present invention are known per se or may be prepared by known methods.

Pharmacological Activities

The potency of inhibitory activity against each matrix metalloproteinases is confirmed as below. The $IC_{50}$ value for inhibition of gelatinase A activity is determined as follows.

(1) Inhibitory activity against gelatinase A

[Method]

The progelatinase A (7 μl; in assay buffer (90 μl)) was purified from human normal skin dermal fibroblasts (HNDF). It was activated by the addition of 10 mM of p-aminophenylmercuric acetate (APMA) (10 μl) for 1 hour at 37° C.

The solution of activated gelatinase A (7 μl/tube, 98 μl) was mixed with various concentrations of the test compound or dimethylsulfoxide (2 μl) and gelatin (100 μl) labeled with 0.05% fluorescein isothiocyanate (FITC) and incubated for 2 hours at 37° C. The reaction was terminated by the addition of 0.1M Tris-HCl (pH9.5) containing 94.7% ethanol (750 μl). The mixture was stirred and then allowed to stand for 30 minutes at 0° C. The mixture was centrifuged for 30 minutes at 900×g. The $IC_{50}$ was determined by measuring the fluorescent intensity in supernatant (Ex=495 nm, and Em=520 nm). The results are shown in table 24.

TABLE 24

| Example No. | $IC_{50}$ (μM) |
|---|---|
| 2 | 0.11 |
| 2(10) | 0.66 |
| 2(11) | 0.80 |
| 2(35) | 0.013 |
| 2(63) | 0.0023 |
| 3(13) | 0.0027 |
| 6 | 0.42 |
| 10(1) | 0.70 |

Toxicity

The toxicity of the compounds of the present invention is very low and therefore, it may be considered safe for pharmaceutical use.

Application for Pharmaceuticals

To inhibit matrix metalloproteinase is useful for prevention and/or treatment of diseases induced by overexpression and excess activity of matrix metalloproteinases, for example, rheumatoid, arthrosteitis, unusual bone resorption, osteoporosis, periodontitis, interstitial nephritis, arteriosclerosis, pulmonary emphysema, cirrhosis, cornea injury, metastasis of, invasion of or growth of tumor cell, autoimmune disease (Crohn's disease, Sjogren's syndrome etc.), disease caused by vascular emigration or infiltration of leukocytes, arterialization in animals including human beings, especially human beings.

For the purpose above described, the compounds of the formula (Ia), of the present invention, non-toxic acid addition salts thereof or hydrate thereof may be normally by administered systematically or locally usually by oral or parenteral administration.

The doses to be administered are determined depending upon age, body weight, symptom, the desired therapeutic effect, the route of administration, and the duration of the treatment etc. In the human adult, the doses per person are generally between 1 mg and 1000 mg, by oral administration, up to several times per day, and between 1 mg and 100 mg, by parenteral administration (preferable intravenous administration), up to several times per day, or continuous administration between 1 and 24 hours per day from vein.

As mentioned above, the doses to be used depend upon various conditions. Therefore, there are cases in which doses lower than or greater than the ranges specified above may be used.

When administration of the compounds of the present invention, it is used as solid compositions, liquid compositions or other compositions for oral administration, as injections, liniments or suppositories etc. for parenteral administration.

Solid compositions for oral administration include compressed tablets, pills, capsules, dispersible powders, and granules.

Capsules include hard capsules and soft capsules.

In such compositions, one or more of the active compound(s) is or are admixed with at least one inert diluent (such as lactose, mannitol, glucose, hydroxypropyl cellulose, microcrystalline cellulose, starch, polyvinylpyrrolidone, magnesium metasilicate aluminate, etc.). The compositions may also comprise, as is normal practice, additional substances other than inert diluents: e.g. lubricating agents (such as magnesium stearate etc.), disintegrating agents (such as cellulose calcium glycolate, etc.), stabilizing agents, and assisting agents for dissolving such as glutamic acid, aspartic acid etc.).

The tablets or pills may, if desired, be coated with a film of gastric or enteric material (such as sugar, gelatin, hydroxypropyl cellulose or hydroxypropylmethyl cellulose phthalate, etc.), or be coated with more than two films. And further, coating may include containment within capsules of absorbable materials such as gelatin.

Liquid compositions for oral administration include pharmaceutically acceptable emulsions, solutions, syrups and elixirs. In such compositions, one or more of the active compound(s) is or are contained in inert diluent(s) commonly used in the art (purified water, ethanol etc.). Besides inert diluents, such compositions may also comprise adjuvants (such as wetting agents, suspending agents, etc.), sweetening agents, flavouring agents, perfuming agents, and preserving agents.

Other compositions for oral administration included spray compositions which may be prepared by known methods and which comprise one or more of the active compound(s). Spray compositions may comprise additional substances other than inert diluents: e.g. stabilizing agents (sodium sulfate etc.), isotonic buffer (sodium chloride, sodium citrate, citric acid, etc.). For preparation of such spray compositions, for example, the method described in the U.S. Pat. Nos. 2,868,691 or 3,095,355 may be used.

Injections for parenteral administration include sterile aqueous or non-aqueous solutions, suspensions and emulsions. Aqueous solutions, suspensions include distilled water for injection and physiological salt solution. Non-aqueous solutions, suspensions include propylene glycol, polyethylene glycol, vegetable oil such as olive oil, alcohol such as ethanol, POLYSORBATE80 (registered trade mark), etc.

Injections may comprise additional other than inert diluents: e.g. preserving agents, wetting agents, emulsifying agents, dispersing agents, stabilizing agent, assisting agents such as assisting agents for dissolving (glutamic acid, aspartic acid, etc.).

They may be sterilized for example, by filtration through a bacteria-retaining filter, by incorporation of sterilizing agents in the compositions or by irradiation. They may also be manufactured in the form of sterile solid compositions and which may be dissolved in sterile water or some other sterile diluent(s) for injection immediately before used.

Other compositions for parenteral administration include liquids for external use, and endermic liniments, ointment, suppositories for rectal administration and pessaries for vaginal administration which comprise one or more of the active compound(s) and may be prepared by per se known methods.

REFERENCE EXAMPLE AND EXAMPLE

The following reference examples and examples illustrate the present invention, but do not limit the present invention.

The solvents in the parentheses show the developing or eluting solvents and the ratios of the solvents used are by volume in chromatographic separations or TLC.

The solvents in the parentheses in NMR show the solvents used in measurement.

Reference Example 1

N-[(4-Nitrophenyl)sulfonyl]glycine t-butyl ester

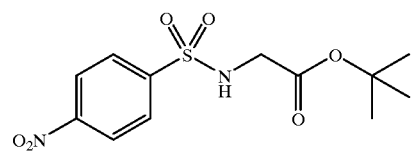

4-Nitrobenzenesulfonyl chloride (46.3 g) was added to a solution of glycine t-butyl ester hydrochloride (35 g) in pyridine (200 ml). The mixture was stirred for 1 hour at room temperature. The reaction mixture was concentrated. The precipitated crystals was washed with water and then a mixture of hexane and ethyl acetate (9:1) and dried to give the title compound (61.4 g) having the following physical data.

TLC: Rf 0.18 (Hexane:Ethyl acetate=4:1).

Reference Example 2

N-[(4-Aminophenyl)sulfonyl]glycine t-butyl ester

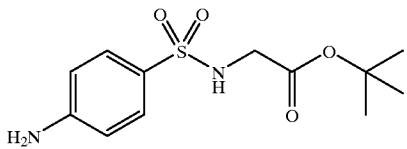

To a solution of the compound prepared in reference example 1 (57.1 g) in ethanol (200 ml) and tetrahydrofuran (200 ml), 10% palladium carbon (2.2 g) was added. The mixture was stirred for 3 hours at room temperature under an atmosphere of hydrogen. The reaction mixture was filtered through celite (registered trade mark). The filtrate was concentrated. The precipitated crystals was washed with a mixture of hexane and ethyl acetate (4:1) and dried to give the title compound (50 g) having the following physical data.

TLC: Rf 0.36 (Hexane:Ethyl acetate=1:1).

Example 1

N-[[4-(p-Toluoylamino)phenyl]sulfonyl]glycine t-butyl ester

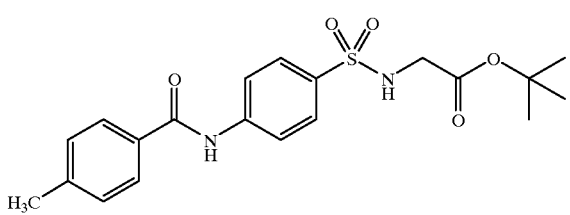

To a solution of the compound prepared in reference example 2 (1.2 g) in pyridine (10 ml), p-toluoyl chloride (0.5 ml) was added at 0° C. The mixture was stirred for 30 minutes at room temperature. To the reaction mixture, 1N hydrochloric acid (100 ml) was added. The mixture was extracted with ethyl acetate. The extract was washed with a saturated aqueous solution of sodium bicarbonate, a saturated aqueous solution of sodium chloride, dried over anhydrous sodium sulfate and concentrated. The residue was washed with ether and dried to give the title compound (1.52 g) having the following physical data.

TLC: Rf 0.56 (Hexane:Ethyl acetate=1:1), NMR (CDCl$_3$); δ 8.08–8.00 (1H, br.s), 7.86 (2H, d, J=9.2 Hz), 7.82 (2H, d, J=9.2 Hz), 7.78 (2H, d, J=8.2 Hz), 7.31 (2H, d, J=8.2 Hz), 5.04 (1H, t, J=5.4 Hz), 3.67 (2H, d, J=5.4 Hz), 2.44 (3H, s), 1.37 (9H, s).

Example 1(1)–1(91)

The compounds having the following physical data were obtained by the same procedure as a series of reaction of Example 1, using a corresponding acyl chloride instead of p-toluoyl chloride.

Example 1(1)

N-[[4-(Isobutyrylamino)phenyl]sulfonyl]glycine t-butyl ester

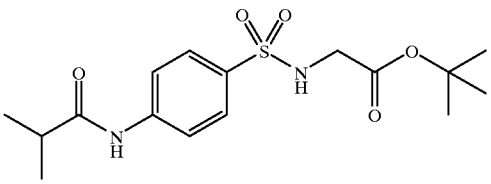

TLC: Rf 0.41 (Hexane:Ethyl acetate=1:1), NMR (CDCl$_3$): δ 7.77 (2H, d, J=9.0 Hz), 7.68 (2H, d, J=9.0 Hz), 5.15 (1H, t, J=5.4 Hz), 3.64 (2H, d, J=5.4 Hz), 2.56 (1H, m), 1.36 (9H, s), 1.25 (6H, d, J=6.8 Hz).

Example 1(2)

N-[[4-(Acetylamino)phenyl]sulfonyl]glycine t-butyl ester

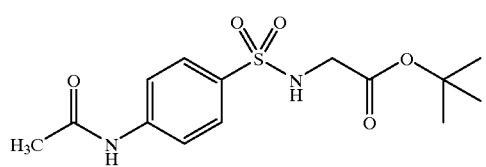

TLC: Rf 0.36 (Hexane:Ethyl acetate=3:7), NMR (CDCl$_3$); δ 7.78 (2H, d, J=8.8 Hz), 7.76–7.72 (1H), 7.65 (2H, d, J=8.8 Hz), 5.11 (1H, t, J=5.4 Hz), 3.65 (2H, d, J=5.4 Hz), 2.21 (3H, s), 1.36 (9H, s).

Example 1(3)

N-[[4-(o-Toluoylamino)phenyl]sulfonyl]glycine t-butyl ester

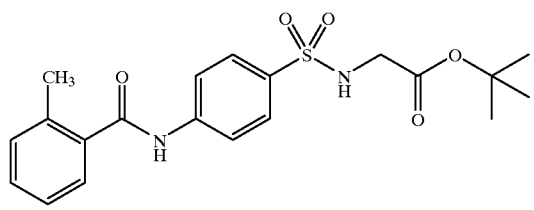

TLC: Rf 0.64 (Hexane Ethyl acetate=1:1), NMR (CDCl$_3$): δ 7.83 (2H, d, J=8.8 Hz), 7.76 (2H, d, J=8.8 Hz), 7.88–7.72 (1H), 7.52–7.22 (4H, m), 5.01 (1H, t, J=5.4 Hz), 3.65 (2H, d, J=5.4 Hz), 2.49 (3H, s), 1.37 (9H, s).

Example 1(4)

N-[[4-(m-Toluoylamino)phenyl]sulfonyl]glycine t-butyl ester

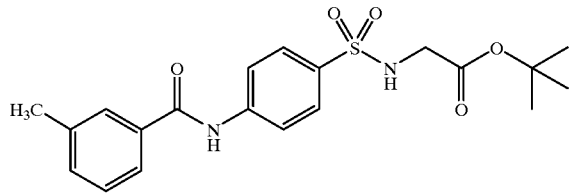

TLC: Rf 0.59 (Hexane:Ethyl acetate=1:1), NMR (CDCl$_3$): δ 8.10–8.04 (1H, br.s), 7.85 (2H, d, J=9.2 Hz), 7.80 (2H, d, J=9.2 Hz), 7.72–7.60 (2H, m), 7.43–7.36 (2H, m), 5.05 (1H, t, J=5.4 Hz), 3.67 (2H, d, J=5.4 Hz), 2.44 (3H, s), 1.37 (9H, s).

Example 1(5)

N-[[4-(2-Chlorobenzoylamino)phenyl]sulfonyl] glycine t-butyl ester

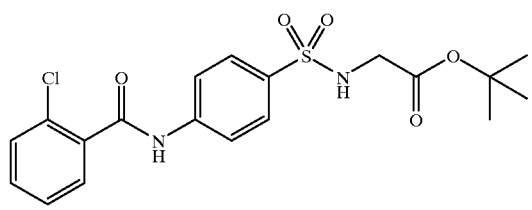

TLC: Rf 0.52 (Hexane:Ethyl acetate=1:1), NMR (CDCl$_3$): δ 8.22–8.12 (1H, br.s), 7.87 (2H, d, J=8.6 Hz), 7.84–7.74 (1H, m), 7.79 (2H, d, J=8.6 Hz), 7.50–7.36 (3H, m), 5.03 (1H, t, J=5.6 Hz), 3.67 (2H, d), J=5.6 Hz), 1.36 (9H, s).

Example 1(6)

N-[[4-(3-Chlorobenzoylamino)phenyl]sulfonyl] glycine t-butyl ester

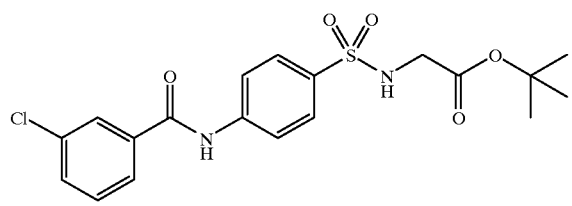

TLC: Rf 0.58 (Hexane:Ethyl acetate=1:1), NMR (CDCl$_3$): δ 8.02–7.94 (1H, br.s), 7.92–7.72 (6H, m), 7.61–7.40 (2H, m), 5.02 (1H, t, J=5.4 Hz), 3.68 (2H, d, J=5.4 Hz), 1.37 (9H, s).

Example 1(7)

N-[[4-(4-Chlorobenzoylamino)phenyl]sulfonyl] glycine t-butyl ester

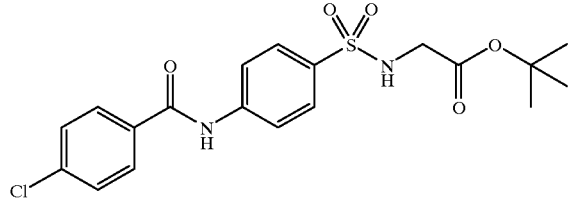

TLC: Rf 0.64 (Hexane:Ethyl acetate=1:1), NMR (CDCl$_3$): δ 8.00–7.90 (1H, br.s), 7.87 (2H, d, J=8.6 Hz), 7.83 (2H, d, J=8.8 Hz), 7.78 (2H, d, J=8.6 Hz), 7.49 (2H, d, J=8.8 Hz), 5.00 (1H, t, J=5.4 Hz), 3.67 (2H, d, J=5.4 Hz), 1.37 (9H, s).

Example 1(8)

N-[[4-(2-Methoxybenzoylamino)phenyl]sulfonyl] glycine t-butyl ester

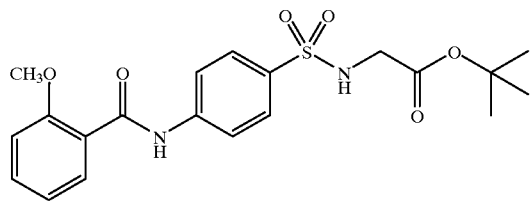

TLC: Rf 0.42 (Hexane:Ethyl acetate=1:1), NMR (CDCl$_3$); δ 10.08–10.00 (1H, br.s), 8.28 (1H, dd, J=2.0, 8.0 Hz), 7.87 (2H, d, J=9.4 Hz), 7.82 (2H, d, J=9.4 Hz), 7.60–7.48 (1H, m), 7.21–7.11 (1H, m), 7.06 (1H, d, J=8.4 Hz), 4.99 (1H, t, J=5.4 Hz), 4.09 (3H, s), 3.67 (2H, d, J=5.4 Hz), 1.37 (9H, s).

Example 1(9)

N-[[4-(3-Methoxybenzoylamino)phenyl]sulfonyl] glycine t-butyl ester

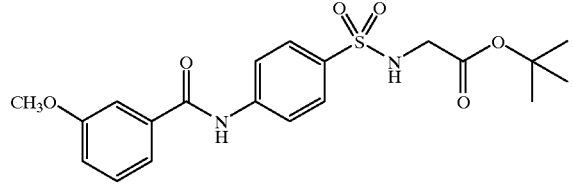

TLC: Rf 0.52 (Hexane:Ethyl acetate=1:1), NMR (CDCl$_3$): δ 8.02–7.96 (1H, br.s), 7.87 (2H, d, J=9.2 Hz), 7.80 (2H, d, J=9.2 Hz), 7.47–7.36 (3H, m), 7.15–7.08 (1H, m), 5.01 (1H, t, J=5.4 Hz), 3.88 (3H, s), 3.68 (2H, d, J=5.4 Hz), 1.37 (9H, s).

Example 1(10)

N-[[4-(Benzoylamino)phenyl]sulfonyl]glycine t-butyl ester

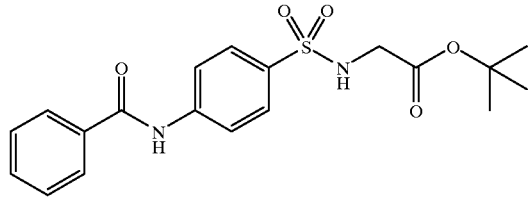

TLC: Rf 0.70 (Ethyl acetate), NMR (CDCl$_3$); δ 8.02 (1H, s), 7.9–7.8 (6H, m), 7.6–7.3 (3H, m), 5.02 (1H, t, J=5.4 Hz), 3.68 (2H, d, J=5.4 Hz), 1.37 (9H, s).

Example 1(11)

N-[[4-(4-Fluorobenzoylamino)phenyl]sulfonyl] glycine t-butyl ester

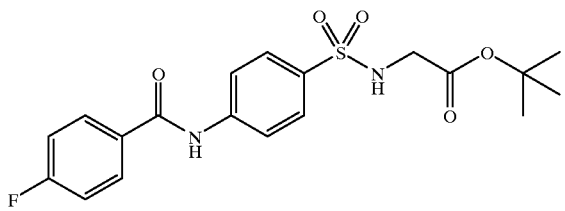

TLC: Rf 0.53 (Hexane:Ethyl acetate=1:1), NMR (CDCl$_3$+CD$_3$OD): δ 7.88 (2H, dd, J=5.2, 8.8 Hz), 7.82–7.75 (4H, m), 7.11 (2H, t, J=8.8 Hz), 3.60 (2H, s), 1.31 (9H, s).

Example 1(12)

N-[[4-(4-Methoxybenzoylamino)phenyl]sulfonyl] glycine t-butyl ester

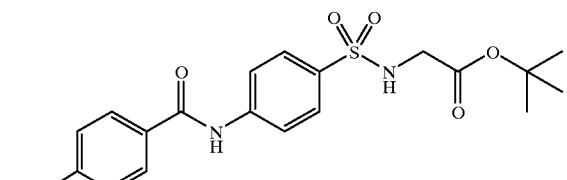

TLC: Rf 0.40 (Hexane:Ethyl acetate=1:1), NMR (CDCl$_3$): δ 7.94–7.90 (1H, br.s), 7.86 (2H, d, J=9.2 Hz), 7.85 (2H, d, J=8.8 Hz), 7.79 (2H, d, J=9.2 Hz), 6.99 (2H, d, J=8.8 Hz), 5.00 (1H, t, J=5.4 Hz), 3.89 (3H, s), 3.67 (2H, d, J=5.4 Hz), 1.37 (9H, s).

Example 1(13)

N-[[4-(2-Nitrobenzoylamino)phenyl]sulfonyl] glycine t-butyl ester

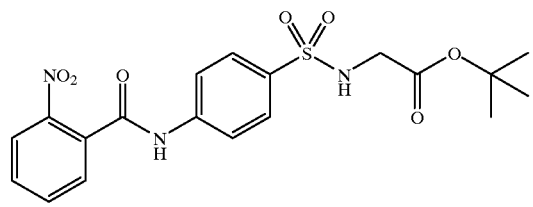

TLC: Rf 0.62 (Ethyl acetate), NMR (CD$_3$OD): δ 8.19 (1H d, J=8.4 Hz), 7.9–7.7 (7H, m), 3.65 (2H, s), 1.35 (9H, s).

Example 1(14)

N-[[4-(3-Nitrobenzoylamino)phenyl]sulfonyl] glycine t-butyl ester

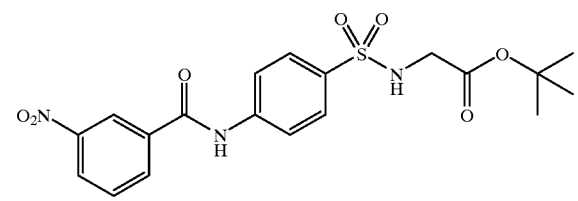

TLC: Rf 0.72 (Ethyl acetate), NMR (CDCl$_3$+CD3OD): δ 8.85 (1H, s), 8.43 (1H, d, J=8.0 Hz), 8.35 (1H, d, J8.0 Hz), 7.94 (2H, d, J=8.8 Hz), 7.85 (2H, d, J=8.8 Hz), 7.73 (1H, t, J=8.0 Hz), 3.68 (2H, s), 1.38 (9H, s).

Example 1(15)

N-[[4-(4-Nitrobenzoylamino)phenyl]sulfonyl] glycine t-butyl ester

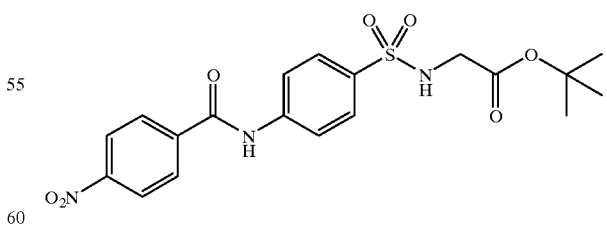

TLC: Rf 0.74 (Ethyl acetate), NMR (DMSO-d$_6$): δ 10.88 (1H, s), 8.39 (2H, d, J=8.8 Hz), 8.20 (2H, d, J=8.8 Hz), 8.01 (1H, t, J=6.0 Hz), 7.97 (2H, d, J=8.8 Hz), 7.79 (2H, d, J=8.8 Hz), 3.58 (2H, d, J=6.0 Hz), 1.32 (9H, s).

Example 1 (16)

N-[[4-(4-Ethylbenzoylamino)phenyl]sulfonyl]
glycine t-butyl ester

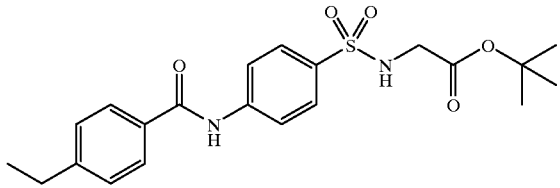

TLC: Rf 0.56 (Hexane:Ethyl acetate=1:1), NMR (CDCl$_3$): δ 8.00–7.98 (1H, br.s), 7.87 (2H, d, J=8.4 Hz), 7.81 (2H, d, J=8.4 Hz), 7.80 (2H, d, J=8.2 Hz), 7.34 (2H, d, J=8.2 Hz), 5.00 (1H, t, J=5.4 Hz), 3.67 (2H, d, J=5.4 Hz), 2.74 (2H, q, J=7.4 Hz), 1.37 (9H, s), 1.28 (3H, t, J=7.4 Hz).

Example 1 (17)

N-[[4-[4-Propylbenzoylamino)phenyl]sulfonyl]
glycine t-butyl ester

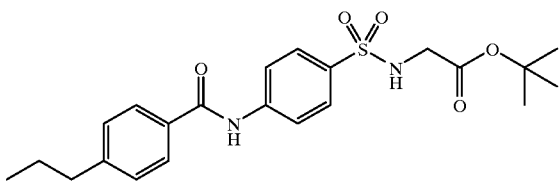

TLC: Rf 0.62 (Hexane:Ethyl acetate=1:1), NMR (CDCl$_3$): δ 8.02–7.95 (1H, br.s), 7.86 (2H, d, J=8.8 Hz), 7.81 (2H, d, J=8.8 Hz), 7.80 (2H, d, J=8.4 Hz), 7.31 (2H, d, J=8.4 Hz), 5.01 (1H, t, J=5.4 Hz), 3.67 (2H, d, J=5.4 Hz), 2.67 (2H, t, J=7.4 Hz), 1.80–1.60 (2H, m), 1.37 (9H, s), 0.96 (3H, t, J=7.4 Hz).

Example 1(18)

N-[[4-(2-Fluorobenzoylamino)phenyl]sulfonyl]
glycine t-butyl ester

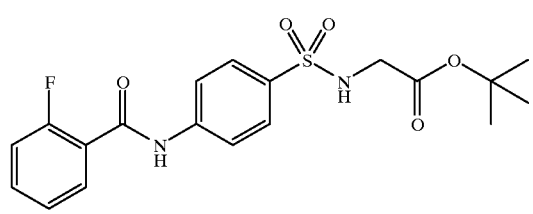

TLC: Rf 0.53 (Hexane:Ethyl acetate=1:1), NMR (CDCl$_3$): δ 8.65 (1H, br.s), 8.18 (1H, dt, J=2.0, 8.0 Hz), 7.88 (2H, d, J=8.8 Hz), 7.83 (2H, d, J=8.8 Hz), 7.64–7.51 (1H, m), 7.35 (1H, dt, J=1.0, 7.4 Hz), 7.28–7.15 (1H, m), 5.02 (1H, t, J=5.4 Hz), 3.68 (2H, d, J=5.4 Hz), 1.36 (9H, s).

Example 1 (19)

N-[[4-(3-Fluorobenzoylamino)phenyl]sulfonyl]
glycine t-butyl ester

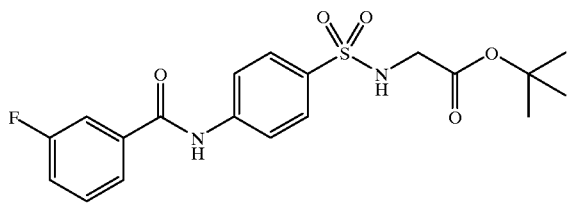

TLC: Rf 0.53 (Hexane:Ethyl acetate=1:1), NMR (CDCl$_3$): δ 8.00–7.93 (1H, br.s), 7.88 (2H, d, J=8.8 Hz), 7.80 (2H, d, J=8.8 Hz), 7.68–7.44 (3H, m), 7.35–7.27 (1H, m), 5.01 (1H, t, J=5.4 Hz), 3.68 (2H, d, J=5.4 Hz), 1.37 (9H, s).

Example 1(20)

N-[[4-(Cyclohexylcarbonylamino)phenyl]sulfonyl]
glycine t-butyl ester

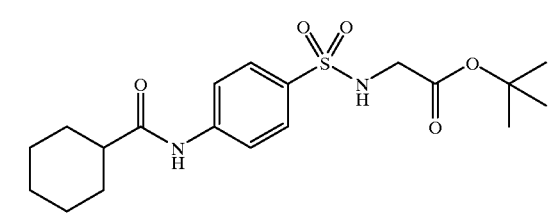

TLC: Rf 0.55 (Hexane:Ethyl acetate=1:1), NMR (CDCl$_3$): δ 7.80 (2H, d, J=8.8 Hz), 7.68 (2H, d, J=8.8 Hz), 7.44–7.32 (1H, br.s), 5.00 (1H, t, J=5.0 Hz), 3.65 (2H, d, J=5.0 Hz), 2.35–2.18 (1H, m), 2.04–1.20 (10H, m), 1.36 (9H, s).

Example 1(21)

N-[[4-(4-Trifluoromethylbenzoylamino)phenyl]
sulfonyl]glycine t-butyl ester

TLC: Rf 0.65 (Hexane:Ethyl acetate=1:1), NMR (DMSO-d$_6$): δ 10.83 (1H, s), 8.18 (2H, d, J=8.0 Hz), 8.04–7.95 (1H), 7.98 (2H, d, J=8.8 Hz), 7.91 (2H, d, J=8.0 Hz), 7.77 (2H, d, J=8.8 Hz), 3.55 (2H, d, J=6.2 Hz), 1.32 (9H, s).

Example 1(22)

N-[[4-(2-Thienylcarbonylamino)phenyl]sulfonyl] glycine t-butyl ester

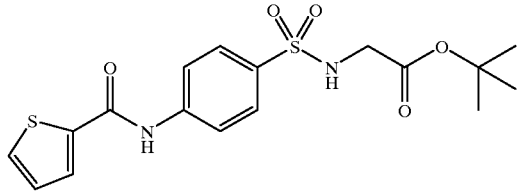

TLC: Rf 0.26 (Hexane:Ethyl acetate=1:1), NMR (CDCl₃): δ 7.95 (1H, s), 7.84 (2H, d, J=8.8 Hz), 7.77 (2H, d, J=8.8 Hz), 7.68 (1H, dd, J=1.0, 3.8 Hz), 7.61 (1H, dd, J=1.0, 4.8 Hz), 7.16 (1H, dd, J=3.8, 4.8 Hz), 5.05 (1H, t, J=5.4 Hz), 3.68 (2H, d, J=5.4 Hz), 1.37 (9H, S).

Example 1(23)

N-[[4-(2-Furylcarbonylamino)phenyl]sulfonyl] glycine t-butyl ester

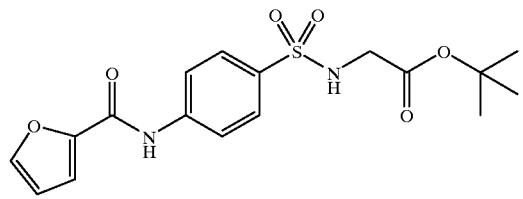

TLC: Rf 0.19 (Hexane:Ethyl acetate=1:1), NMR (CDCl₃): δ 8.25 (1H, s), 7.86–7.82 (4H, m), 7.55 (1H, d, J=1.8 Hz), 7.30 (1H, d, J=3.6 Hz), 6.60 (1H, dd, J=1.8, 3.6 Hz), 5.03 (1H, t, J=5.6 Hz), 3.68 (2H, d, J=5.6 Hz), 1.36 (9H, s).

Example 1(24)

N-[[4-(2-Pyridylcarbonylamino)phenyl]sulfonyl] glycine t-butyl ester

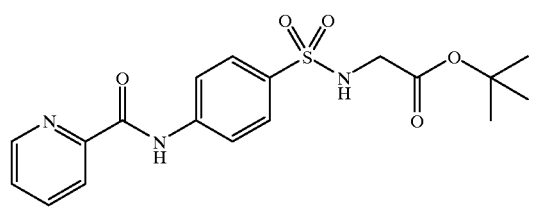

TLC: Rf 0.45 (Hexane:Ethyl acetate=1:1), NMR (CDCl₃): δ 10.33–10.20 (1H, br.s), 8.64–8.60 (1H, m), 8.31 (1H, d, J=7.8Hz), 8.00–7.85 (1H, m), 7.95 (2H, d, J=9.0 Hz), 7.88 (2H, d, J=9.0 Hz), 7.53 (1H, m), 5.02 (1H, t, J=5.4 Hz), 3.68 (2H, d, J=5.4 Hz), 1.36 (9H, s).

Example 1(25)

N-[[4-(3-Pyridylcarbonylamino)phenyl]sulfonyl] glycine t-butyl ester

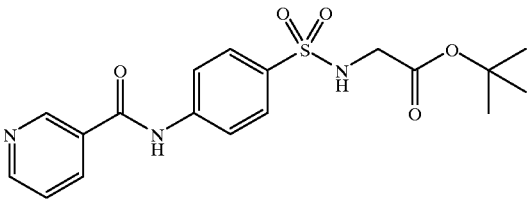

TLC: Rf 0.40 (Ethyl acetate), NMR (CDCl₃): δ 9.11 (1H, br.s), 8.81 (1H, dd, J=1.6, 4.8 Hz), 8.27–8.20 (1H, m), 8.20–8.10 (1H, br.s), 7.88 (2H, d, J=9.0 Hz), 7.81 (2H, d, J=9.0 Hz), 7.53–7.44 (1H, m), 5.10 (1H, t, J=5.4 Hz), 3.69 (2H, d, J=5.4 Hz), 1.37 (9H, s).

Example 1(26)

N-[[4-(4-Pyridylcarbonylamino)phenyl]sulfonyl] glycine t-butyl ester

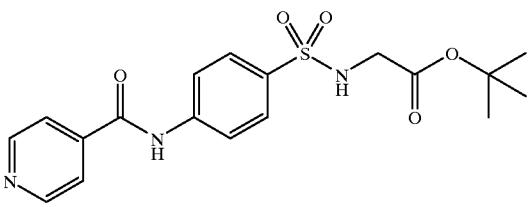

TLC: Rf 0.36 (Ethyl acetate), NMR (CDCl₃+CD₃OD(10 drops)): δ 8.76–8.71 (2H, m), 7.93 (2H, d, J=9.0 Hz), 7.89–7.82 (2H, m), 7.85 (2H, d, J=9.0 Hz), 3.66 (2H, s), 1.37 (9H, s).

Example 1(27)

N-[[4-(3-Thienylcarbonylamino)phenyl]sulfonyl] glycine t-butyl ester

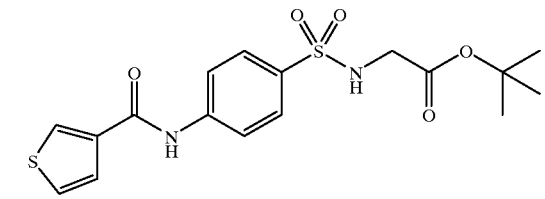

TLC: Rf 0.27 (Hexane:Ethyl acetate=1:1), NMR (CDCl₃+CD₃OD): δ 8.16 (1H, m), 7.87 (2H, d, J=9.0 Hz), 7.82 (2H, d, J=9.0 Hz), 7.61 (1H, m), 7.40 (1H, m), 3.66 (2H, s), 1.36 (9H, s).

Example 1(28)

N-[[4-(3-Furylcarbonylamino)phenyl]sulfonyl]
glycine t-butyl ester

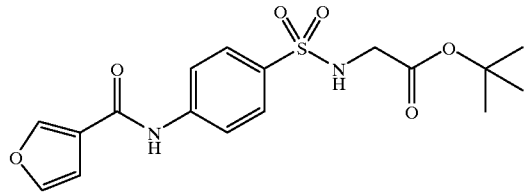

TLC: Rf 0.29 (Hexane:Ethyl acetate=1:1), NMR (CDCl$_3$+CD$_3$OD): δ 8.17 (1H, m), 7.84 (2H, d, J=9.0 Hz), 7.82 (2H, d, J=9.0 Hz), 7.49 (1H, m), 6.88 (1H, m), 3.66 (2H, s), 1.37 (9H, s).

Example 1(29)

N-[[4-(4-Methoxycarbonylbenzoylamino)phenyl]
sulfonyl]glycine t-butyl ester

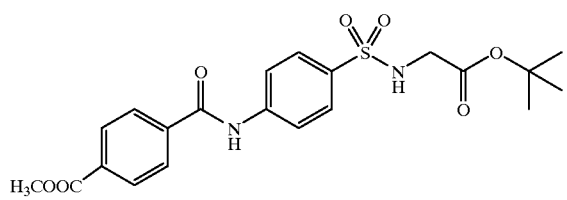

TLC: Rf 0.43 (Hexane:Ethyl acetate=1:1), NMR (CDCl$_3$): δ 8.05–7.98 (1H, br.s), 7.94 (2H, d, J=8.4 Hz), 7.89 (2H, d, J=9.0 Hz), 7.82 (2H, d, J=9.0 Hz), 5.01 (1H, t, J=5.4 Hz), 3.97 (3H, s), 3.69 (2H, d, J=5.4 Hz), 1.37 (9H, s).

Example 1(30)

N-[[4-(4-Cyanobenzoylamino)phenyl]sulfonyl]
glycine t-butyl ester

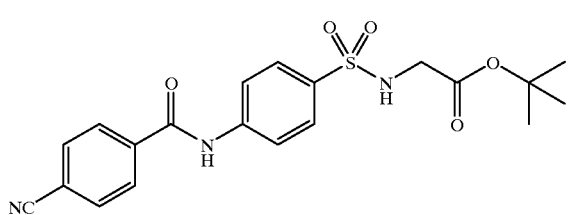

TLC: Rf 0.41 (Hexane:Ethyl acetate=1:1), NMR (CDCl$_3$): δ 8.15 (1H, s), 8.00 (2H, d, J=8.2 Hz), 7.85 (2H, d, J=9.0 Hz), 7.80 (2H, d, J=8.2 Hz), 7.79 (2H, d, J=9.0 Hz), 5.06 (1H, t, J=5.4 Hz), 3.68 (2H, d, J=5.4 Hz), 1.37 (9H, s).

Example 1(31)

N-[[4-(4-Benzyloxybenzoylamino)phenyl]sulfonyl]
glycine t-butyl ester

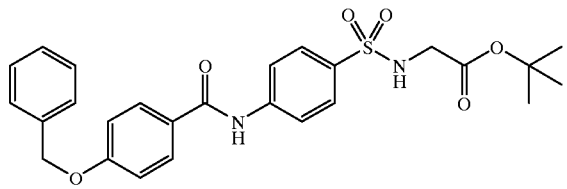

TLC: Rf 0.58 (Hexane:Ethyl acetate=1:1), NMR (DMSO-d$_6$): δ 10.41 (1H, s), 8.04–7.88 (1H, s), 7.97 (2H, d, J=8.4 Hz), 7.96 (2H, d, J=8.4 Hz), 7.74 (2H, d, J=8.4 Hz), 7.52–7.28 (5H, m), 7.16 (2H, d, J=8.4 Hz), 5.21 (2H, s), 3.56 (2H, s), 1.32 (9H, s).

Example 1(32)

N-[[4-(4-Carboxybenzoylamino)phenyl]sulfonyl]
glycine t-butyl ester

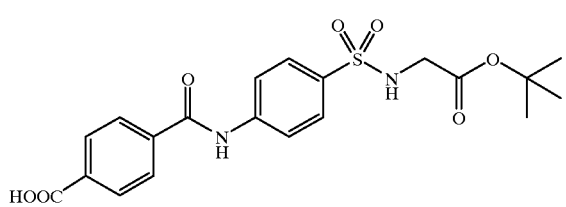

The title compound was not measured the physical data and was used for the next step.

Example 1(33)

N-[[4-(Cinnamoylamino)phenyl]sulfonyl]glycine t-
butyl ester

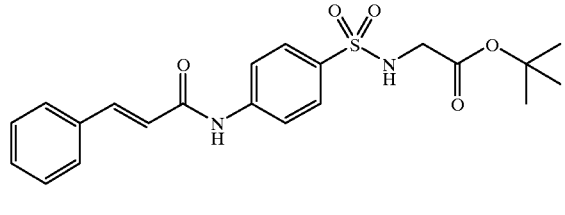

TLC: Rf 0.50 (Hexane:Ethyl acetate=1:1), NMR (CDCl$_3$): δ 7.85 (2H, d, J=8.8 Hz), 7.79 (1H, d, J=15.6 Hz), 7.77 (2H, d, J=8.8 Hz), 7.65–7.50 (3H, m), 7.46–7.38 (3H, m), 6.56 (1H, d, J=15.6 Hz), 5.03 (1H, t, J=5.4 Hz), 3.67 (2H, d, J=5.4 Hz), 1.36 (9H, s).

Example 1(34)

N-[[4-[(4-Butylbenzoylamino)phenyl]sulfonyl]glycine t-butyl ester

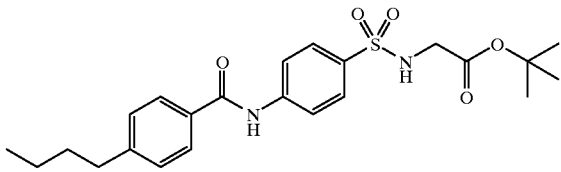

TLC: Rf 0.27 (Hexane:Ethyl acetate=7:3), NMR (CDCl$_3$): δ 7.97 (1H, s), 7.87 (2H, d, J=9.0 Hz), 7.80 (2H, d, J=9.0 Hz), 7.79 (2H, d, J=8.0 Hz), 7.32 (2H, d, J=8.0 Hz), 5.01 (1H, t, J=5.4 Hz), 3.68 (2H, J=5.4 Hz), 2.69 (2H, t, J=7.4 Hz), 1.70–1.50 (2H, m), 1.45–1.20 (2H, m), 1.37 (9H, s), 0.94 (3H, t, J=7.2 Hz).

Example 1(35)

N-[[4-(4-Pentylbenzoylamino)phenyl]sulfonyl]glycine t-butyl ester

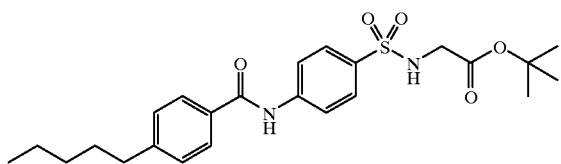

TLC: Rf 0.28 (Hexane:Ethyl acetate=7:3), NMR (CDCl$_3$): δ 7.99 (1H, s), 7.86 (2H, d, J=9.0 Hz), 7.80 (2H, d, J=9.0 Hz), 7.79 (2H, d, J=8.2 Hz), 7.31 (2H, d, J=8.2 Hz), 5.02 (1H, t, J=5.4 Hz), 3.67 (2H, d, J=5.4 Hz), 2.68 (2H, t, J=7.4 Hz), 1.72–1.50 (2H, m), 1.45–1.20 (4H, m), 1.36 (9H, s), 0.89 (3H, t, J=6.6 Hz).

Example 1(36)

N-[[4-(4-Phenylbenzoylamino)phenyl]sulfonyl]glycine t-butyl ester

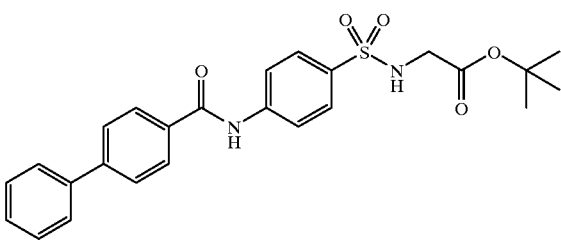

TLC: Rf 0.67 (Hexane:Ethyl acetate=1:1), NMR (DMSO-d$_6$): δ 10.61 (1H, s), 8.08 (2H, d, J=8.4 Hz), 8.04–7.93 (1H, m), 8.00 (2H, d, J=9.0 Hz), 7.85 (2H, d, J=8.4 Hz), 7.82–7.72 (2H), 7.77 (2H, d, J=9.0 Hz), 7.58–7.36 (3H, m), 3.57 (2H, d, J=6.4 Hz), 1.32 (9H, s).

Example 1(37)

N-[[4-(Benzoylamino)phenyl]sulfonyl]-L-valine t-butyl ester

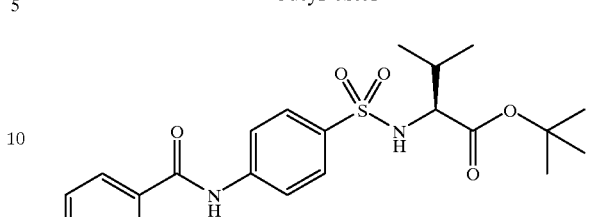

TLC: Rf 0.39 (Hexane:Ethyl acetate=1:1), NMR (CDCl$_3$): δ 8.02 (1H, s), 7.9–7.75 (6H, m), 7.65–7.45 (3H, m), 5.14 (1H, d, J=9.9 Hz), 3.66 (1H, dd, J=4.4, 9.9 Hz), 2.05 (1H, m), 1.26 (9H, s), 1.00 (3H, d, J=7.0 Hz), 0.85 (3H, d, J=7.0 Hz).

Example 1(38)

N-[[4-(1-Naphthoylamino)phenyl]sulfonyl]glycine t-butyl ester

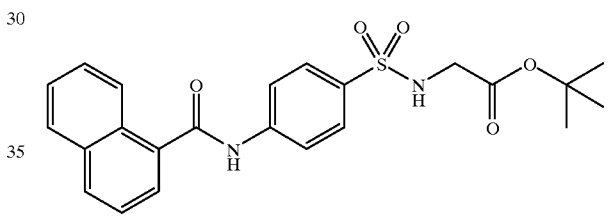

TLC: Rf 0.57 (Hexane:Ethyl acetate=1:1), NMR (CDCl$_3$): δ 8.34–8.24 (1H, m), 8.10 (1H, s), 7.98 (1H, d, J=8.0 Hz), 7.94–7.85 (1H, m), 7.85–7.76 (4H, m), 7.72 (1H, dd, J=1.2, 7.2 Hz), 7.64–7.51 (2H, m), 7.47 (1H, d, J=7.2 Hz), 5.03 (1H, t, J=5.4 Hz), 3.65 (2H, d, J=5.4 Hz), 1.38 (9H, s).

Example 1(39)

N-[[4-(2-Naphthoylamino)phenyl]sulfonyl]glycine t-butyl ester

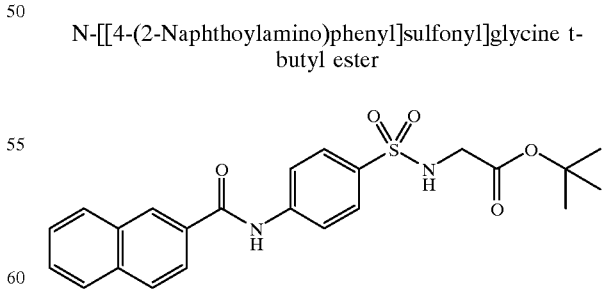

TLC: Rf 0.57 (Hexane:Ethyl acetate=1:1), NMR (CDCl$_3$): δ 8.40 (1H, d, J=0.8 Hz), 8.23 (1H, s), 8.02–7.80 (8H, m), 7.68–7.54 (2H, m), 5.03 (1H, t, J=5.2 Hz), 3.68 (2H, d, J=5.2 Hz), 1.38 (9H, s).

Example 1(40)

N-[[4-(3-Benzyloxybenzoylamino)phenyl]sulfonyl]glycine t-butyl ester

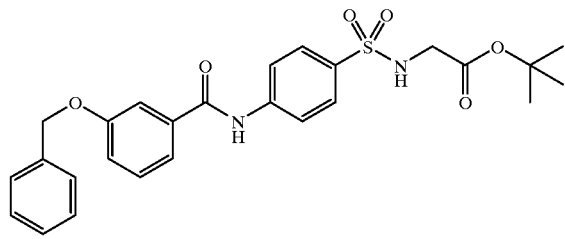

TLC: Rf 0.49 Hexane:Ethyl acetate=1:1), NMR (CDCl₃): δ 7.95 (1H, s), 7.87 (2H, d, J=9.0 Hz), 7.78 (2H, d, J=9.0 Hz), 7.54–7.32 (8H, m), 7.24–7.15 (1H, m), 5.14 (2H, s), 5.00 (1H, t, J=5.4 Hz), 3.67 (2H, d, J=5.4 Hz), 1.37 (9H, s).

Example 1(41)

N-[[4-(2-Benzyloxybenzoylamino)phenyl]sulfonyl]glycine t-butyl ester

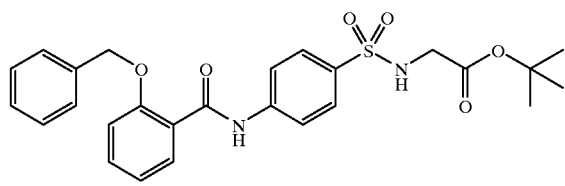

TLC: Rf 0.53 (Hexane:Ethyl acetate=1:1), NMR (CDCl₃): δ 10.25 (1H, s), 8.32 (1H, d, J=7.8 Hz), 7.66 (2H, d, J=8.8 Hz), 7.62–7.47 (5H, m), 7.32–7.22 (1H, m), 7.27 (2H, d, J=8.8 Hz), 7.17 (2H, m), 5.23 (2H, s), 4.94 (1H, t, J=5.4 Hz), 3.62 (2H, d, J=5.4 Hz), 1.34 (9H, s).

Example 1(42)

N-[[4-(Benzoylamino)phenyl]sulfonyl]-L-aspartic acid di-t-butyl ester

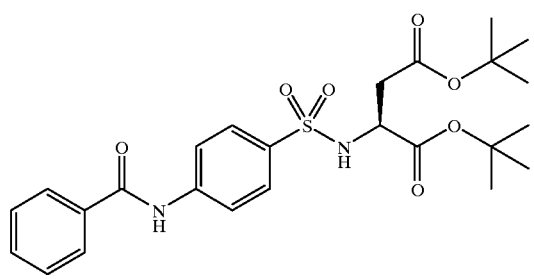

TLC: Rf 0.46 (Hexane:Ethyl acetate=1:1), NMR (CDCl₃): δ 8.02 (1H, s), 7.90–7.75 (6H, m), 7.65–7.45 (3H, m), 5.63 (1H, d, J=8.2 Hz), 4.00 (1H, m), 2.82 (1H, dd, J=4.6, 16.8 Hz), 2.72 (1H, dd, J=4.8, 16.8 Hz), 1.44 (9H, s), 1.33 (9H, s).

Example 1(43)

N-[[4-(Benzoylamino)phenyl]sulfonyl]-L-glutamic acid di-t-butyl ester

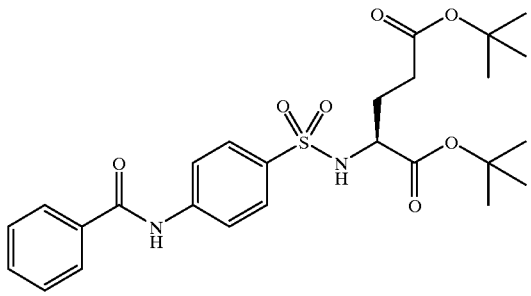

TLC: Rf 0.42 (Hexane:Ethyl acetate=1:1), NMR (CDCl₃): δ 8.08 (1H, s), 7.9–7.8 (6H, m), 7.65–7.25 (3H, m), 5.26 (1H, d, J=9.4 Hz), 3.83 (1H, m), 2.40 (2H, m), 2.15–1.65 (2H, m), 1.46 (9H, s), 1.28 (9H, s).

Example 1(44)

N-[[4-(Phenylacetylamino)phenyl]sulfonyl]glycine t-butyl ester

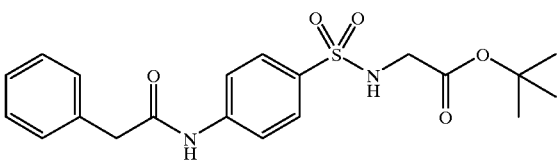

TLC: Rf 0.41 (Hexane:Ethyl acetate=1:1), NMR (CDCl₃): δ 7.75 (2H, d, J=8.8 Hz), 7.57 (2H, d, J=8.8 Hz), 7.48–7.29 (6H, m), 5.03 (1H, t, J=5.4 Hz), 3.76 (2H, s), 3.63 (2H, d, J=5.4 Hz), 1.35 (9H, s).

Example 1(45)

N-[[4-(Benzoylamino)phenyl]sulfonyl]-L-leucine t-butyl ester

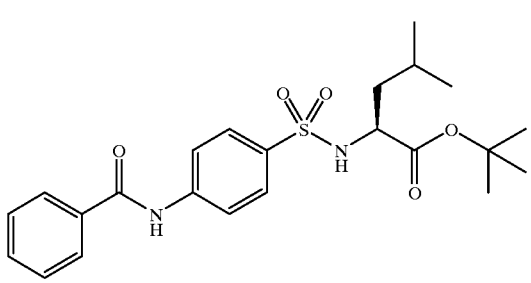

TLC: Rf 0.45 (Hexane:Ethyl acetate=1:1), NMR (DMSO-d₆): δ 10.29 (1H, s), 8.2–8.05 (1H), 7.96 (2H, dd, J=1.6,8.2 Hz), 7.72 (2H, d, J=8.8 Hz), 7.6–7.45 (5H, m), 3.86 (1H, m), 1.8–1.5 (3H, m), 1.46 (9H, s), 0.91 (3H, d, J=6.2 Hz), 0.90 (3H, d, J=6.2 Hz).

Example 1(46)

N-[[4-(Benzoylamino)phenyl]sulfonyl]-D-leucine t-butyl ester

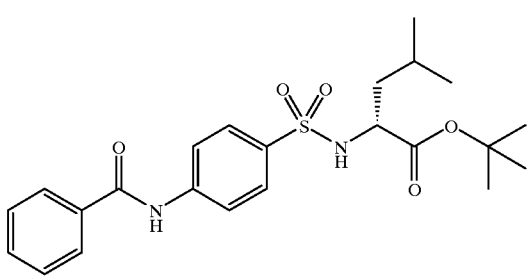

TLC: Rf 0.45 (Hexane:Ethyl acetate=1:1), NMR (DMSO-$d_6$): δ 10.29 (1H, s), 8.2–8.05 (1H), 7.96 (2H, dd, J=1.6, 8.0 Hz), 7.72 (2H, d, J=8.8 Hz), 7.6–7.45 (5H, m), 3.86 (1H, m), 1.8–1.5 (3H, m), 1.46 (9H, s), 0.91 (3H, d, J=6.2 Hz), 0.90 (3H, d, J=6.2 Hz).

Example 1(47)

N-[[4-(Phenoxycarbonylamino)phenyl]sulfonyl] glycine t-butyl ester

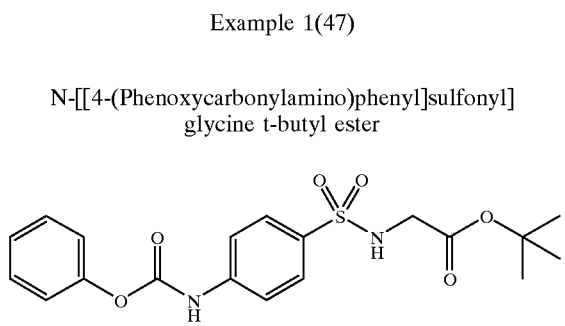

TLC: Rf 0.55 (Hexane:Ethyl acetate=1:1), NMR (CDCl$_3$): δ 7.84 (2H, d, J=8.8 Hz), 7.59 (2H, d, J=8.8 Hz), 7.48–7.36 (2H, m), 7.33–7.16 (4H, m), 5.01 (1H, t, J=5.4 Hz), 3.67 (2H, d, J=5.4 Hz), 1.37 (9H, s).

Example 1(48)

N-[[4-(4-Dimethylaminobenzoylamino)phenyl] sulfonyl]glycine t-butyl ester

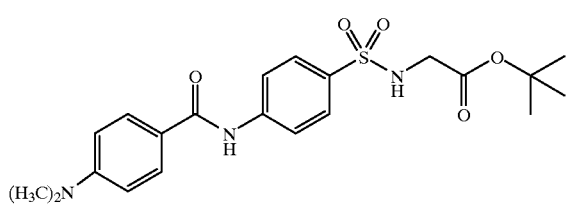

TLC: Rf 0.23 (Hexane:Ethyl acetate=1:1), NMR (DMSO-d6): δ 10.18 (1H, s), 8.0–7.85 (5H, m), 7.72 (2H, d, J=8.8 Hz), 6.77 (2H, d, J=9.0 Hz), 3.56 (2H, d, J=6.0 Hz), 3.01 (6H, s), 1.32 (9H, s).

Example 1(49)

N-[[4-(Benzoylamino)phenyl]sulfonyl]-D-valine t-butyl ester

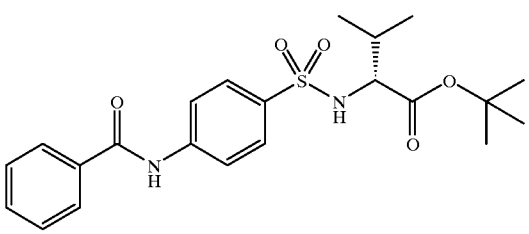

TLC: Rf 0.43 (Hexane:Ethyl acetate=1:1), NMR (CDCl$_3$): δ 7.99 (1H, s), 7.9–7.75 (6H, m), 7.6–7.45 (3H, m), 5.13 (1H, d, J=9.8 Hz), 3.65 (1H, dd, J=4.4, 9.8 Hz), 2.05 (1H, m), 1.26 (9H, s), 1.00 (3H, d, J=6.8 Hz), 0.85 (3H, d, J=6.8 Hz).

Example 1(50)

N-[[4-(Benzoylamino)phenyl]sulfonyl]-L-Phenylalanine t-butyl ester

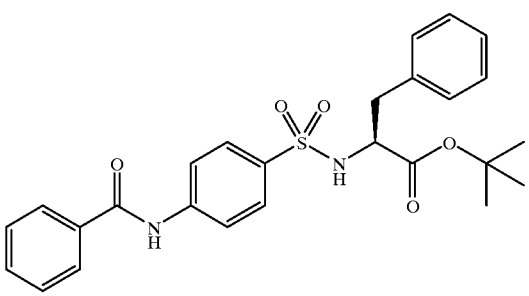

TLC: Rf 0.44 (Hexane:Ethyl acetate=1:1), NMR (CDCl$_3$): δ 8.02 (1H, s), 7.87 (2H, m), 7.76 (4H, s), 7.65–7.45 (3H, m), 7.3–7.1 (5H, m), 5.13 (1H, d, J=9.0 Hz), 4.10 (1H, dt, J=9.0, 6.0 Hz), 3.03 (2H, d, J=6.0 Hz), 1.23 (9H, s).

Example 1(51)

N-[[4-(Benzoylamino)phenyl]sulfonyl]-D-Phenylalanine t-butyl ester

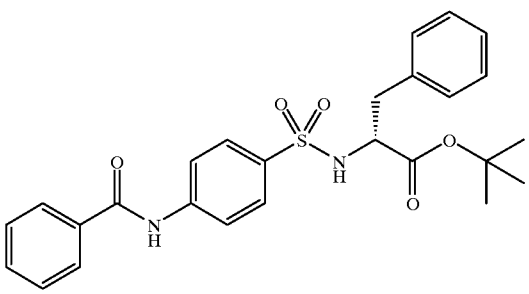

TLC: Rf 0.44 (Hexane:Ethyl acetate=1:1), NMR (CDCl$_3$): δ 7.98 (1H, s), 7.88 (2H, m), 7.76 (4H, s), 7.65–7.45 (3H, m), 7.3–7.1 (5H, m), 5.11 (1H, d, J=9.2 Hz), 4.10 (1H, dt, J=9.2, 6.0 Hz), 3.03 (2H, d, J=6.0 Hz), 1.23 (9H, s).

Example 1(52)

N-[[4-(Benzoylamino)phenyl]sulfonyl]-L-alanine di-t-butyl ester

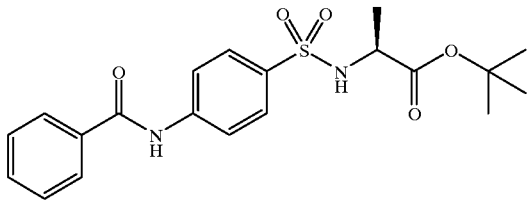

TLC: Rf 0.37 (Hexane:Ethyl acetate=1:1), NMR (CDCl$_3$): δ 8.15 (1H, br.s), 7.89 (2H, dd, J=1.6, 8.4 Hz), 7.81 (4H, s), 7.65–7.45 (3H, m), 5.30 (1H, br.d, J=8.2 Hz), 3.86 (1H, m), 1.36 (3H, d, J=7.2 Hz), 1.32 (9H, s).

Example 1(53)

N-[[4-(Benzoylamino)phenyl]sulfonyl]-D-alanine t-butyl ester

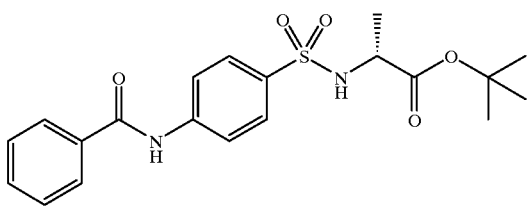

TLC: Rf 0.37 (Hexane:Ethyl acetate=1:1), NMR (CDCl$_3$): δ 8.10 (1H, br.s), 7.88 (2H, dd, J=1.6, 8.4 Hz), 7.81 (4H, s), 7.65–7.45 (3H, m), 5.28 (1H, d, J=8.2 Hz), 3.86 (1H, m), 1.36 (3H, d, J=7.0 Hz), 1.32 (9H, s).

Example 1(54)

N-[[4-(Benzoylamino)phenyl]sulfonyl]-t-butoxycarbonyl-L-lysine t-butyl ester

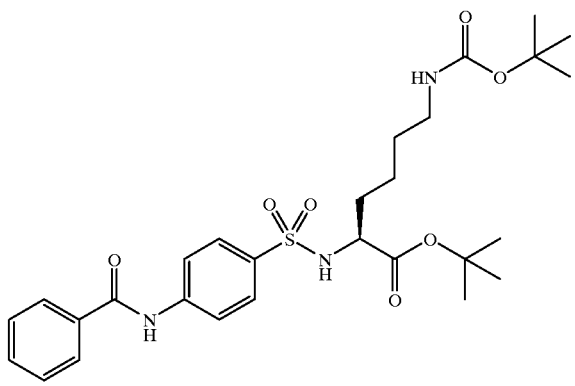

TLC: Rf 0.28 (Hexane:Ethyl acetate=1:1), NMR (CDCl$_3$): δ 8.13 (1H, br.s), 7.91 (2H, m), 7.83 (4H, s), 7.65–7.45 (3H, m), 5.23 (1H, d, J=9.0 Hz), 4.38 (1H, m), 3.79 (1H, m), 3.03 (2H, m), 1.9–1.3 (6H, m), 1.44 (9H, s), 1.30 (9H, s).

Example 1(55)

N-[[4-(Benzoylamino)phenyl]sulfonyl]-t-butoxycarbonyl-D-lysine t-butyl ester

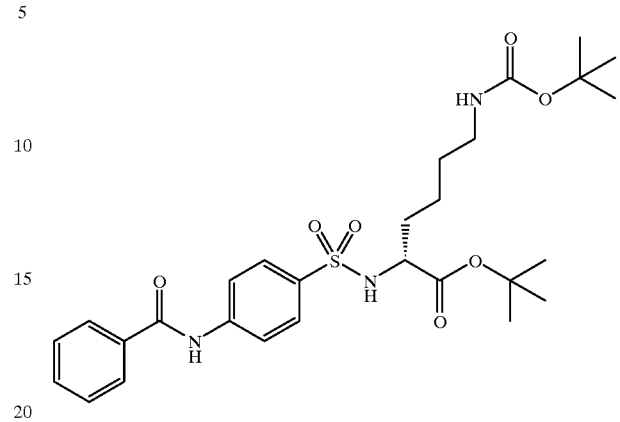

TLC: Rf 0.28 (Hexane:Ethyl acetate=1:1), NMR (CDCl$_3$): δ 8.19 (1H, br.s), 7.91 (2H, m), 7.85 (2H, d, J=8.8 Hz), 7.80 (2H, d, J=8.8 Hz), 7.65–7.45 (3H, m), 5.22 (1H, d, J=8.8 Hz), 4.57 (1H, m), 3.79 (1H, m), 3.03 (2H, m), 1.90–1.25 (6H, m), 1.44 (9H, s), 1.30 (9H, s).

Example 1(56)

N-[[4-(Benzoylamino)phenyl]sulfonyl]-D-glutamic acid di-t-butyl ester

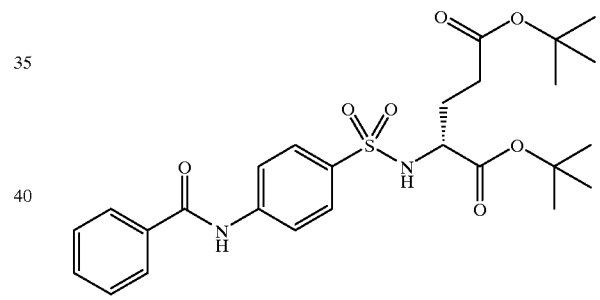

TLC: Rf 0.41 (Hexane:Ethyl acetate=1:1), NMR (CDCl$_3$): δ 8.11 (1H, s), 7.88 (2H, d, J=8.4 Hz), 7.81 (4H, s), 7.65–7.45 (3H, m), 5.26 (1H, d, J=9.0 Hz), 3.82 (1H, m), 2.4 (2H, m), 2.05 (1H, m), 1.79 (1H, m), 1.46 (9H, s), 1.28 (9H, s).

Example 1(57)

N-[[4-(4-Dodecylbenzoylamino)phenyl]sulfonyl] glycine t-butyl ester

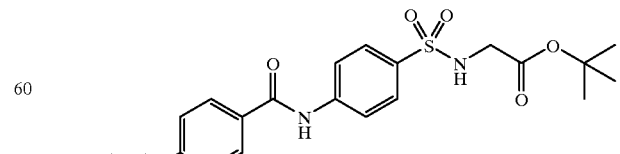

TLC: Rf 0.33 (Hexane:Ethyl acetate=7:3), NMR (CDCl$_3$): δ 7.98 (1H, s), 7.86 (2H, d, J=9.0 Hz), 7.80 (2H, d, J=9.0 Hz), 7.79 (2H, d, J=8.4 Hz), 7.31 (2H, d, J=8.4 Hz), 5.01 (1H, t, J=5.4 Hz), 3.67 (2H, d, J=5.4 Hz), 2.86 (2H, t, J=7.4 Hz), 1.74–1.50 (2H, m), 1.37 (9H, s), 1.36–1.10 (18H, m), 0.88 (3H, t, J=6.8 Hz).

Example 1(58)

4-[N-[[4-(Benzoylamino)phenyl]sulfonyl]amino]butyric acid t-butyl ester

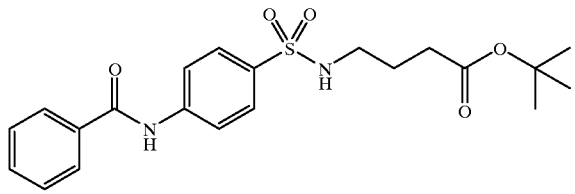

TLC: Rf 0.31 (Hexane:Ethyl acetate=1:1), NMR (CDCl$_3$): δ 8.09 (1H, s), 7.9–7.75 (6H, m), 7.65–7.45 (3H, m), 4.80 (1H, t, J=6.4 Hz), 3.00 (2H, q, J=6.4 Hz), 2.27 (2H, t, J=6.8 Hz), 1.76 (2H, m), 1.43 (9H, s).

Example 1(59)

2-[N-[[4-(Benzoylamino)phenyl]sulfonyl]amino]-3-t-butoxy-L-propionic acid t-butyl ester

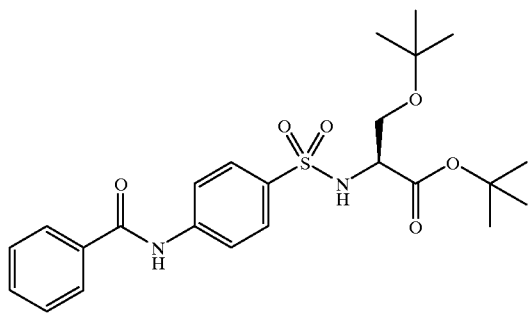

TLC: Rf 0.44 (Hexane:Ethyl acetate=1:1), NMR (CDCl$_3$): δ 8.09 (1H, br.s), 7.9–7.75 (6H, m), 7.65–7.45 (3H, m), 5.45 (1H, d, J=9.4 Hz), 4.0–3.95 (1H, m), 3.69 (1H, dd, J=3, 8.5 Hz), 3.52 (1H, dd, J=3.2, 8.5 Hz), 1.32 (9H, s), 1.11 (9H, s).

Example 1(60)

2-[N-[[4-(Benzoylamino)phenyl]sulfonyl]amino]-3-t-butoxy-D-propionic acid t-butyl ester

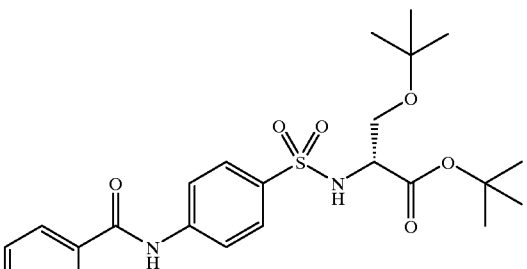

TLC: Rf 0.44 (Hexane:Ethyl acetate=1:1), NMR (CDCl$_3$): δ 8.04 (1H, br.s), 7.9–7.75 (6H, m), 7.65–7.45 (3H, m), 5.44 (1H, d, J=9.2 Hz), 4.0–3.95 (1H, m), 3.69 (1H, dd, J=3.0, 8.6 Hz), 3.52 (1H, dd, J=3.2, 8.6 Hz), 1.32 (9H, s), 1.11 (9H, s).

Example 1(61)

N-[[4-(Benzoylamino)phenyl]sulfonyl]-D-aspartic acid di-t-butyl ester

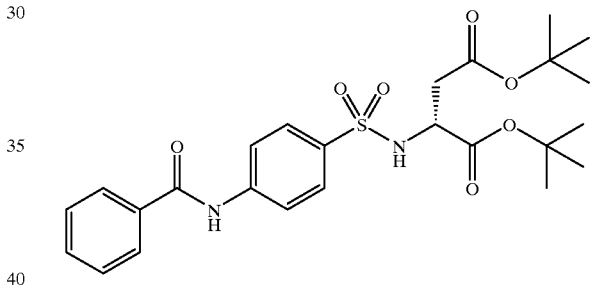

TLC: Rf 0.40 (Hexane:Ethyl acetate=1:1), NMR (CDCl$_3$): δ 8.17 (1H, s), 7.9–7.75 (6H, m), 7.6–7.45 (3H, m), 5.64 (1H, d, J=8.0 Hz), 3.99 (1H, m), 2.81 (1H, dd, J=4.6, 16.8 Hz), 2.72 (1H, dd, J=4.6, 16.8 Hz), 1.43 (9H, s), 1.33 (9H, s).

Example 1(62)

N-[[4-(p-Toluoylamino)phenyl]sulfonyl]-D-phenylalanine t-butyl ester

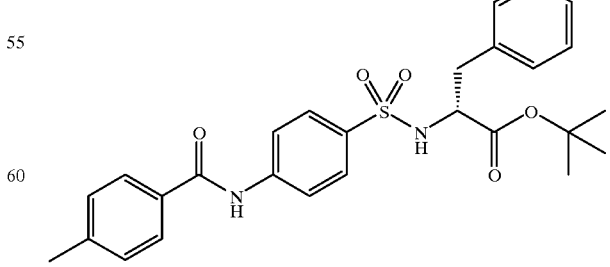

TLC: Rf 0.43 (Hexane:Ethyl acetate=1:1), NMR (CD$_3$OD+CDCl$_3$ (1:1)): δ 7.9–7.8 (4H, m), 7.71 (2H, d, J=8.8 Hz), 7.35–7.1 (7H, m), 4.04 (1H, t, J=6.6 Hz), 2.98 (2H, d, J=6.6 Hz), 2.44 (3H, s), 1.23 (9H, s).

Example 1(63)

N-[[4-(4-Pentylbenzoylamino)phenyl]sulfonyl]-D-phenylalanine t-butyl ester

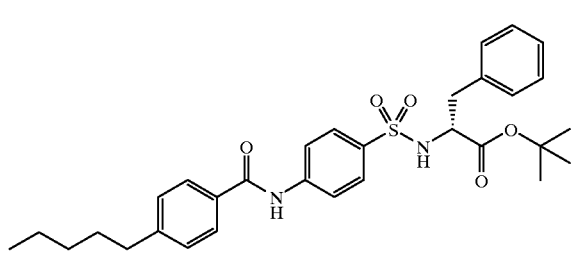

TLC: Rf 0.66 (Hexane:Ethyl acetate=3:2), NMR (CDCl$_3$): δ 7.95 (1H, s), 7.84–7.68 (6H, m), 7.35–7.08 (7H, m), 5.10 (1H, d, J=10.0 Hz), 4.14–4.00 (1H, m), 3.02 (2H, d, J=6.0 Hz), 2.67 (2H, t, J=7.8 Hz), 1.72–1.56 (2H, m), 1.48–1.25 (4H, m), 1.21 (9H, s), 0.89 (3H, t, J=5.0 Hz).

Example 1(64)

N-[[4-(p-Toluoylamino)phenyl]sulfonyl]-L-valine t-butyl ester

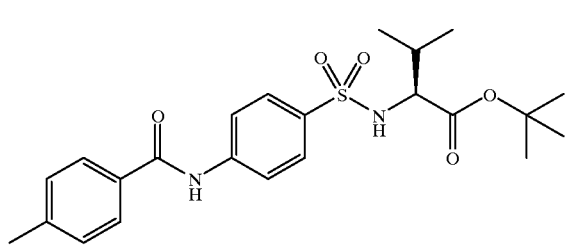

TLC: Rf 0.54 (Hexane:Ethyl acetate=3:2), NMR (CDCl$_3$): δ 7.93 (1H, s), 7.83 (2H, d, J=9.0 Hz), 7.77 (2H, d, J=9.0 Hz), 7.76 (2H, d, J=8.0 Hz), 7.30 (2H, d, J=8.0 Hz), 5.08 (1H, d, J=10.8 Hz), 3.62 (1H, dd, J=4.4, 10.8 Hz), 2.44 (3H, s), 2.15–1.90 (1H, m), 1.25 (9H, s), 1.00 (3H, d, J=6.6 Hz), 0.85 (3H, d, J=6.6 Hz).

Example 1(65)

N-[[4-(4-Hexylbenzoylamino)phenyl]sulfonyl] glycine t-butyl ester

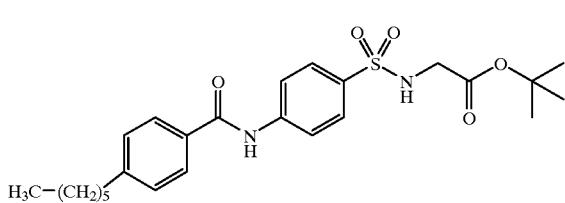

TLC: Rf 0.26 (Hexane:Ethyl acetate=7:3), NMR (CDCl$_3$): δ 8.04 (1H, s), 7.85 (2H, d, J=9.0 Hz), 7.79 (4H, m), 7.30 (2H, d, J=8.0 Hz), 5.04 (1H, t, J=5.2 Hz), 3.67 (2H, d, J=5.2 Hz), 2.68 (2H, t, J=8.0 Hz), 1.76–1.50 (2H, m), 1.37 (9H, s), 1.35–1.20 (6H, m), 0.88 (3H, t, J=6.8 Hz).

Example 1(66)

N-[[4-(4-Heptylbenzoylamino)phenyl]sulfonyl] glycine t-butyl ester

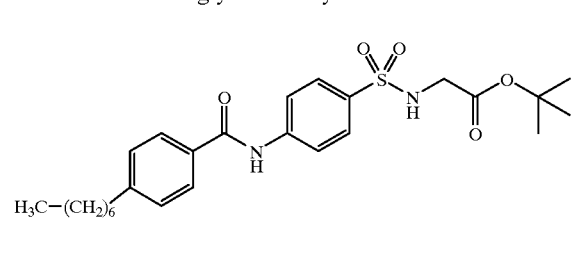

TLC: Rf 0.29 (Hexane:Ethyl acetate=7:3), NMR (CDCl$_3$): δ 8.03 (1H, s), 7.85 (2H, d, J=9.0 Hz), 7.79 (4H, m), 7.31 (2H, d, J=8.2 Hz), 5.03 (1H, t, J=5.6 Hz), 3.67 (2H, d, J=5.6 Hz), 2.68 (2H, t, J=8.2 Hz), 1.72–1.50 (2H, m), 1.37 (9H, s), 1.35–1.10 (8H, m), 0.88 (3H, t, J=6.8 Hz).

Example 1(67)

N-[[4-(4-Isopropylbenzoylamino)phenyl]sulfonyl] glycine t-butyl ester

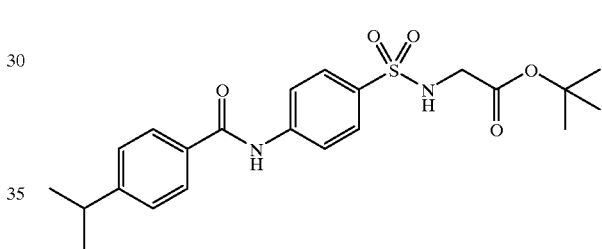

TLC: Rf 0.19 (Hexane:Ethyl acetate=7:3), NMR (CDCl$_3$): δ 8.01 (1H, s), 7.86 (2H, d, J=9.0 Hz), 7.82–7.72 (4H, m), 7.36 (2H, d, J=8.4 Hz), 5.01 (1H, t, J=5.4 Hz), 3.67 (2H, d, J=5.4 Hz), 2.99 (1H, m), 1.37 (9H, s), 1.29 (6H, d, J=6.8 Hz).

Example 1(68)

N-[[4-(4-Isobutylbenzoylamino)phenyl]sulfonyl] glycine t-butyl ester

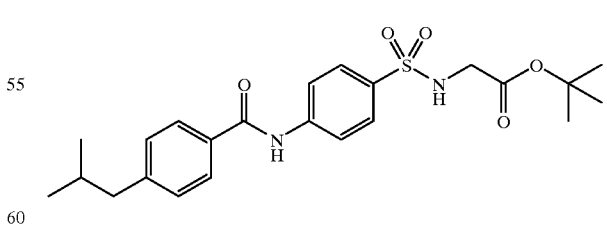

TLC: Rf 0.23 (Hexane:Ethyl acetate=7:3), NMR (CDCl$_3$): δ 8.04 (1H, s), 7.86 (2H, d, J=9.0 Hz), 7.82–7.72 (4H, m), 7.27 (2H, d, J=8.2 Hz), 5.03 (1H, t, J=5.4 Hz), 3.67 (2H, d, J=5.4 Hz), 2.56 (2H, d, J=7.0 Hz), 1.91 (1H, m), 1.37 (9H, s), 0.92 (6H, d, J=6.6 Hz).

Example 1(69)

N-[[4-(Benzoylamino)phenyl]sulfonyl]-2,2-dimethylglycine t-butyl ester

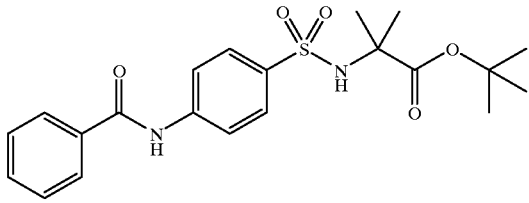

TLC: Rf 0.40 (Hexane:Ethyl acetate=1:1), NMR (CDCl$_3$): δ 8.03 (1H, s), 7.9–7.75 (6H, m), 7.65–7.45 (3H, m), 5.42 (1H, s), 1.45 (9H, s), 1.41 (6H, s).

Example 1(70)

2-[N-[[4-(p-Toluoylamino)phenyl]sulfonyl]amino]-3-t-butoxy-D-propionic acid t-butyl ester

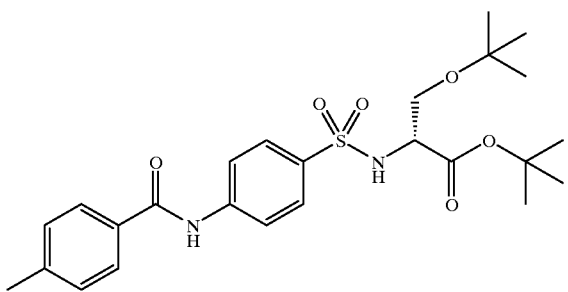

TLC: Rf 0.69 (Hexane:Ethyl acetate=1:1), NMR (CDCl$_3$): δ 7.99 (1H, s), 7.85 (2H, d, J=8.0 Hz), 7.78 (4H, d, J=8.0 Hz), 7.30 (2H, d, J=8.0 Hz), 5.43 (1H, d, J=9.2 Hz), 3.97 (1H, td, J=3.0 Hz, 9.2 Hz), 3.69 (1H, dd, J=3.0 Hz, 8.6 Hz), 3.51 (1H, dd, J=3.0 Hz, 8.6 Hz), 2.43 (3H, s), 1.31 (9H, s), 1.10 (9H, s).

Example 1(71)

N-[[4-(p-Toluoylamino)phenyl]sulfonyl]-L-leucine t-butyl ester

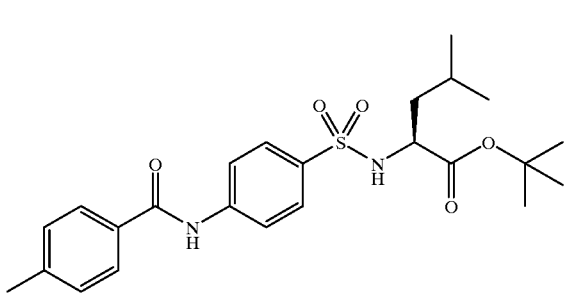

TLC: Rf 0.50 (Hexane:Ethyl acetate=1:11), NMR (CDCl$_3$): δ 7.90 (1H, s), 7.85–7.70 (6H, m), 7.32 (2H, d, J=8.0 Hz), 5.02 (1H, d, J=10 Hz), 3.90–3.75 (1H, m), 2.45 (3H, s), 1.9–1.75 (1H, m), 1.46 (2H, m), 1.26 (9H, s), 0.93 (6H, d, J=6.6 Hz).

Example 1(72)

N-[[4-(p-Toluoylamino)phenyl]sulfonyl]-D-alanine t-butyl ester

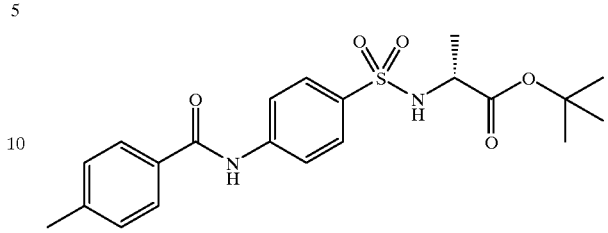

TLC: Rf 0.57 (Hexane:Ethyl acetate=1:1), NMR (DMSO-d6): δ 10.47 (1H, s), 8.08 (1H, d, J=8.6 Hz), 7.96 (2H, d, J=8.8 Hz), 7.88 (2H, d, J=8.8 Hz), 7.74 (2H, d, J=8.8 Hz), 7.35 (2H, d, J=8.2 Hz), 3.80–3.64 (1H, m), 2.39 (3H, s), 1.28 (9H, s), 1.15 (3H, d, J=7.0 Hz).

Example 1(73)

N-[[4-(p-Toluoylamino)phenyl]sulfonyl]-D-valine t-butyl ester

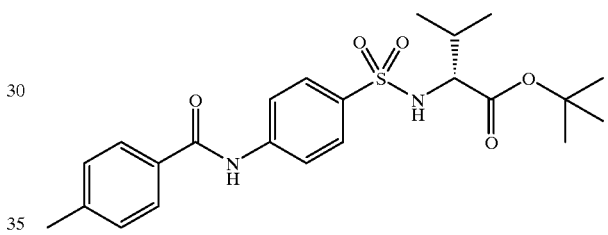

TLC: Rf 0.65 (Hexane:Ethyl acetate=1:1), NMR (DMSO-d6): δ 10.45 (1H, s), 8.02–7.92 (3H, m), 7.88 (2H, d, J=8.0 Hz), 7.72 (2H, d, J=8.8 Hz), 7.35 (2H, d, J=8.0 Hz), 3.48–3.38 (1H, m), 2.39 (3H, s), 2,02–1.80 (1H, m), 1.22 (9H, s), 0.83 (6H, t, J=5.6 Hz).

Example 1(74)

N-[[4-(p-Toluoylamino)phenyl]sulfonyl]-D-leucine t-butyl ester

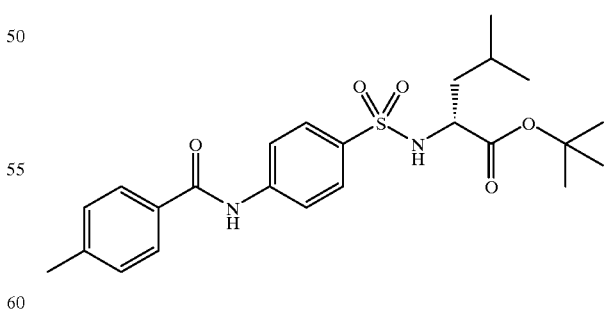

TLC: Rf 0.68 (Hexane:Ethyl acetate=1:1), NMR (DMSO-d6): δ 10.45 (1H, s), 8.07 (1H, d, J=9.0H), 7.95 (2H, d, J=8.8 Hz), 7.88 (2H, d, J=8.2 Hz), 7.71 (2H, d, J=8.8 Hz), 7.35 (2H, d, J=8.2 Hz), 3.70–3.54 (1H, m), 2.39 (3H, s), 1.72–1.50 (1H, m), 1.44–1.30 (2H, m), 1.23 (9H, s), 0.84 (3H, d, J=6.6 Hz), 0.76 (3H, d, J=6.6 Hz).

Example 1(75)

N-[[2-Methyl-4-(p-Toluoylamino)phenyl]sulfonyl] glycine t-butyl ester

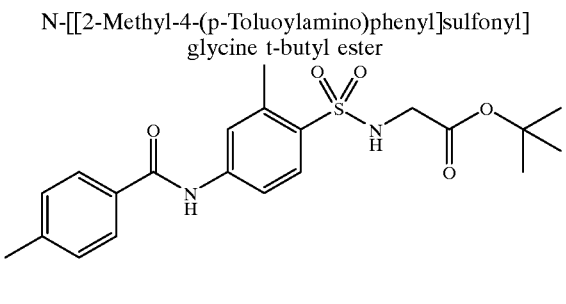

TLC: Rf 0.29 (Hexane:Ethyl acetate=1:1), NMR (CDCl$_3$): δ 7.95 (2H, d, J=8.3 Hz), 7.77 (2H, d, J=6.4 Hz), 7.75–7.57 (2H, m), 7.31 (2H, d, J=8.3 Hz), 5.10 (1H, m), 3.63 (2H, d, J=2.2 Hz), 2.68 (3H, s), 2.44 (3H, s), 1.37 (9H, s).

Example 1(76)

N-[[3-Methyl-4-(p-Toluoylamino)phenyl]sulfonyl] glycine t-butyl ester

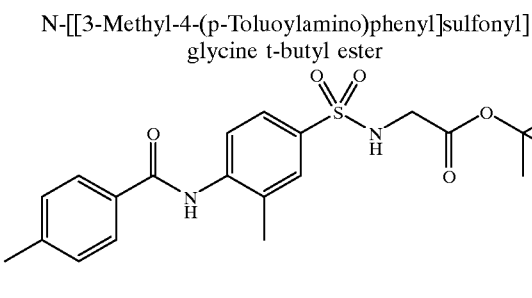

TLC: Rf 0.48 (Chloroform:Methanol=97:3) NMR (CDCl$_3$): δ 8.38 (1H, d, J=8.4 Hz), 7.82–7.73 (4H, m), 7.33 (2H, d, J=7.8 Hz), 5.00 (1H, t, J=4.7 Hz), 3.67 (2H, d, J=4.7 Hz), 2.45 (3H, s), 2.40 (3H, s), 1.38 (9H, s).

Example 1(77)

N-[[4-(2-Hydroxy-4-methylbenzoylamino)phenyl] sulfonyl]-D-alanine t-butyl ester

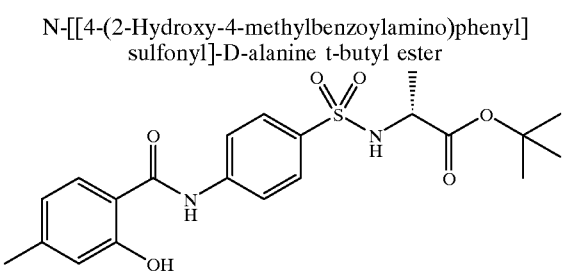

TLC: Rf 0.29 (Chloroform:Methanol=97:3) NMR (CDCl$_3$): δ 11.64 (1H, s), 8.09 (1H, br.s), 7.85 (2H, d, J=8.3 Hz), 7.74 (2H, d, J=8.3 Hz), 7.43 (1H, d, J=7.5 Hz), 6.86 (1H, s), 6.75 (1H, d, J=7.5 Hz), 5.25 (1H, t, J=7.6 Hz), 3.87 (2H, quint, J=7.6 Hz), 2.37 (3H, s), 1.37 (3H, d, J=7.6 Hz), 1.32 (9H, s).

Example 1(78)

N-[[4-(Benzoylamino)phenyl]sulfonyl]-L-tryptophan benzyl ester

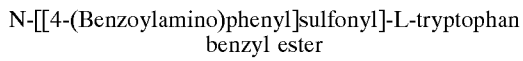

TLC: Rf 0.43 (Hexane:Ethyl acetate=1:1), NMR (CDCl$_3$): δ 9.19 (1H, s), 7.94 (2H, dd, J=1.4, 7.8 Hz), 7.68–7.40 (7H, m), 7.36–7.24 (5H, m), 7.18–6.98 (5H, m), 6.84 (1H, s), 4.91 (2H, s), 4.25 (1H, dd, J=5.2, 6.8 Hz), 3.30–3.06 (2H, m).

Example 1(79)

N-[[4-(Benzoylamino)phenyl]sulfonyl]-L-tyrosine benzyl ester

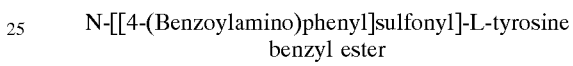

TLC: Rf 0.34 (Hexane:Ethyl acetate=1:1), NMR (CDCl$_3$+CD$_3$OD(10 drops)): δ 8.58 (1H, s), 7.80–7.78 (2H, m), 7.71 (2H, d, J=8.8 Hz), 7.65–7.29 (8H, m), 7.25–7.17 (2H, m), 6.81 (2H, d, J=8.6 Hz), 6.62 (2H, d, J=8.6 Hz), 4.97 (2H, s), 4.10 (1H, dd, J=5.8, 7.8 Hz), 2.99 (1H, dd, J=5.8, 14.0 Hz), 2.81 (1H, dd, J=7.8, 14.0 Hz).

Example 1(80)

N-[[4-(Benzoylamino)phenyl]sulfonyl]-D-tryptophan benzyl ester

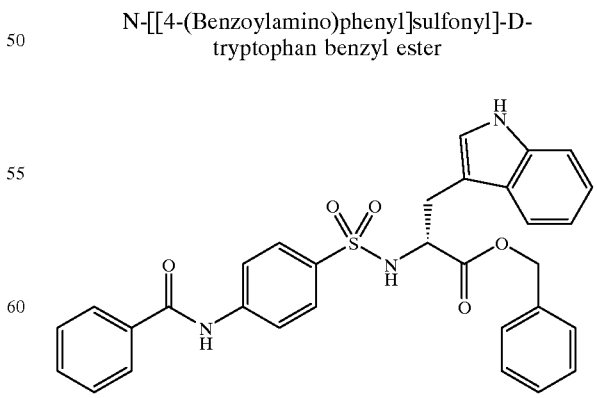

TLC: Rf 0.34 (Hexane:Ethyl acetate=1:1), NMR (CDC$_3$+CD$_3$OD): δ 7.98–7.90 (2H, m), 7.63 (2H, d, J=8.8 Hz), 7.60–7.39 (6H, m), 7.35–7.25 (5H, m), 7.17–6.97 (3H, m), 6.85 (1H, s), 4.91 (2H, s), 4.25 (1H, t, J=6.4 Hz), 3.30–3.06 (2H, m).

Example 1(81)

N-[[4-(Benzoylamino)phenyl]sulfonyl]-D-tyrosine benzyl ester

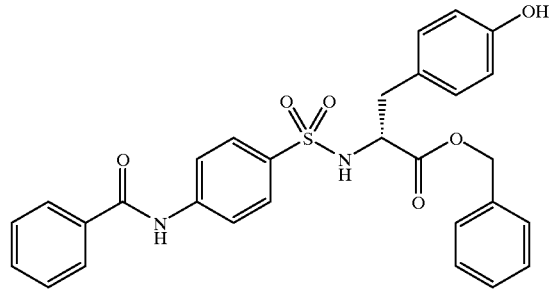

TLC: Rf 0.31 (Hexane:Ethyl acetate=1:1), NMR (CDCl$_3$): δ 8.64–8.57 (1H, m), 8.15 (1H, s), 7.91 (2H, d, J=8.0 Hz), 7.80–7.42 (6H, m), 7.40–7.20 (6H, m), 6.76 (2H, d, J=8.4 Hz), 6.58 (2H, d, J=8.4 Hz), 5.17 (1H, d, J=9.2 Hz), 5.04 (2H, s), 4.18–4.04 (1H, m), 3.01 (1H, dd, J=5.0, 14.2 Hz), 2.75 (1H, dd, J=7.8, 14.2 Hz).

Example 1(82)

N-[[4-(Benzoylamino)phenyl]sulfonyl]-D-histidine benzyl ester

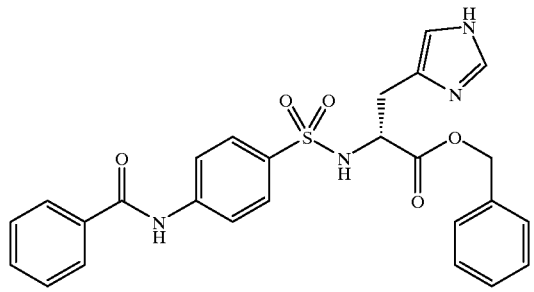

TLC: Rf 0.31 (Chloroform:Methanol=9:1), NMR (CDCl$_3$+CD$_3$OD): δ 8.17 (1H, s), 7.96–7.80 (6H, m), 7.68–7.42 (3H, m), 7.40–7.22 (5H, m), 7.04 (1H, s), 5.10 (2H, s), 3.80 (1H, dd, J=4.6 Hz, 7.6 Hz), 2.98 (1H, dd, J=4.6, 14.6 Hz), 2.81 (1H, dd, J=7.6, 14.6 Hz).

Example 1(83)

2-[N-[4-(Benzoylamino)phenyl]sulfonylamino]-(3-pyridyl)-D-alanine benzyl ester

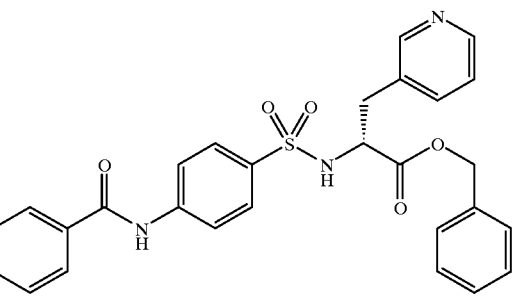

TLC: Rf 0.32 (Hexane:Ethyl acetate=1:5), NMR (CDCl$_3$): δ 8.41 (1H, dd, J=2.0 Hz, 5.0 Hz), 8.25 (1H, d, J=2.0 Hz), 8.08 (1H, s), 7.81 (2H, m), 7.74 (4H, s), 7.65–7.45 (3H, m), 7.35–7.3 (4H, m), 7.25–7.15 (2H, m), 7.09 (1H, dd, J=5, 8.0 Hz), 5.58 (1H, d, J=8.0 Hz), 4.97 (1H, s), 4.27 (1H, dt, J=6.0 Hz, 8.0 Hz), 3.05 (2H, d, J=6.0 Hz).

Example 1(84)

N-[[4-(p-Toluoylamino)phenyl]sulfonyl]-D-tryptophan benzyl ester

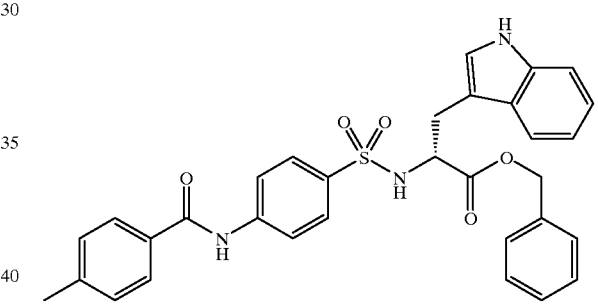

TLC: Rf 0.32 (Hexane:Ethyl acetate=1:1), NMR (CDCl$_3$+CD$_3$OD): δ 7.81 (2H, d, J=8.0 Hz), 7.56 (4H, s), 7.43 (1H, d, J=7.0 Hz), 7.35–7.25 (6H, m), 7.15–7.00 (4H, m), 6.81 (1H, s), 4.92 (2H, s), 4.25 (1H, m), 3.18 (2H, m), 2.45 (3H, s).

Example 1(85)

N-[[4-(Benzoylamino)phenyl]sulfonyl]glycine ethyl ester

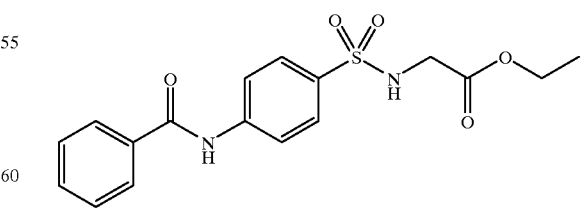

TLC: Rf 0.26 (Hexane:Ethyl acetate=1:1), NMR (DMSO-d6): δ 10.59 (1H, s), 8.09 (1H, t, J=6.2 Hz), 8.0–7.95 (4H, m), 7.77 (2H, d, J=8.8 Hz), 7.65–7.5 (3H, m), 4.00 (2H, q, J=7.0 Hz), 3.68 (2H, d, J=6.2 Hz), 1.12 (3H, t, J=7.0 Hz).

Example 1(86)

N-[[4-(p-Toluylamino)phenyl]sulfonyl]-D-alanine pivaloyloxymethyl ester

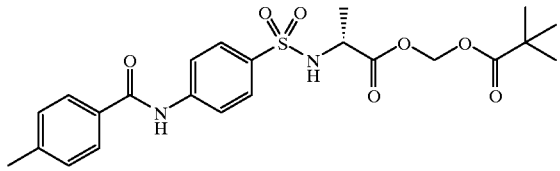

TLC: Rf 0.38 (Hexane:Ethyl acetate=1:1), NMR (CDCl$_3$): δ 8.05 (1H, br.s), 7.82 (4H, s), 7.78 (2H, d, J=8.0 Hz), 7.31 (2H, d, J=8.0 Hz), 5.67 (1H, d, J=14.6 Hz), 5.59 (1H, d, J=14.6 Hz), 5.15 (1H, br.d, J=8.8 Hz), 4.03 (1H, m), 2.44 (3H, s), 1.39 (3H, d, J=7.0 Hz), 1.17 (9H, s).

Example 1(87)

N-[[4-(p-Toluylamino)phenyl]sulfonyl]-D-alanine dimethyl aminocarbonyl ester

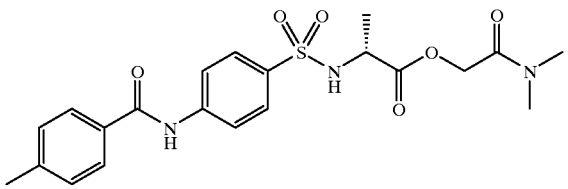

TLC: Rf 0.42 (Chloroform:Methanol:Acetic acid:Water= 100:10:1:1), NMR (CDCl$_3$+CD$_3$OD (3 drops)): δ 7.82 (6H, m), 7.31 (2H, d, J=8.2 Hz), 4.56 (1H, d, J=14.6 Hz), 4.37 (1H, d, J=14.6 Hz), 4.10 (1H, q, J=7.4 Hz), 2.94 (3H, s), 2.90 (3H, s), 2.44 (3H, s), 1.46 (3H, d, J=7.4 Hz).

Example 1(88)

N-([4-(p-Toluylamino)phenyl]sulfonyl]-D-alanine benzyl ester

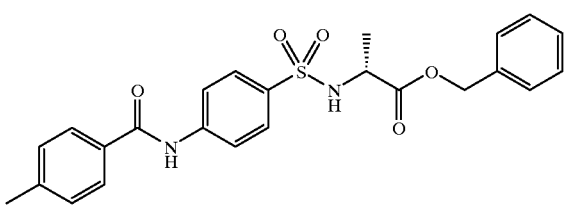

TLC: Rf 0.56 (Chloroform:Methanol:Acetic acid:Water= 100:10:1:1), NMR (DMSO-d6): δ 10.49 (1H, s), 7.96 (3H, m), 7.89 (2H, d, J=8.0 Hz), 7.74 (2H, d, J=8.8 Hz), 7.4–7.25 (7H, m), 4.96 (2H, s), 3.94 (1H, m), 2.40 (3H, s), 1.19 (3H, d, J=7.2 Hz).

Example 1(89)

N-[[4-(2-Thienylcarbonylamino)phenyl]sulfonyl]-D-alanine t-butyl ester

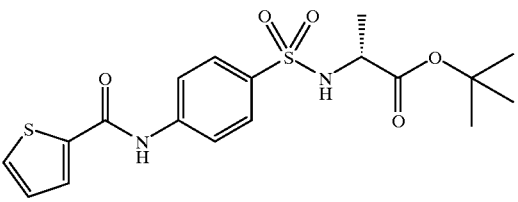

TLC: Rf 0.25 (Hexane:Ethyl acetate=2:1), NMR (DMSO-d$_6$): δ 10.51 (1H, s), 8.12–8.05 (2H, m), 7.94–7.88 (3H, m), 7.74 (2H, d, J=8.8 Hz), 7.24 (1H, t, J=3.8 Hz), 3.72 (1H, quint, J=7.4 Hz), 1.27 (9H, s), 1.14 (3H, d, J=7.4 Hz).

Example 1(90)

N-[[3-(Benzoylamino)phenyl]sulfonyl]glycine t-butyl ester

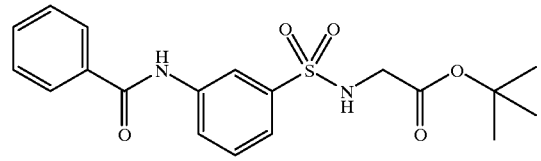

TLC: Rf 0.65 (Hexane:Ethyl acetate=1:1), NMR (CDCl$_3$): δ 8.26–8.16 (2H, m), 8.00 (1H, t, J=1.8 Hz), 7.94–7.87 (2H, m), 7.66–7.46 (5H, m), 5.24 (1H, t, J=5.4 Hz), 3.70 (2H, d, J=5.4 Hz), 1.35 (9H, s).

Example 1(91)

N-[[2-(Benzoylamino)phenyl]sulfonyl]glycine t-butyl ester

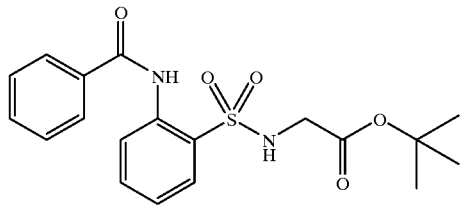

TLC: Rf 0.51 (Hexane:Ethyl acetate=3:2), NMR (CDCl$_3$): δ 10.27 (1H, s), 8.73 (1H, d, J=8.4 Hz), 8.05–7.94 (2H, m), 7.90 (1H, dd, J=1.8 Hz, 8.0 Hz), 7.70–7.45 (4H, m), 7.30–7.18 (1H, m), 5.20 (1H, t, J=5.2 Hz), 3.61 (2H, d, J=5.2 Hz), 1.33 (9H, s).

Example 2

N-[[4-(p-Toluoylamino)phenyl]sulfonyl]glycine

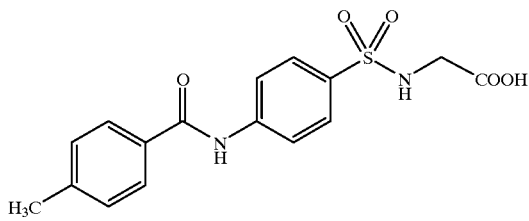

A mixture of the compound prepared in example 1 (1.45 g) in trifluoroacetic acid (10 ml) and water (1 ml) was stirred for 1 hour at room temperature. The reaction mixture was concentrated. The residue was washed with ether and dried to give the title compound (1.16 g) having the following physical data.

TLC: Rf 0.48 (Chloroform:Methanol:acetic acid=16:3:1), NMR (DMSO-d6): δ 10.46 (1H, s), 8.02–7.84 (1H), 7.97 (2H, d, J=9.0 Hz), 7.88 (2H, d, J=8.0 Hz), 7.75 (2H, d, J=9.0 Hz), 7.34 (2H, d, J=8.0 Hz), 3.55 (2H, d, J=6.2 Hz), 2.40 (3H, s).

Example 2(1)–2(80)

The compounds having the following physical data were obtained by the same procedure as a series of reaction of Example 2, or converting to a corresponding salt by conventional method, using the compound prepared in example 1(1)–1(77) and 1(89)–1(91) instead of the compound prepared in example 1.

Example 2(1)

N-[[4-(Isobutyrylamino)phenyl]sulfonyl]glycine

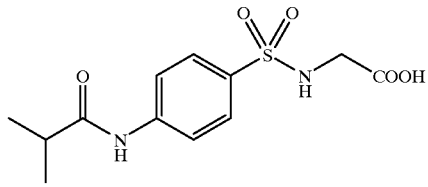

TLC: Rf 0.34 (Chloroform:Methanol:Acetic acid=16:3:1), NMR (CD$_3$OD): δ 7.80 (2H, d, J=9.5 Hz), 7.76 (2H, d, J=9.5 Hz), 3.67 (2H, s), 2.64 (1H, m), 1.19 (6H, d, J=6.8 Hz).

Example 2(2)

N-[[4-(Acetylamino)phenyl]sulfonyl]glycine

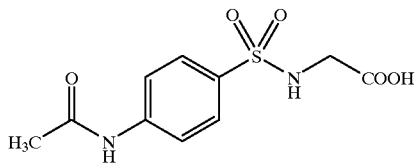

TLC: Rf 0.23 (Chloroform:Methanol:Acetic acid=16:3:1), NMR (DMSO-d6): δ 10.26 (1H, s), 7.84 (1H, t, J=6.0 Hz), 7.73 (2H, d, J=9.6 Hz), 7.68 (2H, d, J=9.6 Hz), 3.52 (2H, d, J=6.0 Hz), 2.07 (3H, s).

Example 2(3)

N-[[4-(o-Toluoylamino)phenyl]sulfonyl]glycine

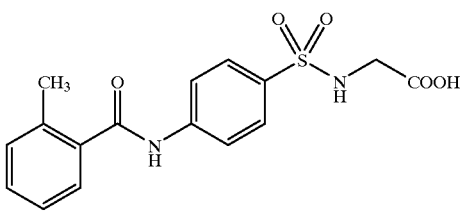

TLC: Rf 0.48 (Chloroform:Methanol:Acetic acid=16:3:1), NMR (DMSO-d$_6$): δ 10.63 (1H, s), 7.91(2H, d, J=9.0 Hz), 7.96–7.84 (1H), 7.74 (2H, d, J=9.0 Hz), 7.51–7.24 (4H, m), 3.54 (2H, d, J=5.8 Hz), 2.39 (3H, s).

Example 2(4)

N-[[4-(3-Methylbenzoylamino)phenyl]sulfonyl]glycine

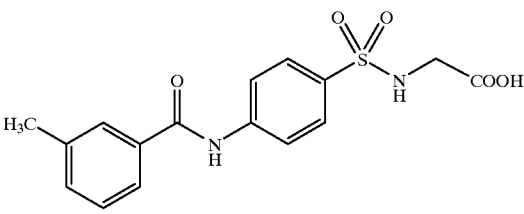

TLC: Rf 0.48 (Chloroform:Methanol:Acetic acid=16:3:1), NMR (DMSO-d6): δ 12.8–12.4 (1H, br.s), 10.49 (1H, s), 7.96(2H, d, J=8.8 Hz), 7.88 (1H, t, J=6.2 Hz), 7.75 (2H, d, J=8.8 Hz), 7.80–7.70 (2H, m), 7.50–7.36 (2H, m), 3.55 (2H, d, J=6.2 Hz), 2.41 (3H, s).

Example 2(5)

N-[[4-(2-Chlorobenzoylamino)phenyl]sulfonyl]glycine

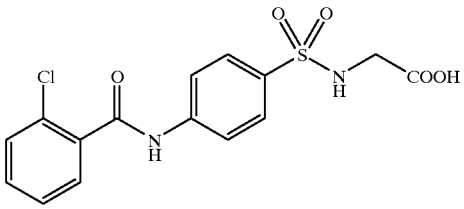

TLC: Rf 0.42 (Chloroform:Methanol:Acetic acid=16:3:1), NMR (CD$_3$OD): δ 7.88 (2H, d, J=9.4 Hz), 7.83 (2H, d, J=9.4 Hz), 7.60–7.38 (4H, m), 3.70 (2H, s).

Example 2(6)

N-[[4-(3-Chlorobenzoylamino)phenyl]sulfonyl]glycine

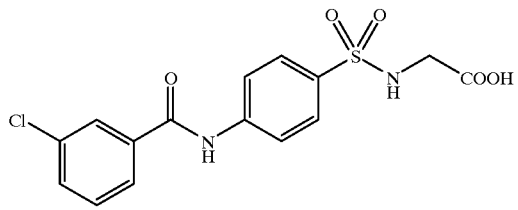

TLC: Rf 0.42 (Chloroform:Methanol:Acetic acid=16:3:1), NMR (CD$_3$OD): δ 7.99–7.94 (1H, m), 7.93 (2H, d, J=9.0 Hz), 7.93–7.80 (1H, m), 7.84 (2H, d, J=9.0 Hz), 7.64–7.46 (2H, m), 3.69 (2H, s).

Example 2(7)

N-[[4-(4-Chlorobenzoylamino)phenyl]sulfonyl]glycine

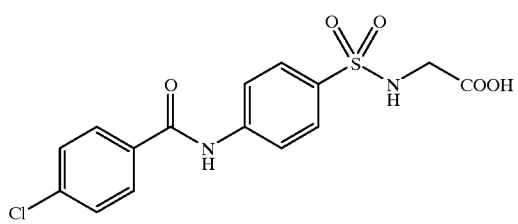

TLC: Rf 0.42 (Chloroform:Methanol:Acetic acid=16:3:1), NMR (CD$_3$OD): δ 7.94 (2H, d, J=8.6 Hz), 7.92 (2H, d, J=9.0 Hz), 7.84 (2H, d, J=9.0 Hz), 7.53 (2H, d, J=8.6 Hz), 3.70 (2H, s).

Example 2(8)

N-[[4-(2-Methoxybenzoylamino)phenyl]sulfonyl]glycine

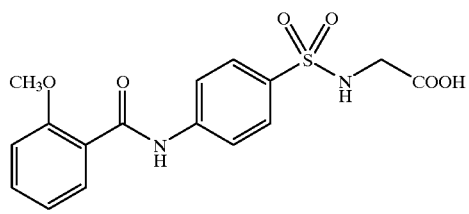

TLC: Rf 0.58 (Chloroform:Methanol:Acetic acid=16:3:1), NMR (DMSO-d6): δ 10.45 (1H, s), 7.91 (1H, t, J=6.2 Hz), 7.90 (2H, d, J=8.8 Hz), 7.75 (2H, d, J=8.8 Hz), 7.61 (1H, dd, J=7.4, 1.6 Hz), 7.52 (1H, ddd, J=8.4, 7.4, 2.0 Hz), 7.18 (1H, d, J=8.0 Hz), 7.07 (1H, td, J=7.6, 1.0 Hz), 3.89 (3H, s), 3.56 (2H, d, J=6.2 Hz).

Example 2(9)

N-[[4-(3-Methoxybenzoylamino)phenyl]sulfonyl]glycine

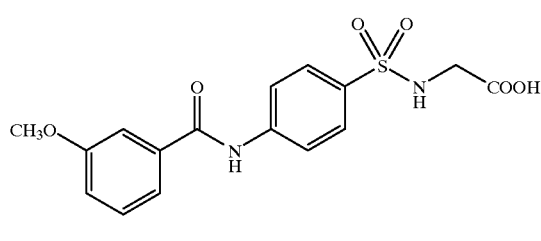

TLC: Rf 0.44 (Chloroform:Methanol:Acetic acid=16:3:1), NMR (DMSO-d6): δ 10.52 (1H, s), 7.96 (2H, d, J=8.8 Hz), 7.91 (1H, t, J=6.2 Hz), 7.76 (2H, d, J=8.8 Hz), 7.58–7.41 (3H, m), 7.21–7.14 (1H, m), 3.84 (3H, s), 3.56 (2H, d, J=6.2 Hz).

Example 2(10)

N-[[4-(Benzoylamino)phenyl]sulfonyl]glycine

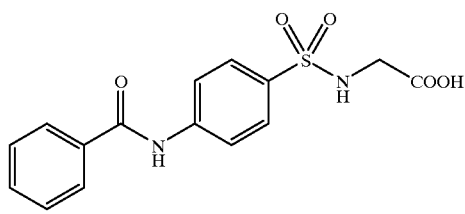

TLC: Rf 0.19 (Chloroform:Methanol:Acetic acid:Water=50:10:1:1), NMR (CD$_3$OD): δ 8.0–7.8 (6H, m), 7.6–7.5 (3H, m), 3.70 (2H, s).

Example 2(11)

N-[[4-(4-Fluorobenzoylamino)phenyl]sulfonyl]glycine

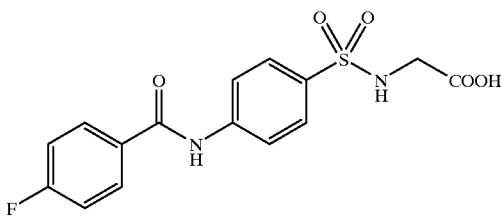

TLC: Rf 0.36 (Chloroform:Methanol:Acetic acid=16:3:1), NMR (DMSO-d6): δ 10.56 (1H, s), 8.05 (2H, dd, J=8.8, 5.4 Hz), 7.96 (2H, d, J=9.2 Hz), 7.91 (1H, t, J=6.2 Hz), 7.77 (2H, d, J=9.2 Hz), 3.56 (2H, d, J=6.2 Hz).

Example 2(12)

N-[[4-(4-Methoxybenzoylamino)phenyl]sulfonyl]
glycine

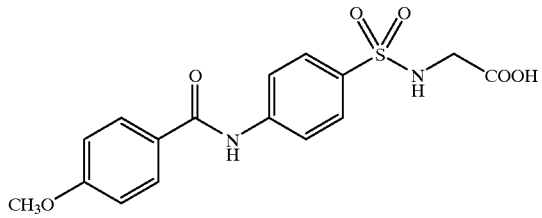

TLC: Rf 0.43 (Chloroform:Methanol:Acetic acid= 16:3:1), NMR (DMSO-d$_6$): δ 10.39 (1H, s), 7.97 (2H, d, J=8.8 Hz), 7.95 (2H, d, J=9.0 Hz), 7.89 (1H, t, J=6.2 Hz), 7.75 (2H, d, J=9.0 Hz), 7.70 (2H, d, J=8.8 Hz), 3.84 (3H, s), 3.55 (2H, d, J=6.2 Hz).

Example 2(13)

N-[[4-(2-Nitrobenzoylamino)phenyl]sulfonyl]
glycine

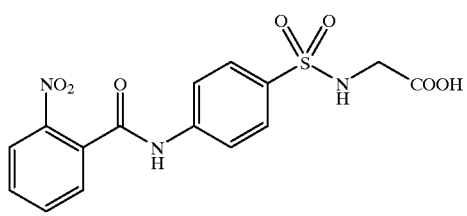

TLC: Rf 0.44 (Chloroform:Methanol:Acetic acid=2:0.1), NMR (DMSO-d6): δ 12.65 (1H, br.s), 11.02 (1H, s), 8.18 (1H, d, J=7.8 Hz), 8.0–7.7 (8H, m), 3.57 (2H, d, J=6.0 Hz).

Example 2(14)

N-[[4-(3-Nitrobenzoylamino)phenyl]sulfonyl]
glycine

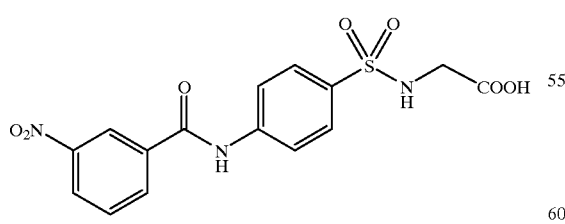

TLC: Rf 0.56 (Chloroform:Methanol:Acetic acid= 2:1:0.1), NMR (DMSO-d6): δ 12.65 (1H, br.s), 10.89 (1H, s), 8.81 (1H, t, J=2.0 Hz), 8.5–8.4 (2H, m), 8.0–7.85 (4H, m), 7.81 (2H, d, J=8.8 Hz), 3.57 (2H, d, J=6.0 Hz).

Example 2(15)

N-[[4-(4-Nitrobenzoylamino)phenyl]sulfonyl]
glycine

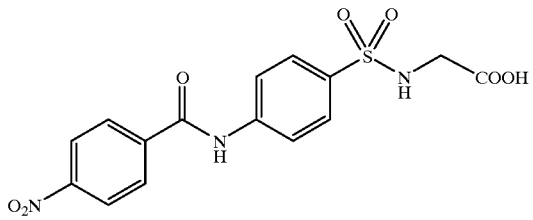

TLC: Rf 0.55 (Chloroform:Methanol Acetic acid= 2:1:0.1), NMR (DMSO-d6): δ 12.65 (1H, br.s), 10.88 (1H, s), 8.39 (2H, d, J=9.0 Hz), 8.20 (2H, d, J=9.0 Hz), 7.98 (d, J=8.8 Hz) and 7.96 (t, J=6.0 Hz) (total 3H), 7.80 (2H, d, J=8.8 Hz), 3.58 (2H, d, J=6.0 Hz).

Example 2(16)

N-[[4-(4-Ethylbenzoylamino)phenyl]sulfonyl]
glycine

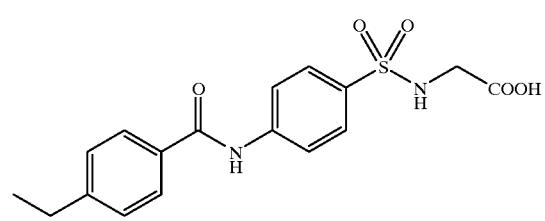

TLC: Rf 0.53 (Chloroform:Methanol:Acetic acid= 16:3:1), NMR (CD$_3$OD): δ 7.93 (2H, d, J=9.0 Hz), 7.87 (2H, d, J=8.6 Hz), 7.83 (2H, d, J=9.0 Hz), 7.36 (2H, d, J=8.6 Hz), 3.69 (2H, s), 2.73 (2H, q, J=7.6 Hz), 1.27 (3H, t, J=7.6 Hz).

Example 2(17)

N-[[4-(4-Propylbenzoylamino)phenyl]sulfonyl]
glycine

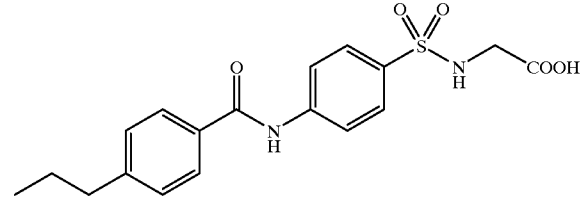

TLC: Rf 0.54 (Chloroform:Methanol:Acetic acid= 16:3:1), NMR (CD$_3$OD): δ 7.93 (2H, d, J=9.0 Hz), 7.86 (2H, d, J=8.2 Hz), 7.83 (2H, d, J=9.0 Hz), 7.33 (2H, d, J=8.2 Hz), 3.69 (2H, s), 2.68 (2H, dd, J=7.4, 8.2 Hz), 1.80–1.60 (2H, m), 0.96 (3H, t, J=7.2 Hz).

Example 2(18)

N-[[4-(2-Fluorobenzoylamino)phenyl]sulfonyl]glycine

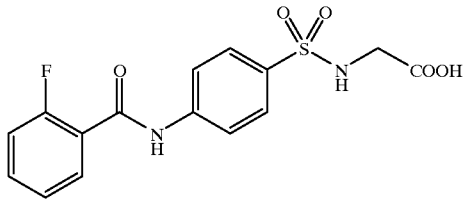

TLC: Rf 0.48 (Chloroform:Methanol:Acetic acid=16:3:1), NMR (DMSO-d6): δ 13.40–11.60 (1H, br.s), 10.74 (1H, s), 7.96–7.84 (1H, t, J=6.0 Hz), 7.89 (2H, d, J=8.8 Hz), 7.76 (2H, d, J=8.8 Hz), 7.72–7.52 (2H, m), 7.42–7.28 (2H, m), 3.55 (2H, d, J=6.0 Hz).

Example 2(19)

N-[[4-(3-Fluorobenzoylamino)phenyl]sulfonyl]glycine

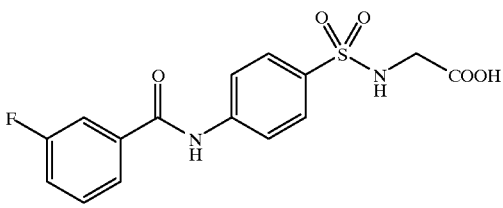

TLC: Rf 0.38 (Chloroform:Methanol:Acetic acid=16:3:1), NMR (DMSO-d6): δ 13.40–11.60 (1H, br.s), 10.61 (1H, s), 7.96 (2H, d, J=8.8 Hz), 7.92 (1H, t, J=6.0 Hz), 7.87–7.72 (2H, m), 7.77 (2H, d, J=8.8 Hz), 7.67–7.40 (2H, m), 3.56 (2H, d, J=6.0 Hz).

Example 2(20)

N-[[4-(Cyclohexylcarbonylamino)phenyl]sulfonyl]glycine

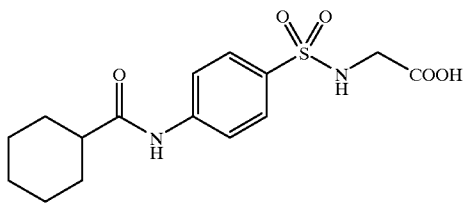

TLC: Rf 0.43 (Chloroform:Methanol:Acetic acid=16:3:1), NMR (CDCl3+CD3OD(10 drops)): δ 7.77 (2H, d, J=8.8 Hz), 7.68 (2H, d, J=8.8 Hz), 3.71 (2H, s), 2.40–2.20 (1H, m), 2.00–1.20 (10H, m).

Example 2(21)

N-[[4-(4-Trifluoromethylbenzoylamino)phenyl]sulfonyl]glycine

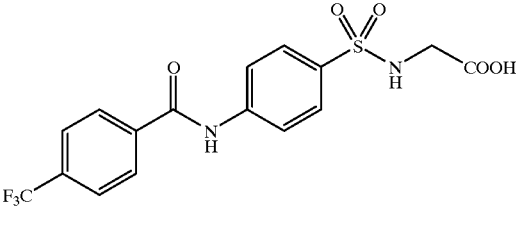

TLC: Rf 0.40 (Chloroform:Methanol:Acetic acid=16:3:1), NMR (DMSO-d6): δ 13.40–11.60 (1H, br.s), 10.76 (1H, s), 8.16 (2H, d, J=8.0 Hz), 8.03–7.87 (1H, t, J=6.2 Hz), 7.97 (2H, d, J=8.8 Hz), 7.91 (2H, d, J=8.0 Hz), 7.78 (2H, d, J=8.8 Hz), 3.57 (2H, d, J=6.2 Hz).

Example 2(22)

N-[[4-(2-Thienylcarbonylamino)phenyl]sulfonyl]glycine

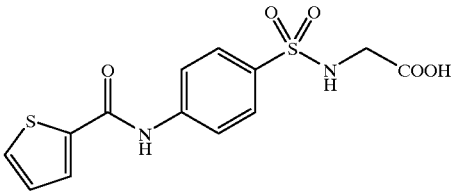

TLC: Rf 0.47 (Chloroform:Methanol:Acetic acid=2:1:0.1), NMR (DMSO-d6): δ 12.60 (1H, br.s), 10.52 (1H, s), 8.06 (1H, d, J=3.8 Hz), 8.0–7.9 (4H, m), 7.77 (2H, d, J=8.8 Hz), 7.25 (1H, dd, J=3.8, 5.0 Hz), 3.57 (2H, d, J=5.8 Hz).

Example 2(23)

N-[[4-(2-Furylcarbonylamino)phenyl]sulfonyl]glycine

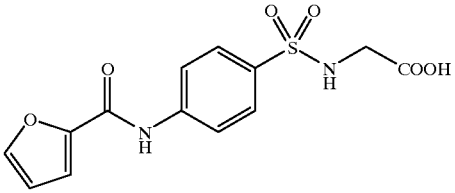

TLC: Rf 0.45 (Chloroform:Methanol:Acetic acid=2:1:0.1), NMR (DMSO-d6): δ 12.65 (1H, br.s), 10.51 (1H, s), 8.0–7.9 (4H, m), 7.75 (2H, d, J=8.8 Hz), 7.40 (1H, d, J=3.4 Hz), 6.73 (1H, dd, J=1.6, 3.4 Hz), 3.57 (2H, d, J=6.0 Hz).

Example 2(24)

N-[[4-(2-Pyridylcarbonylamino)phenyl]sulfonyl]glycine hydrochloride

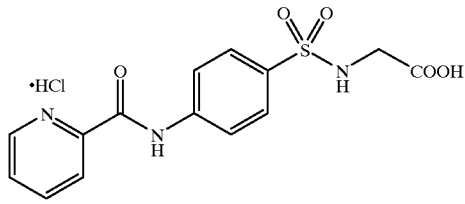

TLC: Rf 0.50 (Chloroform:Methanol:Acetic acid= 16:3:1), NMR (DMSO-d6): δ 10.98 (1H, s), 8.76 (1H, d, J=4.6 Hz), 8.24–8.02 (2H, m), 8.12 (2H, d, J=8.8 Hz), 8.01–7.82 (1H, br.s), 7.77 (2H, d, J=8.8 Hz), 7.74–7.65 (1H, m), 3.57 (2H, d, J=5.4 Hz).

Example 2(25)

N-[[4-(3-Pyridylcarbonylamino)phenyl]sulfonyl]glycine

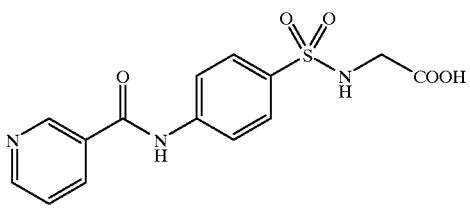

TLC: Rf 0.25 (Chloroform:Methanol:Acetic acid= 16:3:1), NMR (DMSO-d6): δ 13.50–11.50 (1H, br.s), 10.76 (1H, s), 9.12 (1H, d, J=1.8 Hz), 8.77 (1H, dd, J=1.8, 5.0 Hz), 8.31 (1H, dt, J=1.8, 8.2 Hz), 7.97 (2H, d, J=9.0 Hz), 7.93 (1H, t, J=5.4 Hz), 7.79 (2H, d, J=9.0 Hz), 7.58 (1H, dd, J=5.0, 8.2 Hz), 3.57 (2H, d, J=5.4 Hz).

Example 2(26)

N-[[4-(4-Pyridylcarbonylamino)phenyl]sulfonyl]glycine

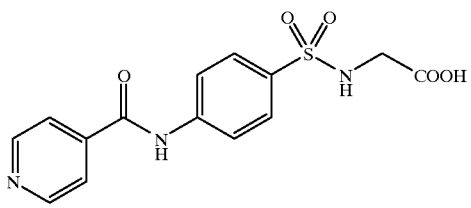

TLC: Rf 0.20 (Chloroform:Methanol:Acetic acid= 16:3:1), NMR (DMSO-d6): δ 13.20–12.00 (1H, br.s), 10.80 (1H, s), 8.83–8.76 (2H, m), 8.02–7.90 (1H, t, J=6.2 Hz), 7.97 (2H, d, J=8.8 Hz), 7.89–7.85 (2H, m), 7.79 (2H, d, J=8.8 Hz), 3.57 (2H, d, J=6.2 Hz).

Example 2(27)

N-[[4-(3-Thienylcarbonylamino)phenyl]sulfonyl]glycine

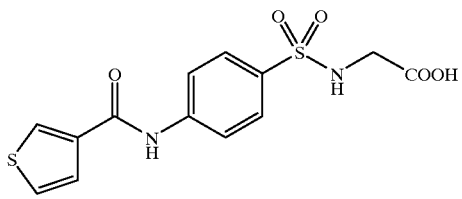

TLC: Rf 0.45 (Chloroform:Methanol:Acetic acid= 2:1:0.1), NMR (DMSO-d6): δ 12.5 (1H, br.s), 10.36 (1H, s), 8.4 (1H, m), 7.95–7.9 (3H, m), 7.76 (2H, d, J=8.9 Hz), 7.65 (2H, m), 3.57 (2H, d, J=6.0 Hz).

Example 2(28)

N-[[4-(3-Furylcarbonylamino)phenyl]sulfonyl]glycine

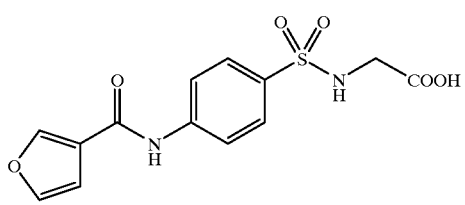

TLC: Rf 0.67 (Chloroform:Methanol:Acetic acid= 2:1:0.1), NMR (DMSO-d6): δ 12.6 (1H, br.s), 10.23 (1H, s), 8.43 (1H, m), 7.95–7.85 (3H, m), 7.82 (1H, m), 7.76 (2H, d, J=8.7 Hz), 7.01 (1H, m), 3.57 (2H, d, J=6.0 Hz).

Example 2(29)

N-[[4-(4-Methoxycarbonylbenzoylamino)phenyl]sulfonyl]glycine

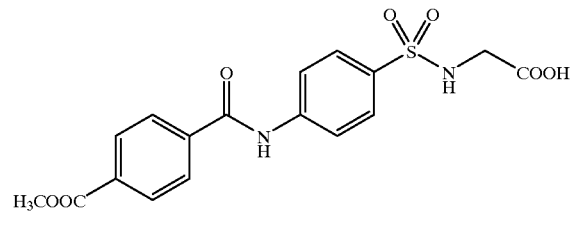

TLC: Rf 0.41 (Chloroform:Methanol:Acetic acid= 16:3:1), NMR (DMSO-d6): δ 13.50–11.50 (1H, br.s), 10.75 (1H, s), 8.12 (2H, d, J=9.2 Hz), 8.07 (2H, d, J=9.2 Hz), 7.98 (2H, d, J=8.8 Hz), 7.94 (1H, t, J=6.0 Hz), 7.78 (2H, d, J=8.8 Hz), 3.90 (3H, s), 3.58 (2H, d, J=6.0 Hz).

Example 2(30)

N-[[4-(4-Cyanobenzoylamino)phenyl]sulfonyl]glycine

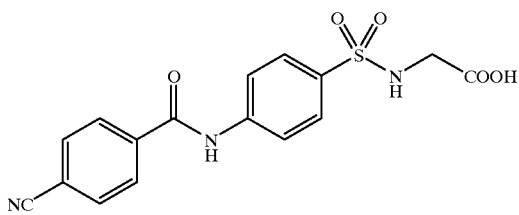

TLC: Rf 0.34 (Chloroform:Methanol:Acetic acid=16:3:1), NMR (DMSO-d6): δ 13.50–11.50 (1H, br.s), 10.79 (1H, s), 8.12 (2H, d, J=8.8 Hz), 8.04 (2H, d, J=8.8 Hz), 8.01–7.90 (1H), 7.96 (2H, d, J=8.8 Hz), 7.79 (2H, d, J=8.8 Hz), 3.58 (2H, d, J=6.2 Hz).

Example 2(31)

N-[[4-(4-Benzyloxybenzoylamino)phenyl]sulfonyl]glycine

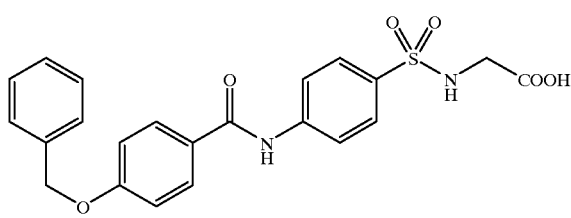

TLC: Rf 0.48 (Chloroform:Methanol:Acetic acid=16:3:1), NMR (DMSO-d6): δ 13.50–11.50 (1H, br.s), 10.41 (1H, s), 7.97 (2H, d, J=8.8 Hz), 7.96 (2H, d, J=8.8 Hz), 7.90 (1H, t, J=6.2 Hz), 7.75 (2H, d, J=8.8 Hz), 7.54–7.28 (5H, m), 7.16 (2H, d, J=8.8 Hz), 5.21 (2H, s), 3.57 (2H, d, J=6.2 Hz).

Example 2(32)

N-[[4-[4-Carboxybenzoylamino)phenyl]sulfonyl]glycine

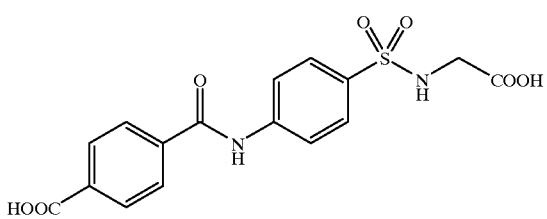

TLC: Rf 0.51 (Chloroform:Methanol:Acetic acid=2:1:0.1), NMR (DMSO-d6): δ 13.3–12.70 (1H, br.s), 10.74 (1H, s), 8.11 (2H, d, J=9.0 Hz), 8.06 (2H, d, J=9.0 Hz), 7.98 (2H, d, J=8.8 Hz), 7.94 (1H, t, J=6.2 Hz), 7.79 (2H, d, J=8.8 Hz), 3.58 (2H, d, J=6.2 Hz).

Example 2(33)

N-[[4-(Cinnamoylamino)phenyl]sulfonyl]glycine

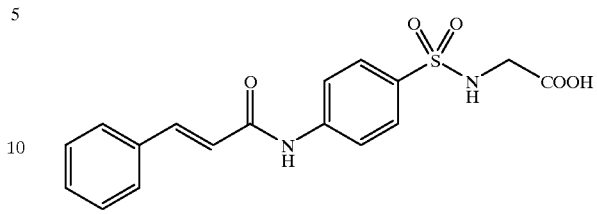

TLC: Rf 0.45 (Chloroform:Methanol:Acetic acid=16:3:1), NMR (DMSO-d6): δ 12.80–12.40 (1H, br.s), 10.57 (1H, s), 7.91 (1H, t, J=6.2 Hz), 7.87 (2H, d, J=8.8 Hz), 7.75 (2H, d, J=8.8 Hz), 7.70–7.52 (3H, m), 7.50–7.38 (3H, m), 6.85 (1H, d, J=15.8 Hz), 3.56 (2H, d, J=6.2 Hz).

Example 2(34)

N-[[4-[(4-Butylbenzoylamino)phenyl]sulfonyl]glycine

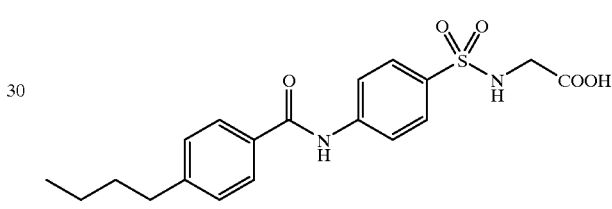

TLC: Rf 0.55 (Chloroform:Methanol:Acetic acid=16:3:1), NMR (DMSO-d6): δ 13.40–11.60 (1H, br.s), 10.47 (1H, s), 7.80 (1H, br.t, J=6.0 Hz), 7.96 (2H, d, J=8.8 Hz), 7.88 (2H, d, J=8.2 Hz), 7.75 (2H, d, J=8.8 Hz), 7.35 (2H, d, J=8.2 Hz), 3.56 (2H, d, J=6.0 Hz), 2.64 (2H, t, J=7.6 Hz), 1.76–1.42 (2H, m), 1.42–1.10 (2H, m), 0.90 (3H, t, J=7.4 Hz).

Example 2(35)

N-[[4-(4-Pentylbenzoylamino)phenyl]sulfonyl]glycine

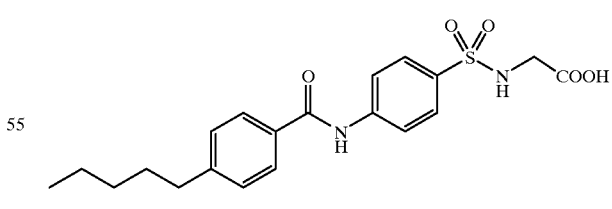

TLC: Rf 0.55 (Chloroform:Methanol:Acetic acid=16:3:1), NMR (DMSO-d6): δ 13.40–11.60 (1H, br.s), 10.48 (1H, s), 7.90 (1H, br.t, J=6.0 Hz), 7.97 (2H, d, J=8.8 Hz), 7.89 (2H, d, J=8.2 Hz), 7.76 (2H, d, J=8.8 Hz), 7.35 (2H, d, J=8.2 Hz), 3.56 (2H, d, J=6.0 Hz), 2.66 (2H, t, J=7.0 Hz), 1.72–1.48 (2H, m), 1.48–1.18 (4H, m), 0.87 (3H, t, J=6.6 Hz).

Example 2(36)

N-[[4-(4-Phenylbenzoylamino)phenyl]sulfonyl]glycine

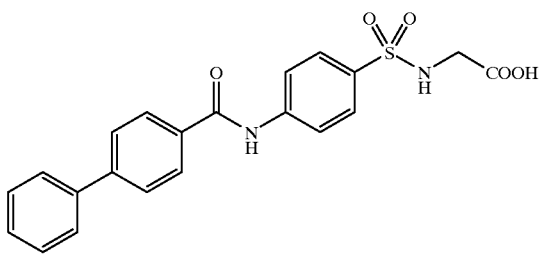

TLC: Rf 0.50 (Chloroform:Methanol:Acetic acid= 16:3:1), NMR (DMSO-d6): δ 13.40–11.60 (1H, br.s), 10.62 (1H, s), 8.08 (2H, d, J=8.4 Hz), 8.01 (2H, d, J=8.8 Hz), 7.93 (1H, t, J=6.0 Hz), 7.90–7.70 (2H, m), 7.85 (2H, d, J=8.4 Hz), 7.77 (2H, d, J=8.8 Hz), 7.60–7.36 (3H, m), 3.58 (2H, d, J=6.0 Hz).

Example 2(37)

N-[[4-(Benzoylamino)phenyl]sulfonyl]-L-valine

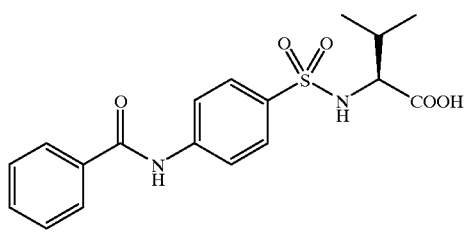

TLC: Rf 0.75 (Chloroform:Methanol:Acetic acid= 2:1:0.1), NMR (DMSO-d6): δ 12.6 (1H, br.s), 10.57 (1H, s), 8.0–7.9 (5H, m), 7.75 (2H, d, J=8.8 Hz), 7.65–7.5 (3H, m), 3.51 (1H, dd, J=6, 9.4 Hz), 2.0–1.85 (1H, m), 0.83 (3H, d, J=6.8 Hz), 0.81 (3H, d, J=6.8 Hz).

Example 2(38)

N-[[4-(1-Naphthoylamino)phenyl]sulfonyl]glycine

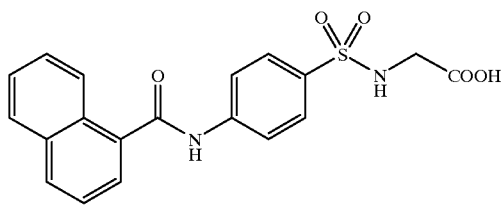

TLC: Rf 0.49 (Chloroform:Methanol:Acetic acid= 16:3:1), NMR (DMSO-d6): δ 13.50–11.50 (1H, br.s), 10.92 (1H, s), 8.26–7.86 (6H, m), 7.85–7.70 (3H, m), 7.68–7.50 (3H, m), 3.58 (2H, d, J=5.8 Hz).

Example 2(39)

N-[[4-(2-Naphthoylamino)phenyl]sulfonyl]glycine

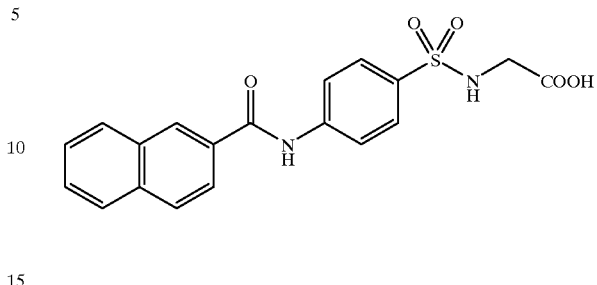

TLC: Rf 0.49 (Chloroform:Methanol:Acetic acid= 16:3:1), NMR (DMSO-d6): δ 13.50–11.50 (1H, br.s), 10.75 (1H, s), 8.61 (1H, s), 8.15–7.99 (6H, m), 7.94 (1H, t, J=6.2 Hz), 7.81 (2H, d, J=9.2 Hz), 7.72–7.58 (2H, m), 3.59 (2H, d, J=6.2 Hz).

Example 2(40)

N-[[4-(3-Benzyloxybenzoylamino)phenyl]sulfonyl]glycine

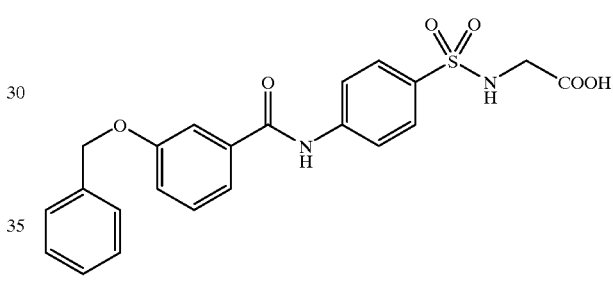

TLC: Rf 0.54 (Chloroform:Methanol:Acetic acid= 16:3:1), NMR (DMSO-d6): δ 13.50–11.50 (1H, br.s), 10.51 (1H, s), 7.96 (2H, d, J=8.8 Hz), 7.90 (1H, t, J=6.2 Hz), 7.76 (2H, d, J=8.8 Hz), 7.62–7.22 (9H, m), 5.19 (2H, s), 3.56 (2H, d, J=6.2 Hz).

Example 2(41)

N-[[4-(2-Benzyloxybenzoylamino)phenyl]sulfonyl]glycine

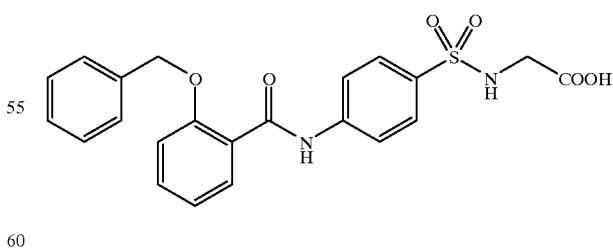

TLC: Rf 0.73 (Chloroform:Methanol:Acetic acid= 16:3:1), NMR (DMSO-d6): δ 13.50–11.50 (1H, br.s), 10.50 (1H, s), 7.89 (1H, t, J=6.2 Hz), 7.78–7.67 (4H, m), 7.68 (1H, dd, J=1.6, 7.6 Hz), 7.60–7.48 (3H, m), 7.44–7.25 (4H, m), 7.10 (1H, dt, J=0.8, 7.6 Hz), 5.24 (2H, s), 3.54 (2H, d, J=6.2 Hz).

Example 2(42)

N-[[4-(Benzoylamino)phenyl]sulfonyl]-L-aspartic acid

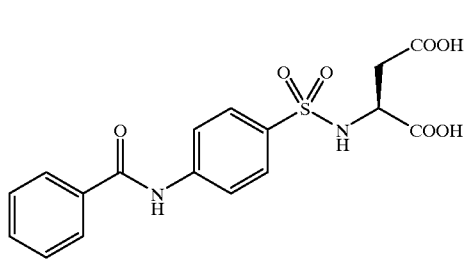

TLC: Rf 0.35 (Chloroform:Methanol:Acetic acid= 2:1:0.1), NMR (CD$_3$OD): δ 8.00–7.80 (6H, m), 7.65–7.50 (3H, m), 4.22 (1H, t, J=9.0 Hz), 2.73 (2H, d, J=6.0 Hz).

Example 2(43)

N-[[4-(Benzoylamino)phenyl]sulfonyl]-L-glutamic acid

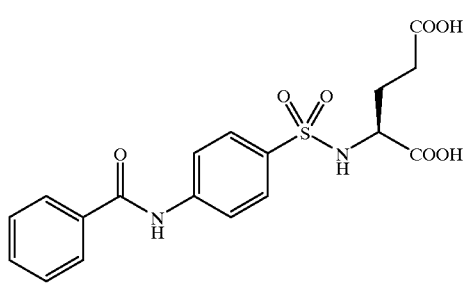

TLC: Rf 0.49 (Chloroform:Methanol:Acetic acid= 2:1:0.1), NMR (CD$_3$OD): δ 8.00–7.80 (6H, m), 7.65–7.50 (3H, m), 3.93 (1H, dd, J=2.8, 9.0 Hz), 2.41 (2H, t, J=7.5 Hz), 2.15–1.95 (1H, m), 1.90–1.75 (1H, m).

Example 2(44)

N-[[4-(Phenylacetylamino)phenyl]sulfonyl]glycine

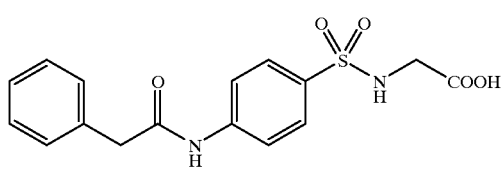

TLC: Rf 0.44 (Chloroform:Methanol:Acetic acid= 16:3:1), NMR (DMSO-d6): δ 10.51 (1H, s), 7.86 (1H, t, J=6.2 Hz), 7.76 (2H, d, J=8.8 Hz), 7.69 (2H, d, J=8.8 Hz), 7.40–7.18 (5H, m), 3.67 (2H, s), 3.53 (2H, d, J=6.2 Hz).

Example 2(45)

N-[[4-(Benzoylamino)phenyl]sulfonyl]-L-leucine

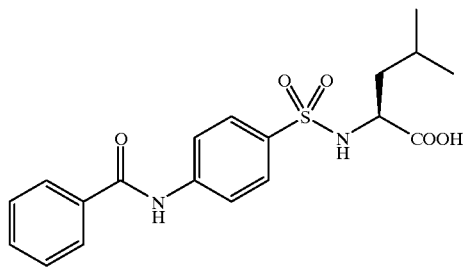

TLC: Rf 0.41 (Chloroform:Methanol:Acetic acid= 2:10.1), NMR (DMSO-d6): δ 10.29 (1H, s), 8.16 (1H, br.t, J=9.0 Hz), 7.97 (2H, m), 7.72 (2H, d, J=8.6 Hz), 7.6–7.45 (5H, m), 3.86 (1H, m), 1.8–1.5 (3H, m), 0.91 (6H, d, J=5.4 Hz).

Example 2(46)

N-[[4-(Benzoylamino)phenyl]sulfonyl]-D-leucine

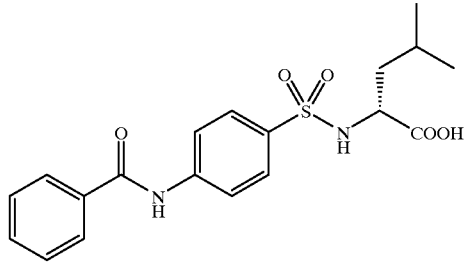

TLC: Rf 0.41 (Chloroform:Methanol:Acetic acid= 2:1:0.1), NMR (DMSO-d6): δ 10.29 (1H, s), 8.16 (1H, br.t, J=9.0 Hz), 7.97 (2H, m), 7.72 (2H, d, J=8.8 Hz), 7.6–7.45 (5H, m), 3.86 (1H, m), 1.8–1.5 (3H, m), 0.90 (6H, d, J=6.2 Hz).

Example 2(47)

N-[[4-(Phenoxycarbonylamino)phenyl]sulfonyl] glycine

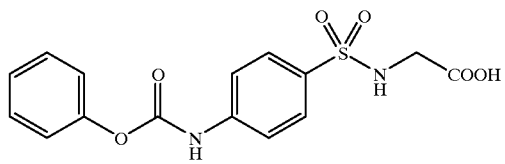

TLC: Rf 0.44 (Chloroform:Methanol:Acetic acid= 16:3:1), NMR (DMSO-d6): δ 13.20–12.00 (1H, br.s), 10.64 (1H, s), 7.89 (1H, t, J=6.2 Hz), 7.75 (2H, d, J=8.8 Hz), 7.65 (2H, d, J=8.8 Hz), 7.51–7.38 (2H, m), 7.33–7.20 (3H, m), 3.55 (2H, d, J=6.2 Hz).

Example 2(48)

N-[[4-(4-Dimethylaminobenzoylamino)phenyl]sulfonyl]glycine

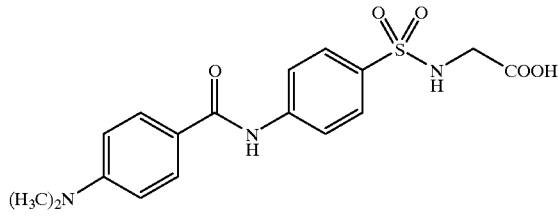

TLC: Rf 0.54 (Chloroform:Methanol:Acetic acid= 2:1:0.1), NMR (DMSO-d6): δ 10.18 (1H, s), 8.00–7.80 (5H, m), 7.73 (2H, d, J=8.8 Hz), 6.77 (2H, d, J=9.0 Hz), 3.55 (2H), 3.03 (6H, s).

Example 2(49)

N-[[4-(Benzoylamino)phenyl]sulfonyl]-D-valine

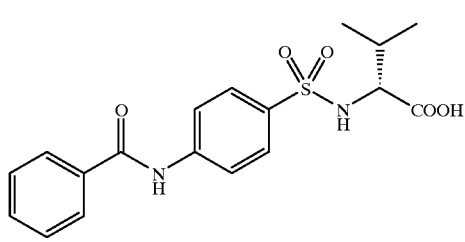

TLC: Rf 0.73 (Chloroform:Methanol:Acetic acid= 2:1:0.1), NMR (DMSO-d6): δ 12.6 (1H, br.s), 10.56 (1H, s), 8.0–7.85 (5H, m), 7.75 (2H, d, J=8.8 Hz), 7.65–7.5 (3H, m), 3.51 (1H, dd, J=6.1, 9.3 Hz), 2.0–1.85 (1H, m), 0.83 (3H, d, J=6.8 Hz), 0.81 (3H, d, J=6.8 Hz).

Example 2(50)

N-[[4-(Benzoylamino)phenyl]sulfonyl]-L-Phenylalanine

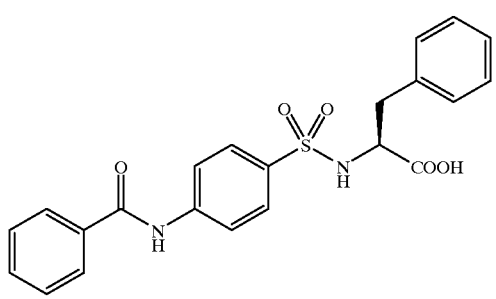

TLC: Rf 0.68 (Chloroform:Methanol:Acetic acid= 2:1:0.1), NMR (DMSO-d6): δ 12.71 (1H, br.s), 10.54 (1H, s), 8.17 (1H, d, J=9.0 Hz), 7.97 (2H, m), 7.86 (2H, m), 7.65–7.5 (5H, m), 7.25–7.1 (5H, m), 3.95–3.8 (1H, m), 2.94 (1H, dd, J=5.8, 13.8 Hz), 2.72 (1H, dd, J=8.8, 13.8 Hz).

Example 2(51)

N-[[4-(Benzoylamino)phenyl]sulfonyl]-D-Phenylalanine

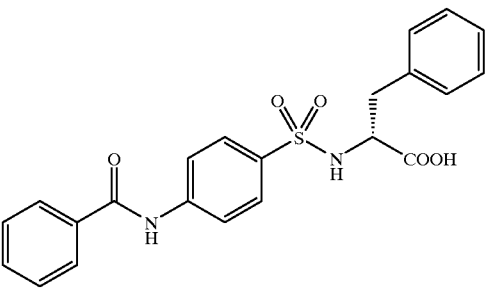

TLC: Rf 0.68 (Chloroform:Methanol:Acetic acid= 2:1:0.1), NMR (DMSO-d6): δ 12.71 (1H, br.s), 10.53 (1H, s), 8.17 (1H, d, J=9.0 Hz), 7.97 (2H, m), 7.86 (2H, m), 7.65–7.5 (5H, m), 7.3–7.1 (5H, m), 3.95–3.8 (1H, m), 2.94 (1H, dd, J=5.8, 13.8 Hz), 2.73 (1H, dd, J=8.4, 13.8 Hz).

Example 2(52)

N-[[4-(Benzoylamino)phenyl]sulfonyl]-L-alanine

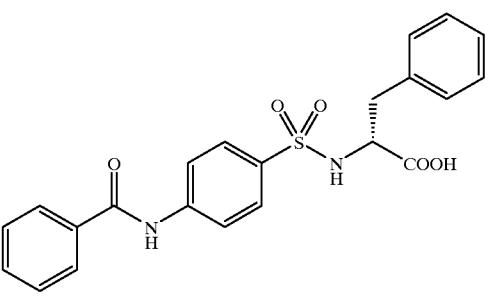

TLC: Rf 0.62 (Chloroform:Methanol:Acetic acid= 2:1:0.1), NMR (DMSO-d6): δ 12.6 (1H, br.s), 10.58 (1H, s), 8.04 (1H, d, J=8.6 Hz), 8.0–7.9 (4H, m), 7.76 (2H, d, J=8.8 Hz), 7.65–7.5 (3H, m), 3.75 (1H, m), 1.16 (3H, d, J=7.4 Hz).

Example 2(53)

N-[[4-(Benzoylamino)phenyl]sulfonyl]-D-alanine

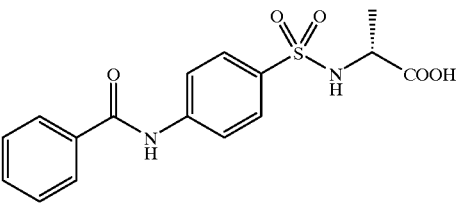

TLC: Rf 0.62 (Chloroform:Methanol:Acetic acid= 2:1:0.1), NMR (DMSO-d6): δ 12.6 (1H, br.s), 10.58 (1H, s), 8.04 (1H, d, J=8.6 Hz), 8.0–7.9 (4H, m), 7.77 (2H, d, J=8.8 Hz), 7.65–7.5 (3H, m), 3.76 (1H, m), 1.16 (3H, d, J=7.4 Hz).

Example 2(54)

N-[[4-(Benzoylamino)phenyl]sulfonyl]-L-lysine

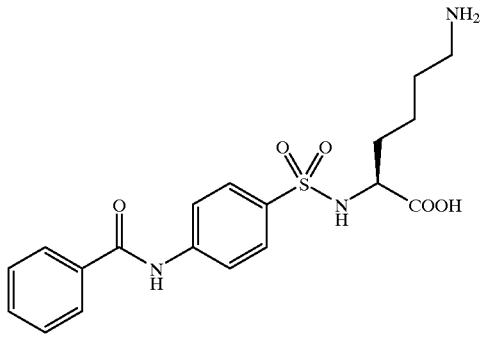

TLC: Rf 0.19 (Chloroform:Methanol:Acetic acid:Water= 2:1:0.1:tailing), NMR (DMSO-d6+CF$_3$COOH(1 drop)): δ 10.59 (1H, s), 8.05–7.95 (5H, m), 7.80–7.50 (4H, m), 3.70–3.60 (1H, m), 2.80–2.65 (2H, m), 1.70–1.20 (6H, m).

Example 2(55)

N-[[4-(Benzoylamino)phenyl]sulfonyl]-D-lysine

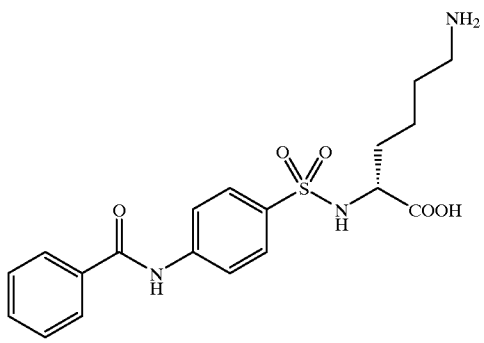

TLC: Rf 0.19 (Chloroform:Methanol:Acetic acid:Water= 2:1:0.1:tailing), NMR (DMSO—d6+CF$_3$COOH(1 drop)): δ 10.59 (1H, s), 8.05–7.95 (5H, m), 7.80–7.50 (4H, m), 3.70–3.60 (1H, m), 2.80–2.65 (2H, m), 1.70–1.20 (6H, m).

Example 2(56)

N-[[4-(Benzoylamino)phenyl]sulfonyl]-D-glutamic acid

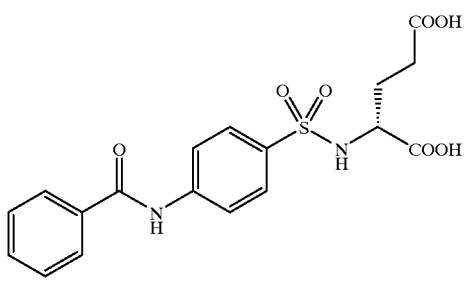

TLC: Rf 0.45 (Chloroform:Methanol:Acetic acid= 2:10.1), NMR (DMSO-d6): δ 12.4 (2H, br.s), 10.57 (1H, s), 8.05 (1H, d, J=9.0 Hz), 7.97 (4H, m), 7.74 (2H, d, J=8.8 Hz), 7.65–7.5 (3H, m), 3.76 (1H, m), 2.23 (2H, t, J=7.4 Hz), 1.95–1.55 (2H, m).

Example 2(57)

N-[[4-(4-Dodecylbenzoylamino)phenyl]sulfonyl] glycine

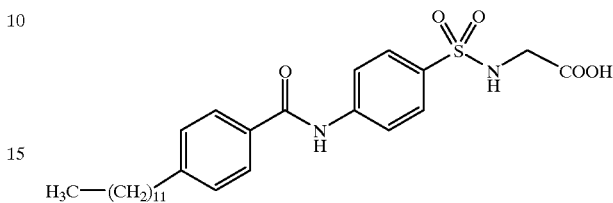

TLC: Rf 0.68 (Chloroform:Methanol:Acetic acid= 16:3:1), NMR (DMSO-d6): δ 13.50–11.50 (1H, br.s), 10.46 (1H, s), 7.97 (2H, d, J=8.8 Hz), 7.89 (1H, t, J=6.2 Hz), 7.88 (2H, d, J=8.4 Hz), 7.76 (2H, d, J=8.8 Hz), 7.34 (2H, d, J=8.4 Hz), 3.55 (2H, d, J=6.2 Hz), 2.65 (2H, t, J=7.8 Hz), 1.70–1.48 (2H, m), 1.40–1.10 (18H, m), 0.85 (3H, t, J=6.6 Hz).

Example 2(58)

4-[N-[[4-(Benzoylamino)phenyl]sulfonyl]amino] butyric acid

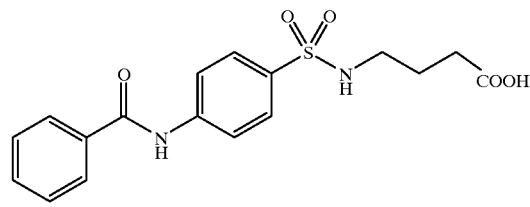

TLC: Rf 0.76 (Chloroform:Methanol:Acetic acid= 2:1:0.1), NMR (DMSO-d6): δ 12.05 (1H, br.s), 10.59 (1H, s), 8.05–7.95 (4H, m), 7.76 (2H, d, J=8.8 Hz), 7.65–7.45 (4H, m), 2.75 (2H, q, J=6.8 Hz), 2.22 (2H, d, J=7.2 Hz), 1.60 (2H, m).

Example 2(59)

N-[[4-(Benzoylamino)phenyl]sulfonyl]amino]-L-serine

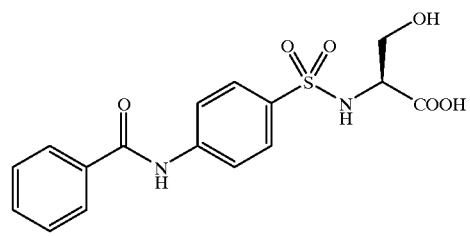

TLC: Rf 0.42 (Chloroform:Methanol:Acetic acid= 2:1:0.1), NMR (DMSO-d6): δ 10.57 (1H, s), 8.0–7.95 (4H, m), 7.88 (1H, d, J=8.6 Hz), 7.76 (2H, d, J=8.6 Hz), 7.65–7.5 (3H, m), 3.74 (1H, m), 3.49 (2H, d, J=5.2 Hz).

Example 2(60)

N-[[4-(Benzoylamino)phenyl]sulfonyl]amino]-D-serine

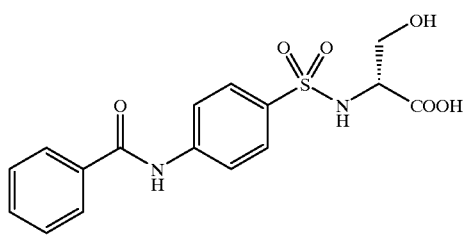

TLC: Rf 0.42 (Chloroform:Methanol:Acetic acid= 2:1:0.1), NMR (DMSO-d6): δ 10.57 (1H, s), 8.0–7.9 (4H, m), 7.88 (1H, d, J=8.6 Hz), 7.76 (2H, d, J=8.8 Hz), 7.65–7.5 (3H, m), 3.75 (1H, m), 3.49 (2H, d, J=5.4 Hz).

Example 2(61)

N-[[4-(Benzoylamino)phenyl]sulfonyl]-D-aspartic acid

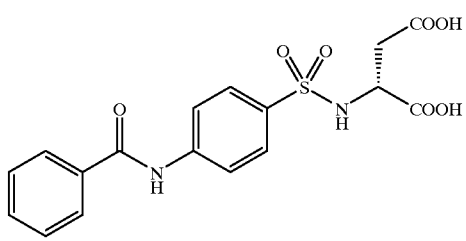

TLC: Rf 0.35 (Chloroform:Methanol:Acetic acid= 2:1:0.1), NMR (DMSO-d6): δ 10.57 (1H, s), 8.07 (1H, d, J=8.6 Hz), 8.0–7.9 (4H, m), 7.76 (2H, d, J=8.8 Hz), 7.65–7.5 (3H, m), 4.05 (1H, m), 2.59 (1H, dd, J=6.6, 16.8 Hz), 2.40 (1H, dd, J=6.6, 16.8 Hz).

Example 2(62)

N-[[4-(p-Toluoylamino)phenyl]sulfonyl]-D-phenylalanine

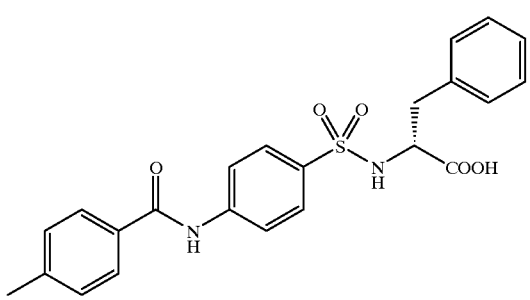

TLC: Rf 0.28 (Chloroform:Methanol:Acetic acid:Water= 100:10:1:1), NMR (DMSO-d6): δ 12.9–12.4 (1H, br.s), 10.44 (1H, s), 8.17 (1H, d, J=9.2 Hz), 7.9–7.8 (4H, m), 7.54 (2H, d, J=8.6 Hz), 7.36 (2H, d, J=8.2 Hz), 7.3–7.1 (5H, m), 3.9–3.8 (1H, m), 2.93 (1H, dd, J=6.0, 14 Hz), 2.72 (1H, dd, J=8.8, 14 Hz), 2.40 (3H, s).

Example 2(63)

N-[[4-(4-Pentylbenzoylamino)phenyl]sulfonyl]-D-phenylalanine

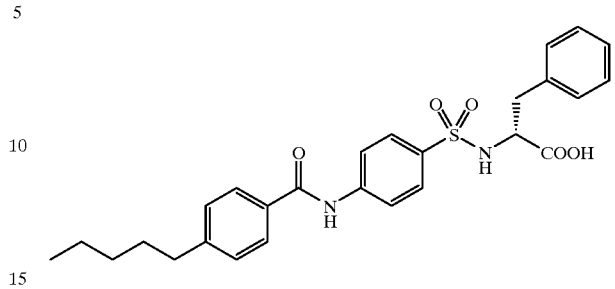

TLC: Rf 0.21 (Chloroform:Methanol:Acetic acid= 95:4:1), NMR (DMSO-d6): δ 13.00–12.20 (1H, br.s), 10.40 (1H, s), 8.11 (1H, d, J=9.0 Hz), 7.88 (2H, d, J=8.6 Hz), 7.84 (2H, d, J=8.4 Hz), 7.52 (2H, d, J=8.6 Hz), 7.34 (2H, d, J=8.4 Hz), 7.28–7.08 (5H, m), 3.92–3.78 (1H, m), 2.93 (1H, dd, J=5.8, 13.4 Hz), 2.71 (1H, dd, J=8.8, 13.4 Hz), 2.66 (2H, t, J=8.2 Hz), 1.70–1.50 (2H, m), 1.44–1.18 (4H, m), 0.87 (3H, t, J=6.8 Hz).

Example 2(64)

N-[[4-(p-Toluoylamino)phenyl]sulfonyl]-L-valine

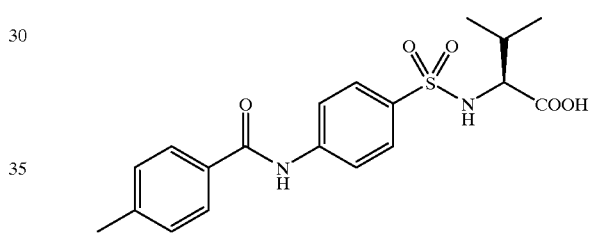

TLC: Rf 0.45 (Chloroform:Methanol:Acetic acid= 45:4:1), NMR (DMSO-d6): δ 12.90–12.30 (1H, br.s), 10.45 (1H, s), 7.94 (1H, br.d, J=9.6 Hz), 7.95 (2H, d, J=8.8 Hz), 7.88 (2H, d, J=8.2 Hz), 7.73 (2H, d, J=8.8 Hz), 7.34 (2H, d, J=8.2 Hz), 3.49 (1H, dd, J=6.2, 9.6 Hz), 2.39 (3H, s), 2.00–1.90 (1H, m), 0.83 (3H, d, J=6.8 Hz), 0.80 (3H, d, J=6.8 Hz).

Example 2(65)

N-[[4-(4-Hexylbenzoylamino)phenyl]sulfonyl] glycine

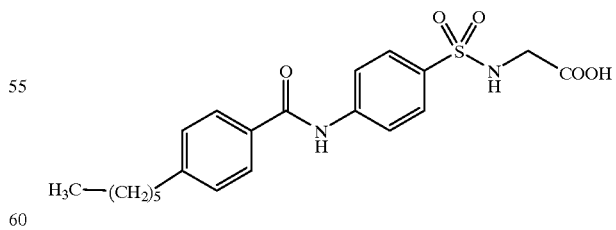

TLC: Rf 0.18 (Chloroform:Methanol:Acetic acid= 90:10:1), NMR (DMSO-d6): δ 13.40–12.00 (1H, br.s), 10.46 (1H, s), 7.97 (3H, m), 7.88 (2H, d, J=8.0 Hz), 7.87 (1H), 7.75 (2H, d, J=8.8 Hz), 7.34 (2H, d, J=8.0 Hz), 3.55 (2H, d, J=5.8 Hz), 2.66 (2H, t, J=7.8 Hz), 1.70–1.50 (2H, m), 1.40–1.15 (6H, m), 0.86 (3H, t, J=6.6 Hz).

Example 2(66)

N-[[4-(4-Heptylbenzoylamino)phenyl]sulfonyl]glycine

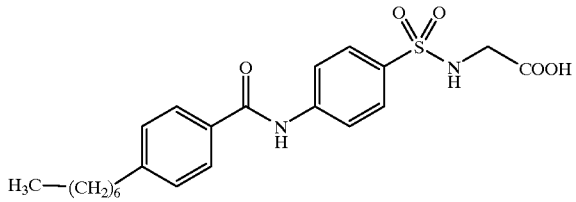

TLC: Rf 0.18 (Chloroform:Methanol:Acetic acid= 90:10:1), NMR (DMSO-d6): δ 13.00–12.40 (1H, br.s), 10.48 (1H, s), 7.97 (3H, m), 7.89 (2H, d, J=8.2 Hz), 7.87 (1H), 7.77 (2H, d, J=9.0 Hz), 7.35 (2H, d, J=8.2 Hz), 3.57 (2H, d, J=6.2 Hz), 2.66 (2H, t, J=7.8 Hz), 1.70–1.44 (2H, m), 1.40–1.10 (8H, m), 0.86 (3H, t, J=7.0 Hz).

Example 2(67)

N-[[4-(4-Isopropylbenzoylamino)phenyl]sulfonyl]glycine

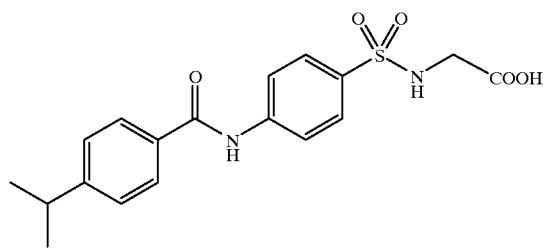

TLC: Rf 0.51 (Chloroform:Methanol:Acetic acid= 16:3:1), NMR (DMSO-d6): δ 13.20–12.00 (1H, br.s), 10.48 (1H, s), 7.96 (3H, m), 7.89 (2H, d, J=8.2 Hz), 7.76 (2H, d, J=8.8 Hz), 7.41 (2H, d, J=8.2 Hz), 3.57 (2H, d, J=6.0 Hz), 2.99 (1H, m), 1.24 (6H, d, J=6.8 Hz).

Example 2(68)

N-[[4-(4-Isobutylbenzoylamino)phenyl]sulfonyl]glycine

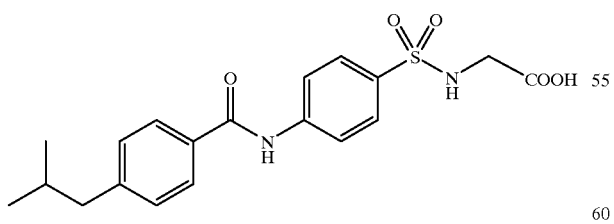

TLC: Rf 0.53 (Chloroform:Methanol:Acetic acid= 16:3:1), NMR (DMSO-d6): δ 13.20–12.00 (1H, br.s), 10.49 (1H, s), 7.96 (3H, m), 7.89 (2H, d, J=8.2 Hz), 7.76 (2H, d, J=8.8 Hz), 7.33 (2H, d, J=8.2 Hz), 3.57 (2H, d, J=6.0 Hz), 2.54 (2H, d, J=7.2 Hz), 1.88 (1H, m), 0.89 (6H, d, J=6.4 Hz).

Example 2(69)

N-[[4-(Benzoylamino)phenyl]sulfonyl]-2,2-dimethylglycine

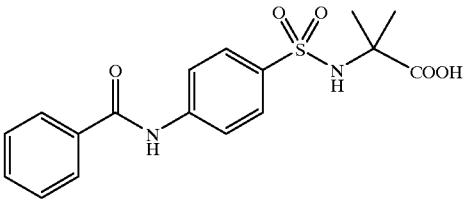

TLC: Rf 0.14 (Chloroform:Methanol:Acetic acid:Water= 100:10:1:1), NMR (DMSO-d6): δ 12.55 (1H, br.s), 10.56 (1H, s), 8.0–7.85 (5H, m), 7.77 (2H, d, J=8.8 Hz), 7.65–7.5 (3H, m), 1.27 (6H, s).

Example 2(70)

N-[[4-(p-Toluoylamino)phenyl]sulfonyl]amino]-D-serine

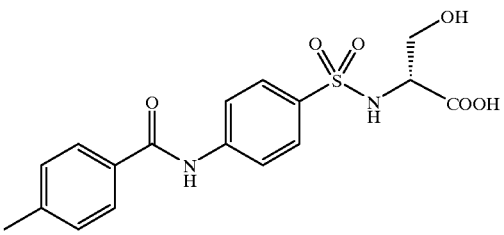

TLC: Rf 0.25 (Chloroform:Methanol:Acetic acid= 16:3:1), NMR (DMSO-d6): δ 13.40–11.60 (1H, br.s), 10.47 (1H, s), 7.95 (2H, d, J=8.8 Hz), 7.88 (2H, d, J=8.2 Hz), 7.86 (1H, d, J=8.4 Hz), 7.75 (2H, d, J=8.8 Hz), 7.35 (2H, d, J=8.2 Hz), 3.80–3.68 (1H, m), 3.53–3.47 (2H), 2.39 (3H, s).

Example 2(71)

N-[[4-(p-Toluoylamino)phenyl]sulfonyl]-L-leucine

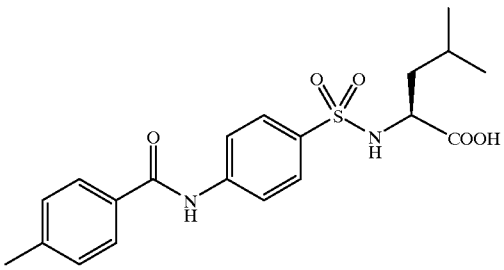

TLC: Rf 0.22 (Chloroform:Methanol:Acetic acid:Water= 100:10:1:1), NMR (DMSO-d6): δ 12.55 (1H, br.s), 10.48 (1H, s), 8.04 (1H, d, J=8.8 Hz), 7.96 (2H, d, J=8.8 Hz), 7.89 (2H, d, J=8.2 Hz), 7.73 (2H, d, J=8.8 Hz), 7.36 (2H, d, J=8.2 Hz), 3.65 (1H, m), 2.40 (3H, s), 1.59 (1H, m), 1.37 (2H, m), 0.82 (3H, d, J=6.6 Hz), 0.72 (3H, d, J=6.4 Hz).

Example 2(72)

N-[[4-(p-Toluoylamino)phenyl]sulfonyl]-D-alanine

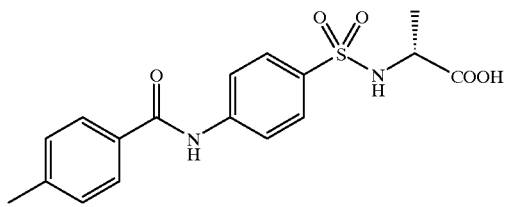

TLC: Rf 0.30 (Chloroform:Methanol:Acetic acid= 90:10:1), NMR (DMSO-d6): δ 13.20–12.00 (1H, br.s), 10.48 (1H, s), 8.02 (1H, d, J=8.2 Hz), 7.97 (2H, d, J=8.8 Hz), 7.88 (2H, d, J=8.4 Hz), 7.75 (2H, d, J=8.8 Hz), 7.35 (2H, d, J=8.4 Hz), 3.82–3.66 (1H, m), 2.39 (3H, s), 1.15 (3H, d, J=7.0 Hz).

Example 2(73)

N-[[4-(p-Toluoylamino)phenyl]sulfonyl]-D-valine

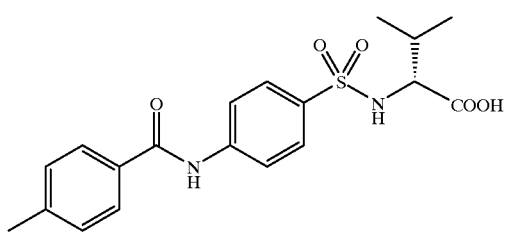

TLC: Rf 0.53 (Chloroform:Methanol:Acetic acid= 90:10:1), NMR (DMSO-d6): δ 12.80–12.40 (1H, br.s), 10.46 (1H, s), 7.95 (2H, d, J=8.8 Hz), 7.94–7.90 (1H), 7.89 (2H, d, J=8.2 Hz), 7.74 (2H, d, J=8.8 Hz), 7.35 (2H, J=8.2 Hz), 3.60–3.45 (1H, m), 2.39 (3H, s), 2.02–1.80 (1H, m), 0.81 (6H, d, J=6.8 Hz).

Example 2(74)

N-[[4-(p-Toluoylamino)phenyl]sulfonyl]-D-leucine

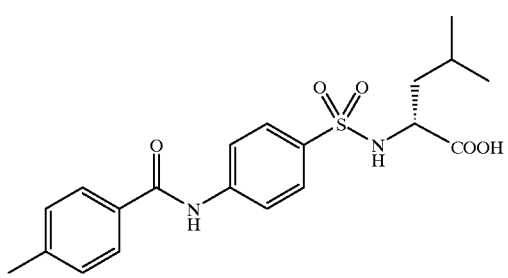

TLC: Rf 0.54 (Chloroform:Methanol:Acetic acid= 90:10:1), NMR (DMSO-d6): δ 12.80–12.30 (1H, br.s), 10.46 (1H, s), 8.02 (1H, d, J=9.0 Hz), 7.96 (2H, d, J=8.8 Hz), 7.89 (2H, d, J=8.2 Hz), 7.73 (2H, d, J=8.8 Hz), 7.35 (2H, d, J=8.2 Hz), 3.75–3.55 (1H, m), 2.39 (3H, s), 1.70–1.48 (1H, m), 1.46–1.30 (2H, m), 0.82 (3H, d, J=6.6 Hz), 0.72 (3H, d, J=6.6 Hz).

Example 2(75)

N-[[2-Methyl-4-(p-Toluoylamino)phenyl]sulfonyl]glycine

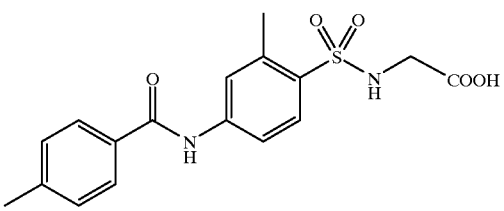

TLC: Rf 0.61 (Chloroform:Methanol=2:1), NMR (DMSO-d6): δ 10.38 (1H, s), 8.02 (1H, t, J=3.6 Hz), 7.88 (2H, d, J=8.1 Hz), 7.80–7.77 (3H, m), 7.34 (2H, d, J=8.1 Hz), 3.58 (2H, d, J=3.6 Hz), 2.59 (3H, s), 2.40 (3H, s).

Example 2(76)

N-[[3-Methyl-4-(p-Toluoylamino)phenyl]sulfonyl]glycine

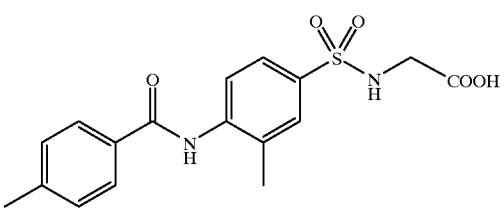

TLC: Rf 0.24 (Chloroform:Methanol=2:1), NMR (DMSO-d6): δ 12.64 (1H, br.s), 9.88 (1H, s), 7.94 (1H, t, J=6.2 Hz), 7.85 (2H, d, J=8.1 Hz), 7.66 (3H, m), 7.30 (2H, d, J=8.1 Hz), 3.55 (2H, d, J=6.2 Hz), 2.36 (3H, s), 2.28 (3H, s).

Example 2(77)

N-[[4-(2-Hydroxy-4-methylbenzoylamino)phenyl]sulfonyl]-D-alanine

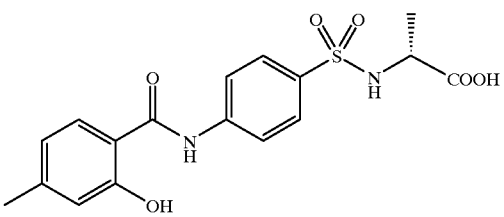

TLC: Rf 0.37 (Chloroform:Methanol=2:1), NMR (DMSO-d6): δ 12.62 (1H, br.s), 11.66 (1H, s), 10.56 (1H, s), 8.06 (1H, d, J=8.6 Hz), 7.93–7.70 (5H, m), 6.82 (1H, s), 6.80 (1H, d, J=7.2 Hz), 3.76 (1H, m), 2.31 (3H, s), 1.15 (3H, d, J=7.2 Hz).

Example 2(78)

N-[[4-(2-Thienylcarbonylamino)phenyl]sulfonyl]-D-alanine

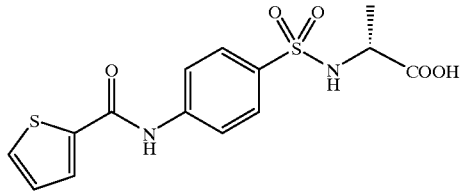

TLC: Rf 0.21 (Chloroform:Methanol:Water=4:1:0.1), NMR (DMSO-d6): δ 12.60 (1H, br.s), 10.49 (1H, s), 8.05–7.98 (2H, m), 7.91–7.85 (3H, m), 7.73 (2H, d, J=8.8 Hz), 7.21 (1H, t, J=3.8 Hz), 3.77–3.68 (1H, m), 1.13 (3H, d, J=7.2 Hz).

Example 2(79)

N-[[3-(Benzoylamino)phenyl]sulfonyl]glycine

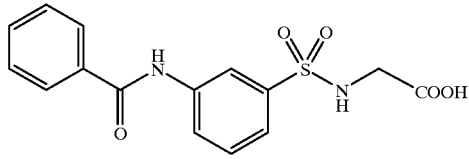

TLC: Rf 0.36 (Chloroform:Methanol:Acetic acid= 16:3:1), NMR (DMSO-d6): δ 10.54 (1H, s), 8.33 (1H, s), 8.14–7.90 (4H, m), 7.68–7.44 (5H, m), 3.60 (2H, d, J=6.0 Hz).

Example 2(80)

N-[[2-(Benzoylamino)phenyl]sulfonyl]glycine

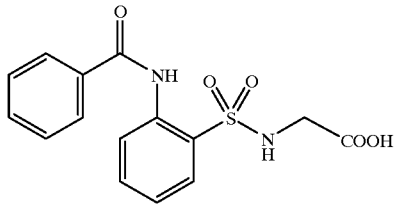

TLC: Rf 0.34 (Chloroform:Methanol:Acetic acid= 90:10:1), NMR (DMSO-d6): δ 13.00–12.60 (1H, br.s), 10.26 (1H, s), 8.67–8.56 (1H), 8.52–8.44 (1H, m), 8.02–7.92 (2H, m), 7.87 (1H, dd, J=1.4, 7.8 Hz), 7.74–7.54 (4H, m), 7.38–7.27 (1H, m), 3.65 (2H, d, J=4.6 Hz).

Example 3

N-[[4-(2-Aminobenzoylamino)phenyl]sulfonyl]glycine

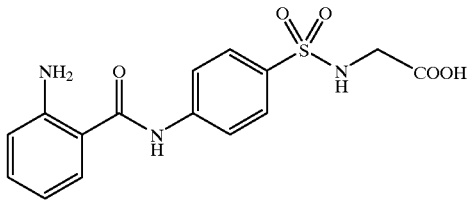

To a solution of the compound prepared in example 2(13) (569 mg) in N,N-dimethylformamide (7.5 ml) and methanol (7.5 ml), 10% palladium carbon (100 mg) and ammonium formate (378 mg) was added. The mixture was stirred for 1 hour at room temperature. The reaction mixture was filtered and the filtrate was concentrated. The residue was washed with water and ether and dried to give the title compound having the following physical data.

TLC: Rf 0.47 (Chloroform:Methanol:acetic acid= 2:1:0.1), NMR (DMSO-d6); δ 12.60 (1H, br.s), 10.30 (1H, s), 7.95–7.85 (3H, m), 7.74 (2H, d, J=8.8 Hz), 7.64 (2H, d, J=8.0 Hz), 7.22 (1H, t, J=8.0 Hz), 6.76 (1H, d, J=8.0 Hz), 6.60 (1H, t, J=8.0 Hz), 6.38 (2H, br), 3.56 (2H, d, J=6.2 Hz).

Example 3(1)–3(13)

The compounds having the following physical data were obtained by the same procedure as a series of reaction of Example 3, using a compound prepared in example 2(14), 2(15), 2(31), 2(33), 2(40), 2(41), 1(78), 1(79), 1(80), 1(81), 1(82), 1(83) and 1(84) instead of a compound prepared in example 2(13).

Example 3(1)

N-[[4-(3-Aminobenzoylamino)phenyl]sulfonyl]glycine

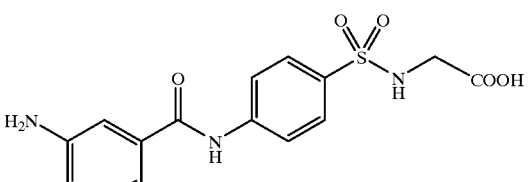

TLC: Rf 0.39 (Chloroform:Methanol:Acetic acid= 2:1:0.1), NMR (DMSO-d6): δ 10.41 (1H, s), 7.85–7.0 (3H, m), 7.74 (2H, d, J=8.4 Hz), 7.2–7.05 (3H, m), 6.77 (1H, d, J=7.6 Hz), 3.56 (2H, d, J=6.0 Hz).

Example 3(2)

N-[[4-(4-Aminobenzoylamino)phenyl]sulfonyl]
glycine

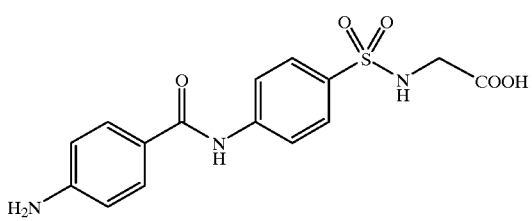

TLC: Rf 0.35 (Chloroform:Methanol:Acetic acid= 2:1:0.1), NMR (DMSO-d6): δ 12.60 (1H, br.s), 10.08 (1H, s), 7.94 (2H, d, J=8.8 Hz), 7.86 (1H, t, J=6.0 Hz), 7.73 and 7.72 (total 4H, each d, both J=8.8 Hz), 6.61 (2H, d, J=8.8 Hz), 5.83 (2H, br), 3.55 (2H, d, J=6.0 Hz).

Example 3(3)

N-[[4-(4-Hydroxybenzoylamino)phenyl]sulfonyl]
glycine

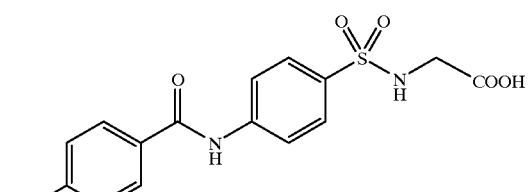

TLC: Rf 0.58 (Chloroform:Methanol:Acetic acid= 20:10:1), NMR (DMSO-d6): δ 10.31 (1H, s), 8.01–7.82 (1H, m), 7.95 (2H, d, J=8.8 Hz), 7.87 (2H, d, J=8.4 Hz), 7.75 (2H, d, J=8.8 Hz), 6.88 (2H, d, J=8.4 Hz), 3.53 (2H, m).

Example 3(4)

N-[[4-[(2-Phenylethyl)carbonylamino]phenyl]
sulfonyl]glycine

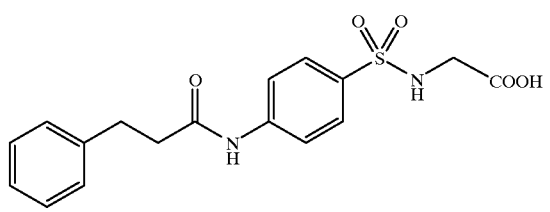

TLC: Rf 0.45 (Chloroform:Methanol:Acetic acid= 16:3:1), NMR (DMSO-d6): δ 10.29 (1H, s), 7.80–7.50 (5H, m), 7.36–7.08 (5H, m), 3.50–3.40 (2H, m), 3.00–2.78 (2H, m), 2.74–2.50 (2H, m).

Example 3(5)

N-[[4-(3-Hydroxybenzoylamino)phenyl]sulfonyl]
glycine

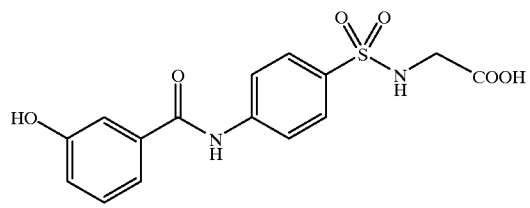

TLC: Rf 0.24 (Chloroform:Methanol:Acetic acid= 16:3:1), NMR (DMSO-d6): δ 10.48 (1H, s), 7.96 (2H, d, J=8.8 Hz), 7.95–7.76 (1H, m), 7.75 (2H, d, J=8.8 Hz), 7.44–7.28 (3H, m), 7.40–6.95 (1H, m), 3.60–3.50 (2H, m).

Example 3(6)

N-[[4-(2-Hydroxybenzoylamino)phenyl]sulfonyl]
glycine

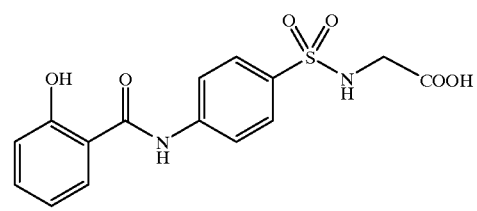

TLC: Rf 0.38 (Chloroform:Methanol:Acetic acid= 16:3:1), NMR (DMSO-d6): δ 13.20–10.80 (1H, br.s), 10.65 (1H, s), 8.00–7.84 (2H, m), 7.92 (2H, d, J=8.8 Hz), 7.78 (2H, d, J=8.8 Hz), 7.44 (1H, m), 7.06–6.92 (2H, m), 3.60–3.48 (2H, m).

Example 3(7)

N-[[4-(Benzoylamino)phenyl]sulfonyl]-L-tryptophan

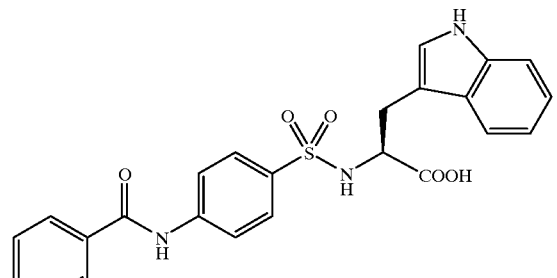

TLC: Rf 0.26 (Chloroform:Methanol:Acetic acid= 90:10:1), NMR (DMSO-d6): δ 13.50–11.60 (1H, br.s), 10.78 (1H, s), 10.49 (1H, s), 8.12–8.00 (1H, m), 7.97 (2H, dd, J=1.6, 7.6 Hz), 7.85 (2H, d, J=9.0 Hz), 7.64–7.49 (5H, m), 7.37–7.25 (2H, m), 7.10–6.86 (3H, m), 4.00–3.80 (1H, m), 3.06 (1H, dd, J=6.6 Hz, 14.4 Hz), 2.87 (1H, dd, J=7.2, 14.4 Hz).

Example 3(8)

N-[[4-(Benzoylamino)phenyl]sulfonyl]-L-tyrosine

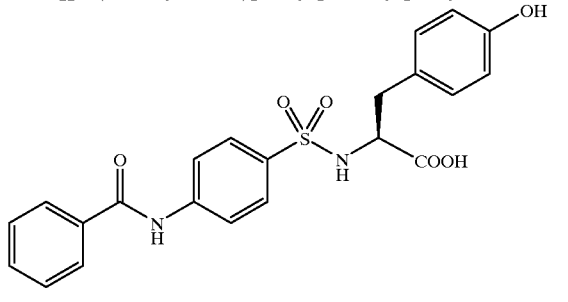

TLC: Rf 0.56 (Chloroform:Methanol:Acetic acid= 16:3:1), NMR (DMSO-d6): δ 10.53 (1H, s), 9.25–9.05 (1H, br.s), 8.00–7.93 (3H, m), 7.89 (2H, d, J=8.8 Hz), 7.61 (2H, d, J=8.8 Hz), 7.60–7.48 (3H, m), 6.92 (2H, d, J=8.4 Hz), 6.60 (2H, d, J=8.4 Hz), 3.80–3.64 (1H, m), 2.80 (1H, dd, J=5.8,13.6 Hz), 2.65 (1H, dd, J=7.6, 13.6 Hz).

Example 3(9)

N-[[4-(Benzoylamino)phenyl]sulfonyl]-D-tryptophan

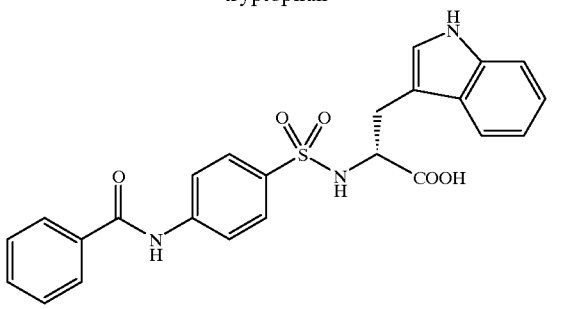

TLC: Rf 0.26 (Chloroform:Methanol:Acetic acid= 90:10:1), NMR (DMSO-d6): δ 12.80–12.30 (1H, br.s), 10.79 (1H, s), 10.50 (1H, s), 8.09 (1H, d, J=8.6 Hz), 8.02–7.93 (2H, m), 7.85 (2H, d, J=8.8 Hz), 7.68–7.50 (5H, m), 7.38–7.25 (2H, m), 7.11–6.87 (3H, m), 4.00–3.81 (1H, m), 3.05 (1H, dd, J=6.6, 14.8 Hz), 2.86 (1H, dd, J=7.8, 14.8 Hz).

Example 3(10)

N-[[4-(Benzoylamino)phenyl]sulfonyl]-D-tyrosine

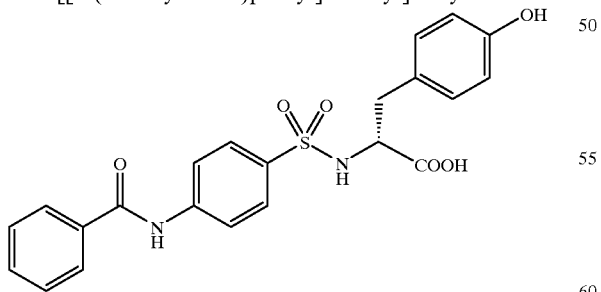

TLC: Rf 0.56 (Chloroform:Methanol:Acetic acid= 16:3:1), NMR (DMSO-d6): δ 12.80–12.00 (1H, br.s), 10.54 (1H, s), 9.20 (1H, s), 8.06 (1H, d, J=8.8 Hz), 8.02–7.93 (2H, m), 7.89 (2H, d, J=8.8 Hz), 7.70–7.50 (5H, m), 6.92 (2H, d, J=8.4 Hz), 6.61 (2H, d, J=8.4 Hz), 3.90–3.70 (1H, m), 2.81 (1H, dd, J=6.4, 13.6 Hz), 2.62 (1H, dd, J=8.2, 13.6 Hz).

Example 3(11)

N-[[4-(Benzoylamino)phenyl]sulfonyl]-D-histidine

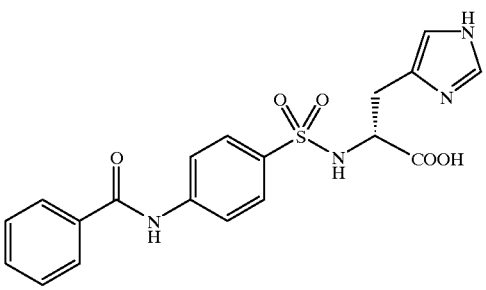

TLC: Rf 0.16 (Chloroform:Methanol:Acetic acid= 14:6:1), NMR (DMSO-d6): δ 10.82 (1H, s), 8.29 (1H, s), 8.10 (2H, d, J=9.0 Hz), 8.04 (2H, d, J=9.0 Hz), 8.00–7.92 (2H, m), 7.68–7.48 (4H, m), 7.45 (1H, s), 3.45–3.35 (1H, m), 3.05 (1H, dd, J=3.6, 15.6 Hz), 2.70 (1H, dd, J=9.0, 15.6 Hz).

Example 3(12)

2-[N-[4-(Benzoylamino)phenyl]sulfonylamino]-(3-pyridyl)-D-alanine

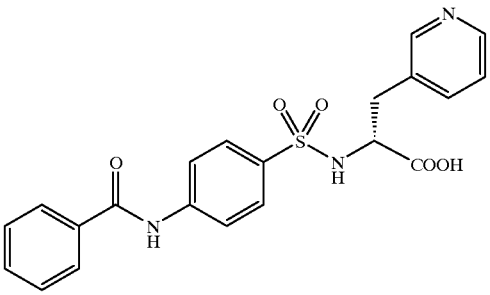

TLC: Rf 0.35 (Chloroform:Methanol:Acetic acid= 2:1:0.1), NMR (DMSO-d6): δ 12.84 (1H, br.s), 10.54 (1H, s), 8.37 (2H, m), 8.02 (1H, d, J=9.0 Hz), 7.96 (2H, m), 7.86 (2H, d, J=8.6 Hz), 7.65–7.5 (6H, m), 7.21 (1H, dd, J=4.9, 7.5 Hz), 3.89 (1H, m), 3.05–2.7 (2H, m).

Example 3(13)

N-[[4-(p-Toluoylamino)phenyl]sulfonyl]-D-tryptophan

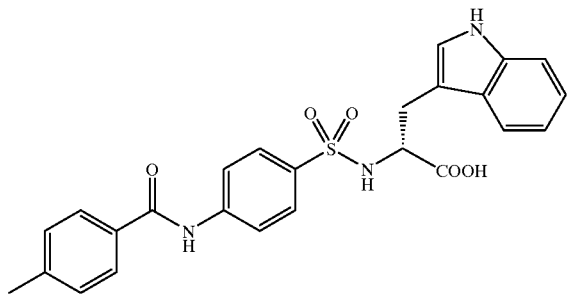

TLC: Rf 0.13 (Chloroform:Methanol:Acetic acid:Water= 100:10:1:1), NMR (DMSO-d6): δ 12.57 (1H, br.s), 10.8

(1H, s), 10.42 (1H, s), 8.13 (1H, d, J=8.8 Hz), 7.9–7.8 (4H, m), 7.59 (2H, d, J=8.8 Hz), 7.4–7.25 (4H, m), 7.1–6.9 (3H, m), 3.95–3.85 (1H, m), 3.04 (1H, dd, J=6.0, 18.0 Hz), 2.84 (1H, dd, J=7.4, 18.0 Hz), 2.39 (3H, s).

Reference Example 3

Sodium 4-(Benzyloxycarbonyloxy)benzenesulfonate

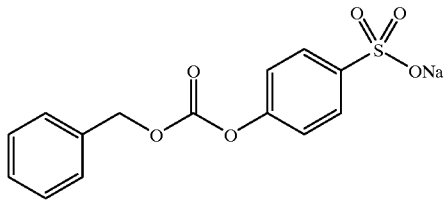

To an aqueous solution (40 ml) of sodium hydride (3.8 g), sodium 4-hydroxybenzenesulfonate dihydroxide (20 g) and tetrahydrofuran (28 ml) was added. To the mixture, benzyl chloroformate (12.3 ml) was added at 0° C. The mixture was stirred for 1 hour at 0° C. and for 1 hour at room temperature. The reaction mixture was concentrated. The precipitated crystals was washed with water and dried to give the title compound (18.1 g) having the following physical data.

NMR (CD$_3$OD): δ 7.85 (2H, d, J=8.0 Hz), 7–50–7.30 (5H, m), 7.25 (2H, d, J=8.0 Hz), 5.25 (2H, s).

Reference Example 4

4-(Benzyloxycarbonyloxy)benzenesulfonyl chloride

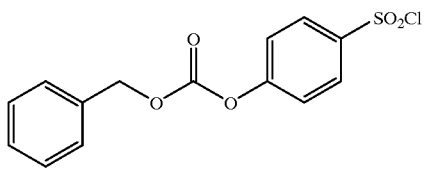

To a suspension of the compound prepared in reference example 3 (10.2 g) in N,N-dimethylformamide (30 ml), sulfonyl chloride (3.4 ml) was added at 0° C. The mixture was stirred for 1 hour at room temperature. The reaction mixture was poured into ice-water (50 ml). The precipitated crystals was washed with water and dried to give the title compound (9.6 g) having the following physical data.

NMR (CD$_3$OD): δ 8.10 (2H, d, J=8.0 Hz), 7.50 (2H, d, J=8.0 Hz), 7.45–7.40 (5H, m), 5.30 (2H, s).

Example 4

N-[[4-(Benzyloxycarbonyloxy)phenyl]sulfonyl] glycine t-butyl ester

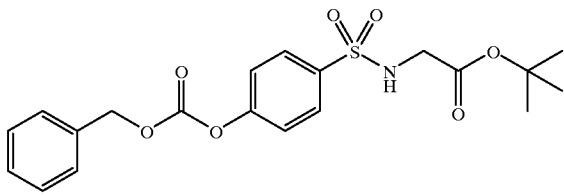

To a solution of glycine t-butyl ester hydrochloride (1.5 g) in pyridine (20 ml), a compound prepared in reference example 4 (3.0 g) was added. The mixture was stirred overnight at room temperature. The reaction mixture was concentrated and the residue was dissolved into ethyl acetate. The solution was washed with 1N hydrochloric acid, water and a saturated aqueous solution of sodium chloride, dried over anhydrous magnesium sulfate and concentrated to give the title compound (2.4 g) having the following physical data.

TLC: Rf 0.78 (Hexane:Ethyl acetate=1:1), NMR (CDCl$_3$); δ 7.90 (2H, d, J=8.0 Hz), 7.50–7.30 (5H, m), 7.35 (2H, d, J=8.0 Hz), 5.30 (2H, s), 5.05 (1H, t, J=6.0 Hz), 3.70 (2H, d, J=6.0 Hz), 1.40 (9H, s).

Reference Example 5

N-[4-(Hydroxyphenyl)sulfonyl]glycine t-butyl ester

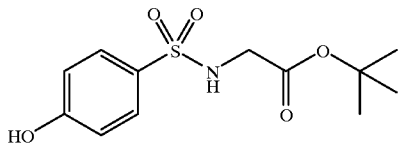

To a solution of a compound prepared in example 4 (2.3 g) in ethanol (50 ml), 10% palladium carbon (200 mg) was added. The mixture was stirred for 2 hours at room temperature under an atmosphere of hydrogen. The reaction mixture was filtered through celite (registered trade mark). The filtrate was concentrated. The residue was purified by column chromatography on silica gel (hexane:ethyl acetate= 3:1→2:1) to give the title compound (1.5 g) having the following physical data.

TLC: Rf 0.19 (Hexane:Ethyl acetate=2:1), NMR (CDCl$_3$): δ 7.70 (2H, d, J=8.0 Hz), 6.90 (2H, d, J=8.0 Hz), 3.75 (1H, br.s), 3.60 (2H, br.s), 1.40 (9H, s).

Example 5

N-[[4-(Benzoyloxy)phenyl]sulfonyl]glycine t-butyl ester

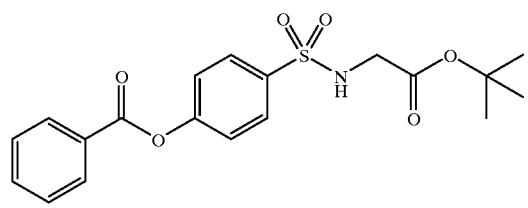

The compounds having the following physical data were obtained by the same procedure as a series of reaction of Example 1, using a compound prepared in reference example 5 instead of a compound prepared in reference example 2, and benzoyl chloride instead of p-toluoyl chloride.

TLC: Rf 0.62 (Hexane:Ethyl acetate=1:1), NMR (CDCl$_3$): δ 8.20 (2H, d, J=7.2 Hz), 7.95 (2H, d, J=9.0 Hz), 7.68 (1H, t, J=7.2 Hz), 7.54 (2H, t, J=7.2 Hz), 7.39 (2H, d, J=9.0 Hz), 5.07 (1H, t, J=5.2 Hz), 3.71 (2H, d, J=5.2 Hz), 1.39 (9H, s).

Example 5(1)–5(6)

The compounds having the following physical data were obtained by the same procedure as a series of reaction of Example 4, using the corresponding amino acid ester derivative instead of glycine t-butyl ester hydrochloride, and then by the same procedure as a series of reaction of reference example 5, and then by the same procedure as a series of reaction of Example 5, using a corresponding acyl chloride derivative or a corresponding carboxylic acid derivative and a condensing agent (e.g. 1,3-dicyclohexylcarbodiimide (DCC), 1-ethyl-3-[3-(dimethylamino)propyl] carbodiimide (EDC)) instead of benzoyl chloride, or converting to a corresponding salt by conventional method.

Example 5(1)

N-[[4-(4-Amidinobenzoyloxy)phenyl]sulfonyl]glycine t-butyl ester

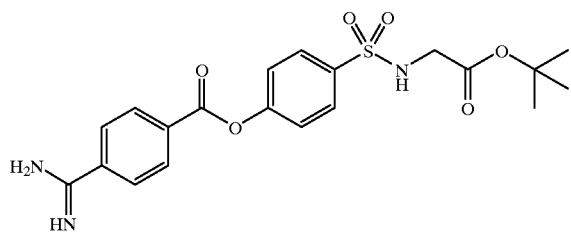

TLC: Rf 0.41 (Chloroform:Methanol:Acetic acid=10:2:1).

Example 5(2)

N-[[4-(4-Guanidinobenzoyloxy)phenyl]sulfonyl]glycine t-butyl ester

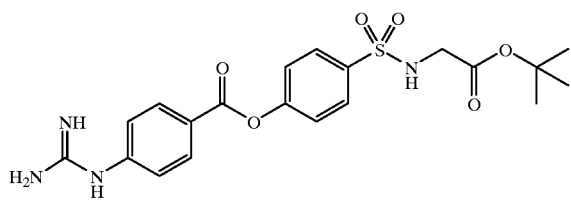

TLC: Rf 0.35 (Chloroform:Methanol:acetic acid=10:2:1).

Example 5(3)

N-[[4-(4-Amidinobenzoyloxy)phenyl]sulfonyl]-L-phenylalanine t-butyl ester

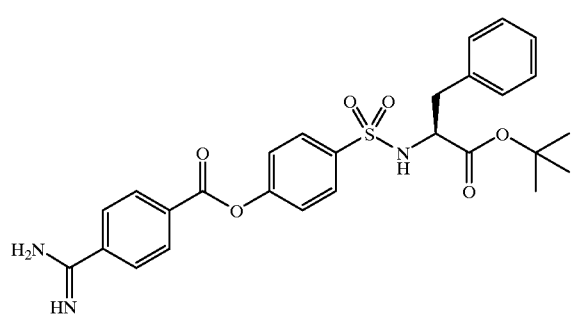

TLC: Rf 0.43 (Chloroform:Methanol:Acetic acid=10:2:1).

Example 5(4)

N-[[4-(Benzoyloxy)phenyl]sulfonyl]glycine ethyl ester

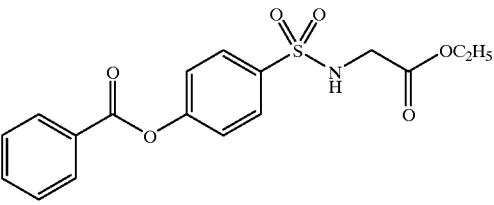

TLC: Rf 0.44 (Hexane:Ethyl acetate=1:1), NMR (CDCl$_3$): δ 8.20 (2H, d, J=7.0 Hz), 7.95 (2H, d, J=8.7 Hz), 7.68 (1H, m), 7.53 (2H, m), 7.40 (2H, d, J=8.7 Hz), 5.11(1H, t, J=5.4 Hz), 4.13 (2H, q, J=7.1 Hz), 3.82 (2H, d, J=5.4 Hz), 1.23 (3H, t, J=7.1 Hz).

Example 5(5)

N-[[4-(Benzoyloxy)phenyl]sulfonyl]-β-alanine t-butyl ester

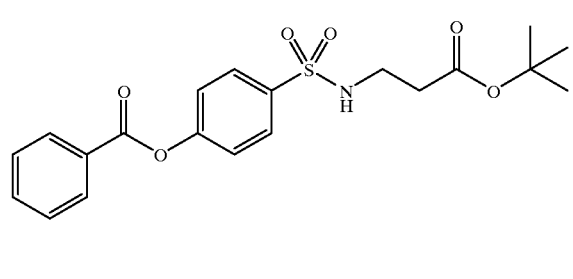

TLC Rf 0.77 (Ethyl acetate), NMR (CDCl$_3$): δ 8.21 (2H, d, J=8.0 Hz), 7.95 (2H, d, J=9.0 Hz), 7.68 (1H, t, J=8.0 Hz), 7.54 (2H, t, J=8.0 Hz), 7.40 (2H, d, J=9.0 Hz), 5.31 (1H, t, J=6.0 Hz), 3.19 (2H, q, J=6.0 Hz), 2.49 (2H, t, J=6.0 Hz), 1.44 (9H, s).

Example 5(6)

N-[[4-(4-Amidinobenzoyloxy)phenyl]sulfonyl]-β-alanine t-butyl ester acetate

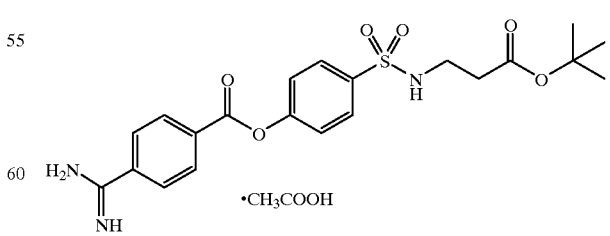

TLC: Rf 0.36 (Chloroform:Methanol:Acetic acid=10:2:1).

Example 6

N-[[4-(Benzoyloxy)phenyl]sulfonyl]glycine

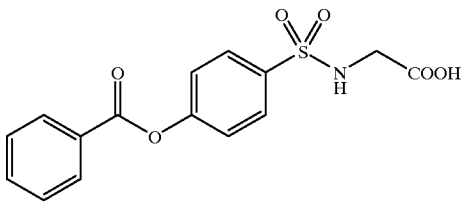

The title compound having the following physical data were obtained by the same procedure as a series of reaction of Example 2, using a compound prepared in example 5 instead of a compound prepared in example 1.

TLC: Rf 0.12 (Chloroform:Methanol:Water=90:10:1), NMR (CDCl$_3$+CD$_3$OD); δ 8.16 (2H, d, J=7.6 Hz), 7.93 (2H, d, J=9.0 Hz), 7.66 (1H, t, J=7.6 Hz), 7.55 (2H, t, J=7.6 Hz), 7.34 (2H, d, J=9.0 Hz), 3.77 (2H, s).

Example 6(1)–6(5)

The compounds having the following physical data were obtained by the same procedure as a series of reaction of Example 6, if necessary, by converting to corresponding salts by conventional method, using a compound prepared in example 5(1)–5(3), 5(5) and 5(6) instead of a compound prepared in example 5.

Example 6(1)

N-[[4-(4-Amidinobenzoyloxy)phenyl]sulfonyl]glycine methansulfonate

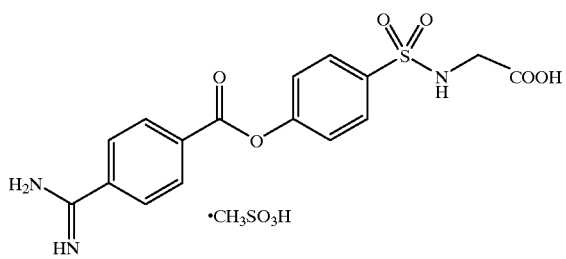

TLC: Rf 0.27 (Chloroform:Methanol:Acetic acid=3:1:1), NMR (DMSO-d6); δ 9.55 (2H, br.), 9.35 (2H, br.), 8.35 (2H, d, J=8.0 Hz), 8.00 (2H, d, J=8.0 Hz), 7.95 (d, J=9.0 Hz), 7.60 (2H, d, J=9.0 Hz), 3.60 (2H, br.), 3.40 (1H, br.), 2.40 (6H, s).

Example 6(2)

N-[[4-[[(4-Guanidinobenzoyloxy)phenyl]sulfonyl]glycine methansulfonate

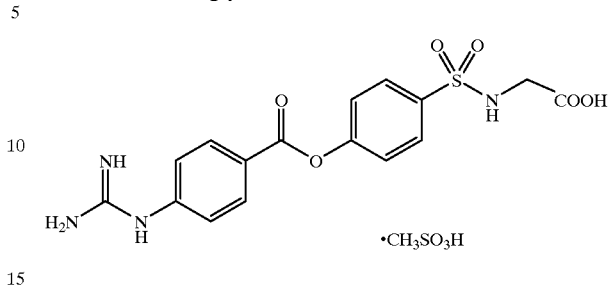

TLC: Rf 0.45 (Chloroform:Methanol:Acetic acid=3:1:1), NMR (CD$_3$OD): δ 8.25 (2H, d, J=8.0 Hz), 7.95 (2H, d, J=8.0 Hz), 7.45 (2H, d, J=8.0 Hz), 7.43 (2H, d, J=8.0 Hz), 3.73 (2H, s), 2.69 (3H, s).

Example 6(3)

N-[[4-[[(4-Amidinobenzoyloxy)phenyl]sulfonyl]-L-phenylalanine acetate

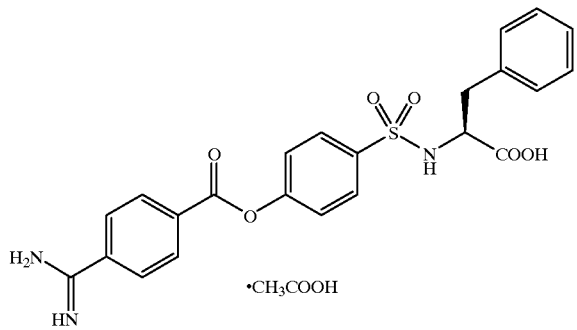

TLC: Rf 0.24 (Chloroform:Methanol:Acetic acid= 10:2:1), NMR (CD$_3$COOD): δ 8.40 (2H, d, J=7.5 Hz), 8.05 (2H, d, J=7.5 Hz), 7.80 (2H, d, J=8.0 Hz), 7.35 (2H, d, J=8.0 Hz), 7.30–7.15 (5H, m), 4.30 (1H, t, J=6.0 Hz), 3.20 (1H, dd, J=15, 6.0 Hz), 2.95 (1H, dd, J=15, 6.0 Hz).

Example 6(4)

N-[[4-(Benzoyloxy)phenyl]sulfonyl]-β-alanine

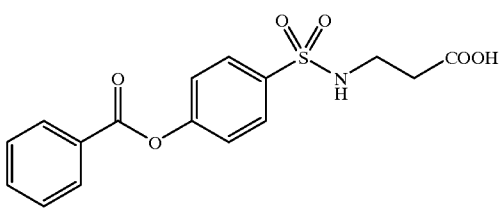

TLC : Rf 0.36 (Chloroform:Methanol:Acetic acid:Water= 100:10:1:1), NMR (CDCl$_3$+CD$_3$OD): δ 8.20 (2H, d, J=7.0 Hz), 7.95 (2H, d, J=9.0 Hz), 7.69 (1H, t, J=7.0 Hz), 7.55 (2H, t, J=7.0 Hz), 7.40 (2H, d, J=9.0 Hz), 3.22 (2H, t, J=6.0 Hz), 2.55 (2H, t, J=6.0 Hz).

Example 6(5)

N-[[4-(4-Amidinobenzoyloxy)phenyl]sulfonyl]-β-alanine

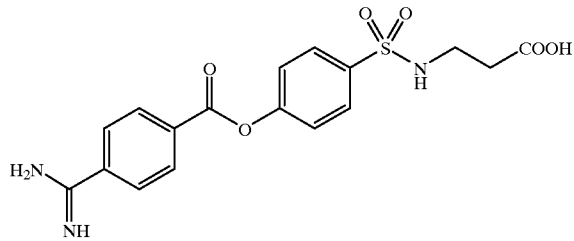

TLC: Rf 0.176 (Chloroform:Methanol:Acetic acid= 10:2:1), NMR (CD$_3$COOD): δ 8.40 (2H, d, J=7.5 Hz), 8.05 (2H, d, J=7.5 Hz), 8.00 (2H, d, J=8.0 Hz), 7.50 (2H, d, J=8.0 Hz), 3.25 (2H, t, J=6.0 Hz), 2.60 (2H, t, J=6.0 Hz).

Reference Example 6

4-(Methoxycarbonyl)benzenesulfonyl chloride

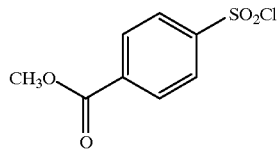

A suspension of 4-Carboxybenzenesulfonyl chloride (2.2 g) in thionyl chloride (10 ml) was refluxed for 1 hour. The reaction mixture was cooled to room temperature and concentrated. The residue was dissolved in methanol (10 ml), and stirred for 1 hours at room temperature. The reaction mixture was concentrated to give the title compound (2.3 g).

Reference Example 7

3-(Methoxycarbonyl)benzenesulfonyl chloride

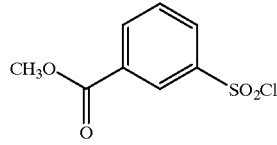

The title compound was obtained by the same procedure as a series of reaction of reference example 6, using 3-carboxybenzenesulfonyl chloride instead of 4-carboxybenzenesulfonyl chloride.

Example 7

N-[[4-(Methoxycarbonyl)phenyl]sulfonyl]glycine t-butyl ester

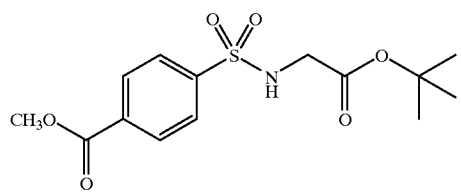

The title compound having the following physical data was obtained by the same procedure as a series of reaction of Example 4, using a compound prepared in reference example 6 instead of a compound prepared in reference example 4.

TLC: Rf 0.56 (Hexane:Ethyl acetate=1:1), NMR (CDCl$_3$): δ 8.16 (2H, d, J=8.8 Hz), 7.93 (2H, d, J=8.8 Hz), 5.09 (1H, t, J=5.4 Hz), 3.95 (3H, s), 3.70 (2H, d, J=5.4 Hz), 1.34 (9H, s).

Example 7(1)–7(8)

The compounds having the following physical data were obtained by the same procedure as a series of reaction of Example 7, using a compound prepared in reference example 6 or 7, and a corresponding amino acid.

Example 7(1)

N-[[4-(Methoxycarbonyl)phenyl]sulfonyl]-L-phenylalanine t-butyl ester

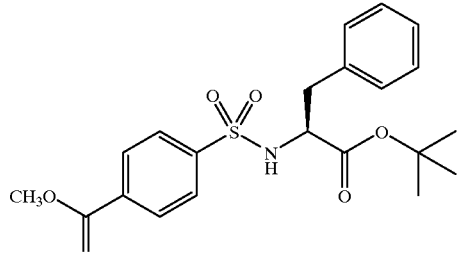

TLC: Rf 0.59 (Hexane:Ethyl acetate =2:1), NMR (CDCl$_3$); δ 8.10 (2H, d, J=8.0 Hz), 7.80 (2H, d, J=8.0 Hz), 7.30–7.20 (3H, m), 7.20–7.10 (2H, m), 5.15 (1H, d, J=9.0 Hz), 4.10 (1H, m), 3.95 (3H, s), 3.00 (2H, d, J=6.0 Hz), 1.20 (9H, s).

Example 7(2)

N-[[4-(Methoxycarbonyl)phenyl]sulfonyl]-L-aspartic acid di-t-butyl ester

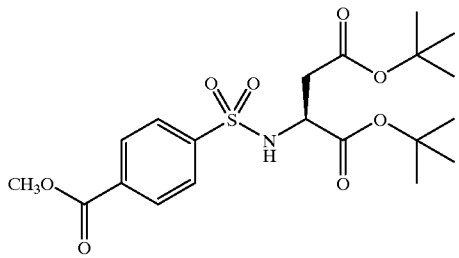

TLC: Rf 0.64 (Hexane:Ethyl acetate=2:1), NMR (CDCl₃): δ 8.10 (2H, d, J=8.0 Hz), 7.90 (2H, d, J=8.0 Hz), 5.65 (1H, d, J=9.0 Hz), 3.95 (1H, m), 3.90 (3H, s), 2.75 (1H, dd, J=15, 5.0 Hz), 2.65 (1H, d, J=15, 5.0 Hz), 1.35 (9H, s), 1.25 (9H, s).

Example 7(3)

N-[[3-(Methoxycarbonyl)phenyl]sulfonyl]glycine t-butyl ester

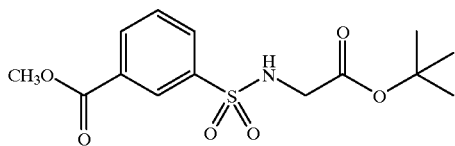

TLC: Rf 0.45 (Hexane:Ethyl acetate=2:1).

Example 7(4)

N-[(4-Methoxycarbonylphenyl)sulfonyl]-L-glutamic acid di-t-butyl ester

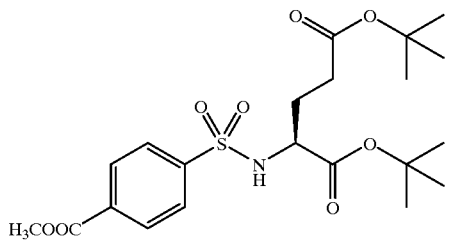

TLC: Rf 0.59 (Hexane:Ethyl acetate=1:1), NMR (CDCl₃): δ 8.14 (2H, d, J=9.0 Hz), 7.90 (2H, d, J=9.0 Hz), 5.31 (1H, d, J=9.0 Hz), 3.96 (3H, s), 3.92–3.80 (1H, m), 2.43–2.35 (2H, m), 2.16–1.98 (1H, m), 1.88–1.66 (1H, m), 1.46 (9H, s), 1.24 (9H, s).

Example 7(5)

N-[[4-Methoxycarbonylphenyl)sulfonyl]-L-aspartic acid di-t-butyl ester

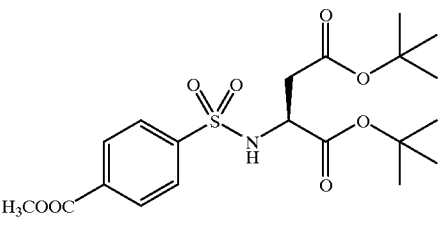

TLC: Rf 0.83 (Hexane:Ethyl acetate=1:1), NMR (CDCl₃): δ 8.15 (2H, d, J=9.0 Hz), 7.94 (2H, d, J=9.0 Hz), 5.72 (1H, d, J=9.0 Hz), 4.08–4.00 (1H, m), 3.96 (3H, s), 2.91–2.65 (2H, m), 1.43 (9H, s), 1.30 (9H, s).

Example 7(6)

N-[(3-Methoxycarbonylphenyl)sulfonyl]-L-aspartic acid di-t-butyl ester

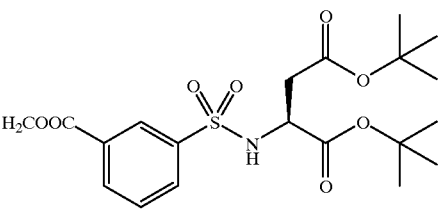

TLC: Rf 0.33 (Hexane:Ethyl acetate=8:2), NMR (CDCl₃): δ 8.51 (1H, t, J=2.0 Hz), 8.24 (1H, dt, J=8.0 Hz, 2 Hz), 8.06 (1H, dt, J=8.0 Hz, 2 Hz), 7.60 (1H, t, J=8.0 Hz), 5.73 (1H, d, J=9.0 Hz), 4.10–4.01 (1H, m), 3.96 (3H, s), 2.91–2.66 (2H, m), 1.41 (9H, s), 1.27 (9H, s).

Example 7(7)

N-[(3-Methoxycarbonylphenyl)sulfonyl]-L-glutamic acid di-t-butyl ester

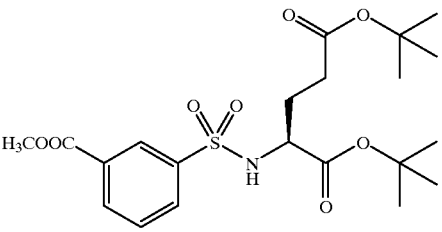

TLC: Rf 0.33 (Hexane:Ethyl acetate=1:1), NMR (CDCl₃): δ 8.48 (1H, t, J=2.0 Hz), 8.23 (1H, dt, J=8.0 Hz, 2 Hz), 8.02 (1H, dt, J=8.0 Hz, 2 Hz), 7.59 (1H, t, J=8.0 Hz), 5.32 (1H, d, J=9.0 Hz), 3.96 (3H, s), 3.92–3.81 (1H, m), 2.40 (2H, t, J=8.0 Hz), 2.13–1.96 (1H, m), 1.87–1.66 (1H, m), 1.46 (9H, s), 1.23 (9H, s).

Example 7(8)

N-[4-(Methoxycarbonylphenyl)sulfonyl]-β-alanine t-butyl ester

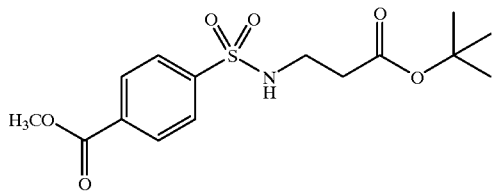

TLC: Rf 0.43 (Hexane:Ethyl acetate=2:1), NMR (CDCl$_3$): δ 8.20 (2H, d, J=8.0 Hz), 7.95 (2H, d, J=8.0 Hz), 5.40 (1H, t, J=6.0 Hz), 4.00 (3H, s), 3.20 (2H, dt, J=6.0 Hz, 6.0 Hz), 2.50 (3H, t, J=6.0Hz), 1.45 (9H, s).

Example 8

N-[(4-Carboxyphenyl)sulfonyl]glycine t-butyl ester

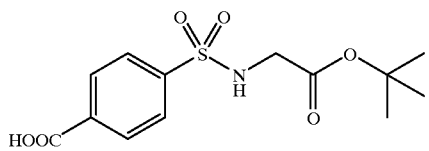

To a solution of a compound prepared in Example 7 (658 mg) in methanol (2 ml) and dioxane (2 ml), 5N aqueous solution of sodium hydroxide (0.8 ml) was added. The mixture was stirred for one day at room temperature. The reaction mixture was neutralized by adding 2N hydrochloric acid and extracted with ethyl acetate. The extract was dried over anhydrous magnesium sulfate and concentrated. The residue was purified by column chromatography on silica gel (methylene chloride:methanol:acetic acid:water= 100:10:1:1) to give the title compound (333 mg) having the following physical data.

TLC: Rf 0.49 (Chloroform:Methanol:Acetic acid:Water= 90:10:1:1), NMR (CD$_3$OD): δ 8.16 (2H, d, J=8.8 Hz), 7.94 (2H, d, J=8.8 Hz), 3.69 (2H, s), 1.31 (9H, s).

Example 8(1)–8(8)

The compounds having the following physical data were obtained by the same procedure as a series of reaction of Example 8, using a compound prepared in example 7(1)–7(8) instead of a compound prepared in example 7.

Example 8(1)

N-[(4-Carboxypheny)sulfonyl]-L-phenylalanine t-butyl ester

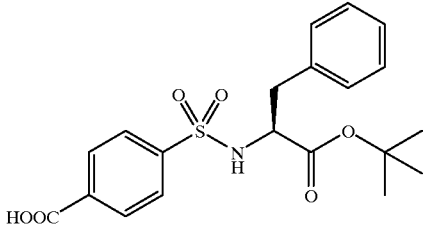

TLC: Rf 0.25 (Chloroform:Methanol=9:1), NMR (CDCl$_3$): δ 8.15 (2H, d, J=8.0 Hz), 7.85 (2H, d, J=8.0 Hz), 7.30–7.20 (3H, m), 7.20–7.10 (2H, m), 5.30 (1H, d, J=9.0 Hz), 4.15 (1H, m), 3.00 (2H, d, J=6.0 Hz), 1.25 (9H, s).

Example 8(2)

N-[(4-Carboxypheny)sulfonyl]-L-aspartic acid di-t-butyl ester

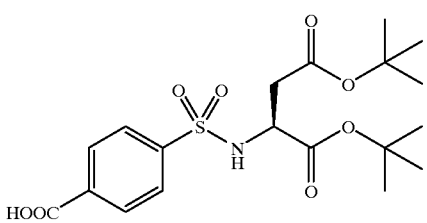

TLC: Rf 0.28 (Chloroform:Methanol=9:1), NMR (CDCl$_3$): δ 8.20 (2H, d, J=8.0 Hz), 8.00 (2H, d, J=8.0 Hz), 5.80 (1H, d, J=9.0 Hz), 4.05 (1H, m), 2.80 (2H, m), 1.40 (9H, s), 1.30 (9H, s).

Example 8(3)

N-[(3-Carboxypheny)sulfonyl]glycine t-butyl ester

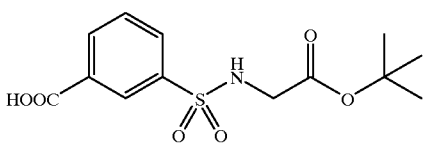

TLC: Rf 0.22 (Chloroform:Methanol=9:1).

Example 8(4)

N-[4-(Carboxypheny)sulfonyl]-L-glutamic acid di-t-butyl ester

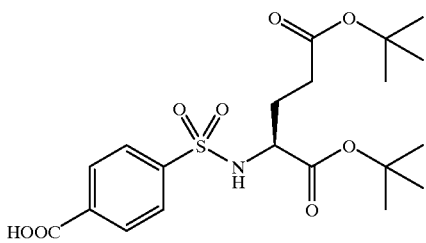

TLC: Rf 0.25 (Chloroform:Methanol=9:1), NMR (CDCl$_3$): δ 8.30–8.10 (2H, br.d, J=8.0 Hz), 8.10–7.80 (2H, br.d, J=8.0 Hz), 5.50–5.30 (1H, br.d, J=9.0 Hz), 4.00–3.78 (1H, m), 2.50–1.60 (8H, m), 1.43 (9H, s), 1.23 (9H, s).

Example 8(5)

N-[(4-Carboxypheny)sulfonyl]-L-aspartic acid di-t-butyl ester

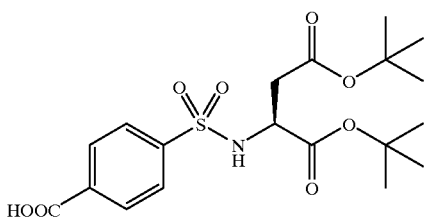

TLC: Rf 0.30 (Chloroform:Methanol=9:1), NMR (CDCl$_3$): δ 8.22–8.04 (2H, br.d, J=8.0 Hz), 7.96–7.76 (2H, br.d, J=8.0 Hz), 6.00–5.82 (1H, br.d, J=9.0 Hz), 4.16–4.00 (1H, m), 2.92–2.63 (2H, m), 1.40 (9H, s), 1.25 (9H, s).

Example 8(6)

N-[(3-Carboxypheny)sulfonyl]-L-aspartic acid di-t-butyl ester

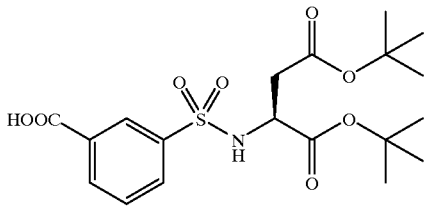

TLC: Rf 0.46 (Chloroform:Methanol:Water=8:2:0.1), NMR (CDCl$_3$): δ 8.63 (1H, t, J=2.0 Hz), 8.29 (1H, dt, J=8.0 Hz, 2.0 Hz), 8.12 (1H, dt, J=8.0 Hz, 2.0 Hz), 7.64 (1H, t, J=8.0 Hz), 6.00 (1H, d, J=9.0 Hz), 4.16–4.07 (1H, m), 2.94–2.69 (2H, m), 1.43 (9H, s), 1.28 (9H, s).

Example 8(7)

N-[(3-Carboxypheny)sulfonyl]-L-glutamic acid di-t-butyl ester

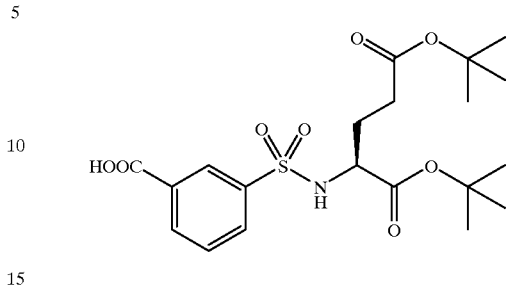

TLC: Rf 0.54 (Chloroform:Methanol:Water=8:2:0.1), NMR (CDCl$_3$): δ 8.57 (1H, t, J=2.0 Hz), 8.29 (1H, dt, J=8.0 Hz, 2.0 Hz), 8.08 (1H, dt, J=8.0 Hz, 2.0 Hz), 7.63 (1H, t, J=8.0 Hz), 5.61 (1H, d, J=9.0 Hz), 3.97–3.86 (1H, m), 2.42 (2H, t, J=7.0 Hz), 2.15–1.98 (1H, m), 1.90–1.72 (1H, m), 1.47 (9H, s), 1.25 (9H, s).

Example 8(8)

N-[(Carboxyphenyl)sulfonyl]-β-alanine t-butyl ester

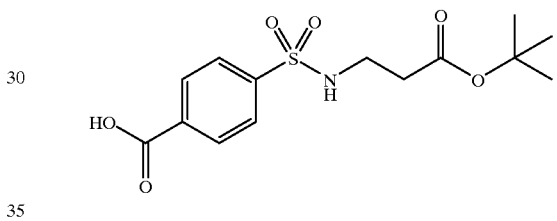

TLC: Rf 0.31 (Chloroform:Methanol=4:1), NMR (CDCl$_3$): δ 8.20 (2H, d, J=8.0 Hz), 7.95 (2H, d, J=8.0 Hz), 3.20 (2H, t, J=6.0 Hz), 2.45 (2H, t, J=6.0 Hz), 1.45 (9H, s).

Example 9

N-[[4-(Phenoxycarbonyl)phenyl]sulfonyl]glycine t-butyl ester

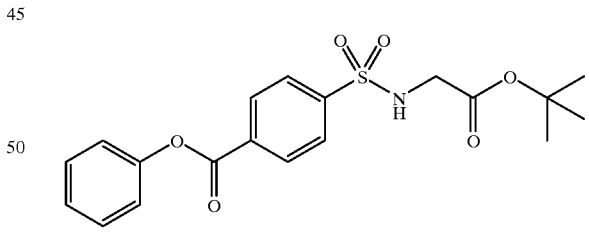

To a solution of a compound prepared in example 8 (221 mg) in pyridine (3.5 ml), phenol (79 mg), N,N-dimethylaminopyridine (9 mg) and dicyclohexylcarbodiimide (159 mg) were added successively. The mixture was stirred overnight and concentrated. The residue was purified by column chromatography on silica gel (hexane:ethyl acetate=5:1) to give the title compound having the following physical data.

TLC: Rf 0.77 (Ethyl acetate), NMR (CDCl$_3$): δ 8.35 (2H, d, J=8.8 Hz), 8.02 (2H, d, J=8.8 Hz), 7.47 (2H, t, J=6.0 Hz), 7.31 (1H, t, J=6.0 Hz), 7.22 (2H, d, J=6.0 Hz), 5.16 (1H, t, J=5.4 Hz), 3.74 (2H, d, J=5.4 Hz), 1.37 (9H, s).

Example 9(1)–9(10)

The compounds having the following physical data were obtained by the same procedure as a series of reaction of Example 9, if necessary, by converting to corresponding salts by conventional method, using a compound prepared in example 8 and 8(1)–8(8) and a corresponding alcohol and amine.

Example 9(1)

N-[[4-(4-Amidinophenoxycarbonyl)phenyl]sulfonyl]-L-phenylalanine t-butyl ester

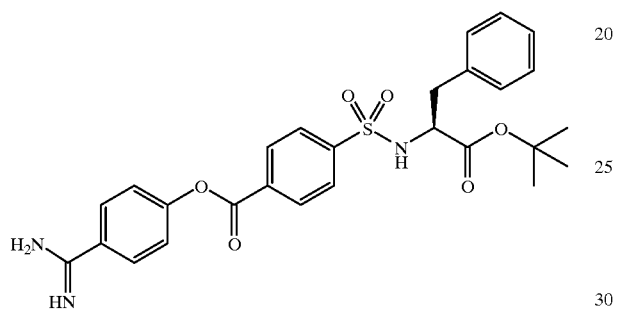

TLC Rf 0.45 (Chloroform:Methanol:Acetic acid=10:2:1), NMR (CD₃OD): δ 8.25 (2H, d, J=8.0 Hz), 7.95 (2H, d, J=8.0 Hz), 7.85 (2H, d, J=8.0 Hz), 7.55 (2H, d, J=8.0 Hz), 7.25–7.10 (5H, m), 4.00 (1H, t, J=7.5 Hz), 3.00 (1H, dd, J=15.0, 7.5 Hz), 2.85 (1H, dd, J=15.0, 7.5 Hz), 1.25 (9H, s).

Example 9(2)

N-[[4-(4-Amidinophenoxycarbonyl)phenyl]sulfonyl]-L-aspartic acid di-t-butyl ester

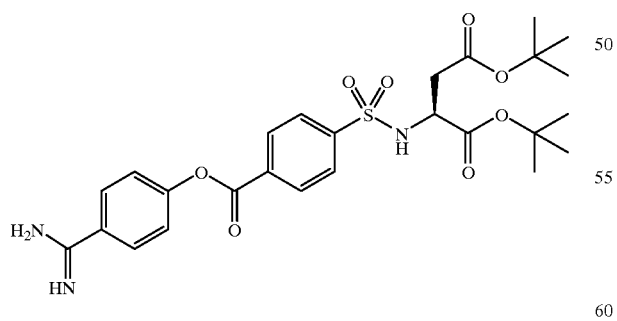

TLC Rf 0.51 (Chloroform:Methanol:Acetic acid=10:2:1), NMR (CD₃OD): δ 8.35 (2H, d, J=8.0 Hz), 8.05 (2H, d, J=8.0 Hz), 7.95 (2H, d, J=9.0 Hz), 7.55 (2H, d, J=9.0 Hz), 4.20 (1H, m), 2.60 (2H, m), 1.45 (9H, s), 1.30 (9H, s).

Example 9(3)

N-[[3-(4-Amidinophenoxycarbonyl)phenyl]sulfonyl]glycine t-butyl ester

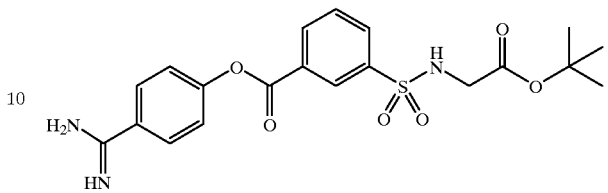

TLC : Rf 0.33 (Chloroform:Methanol:Acetic acid=10:2:1), NMR (CD₃OD): δ 8.60 (1H, s), 8.40 (1H, d, J=8.0 Hz), 8.20 (1H, d, J=8.0 Hz), 7.95 (2H, d, J=9.0 Hz), 7.80 (1H, t, J=8.0 Hz), 7.55 (2H, d, J=9.0 Hz), 3.75 (2H, s), 1.35 (9H, s).

Example 9(4)

N-[[4-(4-Amidinophenoxycarbonyl)phenyl]sulfonyl]glycine t-butyl ester

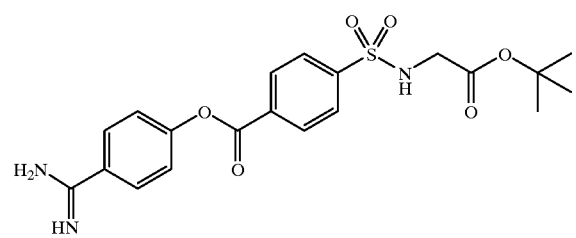

TLC: Rf 0.45 (Chloroform:Methanol:Acetic acid=10:2:1), NMR (CD₃OD): δ 8.35 (2H, d, J=8.0 Hz), 8.05 (2H, d, J=8.0 Hz), 7.95 (2H, d, J=8.0 Hz), 7.55 (2H, d, J=8.0 Hz), 3.75 (2H, s), 1.40 (9H, s).

Example 9(5)

N-[[4-(N-Phenylcarbamoyl)phenyl]sulfonyl]glycine t-butyl ester

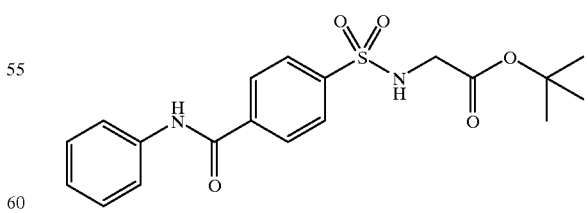

TLC Rf 0.40 (Hexane:Ethyl acetate=1:1), NMR (CDCl₃+CD₃OD); δ 8.04 (2H, d, J=8.8 Hz), 7.95 (2H, d, J=8.8 Hz), 7.69 (2H, d, J=8.0 Hz), 7.39 (2H, t, J=8.0 Hz), 7.18 (1H, t, J=8.0 Hz), 3.70 (2H, s), 1.36 (9H, s).

Example 9(6)

N-[[4-[N-(4-Amidinophenyl)carbamoyl]phenyl]sulfonyl]-L-glutamic acid di-t-butyl ester

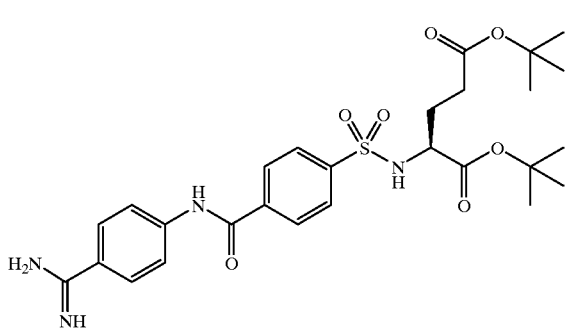

TLC: Rf 0.59 (Chloroform:Methanol:Acetic acid= 10:2:1), NMR (CD₃OD): δ 8.07 (2H, d, J=9.0 Hz), 7.99 (2H, d, J=8.0 Hz), 7.93 (2H, d, J=9.0 Hz), 7.80 (2H, d, J=8.0 Hz), 3.84 (1H, m), 2.35–2.23 (2H, m), 2.03–1.85 (1H, m), 1.76–1.55 (1H, m), 1.39 (9H, s), 1.21 (9H, s).

Example 9(7)

N-[[4-[N-(4-Amidinophenyl)carbamoyl]phenyl]sulfonyl]-L-aspartic acid di-t-butyl ester

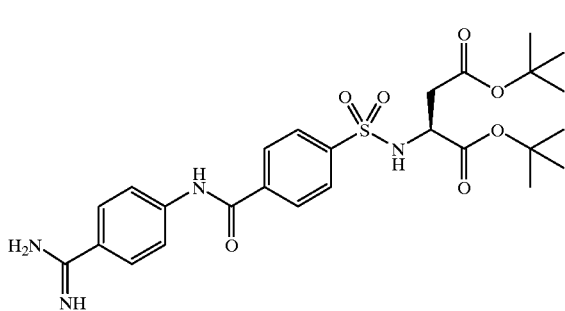

TLC Rf 0.59 (Chloroform:Methanol:Acetic acid=10:2:1), NMR (CD₃OD): δ 8.12 (2H, d, J=9.0 Hz), 8.04 (2H, d, J=8.0 Hz), 8.01 (2H, d, J=9.0 Hz), 7.85 (2H, d, J=8.0 Hz), 4.18 (1H, dd, J=7.0 Hz, 6.0 Hz), 2.70 (1H, dd, J=16 Hz, 6.0 Hz), 2.57 (1H, dd, J=16 Hz, 7 Hz), 1.44 (9H, s), 1.29 (9H, s).

Example 9(8)

N-[[3-[N-(4-Amidinophenyl)carbamoyl]phenyl]sulfonyl]-L-aspartic acid di-t-butyl ester

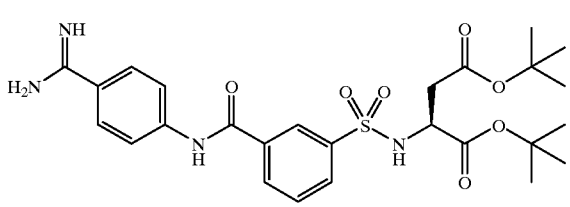

TLC: Rf 0.59 (Chloroform:Methanol:Acetic acid= 10:2:1), NMR (CD₃OD): δ 8.45 (1H, s), 8.20 (1H, d, J=8.0 Hz), 8.09 (1H, d, J=8.0 Hz), 8.05 (2H, d, J=9.0 Hz), 7.86 (2H, d, J=9.0 Hz), 7.73 (1H, t, J8.0 Hz), 4.21 (1H, dd, J=7.0 Hz, 6.0 Hz), 2.70 (1H, dd, J=16 Hz, 6.0 Hz), 2.57 (1H, dd, J=16 Hz, 7 Hz), 1.43 (9H, s), 1.27 (9H, s).

Example 9(9)

N-[[3-[N-(4-Amidinophenyl)carbamoyl]phenyl]sulfonyl]-L-glutamic acid di-t-butyl ester

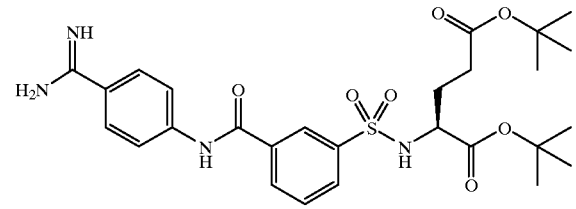

TLC: Rf 0.59 (Chloroform:Methanol:Acetic acid= 10:2:1), NMR (CD₃OD): δ 8.44 (1H, t, J=2.0 Hz), 8.22 (1H, dt, J=8.0 Hz, 2.0 Hz), 8.08 (1H, dt, J=8.0 Hz, 2.0 Hz), 8.06 (2H, d, J=9.0 Hz), 7.87 (2H, d, J=9.0 Hz), 7.74 (1H, t, J=8.0 Hz), 3.92 (1H, dd, J=9.0 Hz, 5.0 Hz), 2.37 (2H, m), 1.98 (1H, m), 1.76 (1H, m), 1.45 (9H, s), 1.25 (9H, s).

Example 9(10)

N-[[4-[(4-Amidinophenoxy)carbonyl]phenyl]sulfonyl]-β-alanine t-butyl ester acetate

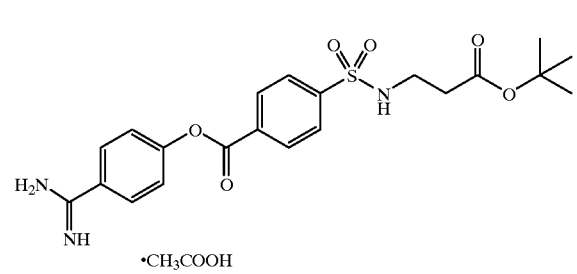

TLC: Rf 0.35 (Chloroform:Methanol:Acetic acid= 10:2:1), NMR (CD₃OD): δ 8.40 (2H, d, J=8.0 Hz), 8.05 (2H, d, J=8.0 Hz), 7.95 (2H, d, J=8.0 Hz), 7.60 (2H, d, J=8.0 Hz), 3.15 (2H, t, J=6.0 Hz), 2.45 (2H, t, J=6.0 Hz), 2.00 (3H, s), 1.45 (9H, s).

Example 10

N-[[4-(Phenoxycarbonyl)phenyl]sulfonyl]glycine

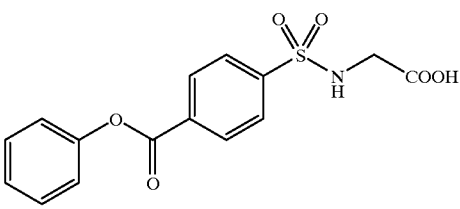

The title compound having the following physical data was obtained by the same procedure as a series of reaction of Example 2, using a compound prepared in example 9 instead of a compound prepared in example 1.

TLC: Rf 0.22 (Chloroform:Ethyl acetate:Acetic acid:Water=90:10:1:1), NMR (CDCl₃+CD₃OD): δ 8.33

(2H, d, J=8.8 Hz), 8.02 (2H, d, J=8.8 Hz), 7.46 (2H, t, J=7.4 Hz), 7.33 (1H, t, J=7.4 Hz), 7.21 (2H, d, J=7.4 Hz), 3.81 (2H, s).

Example 10(1)–10(12)

The compounds having the following physical data were obtained by the same procedure as a series of reaction of Example 10, if necessary, by converting to the corresponding acid addition salts by conventional method, using a compound prepared in example 7, 8 and 9(1)–9(10).

Example 10(1)

N-[[4-(4-Amidinophenoxycarbonyl)phenyl]sulfonyl]-L-phenylalanine methansulfonate

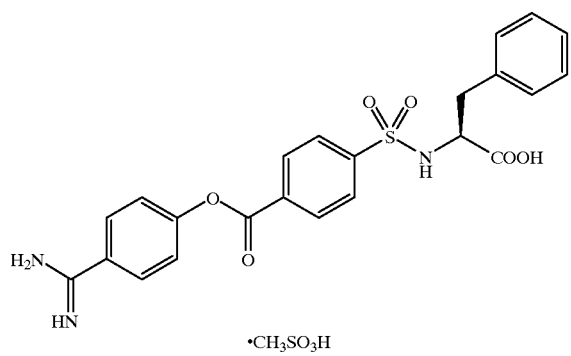

TLC: Rf 0.74 (Chloroform:Methanol:Acetic acid=3:1:1), NMR (CD$_3$OD): δ 8.20 (2H, d, J=8.0 Hz), 7.95 (2H, d, J=8.0 Hz), 7.80 (2H, d, J=8.0 Hz), 7.60 (2H, d, J=8.0 Hz), 7.25–7.10 (5H, m), 4.10 (1H, dd, J=9.0, 5.0 Hz), 3.10 (1H, dd, J=14, 5.0 Hz), 2.85 (1H, dd, J=14, 9.0 Hz), 2.70 (3H, s).

Example 10(2)

N-[[4-(4-Amidinophenoxycarbonyl)phenyl]sulfonyl]-L-aspartic acid methansulfonate

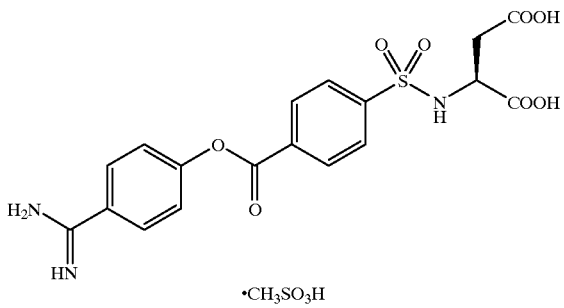

TLC Rf 0.21 (Chloroform:Methanol:Acetic acid=3:1:1), NMR (CD$_3$OD): δ 8.35 (2H, d, J=8.0 Hz), 8.10 (2H, d, J=8.0 Hz), 7.95 (2H, d, J=8.0 Hz), 7.55 (2H, d, J=8.0 Hz), 4.30 (1H, t, J=6.5 Hz), 2.80 (2H, d, J=6.5 Hz), 2.70 (3H, s).

Example 10(3)

N-[[3-(4-Amidinophenoxycarbonyl)phenyl]sulfonyl]glycine methansulfonate

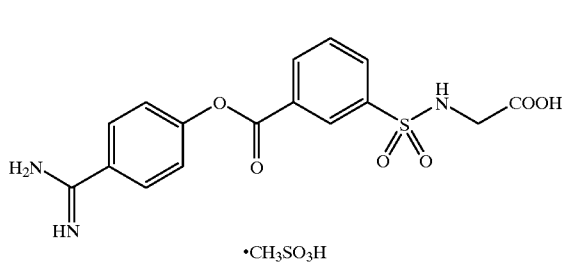

TLC: Rf 0.27 (Chloroform:Methanol:Acetic acid=3:1:1), NMR (CD$_3$OD): δ 8.85 (1H, br.s), 8.40 (1H, d, J=8.0 Hz), 8.20 (1H, d, J=8.0 Hz), 7.95 (2H, d, J=9.0 Hz), 7.80 (1H, t, J=8.0 Hz), 7.60 (2H, d, J=9.0 Hz), 3.80 (2H, s), 2.70 (3H, s).

Example 10(4)

N-[[4-(4-Amidinophenoxycarbonyl)phenyl]sulfonyl]glycine methansulfonate

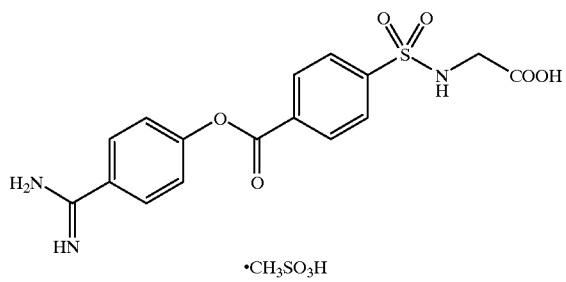

TLC: Rf 0.30 (Chloroform:Methanol:Acetic acid=3:1:1), NMR (CD$_3$OD): δ 8.35 (2H, d, J=8.0 Hz), 8.05 (2H, d, J=8.0 Hz), 7.95 (2H, d, J=9.0 Hz), 7.60 (2H, d, J=9.0 Hz), 3.80 (2H, s), 2.70 (3H, s).

Example 10(5)

N-[[4-(N-Phenylcarbamoyl)phenyl]sulfonyl]glycine

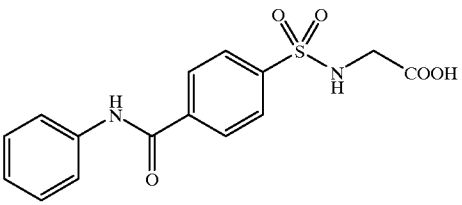

TLC: Rf 0.04 (Chloroform:Methanol:Acetic acid:Water=100:10:1:1), NMR (CDCl$_3$+CD$_3$OD+DMSO-d6): δ 8.10 (2H, d, J=8.3 Hz), 7.95 (2H, d, J=8.3 Hz), 7.75 (2H, d, J=8.0 Hz), 7.35 (2H, t, J=8.0 Hz), 7.13 (1H, t, J=8.0 Hz), 3.67 (2H, s).

Example 10(6)

N-[(4-Methoxycarbonylphenyl)sulfonyl]glycine

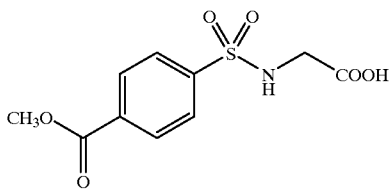

TLC: Rf 0.16 (Chloroform:Methanol:Acetic acid:Water= 90:10:1:1), NMR (CDCl$_3$+CD$_3$OD): δ 8.13 (2H, d, J=8.8 Hz), 7.90 (2H, d, J=8.8 Hz), 3.92 (3H, s), 3.74 (2H, s).

Example 10(7)

N-[(4-Carboxyphenyl)sulfonyl]glycine

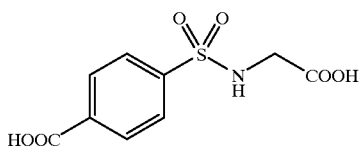

TLC: Rf 0.02 (Chloroform:Methanol:Acetic acid:Water= 90:10:1:1), NMR (DMSO-d6): δ 8.25 (1H, t, J=6.2 Hz), 8.08 (2H, d, J=8.8 Hz), 7.89 (2H, d, J=8.8 Hz), 3.63 (2H, d, J=6.2 Hz).

Example 10(8)

N-[[4-[N-(4-Amidinophenyl)carbamoyl]phenyl]sulfonyl]-L-glutamic acid

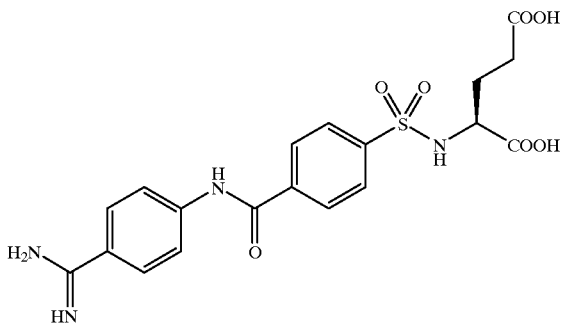

TLC: Rf 0.51 (Ethyl acetate:Acetic acid:Water=3:1:1), NMR (DMSO-d6+MeSO$_3$H(1 drop)): δ 10.85 (1H, s), 9.24 (2H, s), 8.98 (2H, s), 8.39 (1H, d, J=9.0 Hz), 8.15 (2H, d, J=9.0 Hz), 8.03 (2H, d, J=9.0 Hz), 7.93 (2H, d, J=9.0 Hz), 7.87 (2H, d, J=9.0 Hz), 3.85 (1H, dt, J=9.0 Hz, 7 Hz), 2.23 (2H, t, J=7.0 Hz), 2.00–1.60 (2H, m).

Example 10(9)

N-[[4-[N-(4-Amidinophenyl)carbamoyl]phenyl]sulfonyl]-L-aspartic acid

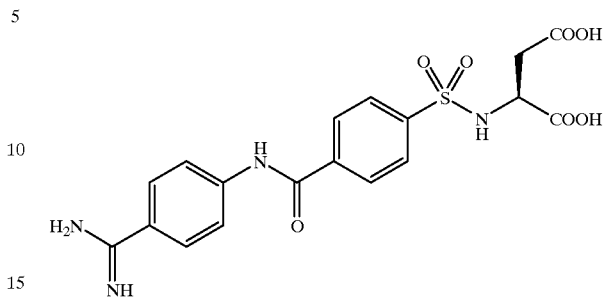

TLC: Rf 0.51 (Ethyl acetate:Acetic acid:Water=3:1:1), NMR (DMSO-d6+MeSO$_3$H(1 drop)): δ 10.85 (1H, s), 9.24 (2H, s), 8.97 (2H, s), 8.43 (1H, d, J=9.0 Hz), 8.14 (2H, d, J=9.0 Hz), 8.03 (2H, d, J=9.0 Hz), 7.95 (2H, d, J=9.0 Hz), 7.87 (2H, d, J=9.0 Hz), 4.13 (1H, dt, J=9.0 Hz, 6.0 Hz), 2.64 (1H, dd, J=16.0 Hz, 6.0 Hz), 2.46 (1H, dd, J=16.0 Hz, 6.0 Hz).

Example 10(10)

N-[[3-[N-(4-Amidinophenyl)carbamoyl]phenyl]sulfonyl]-L-aspartic acid

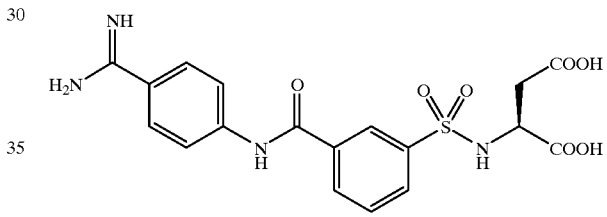

TLC: Rf 0.67 (Ethyl acetate:Acetic acid:Water 3:1:1), NMR (DMSO-d6+MeSO$_3$H(1 drop)): δ 10.88 (1H, s), 9.24 (2H, s), 8.95 (2H, s), 8.40 (1H, s), 8.23 (1H, d, J=8.0 Hz), 8.03 (2H, d, J=9.0 Hz), 8.02 (1H, d, J=8.0 Hz), 7.87 (2H, d, J=9.0 Hz), 7.76 (1H, t, J=8.0 Hz), 4.14 (1H, m), 2.64 (1H, dd, J=16 Hz, 6.0 Hz), 2.46 (1H, dd, J=16 Hz, 6.0 Hz).

Example 10(11)

N-[[3-[N-(4-Amidinophenyl)carbamoyl]phenyl]sulfonyl]-L-glutamic acid

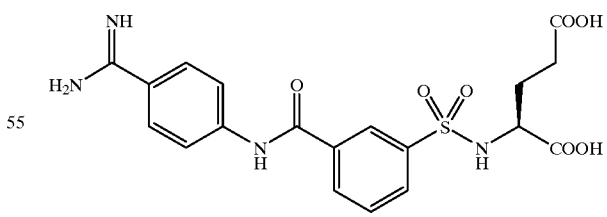

TLC Rf 0.65 (Ethyl acetate:Acetic acid:Water=3:1:1), NMR (DMSO-d6+MeSO$_3$H(1 drop)): δ 10.88 (1H, s), 9.24 (2H, s), 9.01 (2H, s), 8.37 (1H, s), 8.35 (1H, d, J=8.0 Hz), 8.24 (1H, d, J=8.0 Hz), 8.03 (2H, d, J=9.0 Hz), 8.01 (1H, d, J=8.0 Hz), 7.87 (2H, d, J=9.0 Hz), 7.76 (1H, d,J=8.0 Hz), 3.85 (1H, m), 2.22 (2H, t, J=7.0 Hz), 1.90 (1H, m), 1.69 (1H, m).

Example 10(12)

N-[[4-(4-Amidinophenoxycarbonyl)phenyl]sulfonyl]-β-alanine methansulfonate

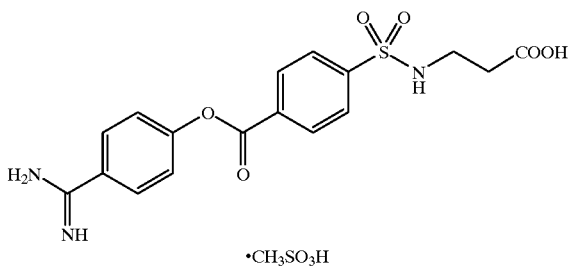

·CH₃SO₃H

TLC: Rf 0.34 (Chloroform:Methanol:Acetic acid= 10:2:1), NMR (CD₃OD): δ 8.40 (2H, d, J=8.0 Hz), 8.05 (2H, d, J=8.0 Hz), 7.95 (2H, d, J=8.0 Hz), 7.60 (2H, d, J=8.0 Hz), 3.20 (2H, t, J=6.5 Hz), 2.75 (3H, s), 2.55 (2H, t, J=6.5 Hz).

Example 11

N-[[4-(N-Phenylureido)phenyl]sulfonyl]glycine t-butyl ester

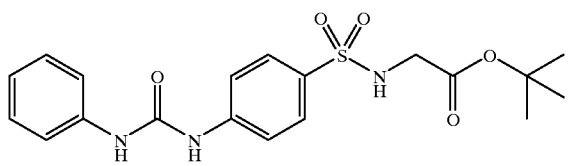

To a solution of a compound prepared in reference example 2 (1.20 g) in acetone (20 ml), phenyl isocyanate (500 µl) was added. After the mixture was stirred for 24 hours at room temperature, phenyl isocyanate (200 µl) was added to the mixture. The mixture was stirred for 24 hours. The additional phenyl isocyanate (500 µl) was added to it and the mixture was stirred for 12 hours. The reaction mixture was concentrated. The residue was washed with ether and dried to give the title compound (1.40 g) having the following physical data.

TLC: Rf 0.25 (Hexane:Ethyl acetate=1:1), NMR (CDCl₃): δ 7.72–7.60 (1H), 7.66 (2H, d, J=8.8 Hz), 7.46–7.20 (5H, m), 7.28 (2H, d, J=8.8 Hz), 7.12–7.00 (1H, m), 5.39 (1H, t, J=5.6 Hz), 3.63 (2H, d, J=5.6 Hz), 1.36 (9H, s).

Example 12

N-[[4-(N-Phenylureido)phenyl]sulfonyl]glycine

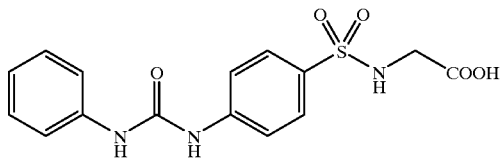

The title compound having the following physical data was obtained by the same procedure as a series of reaction of Example 2, using a compound prepared in example 11.

TLC: Rf 0.34 (Chloroform:Methanol:Acetic acid= 16:3:1), NMR (DMSO-d6): δ 13.50–11.50 (1H, br.s), 9.08 (1H, s), 8.77 (1H, s), 7.82 (1H, t, J=6.2 Hz), 7.69 (2H, d, J=9.0 Hz), 7.60 (2H, d, J=9.0 Hz), 7.52–7.40 (2H, m), 7.28 (2H, t, J=7.4 Hz), 6.98 (1H, t, J=7.4 Hz), 3.53 (2H, d, J=6.2 Hz).

Reference Example 8

2-(4-Chlorosulfonyl)phenylacetophenone

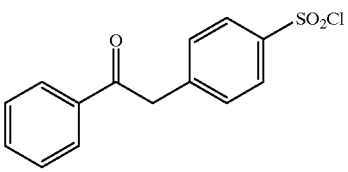

Deoxybenzoine (5.0 g) was added by portions to sulfonyl chloride (8.45 ml) at 0° C. The solution was stirred for 30 minutes at 10–15° C. and then stirred for 15 minutes at 50° C. The reaction mixture was poured into ice-water and extracted with ethyl acetate. The extract was washed with water, a saturated aqueous solution of sodium chloride, dried over anhydrous magnesium sulfate and concentrated. The residue was washed with ether and dried to give the title compound (2.25 g). Besides, the ether layer was purified by column chromatography on silica gel (hexane ethyl acetate =17:3) to give the additional title compound (1.09 g; total 3.34 g) having the following physical data.

TLC: Rf 0.27 (Hexane:Ethyl acetate=9:1).

Example 13

N-[(4-Benzoylmethylphenyl)sulfonyl]glycine t-butyl ester

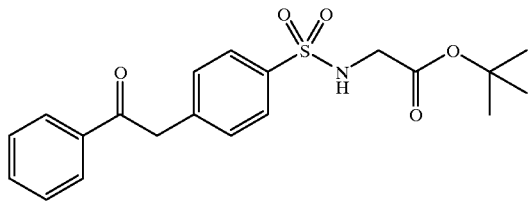

The title compound having the following physical data was obtained by the same procedure as a series of reaction of Example 4, using a compound prepared in reference example 8.

TLC: Rf 0.21 (Hexane:Ethyl acetate=7:3), NMR (CDCl₃): δ 8.05–7.97 (2H, m), 7.83 (2H, d, J=8.6 Hz), 7.65–7.45 (3H, m), 7.41 (2H, d, J=8.6 Hz), 5.05 (1H, t, J=5.4 Hz), 4.35 (2H, s), 3.67 (2H, d, J=5.4 Hz), 1.34 (9H, s).

Example 14

N-[(4-Benzoylmethylphenyl)sulfonyl]glycine

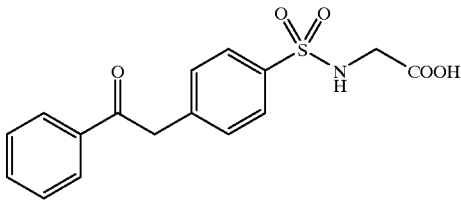

The title compound having the following physical data was obtained by the same procedure as a series of reaction of Example 3, using a compound prepared in example 13.

TLC: Rf 0.56 (Chloroform:Methanol:Acetic acid=6:3:1), NMR (DMSO-d6): δ 13.50–11.50 (1H, br.s), 8.10–8.00 (2H, m), 7.98 (1H, t, J=6.2 Hz), 7.74 (2H, d, J=8.4 Hz), 7.72–7.50 (3H, m), 7.45 (2H, d, J=8.4 Hz), 4.53 (2H, s), 3.57 (2H, d, J=6.2 Hz).

Example 14(1)

N-[4-[(4-Methoxybenzoyl)methyl]sulfonyl]glycine

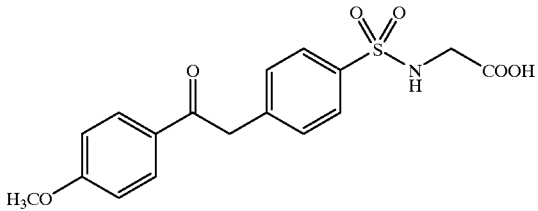

The title compound having the following physical data was obtained by the same procedure as a series of reaction of example 3, using N-[4-[(4-Methoxybenzoyl)methyl]sulfonyl]glycine t-butyl ester which was obtained by the same procedure as a series of reaction of reference example 8 and example 14 using the corresponding compounds.

TLC: Rf 0.35 (Chloroform:Methanol:Acetic acid:Water=50:10:1:1), NMR (CDCl₃+CD₃OD): δ 8.00 (2H, d, J=8.8 Hz), 7.82 (2H, d, J=8.3 Hz), 7.41 (2H, d, J=8.3 Hz), 6.98 (2H, d, J=8.8 Hz), 4.36 (2H, s), 3.90 (3H, s), 3.71 (2H, s).

Reference Example 9

N-[[4-(Benzoylamino)phenyl]sulfonyl]-N-t-butoxycarbonylglycine t-butyl ester

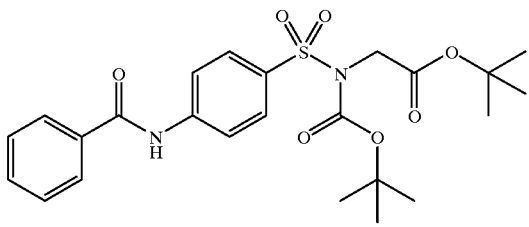

To a solution of a compound prepared in example 1(10) (1.20 g) in acetonitrile (60 ml), 4-dimethylaminopyridine (37 mg) and di-t-butyl dicarbonate (811 μl) were added. The mixture was stirred for 30 minutes at room temperature. The reaction mixture was concentrated and extracted with ethyl acetate. The extract was washed with water, a saturated aqueous solution of sodium bicarbonate, water and a saturated aqueous solution of sodium chloride, successively, dried over anhydrous magnesium sulfate and concentrated to give the title compound (1.61 g) having the following physical data.

TLC: Rf 0.61 (Hexane:Ethyl acetate=1:1).

Reference Example 10

N-[[4-(N-Methyl-N-benzoylamino)phenyl]sulfonyl]-N-tbutoxycarbonylglycine t-butyl ester

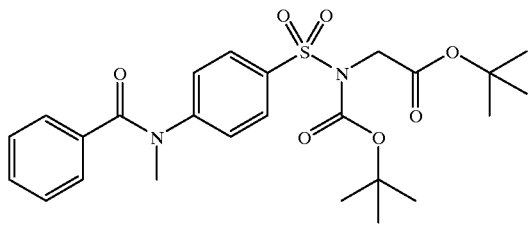

To a solution of a compound prepared in reference example 9 (1.60 g) in dimethylformamide (20 ml), 60% sodium hydride (143 mg) was added at 0° C. The mixture was stirred for 1 hour. To the reaction mixture, Iodomethane (558 μl) was added. The mixture was stirred for 30 minutes. Water was added to the reaction mixture, and then the mixture was extracted with ethyl acetate. The extract was washed a saturated aqueous solution of sodium chloride, dried over anhydrous magnesium sulfate and concentrated. The residue was purified by column chromatography on silica gel (hexane:ethyl acetate=7:3) to give the title compound (1.05 g) having the following physical data.

TLC: Rf 0.54 (Hexane:Ethyl acetate=1:1).

Example 15

N-[[4-(N-Methyl-N-benzoylamino)phenyl]sulfonyl]glycine

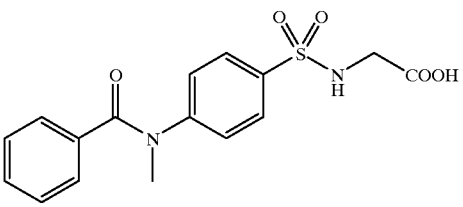

The title compound (641 mg) having the following physical data was obtained by the same procedure as a series of reaction of Example 2, using a compound prepared in reference example 10 (1.00 g).

TLC: Rf 0.47 (Chloroform:Methanol:Acetic acid=16:3:1), NMR (DMSO-d6): δ 13.20–12.00 (1H, br.s), 8.00 (1H, t, J=5.8 Hz), 7.65 (2H, d, J=8.8 Hz), 7.33 (2H, d, J=8.8 Hz), 7.31–7.20 (5H, m), 3.51 (2H, d, J=5.8 Hz), 3.40 (3H, s).

Formulation Example 1

The following components were admixed in conventional method and punched out to obtain 100 tablets each containing 50 mg of active ingredient.

| | |
|---|---|
| N-[[4-(p-Toluoylamino)phenyl]sulfonyl]glycine | 5 g |
| Carboxymethyl Cellulose calcium (disintegrating agent) | 0.2 g |
| Magnesium stearate (lubricating agent) | 0.1 g |
| Microcrystalline cellulose | 4.7 g |

Formulation Example 2

The following components were admixed in conventional method. The solution was sterilized in conventional manner, placed 2 ml portions into 5 ml ampoules and freeze-dried to obtain 100 ampoules each containing 20 mg of the active ingredient.

| | |
|---|---|
| N-[[4-(p-Toluoylamino)phenyl]sulfonyl]glycine | 2.00 g |
| mannitol | 20 g |
| distilled water | 500 ml |

What is claimed is:

1. A method for the treatment of rheumatiod, arthrosteitis, unusual bone resorption, osteoporosis, peridontisis, interstitial nephritis, arteriosclerosis, pulmonary emphysema, cirrhosis, cornea injury, metastasis of, invasion on or growth of tumor cells, autoimmune disease (Chrohn's disease, Sjogren's syndrome), disease caused by vascular emigration or infiltration of leukocytes, arterialization, which comprises the administration of an effective amount of a compound of the formula (Ia):

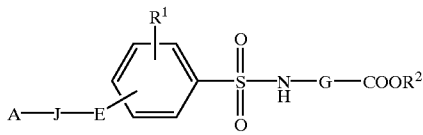

(Ia)

wherein $R^1$ is hydrogen, or C1–4 alkyl;

$R^2$ is (1) hydrogen, (2) C1–8 alkyl, (3) phenyl, or (4) C1–4 alkyl substituted by phenyl, —$OCOR^{16}$, in which $R^{16}$ is C1–4 alkyl; or —$CONR^{17}R^{18}$, in which $R^{17}$ and $R^{18}$ each, independently, is hydrogen or C1–4 alkyl;

E is (1) —$CONR^3$—, in which $R^3$ is hydrogen, C1–4 alkyl, phenyl, C1–4 alkyl substituted by phenyl;
(2) —$NR^3CO$—, in which $R^3$ is the same meaning as hereinbefore defined;
(3) —CO—O—,
(4) —O—CO—,
(5) —$NR^3$—CO—$NR^3$—, in which $R^3$ is the same meaning as hereinbefore defined;
(6) —CO—$CH_2$—,
(7) —CO—,
(8) —O—CO—$NR^3$—, in which $R^3$ is the same meaning as hereinbefore defined;
(9) —$NR^3$—CO—O—, in which $R^3$ is the same meaning as hereinbefore defined;
(10) —O—CO—O—,
(11) —CS—$NR^3$—, in which $R^3$ is the same meaning as hereinbefore defined;
(12) —$NR^3$—CS—, in which $R^3$ is the same meaning as hereinbefore defined;
(13) —$NR^3$—CS—$NR^3$—, in which $R^3$ is the same meaning as hereinbefore defined;
(14) —O—CS—$NR^3$—, in which $R^3$ is the same meaning as hereinbefore defined;
(15) —$NR^3$—CS—O—, in which $R^3$ is the same meaning as hereinbefore defined;
(16) —CS—O—,
(17) —O—CS—,
(18) —O—CS—O—, A is (1) hydrogen, (2) C1–8 alkyl, (3) C3–7 cycloalkyl, or (4) Ar, in which Ar is carbocyclic aryl or heterocyclic aryl, and these rings are unsubstituted or substituted by 1–3 of C1–15 alkyl, C1–15 alkoxy, halogen, nitro, cyano, guanidino, amidino, hydroxy, benzyloxy, —$NR^9R^{10}$, in which $R^9$ and $R^{10}$ each, independently, is hydrogen or C1–4 alkyl; —$COOR^{11}$, in which $R^{11}$ is hydrogen or C1–4 alkyl; trifluoromethyl, phenyl or heterocyclic ring;

J is (1) bond, (2) C2–4 alkylene, (3) C2–4 alkenylene, or (4)

in which $R^4$ and $R^5$ each, independently, is (i) hydrogen, (ii) C1–4 alkyl, (iii) C1–4 alkoxy, or $R^4$ and $R^5$, taken together with the carbon to which they are attached, is C3–7 cycloalkyl, G is (1) —$(CH_2)_m$—, in which m is 2, 3 or 4, or (2)

in which $R^6$ and $R^7$ each, independently, is (i) hydrogen, (ii) C1–8 alkyl, (iii) —$COOR^8$, in which $R^8$ is hydrogen, C1–8 alkyl, phenyl, C1–4 alkyl substituted by phenyl; (iv) Ar, in which Ar is the same meaning as hereinbefore defined; (v) heterocyclic ring, (vi) C1–8 alkyl substituted by —$COOR^8$, in which $R^8$ is the same meaning as hereinbefore defined; C1–4 alkoxy, hydroxy, benzyloxy, —$NR^{12}R^{13}$, in which $R^{12}$ and $R^{13}$ each, independently, is hydrogen or C1–4 alkyl; —$NR^{14}COOR^{15}$, in which $R^{14}$ is hydrogen or C1–4 alkyl, $R^{15}$ is hydrogen, C1–8 alkyl, phenyl, C1–4 alkyl substituted by phenyl; Ar or heterocyclic ring; with the proviso that one of carbon in C1–8 alkyl may be replaced by one of sulfur; or $R^6$ and $R^7$, taken together with the carbon to which they are attached, is C3–7 cycloalkyl; a compound in which E is —O—CO—$NR^3$—, —O—CO—O—, O—CS—$NR^3$—, or O—CS—O—, J is a bond and A is hydrogen, is excluded or non-toxic salts thereof.

2. A method according to claim 1, wherein the compound is selected from group consisting of
N-[[4-(Benzoylamino)phenyl]sulfonyl]glycine,
N-[[3-(Benzoylamino)phenyl]sulfonyl]glycine,
N-[[2-(Benzoylamino)phenyl]sulfonyl]glycine,
N-[[4-(Acetylamino)phenyl]sulfonyl]glycine,
N-[[4-(Phenylacetylamino)phenyl]sulfonyl]glycine,
N-[[4-[(Phenylethylcarbonyl)amino]phenyl]sulfonyl]glycine,
N-[[4-(Cinnamoylamino)phenyl]sulfonyl]glycine,
N-[[4-(N-Phenylureido)phenyl]sulfonyl]glycine, N-[[4-(N-Phenylthioureido)phenyl]sulfonyl]glycine,
N-[[4-[(Benzyloxycarbonyl)amino]phenyl]sulfonyl]glycine,
N-[[4-[(Phenyloxymethylcarbonyl)amino]phenyl]sulfonyl]glycine,
N-[[4-[(Benzyloxymethylcarbonyl)amino]phenyl]sulfonyl]glycine,
N-[[4-(4-Methoxybenzoylamino)phenyl]sulfonyl]glycine,
N-[[4-(4-Fluorobenzoylamino)phenyl]sulfonyl]glycine,
N-[[4-(4-Nitrobenzoylamino)phenyl]sulfonyl]glycine,
N-[[4-(3-Nitrobenzoylamino)phenyl]sulfonyl]glycine,
N-[[4-(2-Nitrobenzoylamino)phenyl]sulfonyl]glycine,
N-[[4-(4-Formylbenzoylamino)phenyl]sulfonyl]glycine,
N-[[4-(Benzoylamino)phenyl]sulfonyl]-D-α-phenylglycine,
N-[[4-(Benzoylamino)phenyl]sulfonyl]-L-α-phenylglycine,
N-[[4-(4-Methylbenzoylamino)phenyl]sulfonyl]-D-α-phenylglycine,
N-[[4-(Methylbenzoylamino)phenyl]sulfonyl]-L-α-phenylglycine,
N-[[4-(4-Methoxybenzoylamino)phenyl]sulfonyl]-D-αphenylglycine,
N-[[4-(4-Methoxybenzoylamino)phenyl]sulfonyl]-L-α-phenylglycine,
N-[[4-(4-Fluorobenzoylamino)phenyl]sulfonyl]-D-α-phenylglycine,
N-[[4-(4-Fluorobenzoylamino)phenyl]sulfonyl]-L-α-phenylglycine,
N-[[4-(4-Nitrobenzoylamino)phenyl]sulfonyl]-D-α-phenylglycine,
N-[[4-(4-Nitrobenzoylamino)phenyl]sulfonyl]-L-α-phenylglycine,
N-[(4-Pivaloyloxyphenyl)sulfonyl]-D, L-α-phenylglycine,
N-[(4-Pivaloyloxyphenyl)sulfonyl]-D, L-phenylalanine,
N-[[4-(2,4-Dichlorobenzoylamino)phenyl]sulfonyl]glycine,
N-[[4-(2,4-Dichlorobenzoylamino)phenyl]sulfonyl]-D, L-alanine ,
N-[[4-(2,4-Dichlorobenzoylamino)phenyl]sulfonyl]-β-alanine,
N-[[4-(2,4-Dichlorobenzoylamino)phenyl]sulfonyl]-L-valine,
N-[[4-(2,4-Dichlorobenzoylamino)phenyl]sulfonyl]-D, L-valine,
N-[[4-(2,4-Dichlorobenzoylamino)phenyl]sulfonyl]-L-leucine,
N-[[4-(2,4-Dichlorobenzoylamino)phenyl]sulfonyl]-D, L-leucine,
N-[[4-(2,4-Dichlorobenzoylamino)phenyl]sulfonyl]-D, L-serine,
N-[[4-(2,4-Dichlorobenzoylamino)phenyl]sulfonyl]-L-phenylalanine,
N-[[4-(2,4-Dichlorobenzoylamino)phenyl]sulfonyl]-L-tyrosine,
N-[[4-(2,4-Dichlorobenzoylamino)phenyl]sulfonyl]-D, L-alanine methyl ester,
N-[[4-(2,4-Dichlorobenzoylamino)phenyl]sulfonyl]-L-valine methyl ester,
N-[[4-(2,4-Dichlorobenzoylamino)phenyl]sulfonyl]-D, L-valine methyl ester,
N-[[4-(2,4-Dichlorobenzoylamino)phenyl]sulfonyl]-L-leucine methyl ester,
N-[[4-(2,4-Dichlorobenzoylamino)phenyl]sulfonyl]-D, L-serine methyl ester,
N-[[4-(2,4-Dichlorobenzoylamino)phenyl]sulfonyl]-L-tyrosine methyl ester,
N-[[4-(3-Nitrobenzoylamino)phenyl]sulfonyl]-L-aspartic acid,
N-[[3-(3-Nitrobenzoylamino)phenyl]sulfonyl]-L-aspartic acid,
N-[[4-(3-Aminobenzoylamino)phenyl]sulfonyl]-L-aspartic acid,
N-[[3-(3-Aminobenzoylamino)phenyl]sulfonyl]-L-aspartic acid,
N-[[4-(Benzoylamino)phenyl]sulfonyl]-L-glutamic acid,
N-[[4-(4-Chlorobenzoylamino)phenyl]sulfonyl]-L-glutamic acid,
N-[[4-(4-Nitrobenzoylamino)phenyl]sulfonyl]-L-glutamic acid,
N-[[4-[2-(4-(1-Pyrrolidinyl)phenyl]butyryloxy]phenyl]sulfonyl]-D, L-3-morpholinoalanine ethyl ester,
N-[[4-[2-(4-(1-Nitrophenyl)butyryloxy]phenyl]sulfonyl]-D, L-3-morpholinoalanine ethyl ester,
N-[[4-(2-Methoxy-2-phenylacetyloxy)phenyl]sulfonyl]-D, L-3-morpholinoalanine ethyl ester,
N-[[4-[[[1-(4-Nitrophenyl)cyclobutyl]carbonyl]oxy]phenyl]sulfonyl]-D,L-3-morpholinoalanine ethyl ester,
N-[[3-Methyl-4-[2-[4-(1-Pyrrolidinyl)phenyl]butyryloxy]phenyl]sulfonyl]-t-butoxycarbonyl-L-lysine,
N-[[4-(2-Phenylbutyryloxy)phenyl]sulfonyl]glycine,
N-[[4-[2-[4-(1-Pyrrolidinyl)phenyl]butyryloxy]phenyl]sulfonyl]-D,L-phenylalanine,
N-[[4-[2-[4-(1-Pyrrolidinyl)phenyl]butyryloxy]phenyl]sulfonyl]-D,L-aspartic acid,
N-[[4-[[[1-(4-Nitrophenyl)cyclobutyl]carbonyl]oxy]phenyl]sulfonyl]-D,L-aspartic acid,
1-[[4-[2-[4-(1-Pyrrolidinyl)phenyl]butyryloxy]phenyl]sulfonylamide]-1-cyclopropanecarboxylic acid,
N-[[4-[2-[4-(1-Pyrrolidinyl)phenyl]butyryloxy]phenyl]sulfonyl]-D,L-2-(2-furanyl)glycine,
N-[[4-[2-[4-(1-Pyrrolidinyl)phenyl]butyryloxy]phenyl]sulfonyl]-D,L-2-(2-thienyl)glycine,
N-[[4-[2-[4-(1-Pyrrolidinyl)phenyl]butyryloxy]phenyl]sulfonyl]-L-valine,
N-[[4-[2-[4-(1-Pyrrolidinyl)phenyl]butyryloxy]phenyl]sulfonyl]-S-carboxymethyl-L-cysteine,
N-[[4-[2-Ethyl-2-(4-methoxyphenyl)butyryloxy]phenyl]sulfonyl]-glycine,
N-[[3-Methyl-4-[2-[4-(1-Pyrrolidinyl)phenyl]butyryloxy]phenyl]sulfonyl]-L-lysine, 5-[N-[[3-Methyl-4-[2-[4-(1-pyrrolidinyl)phenyl]butylyloxy]phenyl]sulfonyl]amino]pentanoic acid, and
N-[[(3-Methyl-4-pivaloyloxy)phenyl]sulfonyl]-β-alanine.

3. A compound of the formula (Ib):

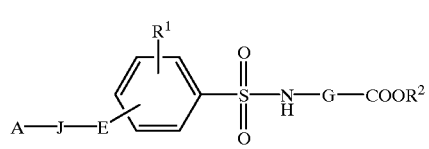

wherein
$R^1$ is hydrogen, or C1–4 alkyl;
$R^2$ is (1) hydrogen, (2) C1–8 alkyl, (3) phenyl, or (4) C1–4 alkyl substituted by phenyl, —OCOR[16], in which R[16] is C1–4 alkyl; or —CONR[17]R[18], in which R[17] and R[18] each, independently, is hydrogen or C1–4 alkyl;
E is (1) —CONR[3]—, in which R[3] is hydrogen, C1–4 alkyl, phenyl, C1–4 alkyl substituted by phenyl;
  (2) —NR[3]CO—, in which R[3] is the same meaning as hereinbefore defined;
  (3) —CO—O—,
  (4) —O—CO—,
  (5) —NR[3]—CO—NR[3]—, in which R[3] is the same meaning as hereinbefore defined;

(6) —CO—CH$_2$—,
(7) —CO—,
(8) —O—CO—NR$^3$—, in which R$^3$ is the same meaning as hereinbefore defined;
(9) —NR$^3$—CO—O—, in which R$^3$ is the same meaning as hereinbefore defined;
(10) —O—CO—O—,
(11) —CS—NR$^3$—, in which R$^3$ is the same meaning as hereinbefore defined;
(12) —NR$^3$—CS—, in which R$^3$ is the same meaning as hereinbefore defined;
(13) —NR$^3$—CS—NR$^3$—, in which R$^3$ is the same meaning as hereinbefore defined;
(14) —O—CS—NR$^3$—, in which R$^3$ is the same meaning as hereinbefore defined;
(15) —NR$^3$—CS—O—, in which R$^3$ is the same meaning as hereinbefore defined;
(16) —CS—O—,
(17) —O—CS—,
(18) —O—CS—O—, A is (1) hydrogen, (2) C1–8 alkyl, (3) C3–7 cycloalkyl, or (4) Ar, in which Ar is carbocyclic a heterocyclic aryl, and these rings are unsubstituted or substituted by 1–3 of C1–15 alkyl, C1–15 alkoxy, halogen, nitro, cyano, guanidino, amidino, hydroxy, benzyloxy, —NR$^9$R$^{10}$, in which R$^9$ and R$^{10}$ each, independently, is hydrogen or C1–4 alkyl; —COOR$^{11}$, in which R$^{11}$ is hydrogen or C1–4 alkyl; trifluoromethyl, phenyl or heterocyclic ring;

J is (1) bond, (2) C2–4 alkylene, (3) C2–4 alkenylene, or (4)

in which R$^4$ and R$^5$ each, independently, is (i) hydrogen, (ii) C1–4 alkyl, (iii) C1–4 alkoxy, or R$^4$ and R$^5$, taken together with the carbon to which they are attached, is C3–7 cycloalkyl, G is (1) —(CH$_2$)$_m$—, in which m is 2, 3 or 4, or (2)

in which R$^6$ and R$^7$ each, independently, is (i) hydrogen, (ii) C1–8 alkyl, (iii) —COOR$^8$, in which R$^8$ is hydrogen, C1–8 alkyl, phenyl, C1–4 alkyl substituted by phenyl; (iv) Ar, in which Ar is the same meaning as hereinbefore defined; (v) heterocyclic ring, (vi) C1–8 alkyl substituted by —COOR$^8$, in which R$^8$ is the same meaning as hereinbefore defined; C1–4 alkoxy, hydroxy, benzyloxy, —NR$^{12}$R$^{13}$, in which R$^{12}$ and R$^{13}$ each, independently, is hydrogen or C1–4 alkyl; —NR$^{14}$COOR$^{15}$, in which R$^{14}$ is hydrogen or C1–4 alkyl, R$^{15}$ is hydrogen, C1–8 alkyl, phenyl, C1–4 alkyl substituted by phenyl; Ar or heterocyclic ring; with the proviso that one of carbon in C1–8 alkyl may be replaced by one of sulfur; or R$^6$ and R$^7$, taken together with the carbon to which they are attached, is C3–7 cycloalkyl; or non-toxic salts thereof; with the proviso that:

1) a compound in which E is —O—CO—NR$^3$—, —O—CO—O—, —O—CS—NR$^3$— or —O—CS—O—, J is bond and A is hydrogen, is excluded;

2) when either of R$^6$ or R$^7$ is hydrogen and the other is C1–8 alkyl substituted by Ar, then Ar is heterocyclic aryl; and 3) the following compounds are excluded:
(1) N-[[4-(Benzoylamino)phenyl]sulfonyl]glycine,
(2) N-[[3-(Benzoylamino)phenyl]sulfonyl]glycine,
(3) N-[[2-(Benzoylamino)phenyl]sulfonyl]glycine,
(4) N-[[4-(Acetylamino)phenyl]sulfonyl]glycine,
(5) N-[[4-(Phenylacetylamino)phenyl]sulfonyl]glycine,
(6) N-[[4-[(Phenylethylcarbonyl)amino]phenyl)sulfonyl]glycine,
(7) N-[[4-(Cinnamoylamino)phenyl]sulfonyl]glycine,
(8) N-[[4-(N-Phenylureido)phenyl]sulfonyl]glycine,
(9) N-[[4-(N-Phenylthioureido)amino]phenyl]sulfonyl]glycine,
(10) N-[[4-[(Benzyloxycarbonyl)amino]phenyl]sulfonyl]glycine,
(11) N-[[4-[(phenyloxymethylcarbonyl)amino]phenyl]sulfonyl]glycine,
(12) N-[[4-[(Benzyloxymethylcarbonyl)amino]phenyl]sulfonyl]glycine,
(13) N-[[4-(4-Methoxybenzoylamino)phenyl]sulfonyl]glycine,
(14) N-[[4-(4-Fluorobenzoylamino)phenyl]sulfonyl]glycine,
(15) N-[[4-(4-Nitrobenzoylamino)phenyl]sulfonyl]glycine,
(16) N-[[4-(3-Nitrobenzoylamino)phenyl]sulfonyl]glycine,
(17) N-[[4-(2-Nitrobenzoylamino)phenyl]sulfonyl]glycine,
(18) N-[[4-(4-Formylbenzoylamino)phenyl]sulfonyl]glycine,
(19) N-[[4-(Benzoylamino)phenyl]sulfonyl]-D-α-phenylglycine,
(20) N-[[4-(Benzoylamino)phenyl]sulfonyl]-L-α-phenylglycine,
(21) N-[[4-(4-Methylbenzoylamino)phenyl]sulfonyl]-D-α-phenylglycine,
(22) N-[[4-(4-Methylbenzoylamino)phenyl]sulfonyl]-L-α-phenylglycine,
(23) N-[[4-(4-Methoxybenzoylamino)phenyl]sulfonyl]-D-α-phenylglycine,
(24) N-[[4-(4-Methoxybenzoylamino)phenyl]sulfonyl]-L-α-phenylglycine,
(25) N-[[4-(4-Fluorobenzoylamino)phenyl]sulfonyl]-D-α-phenylglycine,
(26) N-[[4-(4-Fluorobenzoylamino)phenyl]sulfonyl]-L-α-phenylglycine,
(27) N-[[4-(4-Nitrobenzoylamino)phenyl]sulfonyl]-D-α-phenylglycine,
(28) N-[[4-(4-Nitrobenzoylamino)phenyl]sulfonyl]-L-α-phenylglycine,
(29) N-[(4-Pivaloyloxyphenyl)sulfonyl]-D,L-α-phenylglycine,
(31) N-[[4-(2,4-Dichlorobenzoylamino)phenyl]sulfonyl]glycine,
(32) N-[[4-(2,4-Dichlorobenzoylamino)phenyl]sulfonyl]-D,L-alanine,
(33) N-[[4-(2,4-Dichlorobenzoylamino)phenyl]sulfonyl]-β-alanine,
(34) N-[[4-(2,4-Dichlorobenzoylamino)phenyl]sulfonyl]-L-valine,
(35) N-[[4-(2,4-Dichlorobenzoylamino)phenyl]sulfonyl]-D,L-valine,

(36) N-[[4-(2,4-Dichlorobenzoylamino)phenyl]sulfonyl]-L-leucine,
(37) N-[[4-(2,4-Dichlorobenzoylamino)phenyl]sulfonyl]-D,L-leucine,
(38) N-[[4-(2,4-Dichlorobenzoylamino)phenyl]sulfonyl]-D,L-serine,
(41) N-[[4-(2,4-Dichlorobenzoylamino)phenyl]sulfonyl]-D,L-alanine methyl ester,
(42) N-[[4-(2,4-Dichlorobenzoylamino)phenyl)sulfonyl]-L-valine methyl ester,
(43) N-[[4-(2,4-Dichlorobenzoylamino)phenyl)sulfonyl]-D,L-valine methyl ester,
(44) N-[[4-[[(2,4-Dichlorobenzoylamino)phenyl]sulfonyl]-L-leucine methyl eater,
(45) N-[[4-(2,4-Dichlorobenzoylamino)phenyl]sulfonyl]-D,L-serine methyl ester,
(47) N-[[4-(3-Nitrobenzoylamino)phenyl]sulfonyl]-L-aspartic acid,
(48) N-[[3-(3-Nitrobenzoylamino)phenyl]sulfonyl]-L-aspartic acid,
(49) N-[[4-(3-Aminobenzoylamino)phenyl]sulfonyl]-L-aspartic acid,
(50) N-[[3-(3-Aminobenzoylamino)phenyl]sulfonyl]-L-aspartic acid,
(51) N-[[4-(Benzoylamino)phenyl]sulfonyl]-L-glutamic acid,
(52) N-[[4-(4-Chlorobenzoylamino)phenyl]sulfonyl]-L-glutamic acid,
(53) N-[[4-(4-Nitrobenzoylamino)phenyl]sulfonyl]-L-glutamic acid,
(54) N-[[4-[2-(4-(1-Pyrrolidinyl)phenyl]butyryloxy]phenyl]sulfonyl]-D,L-3-morpholinoalanine ester,
(55) N-[[4-[2-(4-(1-Nitrophenyl)butyryloxy]phenyl]sulfonyl]-D,L-3-morpholino alanine ethyl ester,
(56) N-[[4-(2-Methoxy-2-phenylacetyloxy)phenyl]sulfonyl]-D,L-3-morpholino alanine ethyl ester,
(57) N-[[4-[[[1-(4-Nitrophenyl)cyclobutyl]carbonyl]oxy]phenyl]sulfonyl]-D,L-3-morpholinoalanine ethyl ester,
(58) N-[[3-Methyl-4-[2-[4-(1-Pyrrolidinyl)phenyl]butyryloxy]phenyl]sulfonyl]-t-butoxycarbonyl-L-lysine,
(59) N-[[4-(2-Phenylbutyryloxy)phenyl]sulfonyl]glycine,
(61) N-[[4-[2-[4-(1-Pyrrolidinyl)phenyl]butyryloxy]phenyl]sulfonyl]-D,L-aspartic acid,
(62) N-[[4-[[[1-(4-Nitrophenyl)cyclobutyl]carbonyl]oxy]phenyl]sulfonyl]-D,L-aspartic acid,
(63) 1-[[4-[2-[4-(1-Pyrrolidinyl)phenyl]butyryloxyl phenyl]sulfonylamide]-1-cyclopropanecarboxylic acid,
(64) N-[[4-[2-[4-(1-Pyrrolidinyl)phenyl]butyryloxy]phenyl]sulfonyl]-D,L-2-(2-furanyl)glycine,
(65) N-[[4-[2-[4-(1-Pyrrolidinyl)phenyl]butyryloxy]phenyl]sulfonyl]-D,L-2-(2-thienyl)glycine,
(66) N-[[4-[2-[4-(1-Pyrrolidinyl)phenyl]butyryloxy]phenyl]sulfonyl]-L-valine,
(67) N-[[4-[2-[4-(1-Pyrrolidinyl)phenyl]butyryloxy]phenyl]sulfonyl]-S-carboxymethyl-L-cysteine,
(68) N-[[4-[2-Ethyl-2-(4-methoxyphenyl)butyryloxy]phenyl]sulfonyl]-glycine,
(69) N-[[3-Methyl-4-[2-[4-(1-Pyrrolidinyl)phenyl]butyryloxy]phenyl]sulfonyl]-L-lysine,
(70) 5-[N-[[3-Methyl-4-[2-[4-(1-pyrrolidinyl)phenyl]butylyloxy]phenyl]sulfonyl]amino] pentanoic acid,and
(71) N-[[(3-Methyl-4-pivaloyloxy)phenyl]sulfonyl]-β-alanine.

4. A compound according to claim 3, wherein E is —CONR$^3$—, —NR$^3$CO—, —NR$^3$—CO—NR$^3$—, —O—CO—NR$^3$—, —NR$^3$—CO—O—, —CS—NR$^3$—, —NR$^3$—CS—, —NR$^3$—CS—NR$^3$—, —OCS—NR$^3$—, —NR$^3$—CS—O—, wherein R$^3$ is the same meaning as claim 1.

5. A compound according to claim 3, wherein E is —CO—O—, —O—CO—, —CO—CH$_1$—, —CO—, —O—CO—O—, —CS—O—, —O—CS—, —O—CS—O—.

6. A compound or C1–8 alkyl ester, C1–4 alkyl substituted by phenyl ester thereof or non-toxic salts thereof according to claim 3, which compound is selected from the group consisting of:
N-[[4-(p-Toluoylamino)phenyl]sulfonyl]glycine,
N-[[4-(Isobutyrylamino)phenyl]sulfonyl]glycine,
N-[[4-(Acetylamino)phenyl]sulfonyl]glycine,
N-[[4-(o-Toluoylamino)phenyl]sulfonyl]glycine,
N-[[4-(m-Toluoylamino)phenyl]sulfonyl]glycine,
N-[[4-(2-Chlorobenzoylamino)phenyl]sulfonyl]glycine,
N-[[4-(3-Chlorobenzoylamino)phenyl]sulfonyl]glycine,
N-[[4-(4-Chlorobenzoylamino)phenyl]sulfonyl]glycine,
N-[[4-(2-Methoxybenzoylamino)phenyl]sulfonyl]glycine,
N-[[4-(3-Methoxybenzoylamino)phenyl]sulfonyl]glycine,
N-[[4-(4-Ethylbenzoylamino)phenyl]sulfonyl]glycine,
N-[[4-(4-Propylbenzoylamino)phenyl]sulfonyl]glycine,
N-[[4-(2-Fluorobenzoylamino)phenyl]sulfonyl]glycine,
N-[[4-(3-Fluorobenzoylamino)phenyl]sulfonyl]glycine,
N-[[4-(Cyclohexylcarbonylamino)phenyl]sulfonyl]glycine,
N-[[4-(4-Trifluoromethylbenzoylamino)phenyl]sulfonyl]glycine,
N-[[4-(2-Thienylcarbonylamino)phenyl]sulfonyl]glycine,
N-[[4-(2-Furylcarbonylamino)phenyl]sulfonyl]glycine,
N-[[4-(2-Pyridylcarbonylamino)phenyl]sulfonyl]glycine,
N-[[4-(3-Pyridylcarbonylamino)phenyl]sulfonyl]glycine,
N-[[4-(4-Pyridylcarbonylamino)phenyl]sulfonyl]glycine,
N-[[4-(3-Thienylcarbonylamino)phenyl]sulfonyl]glycine,
N-[[4-(3-Furylcarbonylamino)phenyl]sulfonyl]glycine,
N-[[4-(4-Methoxycarbonylbenzoylamino)phenyl]sulfonyl]glycine,
N-[[4-(4-Cyanobenzoylamino)phenyl]sulfonyl]glycine,
N-[[4-(4-Benzyloxybenzoylamino)phenyl]sulfonyl]glycine,
N-[[4-(4-Carboxybenzoylamino)phenyl]sulfonyl]glycine,
N-[[4-[(4-Butylbenzoylamino)phenyl]sulfonyl]glycine,
N-[[4-(4-Pentylbenzoylamino)phenyl]sulfonyl]glycine,
N-[[4-(4-Phenylbenzoylamino)phenyl]sulfonyl]glycine,
N-[[4-(Benzoylamino)phenyl)sulfonyl]-L-valine,
N-[[4-(1-Naphthoylamino)phenyl)sulfonyl]glycine,
N-[[4-(2-Naphthoylamino)phenyl]sulfonyl]glycine,
N-[[4-(3-Benzyloxybenzoylamino)phenyl]sulfonyl]glycine,
N-[[4-(2-Benzyloxybenzoylamino)phenyl]sulfonyl]glycine,
N-[[4-(Benzoylamino)phenyl]sulfonyl]-L-aspartic acid,
N-[[4-(Benzoylamino)phenyl]sulfonyl]-L-leucine,
N-[[4-(Benzoylamino)phenyl]sulfonyl]-D-leucine,
N-[[4-(Phenoxycarbonylamino)phenyl]sulfonyl]glycine,
N-[[4-(4-Dimethylaminobenzoylamino)phenyl]sulfonyl]glycine,
N-[[4-(Benzoylamino)phenyl]sulfonyl]-D-valine,
N-[[4-(Benzoylamino)phenyl]sulfonyl]-L-alanine,
N-[[4-(Benzoylamino)phenyl]sulfonyl]-D-alanine,
N-[[4-(Benzoylamino)phenyl]sulfonyl]-L-lysine,
N-[[4-(Benzoylamino)phenyl]sulfonyl]-D-lysine,
N-[[4-(Benzoylamino)phenyl]sulfonyl]-D-glutamic acid,
N-[[4-(4-Dodecylbenzoylamino)phenyl]sulfonyl]glycine,
4-[N-[[4-(Benzoylamino)phenyl]sulfonyl]amino]butyric acid,
N-[[4-(Benzoylamino)phenyl]sulfonyl]amino]-L-serine,
N-[[4-(Benzoylamino)phenyl]sulfonyl]amino]-D-serine, N-[[4-(Benzoylamino)phenyl]sulfonyl]-D-aspartic acid,
N-[[4-(p-Toluoylamino)phenyl]sulfonyl]-L-valine,
N-[[4-(4-Hexylbenzoylamino)phenyl]sulfonyl]glycine,
N-[[4-(4-Heptylbenzoylamino)phenyl]sulfonyl]glycine,
N-[[4-(4-Isopropylbenzoylamino)phenyl]sulfonyl]glycine,
N-[[4-(4-Isobutylbenzoylamino)phenyl]sulfonyl]glycine,
N-[[4-(Benzoylamino)phenyl]sulfonyl]-2,2-dimethylglycine,
N-[[4-(p-Toluoylamino)phenyl]sulfonyl]amino]-D-serine,
N-[[4-(p-Toluoylamino)phenyl]sulfonyl]-L-leucine,
N-[[4-(p-Toluoylamino)phenyl]sulfonyl]-D-alanine,
N-[[4-(p-Toluoylamino)phenyl]sulfonyl)-D-valine,
N-[[4-(p-Toluoylamino)phenyl]sulfonyl]-D-leucine,
N-[[2-Methyl-4-(p-Toluoylamino)phenyl]sulfonyl]glycine,
N-[[3-Methyl-4-(p-Toluoylamino)phenyl]sulfonyl]glycine,
N-[[4-(2-Hydroxy-4-methylbenzoylamino)phenyl]sulfonyl]-D-alanine,
N-[[4-(2-Thienylcarbonylamino)phenyl]sulfonyl-D-alanine,
N-[[3-(Benzoylamino)phenyl]sulfonyl]glycine,
N-[[2-(Benzoylamino)phenyl]sulfonyl]glycine,
N-[[4-(2-Aminobenzoylamino)phenyl]sulfonyl]glycine,
N-[[4-(3-Aminobenzoylamino)phenyl]sulfonyl]glycine,
N-[[4-(4-Aminobenzoylamino)phenyl]sulfonyl]glycine,
N-[[4-(4-Hydroxybenzoylamino)phenyl]sulfonyl]glycine,
N-[[4-[(2-Phenylethyl)carbonylamino]phenyl]sulfonyl]glycine,
N-[(4-Methoxycarbonylphenyl)sulfonyl]glycine,
N-[(4-Carboxyphenyl)sulfonyl]glycine,
N-[[4-(4-Amidinophenoxycarbonyl)phenyl]sulfonyl-β-alanine,
N-[(4-Benzoylmethylphenyl)sulfonyl]glycine,and
N-[4-[(4-Methoxybenzoyl)methyl]sulfonyl]glycine.

7. A compound or ester thereof or non-toxic salts thereof according to claim 3, which compound is selected from group consisting of:

N-[[4-(Benzyloxycarbonyloxy)phenyl]sulfonyl]glycine,
N-[[4-(Benzoyloxy)phenyl]sulfonyl]glycine,
N-[[4-(4-Amidinobenzoyloxy)phenyl]sulfonyl]glycine,
N-[[4-[[(4-Guanidinobenzoyloxy)phenyl]sulfonyl]glycine,
N-[[4-(Benzoyloxy)phenyl]sulfonyl]-β-alanine,
N-[[4-(4-Amidinobenzoyloxy)phenyl]sulfonyl]-β-alanine,
N-[[4-(Phenoxycarbonyl)phenyl]sulfonyl]glycine,
N-[[4-(4-Amidinophenoxycarbonyl)phenyl]sulfonyl]-L-aspartic acid,
N-[[3-(4-Amidinophenoxycarbonyl)phenyl]sulfonyl]glycine,
N-[[4-(4-Amidinophenoxycarbonyl)phenyl]sulfonyl]glycine,
N-[(4-Methoxycarbonylphenyl)sulfonyl]glycine,
N-[(4-Carboxyphenyl)sulfonyl]glycine,
N-[[4-(4-Amidinophenoxycarbonyl)phenyl]sulfonyl-β-alanine,
N-[(4-Benzoylmethylphenyl)sulfonyl]glycine,and
N-[4-[(4-Methoxybenzoyl)methyl]sulfonyl]glycine.

8. A pharmaceutical composition for the treatment of rheumatoid, arthrosteitis, unusual bone resorption, osteoporosis, periodontitis, interstitial nephritis, arteriosclerosis, pulmonary emphysema, cirrhosis, cornea injury, metastasis of, invasion of or growth of tumor cell, autoimmune disease (Crohn's disease, Sjogren's syndrome etc.), disease caused by vascular emigration or infiltration of leukocytes, arterialization, which comprises, as active ingredient, an effective amount of a compound of formula (Ib) depicted in claim 3 or the pharmaceutically acceptable salt thereof, with a pharmaceutically acceptable carrier or coating.

* * * * *